US010532111B2

United States Patent
Kay et al.

(10) Patent No.: US 10,532,111 B2
(45) Date of Patent: Jan. 14, 2020

(54) RECOMBINANT ADENO-ASSOCIATED VIRUS CAPSIDS RESISTANT TO PRE-EXISTING HUMAN NEUTRALIZING ANTIBODIES

(71) Applicant: The Board of Trustees of the Leland Stanford Junior University, Stanford, CA (US)

(72) Inventors: Mark A. Kay, Los Altos, CA (US); Nicole K. Paulk, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 15/681,267

(22) Filed: Aug. 18, 2017

(65) Prior Publication Data
US 2017/0360962 A1 Dec. 21, 2017

Related U.S. Application Data

(63) Continuation of application No. 15/435,212, filed on Feb. 16, 2017, now Pat. No. 10,179,176.

(60) Provisional application No. 62/296,046, filed on Feb. 16, 2016.

(51) Int. Cl.
| | |
|---|---|
| *A61K 48/00* | (2006.01) |
| *C12N 15/85* | (2006.01) |
| *A61K 9/127* | (2006.01) |
| *C07K 14/005* | (2006.01) |
| *C07K 14/47* | (2006.01) |
| *C12N 7/00* | (2006.01) |
| *C12N 15/10* | (2006.01) |
| *C12N 15/86* | (2006.01) |
| *A61K 39/23* | (2006.01) |
| *G01N 33/569* | (2006.01) |
| *A61K 39/00* | (2006.01) |

(52) U.S. Cl.
CPC .......... *A61K 48/0058* (2013.01); *A61K 39/23* (2013.01); *C07K 14/005* (2013.01); *C12N 7/00* (2013.01); *C12N 15/1058* (2013.01); *C12N 15/86* (2013.01); *G01N 33/56983* (2013.01); *A61K 2039/575* (2013.01); *C12N 2750/14122* (2013.01); *C12N 2750/14134* (2013.01); *C12N 2750/14143* (2013.01); *C12N 2750/14151* (2013.01); *C12N 2750/14171* (2013.01); *G01N 2333/015* (2013.01); *G01N 2469/20* (2013.01)

(58) Field of Classification Search
CPC .... C07K 14/505; C07K 14/535; C12N 15/85; C12Y 304/21022; A61K 38/1816
See application file for complete search history.

(56) References Cited

FOREIGN PATENT DOCUMENTS

| WO | WO 2013-029030 A1 | 2/2013 |
|---|---|---|
| WO | WO2013029030 | * 2/2013 |
| WO | WO 2014-194132 A1 | 12/2014 |

OTHER PUBLICATIONS

Gearing, "A match made in Heaven: CRISPR and AAV", Addgene's Blog/Post, Jul. 14, 2015:pdf pp. 1-7.*
International Search Report for International Patent Application No. PCT/US2017/018226 filed Jun. 2, 2017 (8 pages).
Grimm, D. et al., "E Pluribus Unum: 50 Years of Research, Millions of Viruses, and One Goal-Tailored Acceleration of AAV Evolution", *Molecular Therapy*, vol. 23, No. 12, 2015, pp. 1819-1831.
Paulk, N. K. et al., "262: Directed Evolution of Improved AAV Capsids for the Ideal Human Liver Vector—Can Hum Liver Tropism and Human Immune Evasion be Achieved?", Molecular Therapy; 18th Annual Meeting of the American-Society-of-Gene-and-Cell-Therapy(ASGCT), vol. 23, No. Suppl. 1, 2015, pp. S104-S105.
Paulk, N. K. et al., "Bioengineered AAV capsids with enhanced human hepatocyte transduction and unique humoral neutralization profiles for use in liver gene therapy", Liver Center Annual Symposium, 2016, San Francisco.
Written Opinion for International Patent Application No. PCT/US2017/018226 filed Jun. 2, 2017 (9 pages).

* cited by examiner

*Primary Examiner* — Barry A Chestnut
(74) *Attorney, Agent, or Firm* — Morgan Lewis & Bockius LLP

(57) ABSTRACT

The present invention relates to variant AAV capsid polypeptides, wherein the variant capsid polypeptides exhibit an enhanced neutralization profile, increased transduction and/or tropism in human liver tissue or hepatocyte cells (i.e., human hepatocyte cells), or both, as compared non-variant parent capsid polypeptides.

50 Claims, 27 Drawing Sheets
(20 of 27 Drawing Sheet(s) Filed in Color)
Specification includes a Sequence Listing.

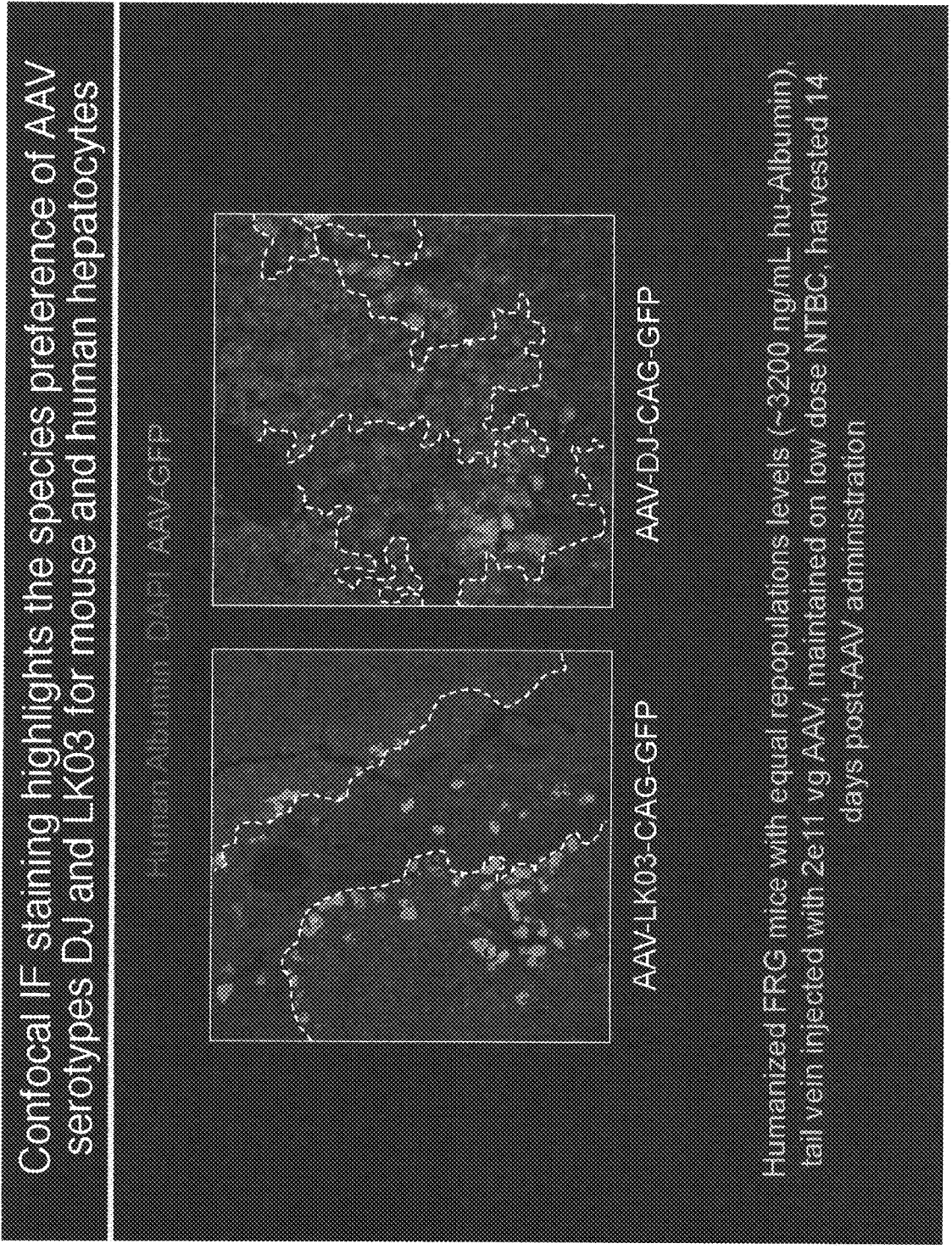

FIG. 11A

>AAV-NP84-nt (SEQ ID NO:1)
ATGGCTGCCGATGGTTATCTTCCAGATTGGCTCGAGGACACTCTCTGAGGAATAAGACAGTGGTGGAAGCTCAAACCTGGCAGA
GCGGCATAAGGACAGACAGCAGGGGTCTTGTGCTTCCTGGGTACAAGCTACCTCCGACCCTTCAACGACTCGACAAGGGAGAGCCGGTCAACGACGCCGGC
CCCTCGAGCGACGACAAAGCCTACGACGGCCAGCTCGAAGCGGCAGTCTTCCAGGCGAGAACCTGGCGCCCTTGAAGACCTGTGTGAACCTCTGAACCTCTGGGCCCTGTTGAACCTCTGGGCCCCGCTAAAAAGAGGACTCAATTTGGTCAGACTGGCGACT
ACGTCTTTTGGGGCAACCTCGGACACTCTCCCTGTGAGCCAGACCAGCAGCAGCCAAGAGCAGGCCAAGACAGGCCCAGAGAACAGGCAGGCCCCCTGTGCTCTGGGAACTCGGGCAGCCCCTCTGTGGAACCTGGAACCCCTGGCCCCTCGTGCCCCCTCAATGGCATTGCCATTCCTCAGGAAATTCCTCAGGAAATTCCTCGAGCCCCAGGCATTGGGCGACAGGTCGGCGTACAGCTGCATCACCAGCCTGGGGTGTATTTGACTTTAACA
CACCTACAACAACATCTCCACACGTGGCTTCCAGCACGTTGCCAATCAGGAGCTTCAAACGACAGAGCTTTGGCTCAGCAACTGGGATGGCACTGGGGGAATTCCAGGAAACCGACACGCGTTGCCAATCAGGAGCTTGGCTACAGACCCTTTGGCTACAGACCCTTTGGCTACAGACCCTTTGGCTACAGACCCTTTGGCTACAGACCCTTAGCCAGGATACAGCCTGCCCAAGAAACTCAGCTTCAAACATCCAAGTTAAA
GAGTCACGCAGAACGATGGCCACGACGTATTGCCATCATAACCTTACCAGCAGCGTCTTCAAGTGTTACTCACCCTGAACACCGTACAACAACCAGAACAACACCAGTACCAGCCCTGTCAGCAGTCAGGGAGCAGTCAGCAGCAGCTACGCTCGGC
GCATCAAGGATGCCTCCCGCCGTTCCTTCCTCAGATGCTGCCGAACAACTTTACCTTCACCTGAACACTCTGCTTCTCCTGGACCCTGTCAGAGAACATGGCTGCTTCCTGGTGAATCCGGCAGCCTCTTCCTCCTCGACACATGCATGGAACATGATATGATATGGGACGAATCGGCCAAGTGTGGACATCACGAAAACAGATGGGACATCACGAAAACAGATGGGACATCAGAAAACAGAAAACCAGAAAACAGAAAACCAGAAAACCAGAAAACCAGAAAACCAGAAAAGGGCTTCCTCAGAAAAGAAGAAATCAGGACAACAATCCGT
ACTCAAGGATGCCTCCCGCCGTTCCTTCCTCAGATGCTGCCGAACAACTTTACCTTCACCTGAACACTCTGCTTCTCCTGGACCCTGTCAGAGAACATGGCTGCTTCCTGGTGAATCCGGCAGCCTCTTCCTCCTCGACACATGCATGGAACATGATATGATATGGGACGAATCGGCCAAGTGTGGACATCACGAAAACAGATGGGACATCACGAAAACAGATGGGACATCAGAAAACAGAAAACCAGAAAACAGAAAACCAGAAAACCAGAAAACCAGAAAACCAGAAAAGGGCTTCCTCAGAAAAGAAGAAATCAGGACAACAATCCGT
GGCCGGAGCGAGCTGAGACTCTTGGGAAGCAAGGCTCAGAGAGAAAACAAATGTGGACATTGAAAAGTCCTTCAGGCTGCTGATTCGGACTCCAGGACAGGCTGAATCGGCGACTGGATTCAAGGGCCCTGATTCAAGGGCCCTGATTCAAGGGACACTGGGACATGGGACATGGGCACACGACACCAGGTTCTTCCAGGACTTCCGGACATCCACGGACAGGT
CAGCTGGAGATCGAGTGGGAGCTCCAGAAGGAAAACAGACAGAAGCTGGAAGCTGGAAGAAAACAGAAAACAGAAGCTGGAATCCAAAACTGGAAGCTGGAATCCAAAACTGGAAGCTGGAATCCAAAACTGGAAGCTGGAATCCAAAACTGGAAGCTGGAATCCAAAACTGGAAGCTGGAATCCCAGAACTTGTTAATGTGAATCTGTAA
TGGACACTAATGGCGTGTATTCAGAGCCTCGCCCATTGGCACCCAGATACCTGTACCGTAATCTGTAA

>AAV-NP84-aa (SEQ ID NO:2)
MAADGYLPDWLEDTLSEGIRQWWKLKPGPPPPKPAERHKDDSRGLVLPGYKYLGPFNGLDKGEPVNEADAAALEHDKAYDRQLDSGDNPYLKYNHADAEFQERLKED
TSFGGNLGRAVFQAKKRVLEPLGLVEEPVKTAPGKKRPVEHSPVEPDSSSGTGKTGQQPAKKRLNFGQTGDSESVPDPQPLGEPPAAPSGLGTNTMATGSGAPMADN
NEGADGVGNSSGNWHCDSQWLGDRVITTSTRTWALPTYNNHLYKQISSQSGASNDNHYFGYSTPWGYFDFNRFHCHFSPRDWQRLINNNWGFRPKKLSFKLFNIQVK
EVTQNDGTTTIANNLTSTVQVFTDSEYQLPYVLGSAHQGCLPFFPADVFMVPQYGYLTLNNGSQAVGRSSFYCLEYFPSQMLRTGNNFTFSYTFEDVPFHSSYAHSQ
SLDRLMNPLIDQYLYYLSRTNTPSGTTTQSRLQFSQAGASDIRDQSRNWLPGPCYRQQRVSKTSADNNNSEYSWTGATKYHLNGRDSLVNPGPAMASHKDDEEEFFP
QSGVLIFGKQGSEKTNVDIEKVMITDEEEIRTTNPVATEQYGSVSTNLQGGNRQAATADVNTQGVLPGMVWQDRDVYLQGPIWAKIPHTDGHFHPSPLMGGFGLKHP
PPQILIKNTPVPANPSTTFSAAKFASFITQYSTGQVSVEIEWELQKENSKRWNPEIQYTSNYNKSVNVDFTVDTNGVYSEPRPIGTRYLTRNL

FIG. 11B

>AAV-NP59-nt (SEQ ID NO:3)

```
ATGGCTGCCGATGGTTATCTTCCAGATTGGCTCGAGGACACTCTCTGAGGAATAAGACAGTGTGGAAGCTCAAACCTGGCCCACCACCAAAGCCCGAGA
GCGGCATAAGGACGACAGCAGGGGTCTTGTGCCTTCTGGGTACAAGTACCTCGGACCCTTCAAGTGGTAAGCGACTGTGTGCGACGGATGAAGAT
CCCTCGAGCACGACAAAGCCTACGACCGGCAGCTGACACCCCGTACCTCAAGTACAACAACCGTACCTCGGCGAAGAGCCGGAGTTTCAGGAGCCGGGAGTTTAAAGAAGAT
ACGTCTTTGGGGCAACCTGCCTCCTCGGACGAGCAGTCTTCCAGGCGGAGAAAAAGAGGGTTCTTGAACCTCTGGGCCTGGTTGAGGAACCTGTTAAGACGACTCCGGGAACAAA
GAGGCCGGTAGAGCACTCCCAGACCCTCAACCTCTCGGAGAACAGGCCAGCAGCCCCTCGGTCTGGGAACTAATACAGATGGCTACAGGCAGTGGCGCACCAATGGCAGACAAT
CAGAGTCAGTCCAGACCCTCAACCTCTCGGAGAACAGGCCAGCAGCCCCTCGGTCTGGGAACTAATACAGATGGCTACAGGCAGTGGCGCACCAATGGCAGACAAT
AACGAGGGCGCCGACGGAGTGGGTAATTCCTCGGGAAATTGCATTCCACATGGATGGCGACAGAGTCATCACCACCCCCGAACCTGGCCCTGCC
CACCTACAACAACCATCTCTACAAGCAAATCTCAGCAGCAGCTTCAAACAACTGGGGATTCCGGCCCAAGAAACTCAGCTTGGCTACAAGTCTTCAACATCCAAGTTAAA
GATTCCACTGCCCACTTCTCACACGCAGCCAATTGCCAATTCTACCAGCACTACTACTTGGCTACAAGAAACTCAGCTTGACTGGGTTTTACTGACTGTTACTGACTGTGTTACTGACTGTGTGCCTGCCTGCGGC
GAGGTCACGCAGAACGATGGCGCCGCGTCCCAGAGCTCTTCATGGTGCCACAGTACCTCACCCTGTTACTCACACTTTTGAGACGTTCCTTCCACAGCGACTAGGAGCGCTCTTCATTTT
ACTGCCCTGGAGTACTTTCCTTCATGAATCTCTCGACCAGTCTGTATTACTTGAGCAGAACAAACTCCAAGTGAACACTCCAAGTCAAAGACATCTGCGGATAACAACAGTGAAT
GGCCGGGAGCGGAGTGACATTCGGGACTACCAAGTGGACCAGTTGGCCTCTCGTGGTGAATCCGGGGCCCAGCAGCAGTATCAAAGACCACCACGAGTCCAGCAGTCGCCAGTCAAAGACAC
ACTCGTGGACTGGGGTTCTCATCTTGGGAAGCAAGGCTCAGAAGAAACAAATGTGGACATTGAAGAGTCATGATTACAGAAGACGAAGAGGAAATCAGGACAACCAATCCCGT
GGCTACGAAGAGATGTGTACCTTCAGGACCCATCGTATCGGAAGACAGACAAAGACAAACAGCAACAGCAACGACCACCTTCAGTGCGCAAAGTTTGCTCTCATCACAACAAGTCTGTTAATGTGGACTTTACTG
CAGCGTGGAGATCGAGTGGGAGCTCGAGATGGGAGAAGAAAACAGCAGAAAACGCTGGAATCCCGAAATTCAGTACACTTCCAACTACACGCTGGAACCAGAGTCTGCTGGAACTCACCACAAGTCTGTTAATGTGGACTTTACTG
TGGACACTGTAATGGCCGTGTATTCAGAAGCCTGCTATTCCAACCAGAGCCTCGCCCCATTGGCACCCAGATACCTGACTGTAATCTGTAA
```

>AAV-NP59-aa (SEQ ID NO:4)

```
MAADGYLPDWLEDTLSEGIRQWWKLKPGPPPPKPAERHKDDSRGLVLPGYKYLGPFNGLDKGEPVNEADAAALEHDKAYDRQLDSGDNPYLKYNHADAEFQERLKED
TSFGGNLGRAVFQAKKRVLEPLGLVEEPVKTAPGKKRPVEHSPVEPDSSSGTGKTGQQPAKKRLNFGQTGDSESVPDPQPLGEPPAAPSGLGTNTMATGSGAPMADN
NEGADGVGNSSGNWHCDSTWMGDRVITTSTRTWALPTYNNHLYKQISSQSGASNDNHYFGYSTPWGYFDFNRFHCHFSPRDWQRLINNNWGFRPKKLSFKLFNIQVK
EVTQNDGTTTIANNLTSTVQVFTDSEYQLPYVLGSAHQGCLPPFPADVFMVPQYGYLTLNNGSQAVGRSSFYCLEYFPSQMLRTGNNFTFSYTFEDVPFHSSYAHSQ
SLDRLMNPLIDQYLYYLSRTNTPSGTTTQSRLQFSQAGASDIRDQSRNWLPGPCYRQQRVSKTSADNNNSEYSWTGATKYHINGRDSLVNPGPAMASHKDDEEKFFP
QSGVLIFGKQGSEKTNVDIEKVMITDEEEIRTTNPVATEQYGSVSTNLQRGNRQAATADVDTQGVLPGMVWQDRDVYLQGPIWAKIPHTDGHFHPSPLMGGFGLKHP
PPQILIKNTPVPANPSTTFSAAKFASFITQYSTGQVSVEIEWELQKENSKRWNPEIQYTSNYNKSVNVDFTVDTNGVYSEPRPIGTRYLTRNL
```

FIG. 11C

>AAV-NP40-nt (SEQ ID NO:5)
ATGGCTGCCGATGGTTATCTTCCAGATTGGCTCGAGGACAACCTTAGTGAAGGAATAAGACAGTGGTGGAAGCTCAAACCTGGCCCACCACCAAAGCCCGCAGA
GCGGCATAAGGACGACAGCAGGGGTCTTGTGCTTCCTGGGTACAAGTACCTCGGACCCTTCAACGGACTCGACAAGGGAGAGCCGGTCAACGAGGCAGACGCCGGG
CCCTCGAGCACGACAAAGCCTACGACCGGCAGCTGGACAGCGGAGAACAACCCTACCTCAAGTACAACCACGCCGAGTTTCAGGAGCCCTTAAAGAAGAT
ACGTCTTTTGGGG

FIG. 11D

>AAV-NP30-nt (SEQ ID NO:7)

```
ATGGCTGCCGATGGTTATCTTCCAGATTGGCTCGAGGACACTCTCTGAGGAATAAGACAGTGGTGGAAGCTCAAACCTGGCGAAGCTCAAACCTGGCCACCACCAAAGCCCGCAGA
GCGGCATAAGGACGACAGCAGGGGTCTTGTGCTTCTGGGTACCAGTCCTCCTGGGTACACCTCCGACCCTTCAACGACTCGACAAGGAGAGCCGTTCAACGAGGAGCGCCGGCGG
CCCTCGAGCACGACAAAGCCTACGACCGGCAGTCCAGCAGCAGTCTTCCAGGCGAGAAAAGAGGGTTCTTGAACCTCTGAGCCTGTTGAACCTGTTAAGACGGCCTTAAAGAGAT
ACGTCTTTTGGGGCCAACCTCGGCCACTCTCCTGTGGACCAGTCCTCTCCTCGGGAACCGGCAAGACAGGCCAGGAACCCAGAGAACCAGGAACTCAATTTTGTCAGACTGGCGACT
CAGAGTCAGTCCCAGACCCTCAACCTCTGGAGAACCACCACAGCCCCTCTGGTCTGGGAACTCTGGGCATTGCAATCCAATGCTGGGCGACAGAGTCATCACCAGCACCCCCTGCC
AACGAGGGTGCCGATGGAGTGGGTAATTCCTCAGGAAATTGGCATTCCAGCAGCTTCAAACGACGAGCTTAACAACAATCCAGCAATCTCCAGCACGTGACTGGCCGATCATTGAG
CACCTACAACCATCTCTACACCACGTGACTGGCGACGAGACAATCAGGACTATCCAGCCAGTCATCACACACGGGATTCAAACAACTCAGCTTCGACTGTTACTGTCTGCCATAAA
GAGGTCACGCAGAACGATGGCCGCGTTCCCTTCTCAGATGCTGCGTACCGAGAAACAACTTTACCTTCACCCTGAACACCACGGAGTCAGGCAGTAGGACGCTACGCTCACAGCCAG
ACTGCCTGGAGTACTTCCTTCATGAATCCTCTCATGAATCCTGTATTACTTGAGCAGAACAACACTCCAAGTGAACCACCACAGCGAGTATCAAAGACCAAGCCAGTGCCGGATAACAACAGTGAAT
GGCCGAGCGAGTGACATTCGGACAAGTACCACCTCAATGGCAGAGAAAACAAATGTGGACATTGAAAGGTCATGATTAACAGACAGCTCAACACAAGGCGACACATTTCACCCCTGCTTTGG
CAGAGCCGGGGTTCTCATCTTTGGGAAGCAAGGCTCAGAGAAATCCAACCTCGGGCAAGATTCCAACACACACCGGACACCTCCCCTCATGGGTGATGTTCTTCCAGGCATGGTCTGGC
GGCTACGGACAGTATGTTACCTTCAGGGCCCATCTGGGACCTGCGAATTCTGCAATCGGGGCCATTGTGATTCGGACTCCAACACAGTCCACCATCTGTTAATGTGGACTTTACTG
AGGACAGAGATTCTCATCAAGAACACACCCGGTACCTGCGAATTCTGCAATCAGCAAACGCTGAAATTCAGTACACTTCCAACTACACACCTGACCTGACTCGTAATCTGTAA
CCTCCACAGATTCTCATCAAGAACACACCCCGTTCTTCAATCGAGAATTCAGTACACTTCCAACTACACACCTGACCTGACTCGTAATCTGTAA
CAGCGTGGAGATCGAGTGGAGCTGCAGAAGGAGAAAACAGCAAACGCTGAAATTCAGTACACTTCCAACTACACACCTGACCTGACTCGTAATCTGTAA
TGGACACTAATGGCGTGTATTCAGAGCCTCGCCCATTGGCACCCAGATACCTGACCTGACTCGTAATCTGTAA
```

>AAV-NP30-aa (SEQ ID NO:8)

```
MAADGYLPDWLEDTLSEGIRQWWKLKPGPPPPKPAERHKDDSRGLVLPGYKYLGPFNGLDKGEPVNEADAAALEHDKAYDRQLDSGDNPYLKYNHADAEFQERLKED
TSFGGNLGRAVFQAKKRVLEPLGLVEEPVKTAPGKKRKRPVEHSPVEPDSSSGTGKTGQQPAKKRLNFGQTGDSESVPDPQPLGEPPAAPSGLGTNTMATGSGAPMADN
NEGADGVGNSSGNWHCDSQWLGDRVITTSTRTWALPTYNNHLYKQISSQSGASNDNHYFGYSTPWGYFDFNRFHCHFSPRDWQRLINNNWGFRPKKLSFKLFNIQVK
EVTQNDGTTTIANNLTSTVQVFTDSEYQLPYVLGSAHQGCLPPFADVFMVPQYGYLTLNNGSQAVGRSSFYCLEYFPSQMLRTGNNFTFSYTFEDVPFHSSYAHSQ
SLDRLMNPLIDQYLYYLSRTNTPSGTTTQSRLQFSQAGASDIRDQSRNWLPGPCYRQQRVSKTSADNNNSEYSWTGATKYHLNGRDSLVNPGPAMASHKDDEEFFP
QSGVLIFGKQGSEKTNVDIEKVMITDEEEIRTTNPVATEQYGSVSTNLQRGNRQAATADVNTQGVLPGMVWQDRDVYLQGPIWAKIPHTDGHFHPSPLMGGFGLKHP
PPQILIKNTPVPANPSTTFSAAKFASFITQYSTGQVSVEIEWELQKENSKRWNPEIQYTSNYNKSVNVDFTVDTNGVYSEPRPIGTRYLTRNL
```

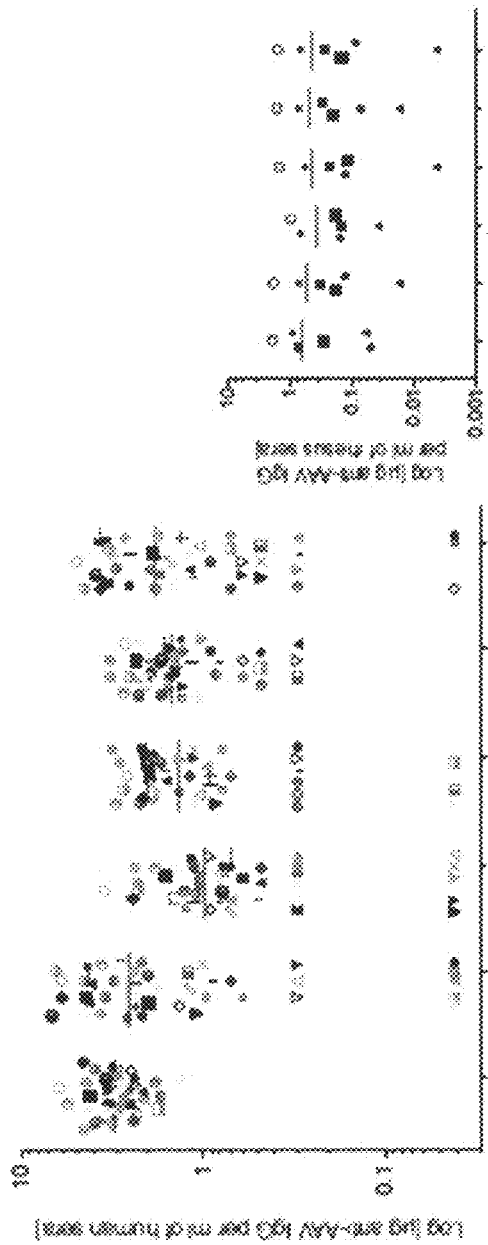
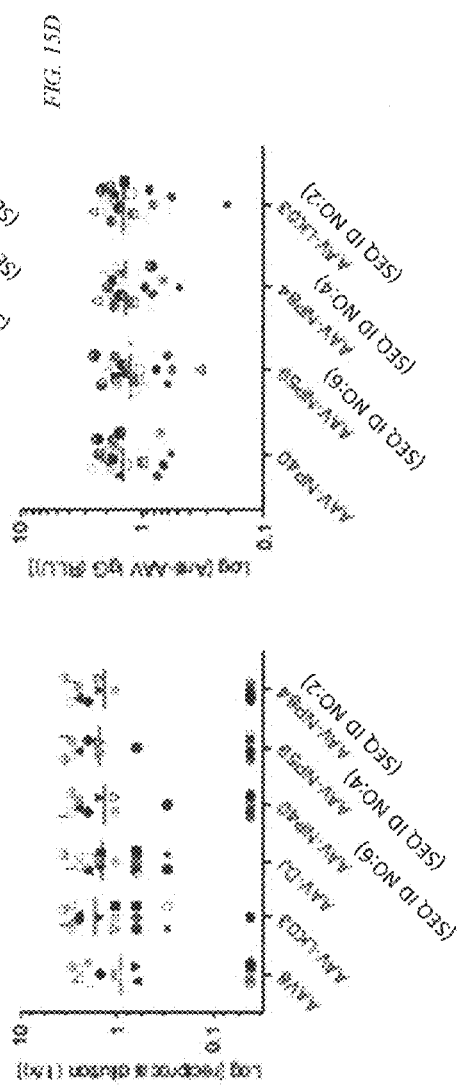
FIG. 15A
FIG. 15B
FIG. 15C
FIG. 15D

FIG. 16A                    FIG. 16B
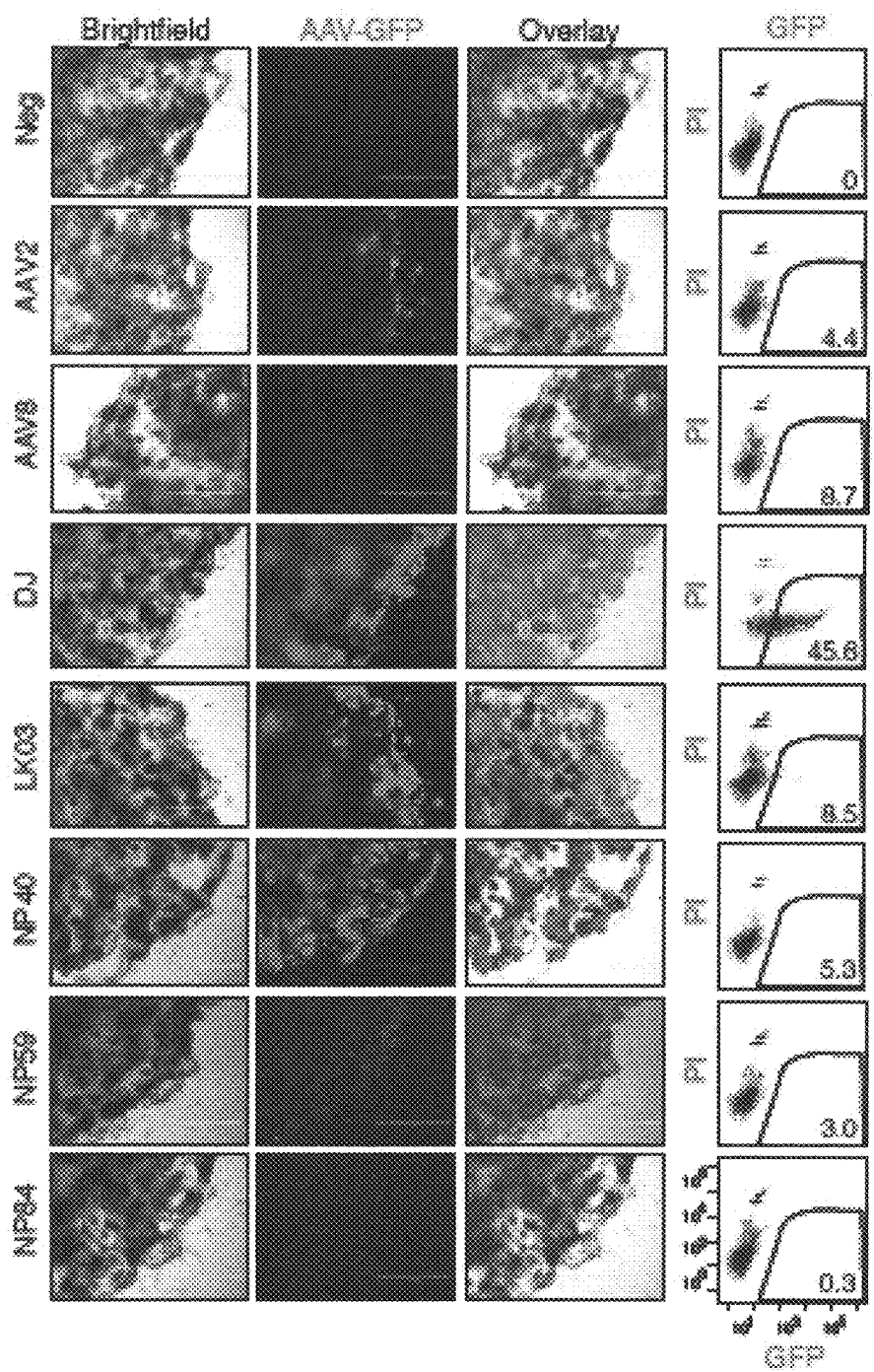

FIG. 17A
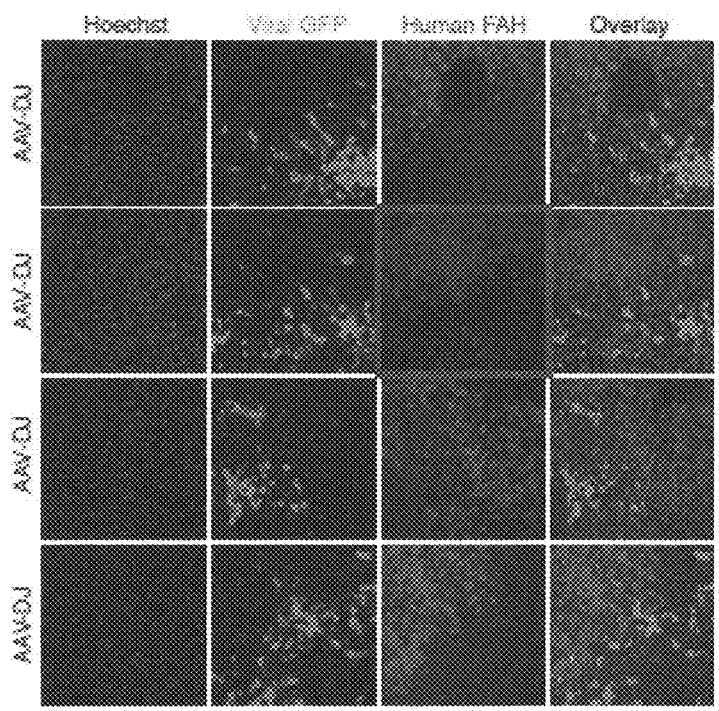
FIG. 17B
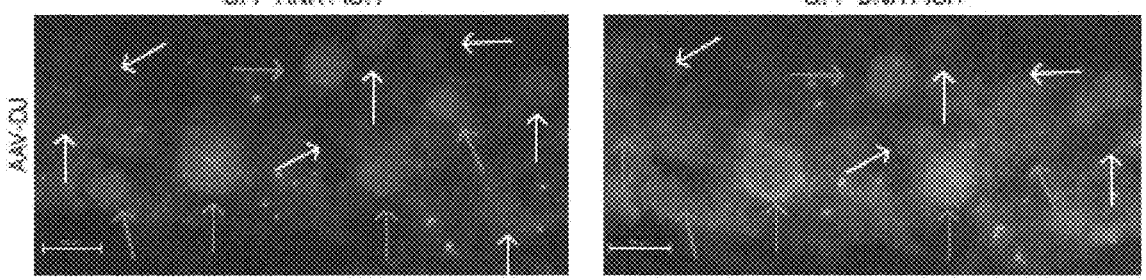
FIG. 17C
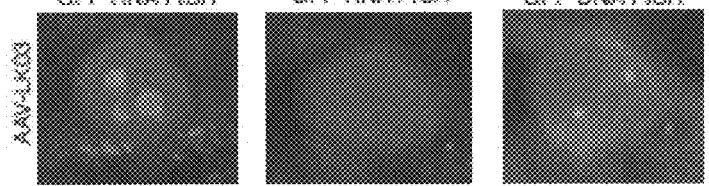
FIG. 17D
FIG. 17E

FIG. 18

FIG. 19A
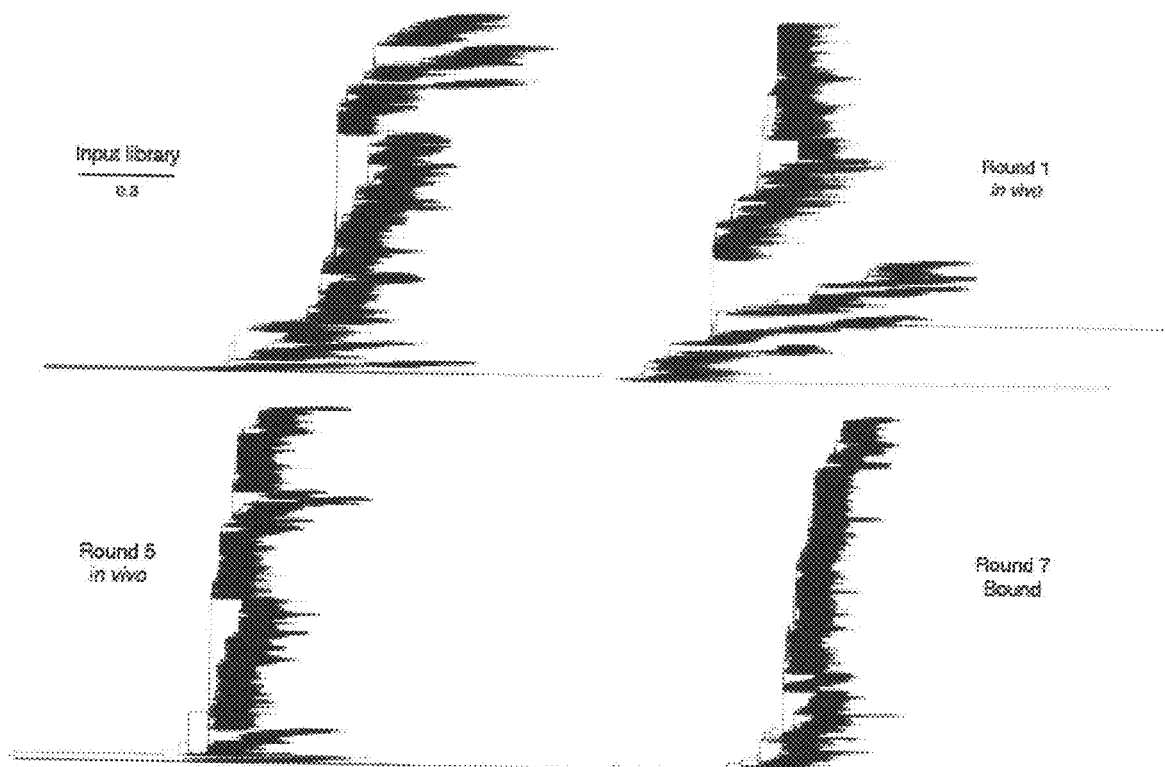
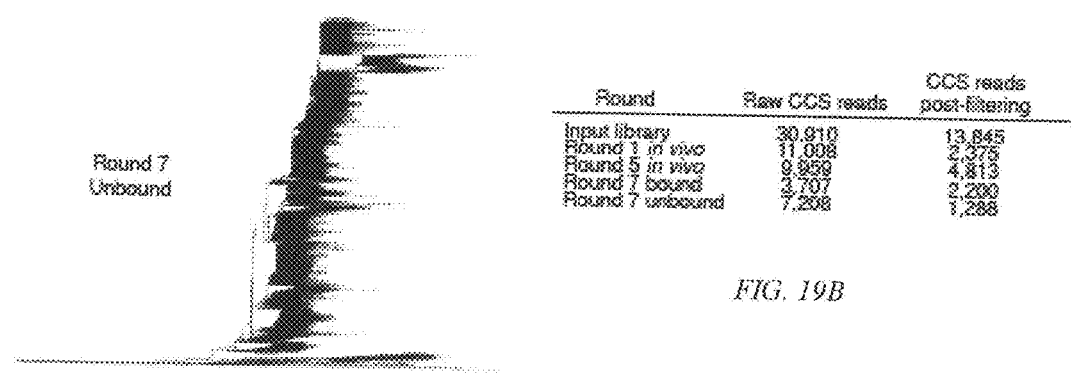
FIG. 19B

FIG. 22A
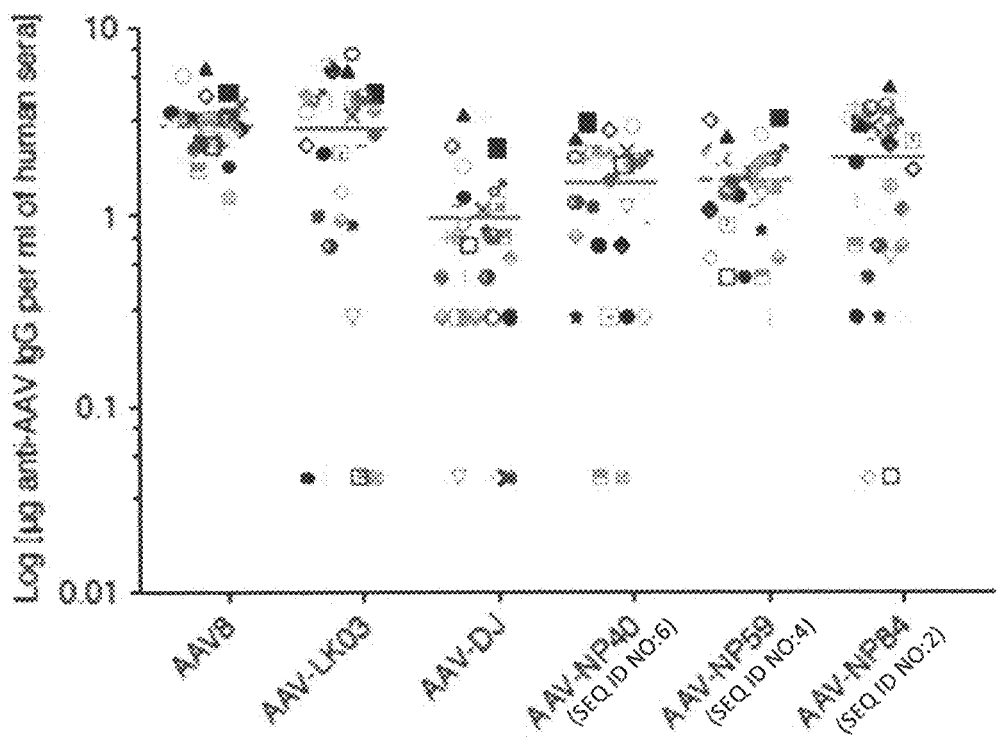
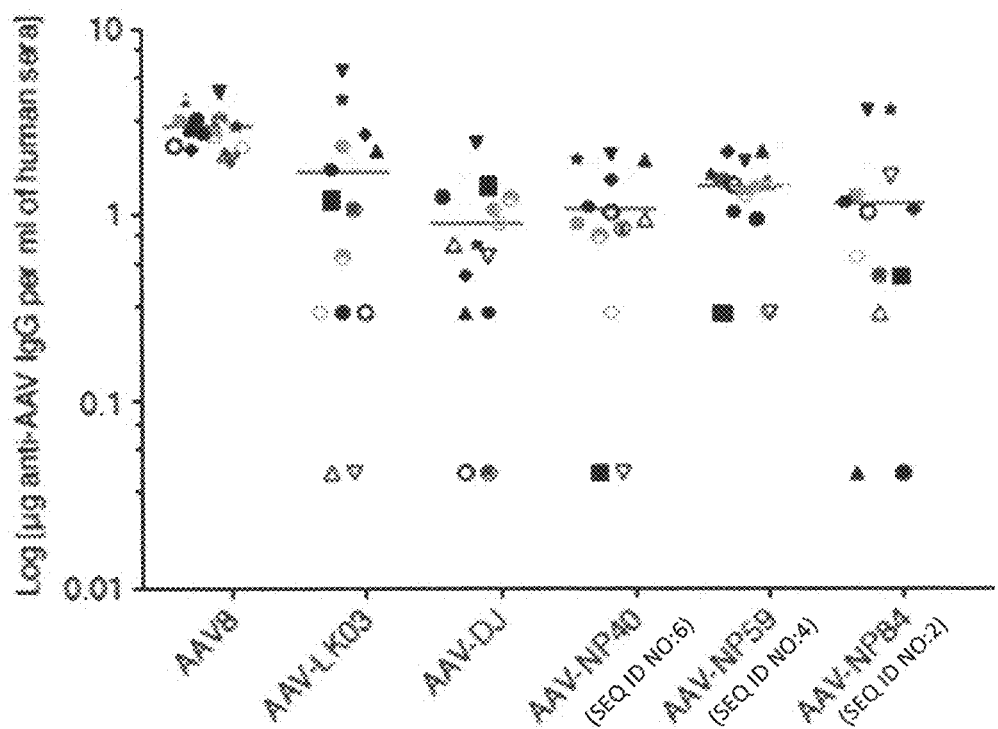
FIG. 22B

Amino acid sequences of selected shuffled capsid variants.

FIG. 23A (A) >NP84 (SEQ ID NO:2)
MAADGYLPDWLEDTLSEGIRQWWKLKPGPPPPKPAERHKDDSRGLVLPGYKYLGPFNGLDKGEPVNEAD
AAALEHDKAYDRQLDSGDNPYLKYNHADAEFQERLKEDTSFGGNLGRAVFQAKKRVLEPLGLVEEPVKT
APGKKRPVEHSPVEPDSSSGTGKTGQQPAKKRLNFGQTGDSESVPDPQPLGEPPAAPSGLGTNTMATGSGA
PMADNNEGADGVGNSSGNWHCDSQWLGDRVITTSTRTWALPTYNNHLYKQISSQSGASNDNHYFGYSTP
WGYFDFNRFHCHFSPRDWQRLINNNWGFRPKKLSFKLFNIQVKEVTQNDGTTTIANNLTSTVQVFTDSEYQ
LPYVLGSAHQGCLPPFPADVFMVPQYGYLTLNNGSQAVGRSSFYCLEYFPSQMLRTGNNFTFSYTFEDVPF
HSSYAHSQSLDRLMNPLIDQYLYYLSRTNTPSGTTTQSRLQFSQAGASDIRDQSRNWLPGPCYRQQRVSKT
SADNNNSEYSWTGATKYHLNGRDSLVNPGPAMASHKDDEEEFFPQSGVLIFGKQGSEKTNVDIEKVMITD
EEEIRTTNPVATEQYGSVSTNLQGGNRQAATADVNTQGVLPGMVWQDRDVYLQGPIWAKIPHTDGHFHPS
PLMGGFGLKHPPPQILIKNTPVPANPSTTFSAAKFASFITQYSTGQVSVEIEWELQKENSKRWNPEIQYTSNY
NKSVNVDFTVDTNGVYSEPRPIGTRYLTRNL

FIG. 23B (B) >NP59 (SEQ ID NO:4)
MAADGYLPDWLEDTLSEGIRQWWKLKPGPPPPKPAERHKDDSRGLVLPGYKYLGPFNGLDKGEPVNEAD
AAALEHDKAYDRQLDSGDNPYLKYNHADAEFQERLKEDTSFGGNLGRAVFQAKKRVLEPLGLVEEPVKT
APGKKRPVEHSPVEPDSSSGTGKTGQQPAKKRLNFGQTGDSESVPDPQPLGEPPAAPSGLGTNTMATGSGA
PMADNNEGADGVGNSSGNWHCDSQWLGDRVITTSTRTWALPTYNNHLYKQISSQSGASNDNHYFGYSTP
WGYFDFNRFHCHFSPRDWQRLINNNWGFRPKKLSFKLFNIQVKEVTQNDGTTTIANNLTSTVQVFTDSEYQ
LPYVLGSAHQGCLPPFPADVFMVPQYGYLTLNNGSQAVGRSSFYCLEYFPSQMLRTGNNFTFSYTFEDVPF
HSSYAHSQSLDRLMNPLIDQYLYYLSRTNTPSGTTTQSRLQFSQAGASDIRDQSRNWLPGPCYRQQRVSKT
SADNNNSEYSWAGATKYHLNGRDSLVNPGPAMASHKDDEEKFFPQSGVLIFGKQGSEKTNVDIEKVMITD
EEEIRTTNPVATEQYGSVSTNLQRGNRQAATADVDTQGVLPGMVWQDRDVYLQGPIWAKIPHTDGHFHPS
PLMGGFGLKHPPPQILIKNTPVPANPSTTFSAAKFASFITQYSTGQVSVEIEWELQKENSKRWNPEIQYTSNY
NKSVNVDFTVDTNGVYSEPRPIGTRYLTRNL

FIG. 23C (C) >NP40 (SEQ ID NO: 6)
MAADGYLPDWLEDNLSEGIRQWWKLKPGPPPPKPAERHKDDSRGLVLPGYKYLGPFNGLDKGEPVNEAD
AAALEHDKAYDRQLDSGDNPYLKYNHADAEFQERLKEDTSFGGNLGRAVFQAKKRVLEPLGLVEEPVKT
APGKKRPVEHSPVEPDSSSGTGKTGQQPAKKRLNFGQTGDSESVPDPQPLGEPPAAPSGLGTNTMATGSGA
PMADNNEGADGVGNSSGNWHCDSQWLGDRVITTSTRTWALPTYNNHLYKQISSQSGASNDNHYFGYSTP
WGYFDFNRFHCHFSPRDWQRLINNNWGFRPKKLSFKLFNIQVKEVTQNDGTTTIANNLTSTVQVFTDSEYQ
LPYVLGSAHQGCLPPFPADVFMVPQYGYLTLNNGSQAVGRSSFYCLEYFPSQMLRTGNNFTFSYTFEDVPF
HSSYAHSQSLDRLMNPLIDQYLYYLSRTNTPSGTTTQSRLQFSQAGASDIRDQSRNWLPGPCYRQQRVSKT
SADNNNSEYSWTGATKYHLNGRDSLVNPGPAMASHKDDEEEFFPQSGVLIFGKQGSEKTNVDIEKVMITD
EEEIRTTNPVATEQYGSVSTNLQRGNRQAATADVNTQGVLPGMVWQDRDVYLQGPIWAKIPHTDGHFHH
SPLMGGFGLKHPPPQILIKNTPVPANPSTTFSAAKFASFITQYSTGQVSVEIEWELQKENSKRWNPEIQYTSN
YNKSVNVDFTVDTNGVYSEPRPIGTRYLTRNL

*FIG. 24*

| AAV group | section ID | FAH (huma) cells | GFP+ve human cells | % GFP transduced human cells | average of % GFP transduced human cells | hum Alb (mg/ml) | mouse gender |
|---|---|---|---|---|---|---|---|
| NP59 | FRG309-5-3-1 | 113 | 106 | 93.8 | 94.5 | 0.25 | male |
| | FRG309-5-3-3 | 148 | 130 | 87.8 | | | |
| | FRG309-5-3-5 | 137 | 122 | 89.1 | | | |
| | FRG309-2-3-1 | 126 | 116 | 92.1 | | | |
| | FRG328-4-2 | 130 | 126 | 96.9 | | 0.36 | female |
| | FRG328-5-3-1 | 81 | 78 | 96.3 | | | |
| | FRG321-5-3-1 | 320 | 310 | 96.9 | | 0.29 | female |
| | FRG321-5-3-2 | 79 | 76 | 96.2 | | | |
| | FRG321-5-3-3 | 307 | 294 | 95.8 | | | |
| | FRG321-2-3-1 | 638 | 613 | 96.1 | | | |
| | FRG321-2-3-2 | 484 | 479 | 99.0 | | | |
| NP40 | FRG319-5-2-1 | 804 | 743 | 92.4 | 72.8 | 4.95 | female |
| | FRG319-5-2-2 | 329 | 89 | 27.1 | | | |
| | FRG319-5-2-3 | 91 | 84 | 92.3 | | | |
| | FRG319-5-2-4 | 83 | 52 | 62.7 | | | |
| | FRG319-1-1-1 | 106 | 92 | 86.8 | | | |
| | FRG323-5-2 | 218 | 200 | 91.7 | | 0.73 | female |
| | FRG323-1-3-1 | 275 | 111 | 40.4 | | | |
| | FRG323-2-3-1 | 338 | 302 | 89.3 | | | |
| | FRG316 | 0 | poorly engrafted. no human cell found in sections | | | 0.1 | male |
| NP84 | FRG313-5-3-1 | 212 | 37 | 17.5 | 27.7 | 0.23 | female |
| | FRG313-5-3-3 | 134 | 47 | 35.1 | | | |
| | FRG313-5-1-3 | 45 | 11 | 24.4 | | | |
| | FRG313-5-2-3 | 84 | 27 | 32.1 | | | |
| | FRG314-5-3-2 | 178 | 26 | 14.6 | | | |
| | FRG314-5-3-1 | 188 | 30 | 16.0 | | | |
| | FRG314-2-3-2 | 87 | 13 | 14.9 | | 0.38 | female |
| | FRG331-2-3-1 | 33 | 13 | 39.4 | | 0.036 | male |
| | FRG331-2-3-2 | 27 | 15 | 55.6 | | | |
| LK03 | FRG322-3-1 | 91 | 45 | 49.5 | 32.6 | 0.06 | female |
| | FRG322-3-4 | 143 | 55 | 38.5 | | | |
| | FRG320-5-3-1 | 243 | 55 | 22.6 | | 0.13 | female |
| | FRG320-5-3-2 | 115 | 23 | 20.0 | | | |
| | FRG316 | 0 | poorly engrafted. no human cell found in sections | | | 0.007 | male |

RECOMBINANT ADENO-ASSOCIATED VIRUS CAPSIDS RESISTANT TO PRE-EXISTING HUMAN NEUTRALIZING ANTIBODIES

CROSS REFERENCE TO RELATED APPLICATIONS

This application is a Continuation of U.S. application Ser. No. 15/435,212, filed Feb. 16, 2017, which claims the benefit of U.S. Provisional Application No. 62/296,046, filed on Feb. 16, 2016, all of which is expressly incorporated herein by reference in their entireties.

STATEMENT AS TO RIGHTS TO INVENTIONS MADE UNDER FEDERALLY SPONSORED RESEARCH OR DEVELOPMENT

This invention was made with Government support under contracts HL092096, AI116698, OD010580 and HL119059 awarded by the National Institutes of Health. The Government has certain rights in the invention.

FIELD OF THE INVENTION

The present invention relates to variant AAV capsid polypeptides, wherein the variant capsid polypeptides exhibit an enhanced neutralization profile, exhibit increased transduction or tropism in human liver tissue or hepatocyte cells (i.e., human hepatocyte cells), or both as compared to non-variant parent capsid polypeptides.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Apr. 15, 2017, entitled 068597_5031_US_ST25.txt which is 61 kilobytes in size.

BACKGROUND OF THE INVENTION

Genetic disorders caused by absence of or a defect in a desirable gene (loss of function) or expression of an undesirable or defective gene (gain of function) lead to a variety of diseases. At present, adeno-associated virus (AAV) vectors are recognized as the gene transfer vectors of choice for therapeutic applications since they have the best safety and efficacy profile for the delivery of genes in vivo. Of the AAV serotypes isolated so far, AAV2, AAV5, AAV6 and AAV8 have been used to target the liver of humans affected by severe hemophilia B. In the case of AAV8, long-term expression of the therapeutic transgene was documented. Recent data from humans showed that targeting the liver with an AAV vector can achieve long-term expression of the FIX transgene at therapeutic levels. Additionally, several Phase 1 and Phase 2 clinical trials using various AAV serotypes have been reported for the treatment of alpha-1 antitrypsin deficiency (M. L. Brantly, J. D. Chulay, L. Wang, C. Mueller, M. Humphries, L. T. Spencer, F. Rouhani, T. J. Conlon, R. Calcedo, M. R. Betts, C. Spencer, B. J. Byrne, J. M. Wilson, T. R. Flotte, Sustained transgene expression despite T lymphocyte responses in a clinical trial of rAAV1-AAT gene therapy. *Proceedings of the National Academy of Sciences of the United States of America* 106, 16363-16368 (2009); T. R. Flotte, B. C. Trapnell, M. Humphries, B. Carey, R. Calcedo, F. Rouhani, M. Campbell-Thompson, A. T. Yachnis, R. A. Sandhaus, N. G. McElvaney, C. Mueller, L. M. Messina, J. M. Wilson, M. Brantly, D. R. Knop, G. J. Ye, J. D. Chulay, Phase 2 clinical trial of a recombinant adeno-associated viral vector expressing alpha1-antitrypsin: interim results. *Human gene therapy* 22, 1239-1247 (2011); C. Mueller, J. D. Chulay, B. C. Trapnell, M. Humphries, B. Carey, R. A. Sandhaus, N. G. McElvaney, L. Messina, Q. Tang, F. N. Rouhani, M. Campbell-Thompson, A. D. Fu, A. Yachnis, D. R. Knop, G. J. Ye, M. Brantly, R. Calcedo, S. Somanathan, L. P. Richman, R. H. Vonderheide, M. A. Hulme, T. M. Brusko, J. M. Wilson, T. R. Flotte, Human Treg responses allow sustained recombinant adeno-associated virus-mediated transgene expression. *The Journal of clinical investigation* 123, 5310-5318 (2013)). Additionally, numerous world-wide trials are underway, including for example, trial ES-0020 with AAV5 for acute intermittent porphyria (AIP) (Phase I); IE-0001 with AAV1 for hAAT (alpha-1 antitrypsin) (Phase II); NL-0037 with AAV5 for hemophilia B (Phase I); UK-0137 with AAV2 for hemophilia B (Phase I); US-0864 with AAV2 for hemophilia B (Phase I); US-1441 with AAV8 for hemophilia B (Phase I/II); US-1355 with AAV8 for hemophilia B (Phase I/II); US-1144 with AAV8 for hypercholesterolemia (Phase I); US-1398 with AAVrh10 for hemophilia B (Phase I/II); US-1446 with AAV2/AAV6 for hemophilia B (Phase I); and US-1520 with AAV8 for Late-Onset Ornithine Transcarbamylase (OTC) deficiency (Phase I/II). See, the World Wide Web at abedia.com/wiley/index.html.

Adeno-associated virus (AAV), a member of the Parvovirus family, is a small nonenveloped, icosahedral virus with single-stranded linear DNA genomes of 4.7 kilobases (kb). AAV is assigned to the genus, Dependovirus, because the virus was discovered as a contaminant in purified adenovirus stocks (D. M Knipe, P. M Howley, *Field's Virology*, Lippincott Williams & Wilkins, Philadelphia, ed. Sixth, 2013). In its wild-type state, AAV depends on a helper virus—typically adenovirus—to provide necessary protein factors for replication, as AAV is naturally replication-defective. The 4.7-kb genome of AAV is flanked by two inverted terminal repeats (ITRs) that fold into a hairpin shape important for replication. Being naturally replication-defective and capable of transducing nearly every cell type in the human body, AAV represents an ideal vector for therapeutic use in gene therapy or vaccine delivery. In its wild-type state, AAV's life cycle includes a latent phase during which AAV genomes, after infection, are site specifically integrated into host chromosomes and an infectious phase during which, following either adenovirus or herpes simplex virus infection, the integrated genomes are subsequently rescued, replicated, and packaged into infectious viruses. When vectorized, the viral Rep and Cap genes of AAV are removed and provided in trans during virus production, making the ITRs the only viral DNA that remains (A. Vasileva, R. Jessberger, *Nature reviews*. Microbiology, 3, 837-847 (2005)). Rep and Cap are then replaced with an array of possible transfer vector configurations to perform gene addition or gene targeting. These vectorized recombinant AAVs (rAAV) transduce both dividing and non-dividing cells, and show robust stable expression in quiescent tissues. The number of rAAV gene therapy clinical trials that have been completed or are ongoing to treat various inherited or acquired diseases is increasing dramatically as rAAV-based therapies increase in popularity. Similarly, in the clinical vaccine space, there have been numerous recent preclinical studies and one ongoing clinical trial using rAAV as a vector to deliver antibody expression cassettes in passive vaccine approaches for human/simian immunodeficiency virus (HIV/SIV), influenza virus, henipavirus, and human papilloma virus (HPV). (See, P. R. Johnson, B. C. Schnepp, J. Zhang, M. J. Connell, S. M. Greene, E. Yuste, R. C. Desrosiers, K. R. Clark, Nature medicine 15, 901-906 (2009); A. B. Balazs, J. Chen, C. M. Hong, D. S. Rao, L. Yang, D. Baltimore, Nature 481, 81-84 (2012); A. B. Balazs, Y. Ouyang, C. M. Hong, J. Chen, S. M. Nguyen, D. S. Rao, D. S. An, D. Baltimore, Nature medicine 20, 296-300 (2014); A. B. Balazs, J. D. Bloom, C. M. Hong, D. S. Rao, D. Baltimore, Nature biotechnology 31, 647-652 (2013); M. P. Limberis, V. S. Adam, G. Wong, J. Gren, D. Kobasa, T. M. Ross, G. P. Kobinger, A. Tretiakova, J. M., Science translational medicine 5, 187ra172 (2013); M. P. Limberis, T. Racine, D. Kobasa, Y. Li, G. F. Gao, G. Kobinger, J. M. Wilson, Vectored expression of the broadly neutralizing antibody F16 in mouse airway provides partial protection against a new avian influenza A virus, H7N9. Clinical and vaccine immunology: CVI 20, 1836-1837 (2013); J. Lin, R. Calcedo, L. H. Vandenberghe, P. Bell, S. Somanathan, J. M. Wilson, Journal of virology 83, 12738-12750 (2009); I. Sipo, M. Knauf, H. Fechner, W. Poller, O. Planz, R. Kurth, S. Norley, Vaccine 29, 1690-1699 (2011); A. Ploquin, J. Szecsi, C. Mathieu, V. Guillaume, V. Barateau, K. C. Ong, K. T. Wong, F. L. Cosset, B. Horvat, A. Salvetti, The Journal of infectious diseases 207, 469-478 (2013); D. Kuck, T. Lau, B. Leuchs, A. Kern, M. Muller, L. Gissmann, J. A. Kleinschmidt, Journal of virology 80, 2621-2630 (2006); K. Nieto, A. Kern, B. Leuchs, L. Gissmann, M. Muller, J. A. Kleinschmidt, Antiviral therapy 14, 1125-1137 (2009); K. Nieto, C. Stahl-Hennig, B. Leuchs, M. Muller, L. Gissmann, J. A. Kleinschmidt, Human gene therapy 23, 733-741 (2012); and L. Zhou, T. Zhu, X. Ye, L. Yang, B. Wang, X. Liang, L. Lu, Y. P. Tsao, S. L. Chen, J. Li, X. Xiao, Human gene therapy 21, 109-119 (2010).) The properties of non-pathogenicity, broad host range of infectivity, including non-dividing cells, and potential site-specific chromosomal integration make AAV an attractive tool for gene transfer.

The first rAAV-based gene therapy to be approved in the Western world (Glybera® for lipoprotein lipase deficiency, approved for use in 2012 in the European Union) has stimulated the gene therapy community, investors and regulators to the real possibility of moving rAAV therapies into the clinic globally. Yet, despite the impressive abilities of rAAV to transduce a variety of tissue and cell types, human liver tissue has been historically a challenging tissue to transduce at high levels sufficient to provide sustained therapeutic levels of expression of delivered transgene products. This likely stems from the fact that preclinical modeling with rAAV to determine the best capsid serotypes for transducing target tissues is done in animal models—typically mice—which do not necessarily recapitulate the tissue and cell tropism each rAAV has in humans, nor the transduction capabilities at treatment, as well as the immunological barriers present in humans.

A variety of published US applications describe AAV vectors and virions, including U.S. Publication Nos. 2015/0176027, 2015/0023924, 2014/0348794, 2014/0242031, and 2012/0164106; all of which are incorporated by reference herein in their entireties.

However, high levels of transduction are needed for gene therapy trials. If a variant AAV capsid polypeptide exhibited an enhanced neutralization profile and/or exhibited increased transduction or tropism in human liver tissue or hepatocyte cells (i.e., human hepatocyte cells), a lower dose and fewer injections would be needed to achieve therapeutic relevance. Similarly, for use as a vaccine delivery tool, high efficiency transduction and stability is needed to achieve robust secretion of antibodies encoded within the AAV to reach therapeutic levels of circulating antibodies in the blood.

There remains, therefore, a need in the art for variant AAV capsids which exhibit an enhanced neutralization profile, exhibit increased transduction or tropism in human liver tissue or hepatocyte cells (i.e., human hepatocyte cells), or variant AAV capsids that exhibit both. The present invention meets this need by providing variant AAV capsid polypeptides which demonstrate an enhanced neutralization profile, increased transduction or tropism in human liver tissue or hepatocyte cells (i.e., human hepatocyte cells), as well as variant AAV capsids that exhibit both properties. The present invention utilizes directed evolution by DNA gene shuffling to characterize and screen for such variant AAV capsid polypeptides which have an enhanced neutralization profile, increased transduction or tropism in human liver tissue or hepatocyte cells (i.e., human hepatocyte cells), as well as variant AAV capsids that exhibit both properties.

BRIEF SUMMARY OF THE INVENTION

The present invention provides variant adeno-associated virus (AAV) capsid polypeptides, where the variant AAV capsid polypeptides exhibit an enhanced neutralization profile as compared to non-variant parent capsid polypeptides.

In some embodiments, the variant AAV capsid polypeptides exhibit an enhanced neutralization profile against pooled human immunoglobulins as compared to non-variant parent capsid polypeptides.

In some embodiments, the variant AAV capsid polypeptides further exhibit increased transduction or tropism in human liver tissue or hepatocyte cells (i.e., human hepatocyte cells) as compared to non-variant parent capsid polypeptides.

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid.

In some embodiments, the variant AAV capsid polypeptide further exhibits increased transduction or tropism in one or more non-liver human tissues or non-hepatocyte human cells as compared to a non-variant parent capsid polypeptide.

In some embodiments, the variant AAV capsid polypeptide exhibits increased transduction of human liver tissue or hepatocyte cells (i.e., human hepatocyte cells) in vivo as compared to a non-variant parent capsid polypeptide.

In some embodiments, the variant AAV capsid polypeptide exhibits increased transduction of human liver tissue or hepatocyte cells (i.e., human hepatocyte cells) in vitro as compared to a non-variant parent capsid polypeptide.

In some embodiments, the variant AAV capsid polypeptide exhibits increased transduction of human liver organoids in 3-dimensional cultures in vitro as compared to a non-variant parent capsid polypeptide.

In some embodiments, the variant AAV capsid polypeptide is part of a functional AAV capsid, wherein said functional AAV capsid packages a nucleic acid sequence selected from the group consisting of a non-coding RNA, a protein coding sequence, an expression cassette, a multi-expression cassette, a sequence for homologous recombination, a genomic gene targeting cassette, and a therapeutic expression cassette.

In some embodiments, the nucleic acid sequence is contained within an AAV vector.

In some embodiments, the expression cassette is a CRISPR/CAS expression system.

In some embodiments, the therapeutic expression cassette encodes a therapeutic protein or antibody.

In some embodiments, the variant AAV capsid polypeptide allows for enhanced nucleic acid expression as compared to a non-variant parent capsid polypeptide.

In some embodiments, the variant AAV capsid polypeptide sequence is selected from the group consisting of AAV-NP84 (SEQ ID NO:2), AAV-NP59 (SEQ ID NO:4), AAV-NP40 (SEQ ID NO:6), and AAV-NP30 (SEQ ID NO:8).

The present invention also provides a method of using the variant AAV capsid polypeptide in a therapeutic treatment regimen or vaccine.

In some embodiments, the method of using the variant AAV capsid polypeptides of the invention provides for a reduction in the amount of total nucleic acid administered to a subject. In some embodiments, the method comprises administering less total nucleic acid amount to a subject when the nucleic acid is transduced using a variant AAV capsid polypeptide as compared to the amount of nucleic acid administered to a subject when the nucleic acid is transduced using a non-variant parent capsid polypeptide in order to obtain a similar therapeutic effect.

The present invention also provides variant adeno-associated virus (AAV) capsid polypeptides, where the variant AAV capsid polypeptides exhibit increased transduction or tropism in human liver tissue or hepatocyte cells (i.e., human hepatocyte cells) as compared to a non-variant parent capsid polypeptide.

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid.

In some embodiments, the variant AAV capsid polypeptide further exhibits an enhanced neutralization profile as compared to a non-variant parent capsid polypeptide.

In some embodiments, the variant AAV capsid polypeptide exhibits an enhanced neutralization profile against pooled human immunoglobulins as compared to a non-variant parent capsid polypeptide.

In some embodiments, the variant AAV capsid polypeptide further exhibits increased transduction or tropism in one or more non-liver human tissues or non-hepatocyte human cells as compared to a non-variant parent capsid polypeptide.

In some embodiments, the variant AAV capsid polypeptide exhibits increased transduction of human liver tissue or hepatocyte cells (i.e., human hepatocyte cells) in vivo as compared to a non-variant parent capsid polypeptide.

In some embodiments, the variant AAV capsid polypeptide exhibits increased transduction of human liver tissue or hepatocyte cells (i.e., human hepatocyte cells) in vitro as compared to a non-variant parent capsid polypeptide.

In some embodiments, the variant AAV capsid polypeptide exhibits increased transduction of human liver organoids in 3-dimensional cultures in vitro as compared to a non-variant parent capsid polypeptide In some embodiments, the variant AAV capsid polypeptide is part of a functional AAV capsid, wherein said functional AAV capsid packages a nucleic acid sequence selected from the group consisting of a non-coding RNA, a protein coding sequence, an expression cassette, a multi-expression cassette, a sequence for homologous recombination, a genomic gene targeting cassette, and a therapeutic expression cassette.

In some embodiments, the nucleic acid sequence is contained within an AAV vector.

In some embodiments, the expression cassette is a CRISPR/CAS expression system.

In some embodiments, the therapeutic expression cassette encodes a therapeutic protein or antibody.

In some embodiments, the variant AAV capsid polypeptide allows for enhanced nucleic acid expression as compared to a non-variant parent capsid polypeptide.

In some embodiments, the variant AAV capsid polypeptide sequence is selected from the group consisting of AAV-NP84 (SEQ ID NO:2), AAV-NP59 (SEQ ID NO:4), AAV-NP40 (SEQ ID NO:6), and AAV-NP30 (SEQ ID NO:8).

The present invention also provides a method of using the variant AAV capsid polypeptide in a therapeutic treatment regimen or vaccine.

In some embodiments, the method of using the variant AAV capsid polypeptide of the invention provides for a reduction in the amount of total nucleic acid administered to a subject. In some embodiments, the method comprises administering less total nucleic acid amount to a subject when the nucleic acid is transduced using a variant AAV capsid polypeptide as compared to the amount of nucleic acid administered to a subject when the nucleic acid is transduced using a non-variant parent capsid polypeptide in order to obtain a similar therapeutic effect.

The present invention also provides an adeno-associated virus (AAV) vector comprising a nucleic acid sequence encoding a variant AAV capsid polypeptide, where the variant AAV capsid polypeptide exhibits an enhanced neutralization profile as compared to a non-variant parent capsid polypeptide.

In some embodiments, the variant AAV capsid polypeptide exhibits an enhanced neutralization profile against pooled human immunoglobulins as compared to a non-variant parent capsid polypeptide.

In some embodiments, the variant AAV capsid polypeptide exhibits increased transduction or tropism in human liver tissue or hepatocyte cells (i.e., human hepatocyte cells).

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid polypeptide.

In some embodiments, the variant AAV capsid polypeptide further exhibits increased transduction or tropism in one or more non-liver human tissues or non-hepatocyte human cells as compared to a non-variant parent capsid polypeptide.

In some embodiments, the variant AAV capsid polypeptide exhibits increased transduction of human liver tissue or hepatocyte cells (i.e., human hepatocyte cells) in vivo as compared to a non-variant parent capsid polypeptide.

In some embodiments, the variant AAV capsid polypeptide exhibits increased transduction of human liver tissue or hepatocyte cells (i.e., human hepatocyte cells) in vitro as compared to a non-variant parent capsid polypeptide.

In some embodiments, the variant AAV capsid polypeptide exhibits increased transduction of human liver organoids in 3-dimensional cultures in vitro as compared to a non-variant parent capsid polypeptide.

In some embodiments, the vector further comprises a nucleic acid sequence selected from the group consisting of a non-coding RNA, a coding sequence, an expression cassette, a multi-expression cassette, a sequence for homologous recombination, a genomic gene targeting cassette, and a therapeutic expression cassette.

In some embodiments, the variant AAV capsid polypeptide allows for enhanced nucleic acid expression as compared to a non-variant parent capsid polypeptide.

In some embodiments, the expression cassette is a CRISPR/CAS expression system.

In some embodiments, the therapeutic expression cassette encodes a therapeutic protein or antibody.

In some embodiments, the variant AAV capsid polypeptide sequence is selected from the group consisting of AAV-NP84 (SEQ ID NO:2), AAV-NP59 (SEQ ID NO:4), AAV-NP40 (SEQ ID NO:6), and AAV-NP30 (SEQ ID NO:8).

The present invention also provides a method of using the variant AAV capsid polypeptide in a therapeutic treatment regimen or vaccine.

The present invention also provides an adeno-associated virus (AAV) vector comprising a nucleic acid sequence encoding a variant AAV capsid polypeptide, where the variant AAV capsid polypeptide exhibits increased transduction or tropism in human liver tissue or hepatocyte cells (i.e., human hepatocyte cells) as compared to a non-variant parent capsid polypeptide.

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid.

In some embodiments, the variant AAV capsid polypeptide further exhibits an enhanced neutralization profile as compared to a non-variant parent capsid polypeptide.

In some embodiments, the variant AAV capsid polypeptide exhibits an enhanced neutralization profile against pooled human immunoglobulins as compared to a non-variant parent capsid polypeptide.

In some embodiments, the variant AAV capsid polypeptide further exhibits increased transduction or tropism in one or more non-liver human tissues or non-hepatocyte human cells as compared to a non-variant parent capsid polypeptide.

In some embodiments, the variant AAV capsid polypeptide exhibits increased transduction of human liver tissue or hepatocyte cells (i.e., human hepatocyte cells) in vivo as compared to a non-variant parent capsid polypeptide.

In some embodiments, the variant AAV capsid polypeptide exhibits increased transduction of human liver tissue or hepatocyte cells (i.e., human hepatocyte cells) in vitro as compared to a non-variant parent capsid polypeptide.

In some embodiments, the variant AAV capsid polypeptide exhibits increased transduction of human liver organoids in 3-dimensional cultures in vitro as compared to a non-variant parent capsid polypeptide In some embodiments, the vector further comprises a nucleic acid sequence selected from the group consisting of a non-coding RNA, a coding sequence, an expression cassette, a multi-expression cassette, a sequence for homologous recombination, a genomic gene targeting cassette, and a therapeutic expression cassette.

In some embodiments, the variant AAV capsid polypeptide allows for enhanced nucleic acid expression as compared to a non-variant parent capsid polypeptide.

In some embodiments, the said expression cassette is a CRISPR/CAS expression system.

In some embodiments, the said therapeutic expression cassette encodes a therapeutic protein or antibody.

In some embodiments, the variant AAV capsid polypeptide sequence is selected from the group consisting of AAV-NP84 (SEQ ID NO:2), AAV-NP59 (SEQ ID NO:4), AAV-NP40 (SEQ ID NO:6), and AAV-NP30 (SEQ ID NO:8). In some embodiments, the variant AAV capsid polypeptide is selected from the group consisting of AAV-NP84 (SEQ ID NO:2), AAV-NP59 (SEQ ID NO:4), and AAV-NP40 (SEQ ID NO:6). In some embodiments, the variant AAV capsid polypeptide is selected from the group consisting of AAV-NP59 (SEQ ID NO:4), and AAV-NP40 (SEQ ID NO:6). In some embodiments, the variant AAV capsid polypeptide is AAV-NP59 (SEQ ID NO:4). In some embodiments, the variant AAV capsid polypeptide is AAV-NP40 (SEQ ID NO:6).

The present invention also provides a method of using the variant AAV capsid polypeptide in a therapeutic treatment regimen or vaccine.

In some embodiments, the method of using the AAV vector of the invention provides for a reduction in the amount of total AAV vector administered to a subject. In some embodiments, the method comprises administering less total AAV vector amount to said subject when said AAV vector is transduced by a variant AAV capsid polypeptide as compared to the amount of AAV vector administered to said subject when said AAV vector is transduced by a non-variant parent capsid polypeptide in order to obtain a similar therapeutic effect.

The present invention also provides methods for generating variant AAV capsid polypeptides, wherein the variant AAV capsid polypeptide exhibits both an enhanced neutralization profile and increased transduction or tropism in human liver tissue or hepatocyte cells (i.e., human hepatocyte cells) as compared to a non-variant parent capsid polypeptide. In some embodiments, the method comprises:
 a) generating a library of variant AAV capsid polypeptides, wherein said variant AAV capsid polypeptides include a plurality of variant AAV capsid polypeptide sequences from more than one non-variant parent capsid polypeptide;
 b) generating an AAV vector library by cloning said variant AAV capsid polypeptide library into AAV vectors, wherein said AAV vectors are replication competent AAV vectors;
 c) screening said AAV vector library from b) for variant AAV capsid polypeptides for both an enhanced neutralization profile and increased transduction or tropism in human liver tissue or hepatocyte cells (i.e., human hepatocyte cells) as compared to a non-variant parent capsid polypeptide; and
 d) selecting said variant AAV capsid polypeptides from c).

In some embodiments, the method further comprises e) determining the sequence of said variant AAV capsid polypeptides from d).

In some embodiments, the variant AAV capsid polypeptide exhibits an enhanced neutralization profile against pooled human immunoglobulins as compared to a non-variant parent capsid polypeptide In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid polypeptide.

In some embodiments, the variant AAV capsid polypeptide further exhibits increased transduction or tropism in one or more non-liver human tissues or non-hepatocyte human cells as compared to a non-variant parent capsid polypeptide.

In some embodiments, the variant AAV capsid polypeptide exhibits increased transduction of human liver tissue or hepatocyte cells (i.e., human hepatocyte cells) in vivo as compared to a non-variant parent capsid polypeptide.

In some embodiments, the variant AAV capsid polypeptide exhibits increased transduction of human liver tissue or hepatocyte cells (i.e., human hepatocyte cells) in vitro as compared to a non-variant parent capsid polypeptide.

In some embodiments, the variant AAV capsid polypeptide exhibits increased transduction of human liver organoids in 3-dimensional cultures in vitro as compared to a non-variant parent capsid polypeptide In some embodiments, the variant AAV capsid polypeptide exhibits selective transduction of human liver tissue or hepatocyte cells (i.e., human hepatocyte cells) in chimeric mice having undergone xenograft transplants with human liver tissue or hepatocyte cells (i.e., human hepatocyte cells).

Other objects, advantages and embodiments of the invention will be apparent from the detailed description following.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 provides confocal immunofluorescence (IF) staining highlighting the species preference of AAV serotypes DJ and LK03 for mouse and human hepatocytes, respectively.

FIG. 11A-FIG. 11D provides the nucleic acid and amino acid sequences for four AAV capsids: A) AAV-NP84, B) AAV-NP59, C) AAV-NP40, and D) AAV-NP30.

FIG. 15A-FIG. 15D provides immunological assays across key patient groups and nonhuman primates. (A) Seroreactivity ELISA assay for presence of anti-AAV antibodies in normal human serum from 50 U.S. adults. Each patient was assayed in technical triplicates with data points representing the mean minus background. Red line represents the mean. Symbols are consistent across treatments for each patient to allow comparisons. (B) Seroreactivity ELISA assay for presence of anti-AAV antibodies in serum from 6 rhesus macaques. Each dot is 1 macaque. Red line represents the mean. (C) Human 2V6.11 AAV-permissive cells were used to assess rAAV neutralization in the presence of patient serums for 21 E.U. individuals. Data show the reciprocal dilution at which >50% inhibition of transduction was observed. Red line represents the mean. (D) Seroreactivity ELISA assay for presence of anti-AAV antibodies in human serum from 21 adult males with hemophilia B. Red line represents the mean.

FIG. 16A-FIG. 16B provides comparative ex vivo human liver organoid transduction with AAV. (A) Transduction assessments by GFP expression of vectorized variants in primary human liver organoid cultures compared to known hepatotropic AAV control serotypes 2, 8, DJ and LK03. Each serotype was assayed in a 14-day time-course in technical duplicates; day 11 shown. Scale=100-µM. Media from organoid cultures was tested for the presence of human albumin by ELISA (human albumin=58.3-ng/mL). (B) GFP FACS quantitation data on 100,000 dissociated organoid cells from (A) at the end of the study at day 14.

FIG. 17A-FIG. 17E provides data regarding the lack of functional human hepatocyte transduction with AAV-DJ. (A) Representative staining from xenografted FRG livers administered ssAAV-DJ-CAG-GFP at 2E11 vg IV. Sections were stained with Hoechst (blue), viral GFP (green), and human-specific FAH (violet). Scale=100-µM. (B) Summary of analysis from transduced xenografted mice. (C) GFP RNA FISH and GFP protein IF overlay on sections from (A). Human and mouse hepatocytes are differentiated by DAPI labeling (mouse nuclei=large with bright blue heterochromatic punctae (green arrows); human nuclei=small and dull diffuse blue (white arrows)). GFP RNA FISH probed for the AAV-GFP genome (red). Green GFP protein immunofluorescence was then overlaid on top of the GFP RNA probe and image coordinates were recorded. Few human hepatocytes showed DJ-GFP RNA, but none showed concomitant GFP protein expression. Many mouse hepatocytes showed DJ-GFP RNA, and also had concomitant GFP protein expression. Scale=10-µM. (D) Subsequent GFP DNA FISH (red) after RNA FISH on liver sections from (b). Rare human hepatocytes showed nucleoplasmic concatemers of AAV dsDNA (red punctate dots, pink arrow). This cumulatively showed successful AAV uncoating, dsDNA conversion, and in some cases even transcription into RNA, but a block at translating those genomes into GFP protein. (E) In comparison, AAV-LK03-GFP positive control RNA FISH showed abundant cytoplasmic and nucleolar GFP RNA (red). RNAse A treatment followed by GFP RNA FISH eliminated signals seen with RNA FISH alone. Sequential GFP DNA FISH done after RNAse A and RNA FISH showed presence of bright nucleoplasmic GFP DNA signal, confirming that the signal from RNA FISH was ssRNA and not mis-probed ssDNA AAV genome signal.

FIG. 18 provides the modified AAV2 VP1 3'UTR sequence in library cloning plasmid. A modified 3'-UTR sequence from AAV2 was maintained during the cloning of the recipient library plasmid to ensure proper expression and replication of AAV genomes.

FIG. 19A-FIG. 19B provides the phylogenetic trees of screen progress utilizing PacBio full-length capsid sequencing. (A) Comparative phylogenies showing genetic relatedness at the amino acid level among the parental serotypes in the library and all library variants. The decreasing diversity and increasing enrichment going from the unselected AAV library through 5 rounds of in vivo selection and 2 rounds of on-bead IgG selection are shown. (B) Raw and filtered CCS read counts that were used to generate (a) are shown.

FIG. 22A-FIG. 22B provides seroreactivity ELISA profiling separated by gender. Breakdown of human seroreactivity from FIG. 5a by gender. Symbols are consistent across treatments for each patient to allow comparisons. (A) Male patients. (B) Female patients. Line represents the mean.

FIG. 23A-FIG. 23C provides the amino acid sequences of best performing shuffled capsid variants.

FIG. 24 provides data regarding the transduction of human hepatocytes in the humanized mice for each of 4 vectors (NP59, NP40, NP84, and LK03) at a dose $5 \times 10^{10}$ vg.

DETAILED DESCRIPTION OF THE INVENTION

Introduction

Figure 2B:
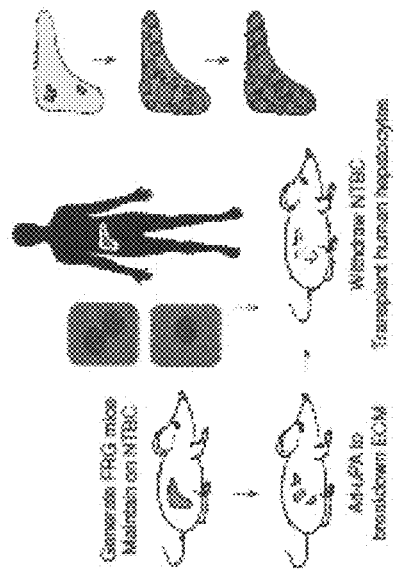
FIG. 2A-FIG. 2D provides a schematic regarding the directed evolution of adeno-associated virus capsids by DNA shuffling and multiplexed sequential screening in humanized liver mice and against pooled human immunoglobulins. (A) AAV capsid genes from ten parental serotypes (1, 2, 3b, 4, 5, 6, 8, 9_hu14, avian and bovine) were PCR-amplified, fragmented with DNaseI digestion and then randomly reassembled through self-priming PCR. Resultant shuffled Cap genes were cloned back into a replication-competent AAV production plasmid via flanking SwaI/NsiI sites downstream of AAV2 Rep. The resultant library production plasmid contained AAV2 ITRs and a modified AAV2 3'UTR. The AAV library was packaged using standard production protocols, dot blot titered and used for selection. (B) Diagram illustrating the procedure for producing humanized liver FRG mice with NTBC selection for selection in humanized liver mice. (C) Diagram illustrating the initial 5-round selection screen with replicating AAV capsid libraries from (A) in humanized liver mice from (B). (D) Diagram illustrating the subsequent 2-round subscreen against pooled human immunoglobulins with the evolved AAV library already screened for human hepatocyte tropism. Capsids which did not bind pooled human immunoglobulins were taken for further characterization.
Figure 2D:
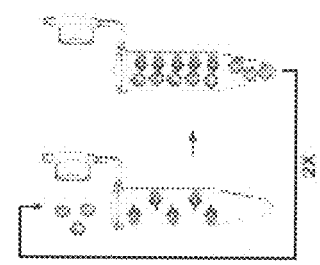
Figure 2A:
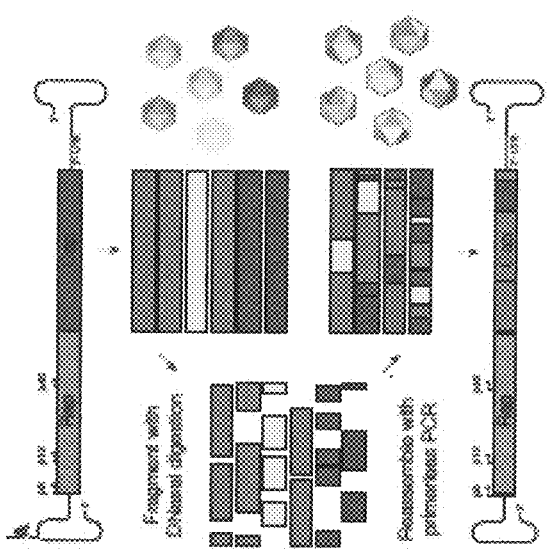
Figure 2C:
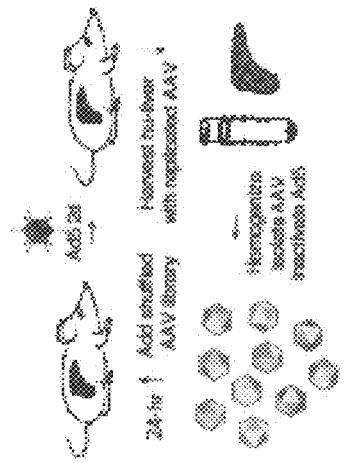

There remains a need in the art for gene therapy vectors capable of exhibiting enhanced neutralization profiles as well as vectors with increased transduction and/or tropism in human liver tissue or hepatocyte cells (i.e., human hepatocyte cells) for gene therapy, so that more therapeutic levels of nucleic acid expression can be achieved. The present invention meets this need and provides variant AAV capsid polypeptides which exhibit an enhanced neutralization profile as compared to non-variant parent capsid polypeptides. The present invention also meets this need and provides variant AAV capsid polypeptides which exhibit increased transduction and/or tropism in human liver tissue or hepatocyte cells (i.e., human hepatocyte cells) as compared to non-variant parent capsid polypeptides. The present invention additionally meets this need by providing variant AAV capsid polypeptides which exhibit both an enhanced neutralization profile as compared to non-variant parent capsid polypeptides and exhibit increased transduction and/or tropism in human liver tissue or hepatocyte cells (i.e., human hepatocyte cells) as compared to non-variant parent capsid polypeptides.

Detailed Description

In various embodiments, the present invention provides variant adeno-associated virus (AAV) capsid polypeptides (i.e., variant AAV capsid polypeptides), where the variant AAV capsid polypeptides exhibit an enhanced neutralization profile as compared to non-variant parent capsid polypeptides. In some embodiments, the variant AAV capsid polypeptides exhibit an enhanced neutralization profile against pooled human immunoglobulins as compared to a non-variant parent capsid polypeptide. In some embodiments, the variant AAV capsid polypeptide further exhibits increased transduction or tropism in human liver tissue or hepatocyte cells (i.e., human hepatocyte cells) as compared to a non-variant parent capsid polypeptides.

In various embodiments, the present invention provides variant adeno-associated virus (AAV) capsid polypeptides, wherein the variant capsid polypeptides exhibit increased transduction or tropism in human liver tissue or hepatocyte cells (i.e., human hepatocyte cells) as compared to non-variant parent capsid polypeptides. In some embodiments, the variant AAV capsid polypeptide further exhibits an enhanced neutralization profile against pooled human immunoglobulins as compared to a non-variant parent capsid polypeptide.

In some embodiments the variant AAV capsid polypeptide is referred to as a variant recombinant AAV capsid polypeptide or variant rAAV capsid polypeptide.

In other various embodiments, the present invention provides AAV vectors comprising a nucleic acid sequence coding for a variant capsid polypeptide, where the variant AAV capsid polypeptides exhibit an enhanced neutralization profile as compared to non-variant parent capsid polypeptides. In some embodiments, the variant AAV capsid polypeptides exhibit an enhanced neutralization profile against pooled human immunoglobulins as compared to a non-variant parent capsid polypeptide. In some embodiments the AAV vector is referred to as a recombinant AAV or rAAV vector.

In other various embodiments, the present invention provides AAV vectors comprising a nucleic acid sequence coding for a variant capsid polypeptide, wherein the variant capsid polypeptide exhibits increased transduction or tropism in human liver tissue or hepatocyte cells (i.e., human hepatocyte cells) as compared to a vector encoding a non-variant parent capsid polypeptide. In some embodiments the AAV vector is referred to as a recombinant AAV or rAAV vector.

In other various embodiments, the present invention provides AAV vectors comprising a nucleic acid sequence coding for a variant capsid polypeptide, wherein the variant capsid polypeptide exhibits both increased transduction or tropism in human liver tissue or hepatocyte cells (i.e., human hepatocyte cells) as compared to a vector encoding a non-variant parent capsid polypeptide and an enhanced neutralization profile as compared to non-variant parent capsid polypeptides. In some embodiments, the variant AAV capsid polypeptides exhibit an enhanced neutralization profile against pooled human immunoglobulins as compared to a non-variant parent capsid polypeptide. In some embodiments the AAV vector is referred to as a recombinant AAV or rAAV vector.

In some embodiments, the present invention provides AAV vectors comprising: a) a variant AAV capsid protein, wherein the variant AAV capsid polypeptide comprises at least one amino acid difference (e.g., amino acid substitution, amino acid insertion, amino acid deletion) relative to a substantially identical non-variant parent AAV capsid protein, and where the variant capsid protein exhibits an enhanced neutralization profile as compared to a vector encoding a non-variant parent capsid polypeptide. In some embodiments, the AAV capsid polypeptide does not comprise an amino acid sequence present in a naturally occurring AAV capsid polypeptide.

In some embodiments, the present invention provides AAV vectors comprising: a) a variant AAV capsid protein, wherein the variant AAV capsid polypeptide comprises at least one amino acid difference (e.g., amino acid substitution, amino acid insertion, amino acid deletion) relative to a substantially identical non-variant parent AAV capsid protein, and where the variant capsid protein exhibits increased transduction or tropism in liver tissue or hepatocyte cells as compared to a vector encoding a non-variant parent capsid polypeptide. In some embodiments, the AAV capsid polypeptide does not comprise an amino acid sequence present in a naturally occurring AAV capsid polypeptide.

In some embodiments, the present invention provides AAV vectors comprising: a) a variant AAV capsid protein, wherein the variant AAV capsid polypeptide comprises at least one amino acid difference (e.g., amino acid substitution, amino acid insertion, amino acid deletion) relative to a substantially identical non-variant parent AAV capsid protein, and where the variant capsid protein exhibits both increased transduction or tropism in human liver tissue or hepatocyte cells (i.e., human hepatocyte cells) as compared to a vector encoding a non-variant parent capsid polypeptide and an enhanced neutralization profile as compared to a vector encoding a non-variant capsid polypeptide. In some embodiments, the AAV capsid polypeptide does not comprise an amino acid sequence present in a naturally occurring AAV capsid polypeptide.

In some embodiments, the present invention provides variant AAV capsid polypeptides, wherein the variant AAV capsid polypeptide comprises at least one amino acid difference (e.g., amino acid substitution, amino acid insertion, amino acid deletion) relative to a substantially identical non-variant parent AAV capsid polypeptide, and where the variant capsid polypeptide exhibits an enhanced neutralization profile as compared to a vector encoding a non-variant parent capsid polypeptide. In some embodiments, the variant AAV capsid polypeptide does not comprise an amino acid sequence present in a naturally occurring AAV capsid polypeptide.

In some embodiments, the present invention provides variant AAV capsid polypeptides, wherein the variant AAV capsid polypeptide comprises at least one amino acid difference (e.g., amino acid substitution, amino acid insertion, amino acid deletion) relative to a substantially identical non-variant parent AAV capsid protein, and where the variant capsid polypeptide exhibits increased transduction or tropism in human liver tissue or hepatocyte cells (i.e., human hepatocyte cells) as compared to a vector encoding a non-variant parent capsid polypeptide. In some embodiments, the variant AAV capsid polypeptide does not comprise an amino acid sequence present in a naturally occurring AAV capsid polypeptide.

In some embodiments, the present invention provides variant AAV capsid polypeptides, wherein the variant AAV capsid polypeptide comprises at least one amino acid difference (e.g., amino acid substitution, amino acid insertion, amino acid deletion) relative to a substantially identical non-variant parent AAV capsid polypeptide, and where the variant capsid polypeptide exhibits both an enhanced neutralization profile as compared to a vector encoding a non-variant parent capsid polypeptide and increased transduction or tropism in human liver tissue or hepatocyte cells (i.e., human hepatocyte cells) as compared to a vector encoding a non-variant parent capsid polypeptide. In some embodiments, the variant AAV capsid polypeptide does not comprise an amino acid sequence present in a naturally occurring AAV capsid polypeptide.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

As described in the present invention, the following terms will be employed, and are defined as indicated below.

Abbreviations

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector").

Definitions

The term "AAV" includes AAV type 1 (AAV1), AAV type 2 (AAV2), AAV type 3 (AAV3), AAV type 3b (AAV3b), AAV type 4 (AAV4), AAV type 5 (AAV5), AAV type 6 (AAV6), AAV type 7 (AAV7), AAV type 8 (AAV8), AAV type 9 (AAV9), AAV 9_hu14, avian AAV, bovine AAV, canine AAV, equine AAV, primate AAV, non-primate AAV, and ovine AAV. "Primate AAV" refers to AAV capable of infecting primates, "non-primate AAV" refers to AAV capable of infecting non-primate mammals, "bovine AAV" refers to AAV capable of infecting bovine mammals, etc.

An "AAV vector" as used herein refers to an AAV vector nucleic acid sequence encoding for various nucleic acid sequences, including in some embodiments a variant capsid polypeptide (i.e., the AAV vector comprises a nucleic acid sequence encoding for a variant capsid polypeptide). The variant capsid polypeptide exhibits an enhanced neutralization profile, an increased transduction or tropism in human liver tissue or hepatocyte cells (i.e., human hepatocyte cells) or, in some embodiments, both, as compared to a non-variant parent capsid polypeptide. The AAV vectors can also comprise a heterologous nucleic acid sequence not of AAV origin as part of the nucleic acid insert. This heterologous nucleic acid sequence typically comprises a sequence of interest for the genetic transformation of a cell. In general, the heterologous nucleic acid sequence is flanked by at least one, and generally by two AAV inverted terminal repeat sequences (ITRs).

The phrase "non-variant parent capsid polypeptide" includes any naturally occurring AAV capsid polypeptide and/or any AAV wild-type capsid polypeptide. In some embodiments, the non-variant parent capsid polypeptide includes AAV1, AAV2, AAV3b, AAV4, AAV5, AAV6, AAV8, AAV9_hu14, bovine AAV and/or avian AAV capsid polypeptides. In some embodiments, the non-variant parent capsid polypeptide can also be a control capsid polypeptide, including for example but not limited to LK03 and/or DJ, as described herein and known in the art. In some embodiments, a control capsid polypeptide is LK03. In some embodiments, a control capsid polypeptide is DJ.

The term "substantially identical" in the context of variant capsid polypeptides and non-variant parent capsid polypeptides refers to sequences with 1 or more amino acid changes. In some embodiments, these changes do not affect the packaging function of the capsid polypeptide. In some embodiments, substantially identical include variant capsid polypeptides about 99%, about 98%, about 97%, about 96%, about 95%, about 94%, about 93%, about 92%, about 91%, or about 90% identical to a non-variant parent capsid polypeptide. In some embodiments, the variant capsid polypeptide can be substantially identical to a non-variant parent capsid polypeptide over a subregion of the variant capsid polypeptide, such as over about 25%, about 50%, about 75%, or about 90% of the total polypeptide sequence length.

An "AAV virion" or "AAV virus" or "AAV viral particle" or "AAV vector particle" refers to a viral particle composed of at least one AAV capsid polypeptide (including both variant capsid polypeptides and non-variant parent capsid polypeptides) and an encapsidated polynucleotide AAV transfer vector. If the particle comprises a heterologous nucleic acid (i.e. a polynucleotide other than a wild-type AAV genome, such as a transgene to be delivered to a mammalian cell), it can be referred to as an "AAV vector particle" or simply an "AAV vector". Thus, production of AAV virion or AAV particle necessarily includes production of an AAV vector as such a vector is contained within an AAV virion or an AAV particle.

"Packaging" refers to a series of intracellular events resulting in the assembly of AAV virions or AAV particles which encapsidate a nucleic acid sequence and/or other therapeutic molecule. Packaging can refer to encapsidation of nucleic acid sequence and/or other therapeutic molecules into a capsid comprising the variant capsid polypeptides described herein.

The phrase "therapeutic molecule" as used herein can include nucleic acids (including, for example, vectors), polypeptides (including, for example, antibodies), and vaccines, as well as any other therapeutic molecule that could be packaged by the variant AAV capsid polypeptides of the invention.

AAV "rep" and "cap" genes refer to polynucleotide sequences encoding replication and encapsidation proteins of adeno-associated virus (AAV). AAV Rep (replication) and Cap (capsid) are referred to herein as AAV "packaging genes."

A "helper virus" for AAV refers to a virus allowing AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used as a helper virus. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome allowing AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virion, virus or viral particle is one comprising a polynucleotide component deliverable into a cell tropic for the viral species. The term does not necessarily imply any replication capacity of the virus. As used herein, an "infectious" virus or viral particle is one that upon accessing a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and are known in the art. Viral infectivity can be expressed as the ratio of infectious viral particles to total viral particles. Total viral particles can be expressed as the number of viral genome copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA) or fluorescence-activated cell sorting (FACS).

A "replication-competent" virion or virus (e.g. a replication-competent AAV) refers to an infectious phenotypically wild-type virus, and is replicable in an infected cell (i.e. in the presence of a helper virus or helper virus functions). In the case of AAV, replication competence generally requires the presence of functional AAV packaging genes. In some embodiments, AAV vectors, as described herein, lack of one or more AAV packaging genes and are replication-incompetent in mammalian cells (especially in human cells). In some embodiments, AAV vectors lack any AAV packaging gene sequences, minimizing the possibility of generating replication-competent AAV by recombination between AAV packaging genes and an incoming AAV vector. In many embodiments, AAV vector preparations as described herein are those containing few if any replication-competent AAV (rcAAV, also referred to as RCA) (e.g., less than about 1 rcAAV per $10^2$ AAV particles, less than about 1 rcAAV per $10^4$ AAV particles, less than about 1 rcAAV per $10^8$ AAV particles, less than about 1 rcAAV per $10^{12}$ AAV particles, or no rcAAV).

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA, tRNA, lncRNA, RNA antagomirs, and inhibitory DNA or RNA (RNAi, e.g., small or short hairpin (sh)RNA, microRNA (miRNA), aptamers, small or short interfering (si)RNA, trans-splicing RNA, or antisense RNA). Polynucleotides also include non-coding RNA, which include for example, but are not limited to, RNAi, miRNAs, lncRNAs, RNA antagomirs, aptamers, and any other non-coding RNAs known to those of skill in the art. Polynucleotides include naturally occurring, synthetic, and intentionally altered or modified polynucleotides as well as analogues and derivatives. The term "polynucleotide" also refers to a polymeric form of nucleotides of any length, including deoxyribonucleotides or ribonucleotides, or analogs thereof, and is synonymous with nucleic acid sequence. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment as described herein encompassing a polynucleotide encompasses both the double-stranded form and each of two complementary single-stranded forms known or predicted to make up the double-stranded form. Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "gene" refers to a polynucleotide containing at least one open reading frame capable of encoding a particular protein or polypeptide after being transcribed and translated.

A "small interfering" or "short interfering RNA" or siRNA is a RNA duplex of nucleotides targeted to a gene interest (a "target gene"). An "RNA duplex" refers to the structure formed by the complementary pairing between two regions of a RNA molecule. siRNA is "targeted" to a gene and the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences forming the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome capable of modulating the productive utilization of mRNA. An artificial microRNA can be any type of RNA sequence, other than endogenous microRNA, capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA fragment of a larger RNA, or a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA cleaved from a microRNA precursor (a "pre-miRNA"), or synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means the polynucleotide is the product of various combinations of cloning, restriction or ligation steps, and other procedures resulting in a construct distinct and/or different from a polynucleotide found in nature. A recombinant virus is a viral particle encapsidating a recombinant polynucleotide. The terms respectively include replicates of the original polynucleotide construct and progeny of the original virus construct.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

"Heterologous" means derived from a genotypically distinct entity from the rest of the entity it is being compared too. For example, a polynucleotide introduced by genetic engineering techniques into a plasmid or vector derived from a different species is a heterologous polynucleotide. A promoter removed from its native coding sequence and operatively linked to a coding sequence it is not naturally found linked to a heterologous promoter. For example, an AAV including a heterologous nucleic acid encoding a heterologous gene product is an AAV including a nucleic acid not normally included in a naturally-occurring, wild-type AAV, and the encoded heterologous gene product is a gene product not normally encoded by a naturally-occurring, wild-type AAV. An AAV including a nucleic acid encoding a variant capsid polypeptide includes a heterologous nucleic acid sequence. Once transferred/delivered into a host cell, a heterologous polynucleotide, contained within the virion, can be expressed (e.g., transcribed, and translated, if appropriate). Alternatively, a transferred/delivered heterologous polynucleotide into a host cell, contained within the virion, need not be expressed. Although the term "heterologous" is not always used herein in reference to polynucleotides, reference to a polynucleotide even in the absence of the modifier "heterologous" is intended to include heterologous polynucleotides in spite of the omission.

The terms "genetic alteration" and "genetic modification" (and grammatical variants thereof) are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alterations may be effected, for example, by transfecting a cell with a recombinant plasmid or other polynucleotide through any process known in the art, such as electroporation, calcium phosphate transfection, or contact with a polynucleotide-liposome complex. Genetic alterations may also be effected, for example, by transduction or infection with a DNA or RNA virus or viral vector. Generally, the genetic element is introduced into a chromosome or mini-chromosome in the cell; but any alteration changing the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced and inheritable by progeny of the altered cell.

The terms "polypeptide," "peptide," and "protein" are used interchangeably herein to refer to polymers of amino acids of any length. The "polypeptides," "proteins" and "peptides" encoded by the "polynucleotide sequences," include full-length native sequences, as with naturally occurring proteins, as well as functional subsequences, modified forms or sequence variants so long as the subsequence, modified form, or variant retains some degree of functionality of the native full-length protein. In methods and uses of as described herein, such polypeptides, proteins, and peptides encoded by the polynucleotide sequences can be but are not required to be identical to the defective endogenous protein, or whose expression is insufficient, or deficient in the treated mammal. The terms also encompass a modified amino acid polymer; for example, disulfide bond formation, glycosylation, lipidation, phosphorylation, methylation, carboxylation, deamidation, acetylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, retaining the desired biochemical function of the intact protein.

As used herein, the abbreviations for the genetically encoded L-enantiomeric amino acids used in the disclosure methods are conventional and are as follows in Table 1.

TABLE 1

Amino acid abbreviations

| Amino Acid | One-Letter Symbol | Common Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydrogen ion. Genetically encoded basic amino acids include His (H), Arg (R) and Lys (K).

"Polar Amino Acid" refers to a hydrophilic amino acid having a side chain uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (I), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO2, —NO, —NH2, —NHR, —NRR, —C(O)R, —C(O)OH, —C(O)OR, —C(O)NH2, —C(O)NHR, —C(O)NRR and the like where each R is independently (C1-C6) alkyl, substituted (C1-C6) alkyl, (C1-C6) alkenyl, substituted (C1-C6) alkenyl, (C1-C6) alkynyl, substituted (C1-C6) alkynyl, (C1-C21)) aryl, substituted (C5-C20) aryl, (C6-C26) alkaryl, substituted (C6-C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The term "non-naturally" with regard to amino acids can include any amino acid molecule not included as one of the 20 amino acids listed in Table 1 above as well as any modified or derivatized amino acid known to one of skill in the art. Non-naturally amino acids can include but are not limited to β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, methionine sulfone, norleucine, norvaline, ornithine, d-ornithine, p-nitro-phenylalanine, hydroxy proline, 1,2,3,4,-tetrahydroisoquinoline-3-carboxylic acid, and thioproline.

The term "variant" or "variants", with regard to polypeptides, such as capsid polypeptides refers to a polypeptide sequence differing by at least one amino acid from a parent polypeptide sequence, also referred to as a non-variant polypeptide sequence (also referred to as a non-variant parent polypeptide). In some embodiments, the polypeptide is a capsid polypeptide and the variant differs by at least one amino acid substitution. Amino acids also include naturally occurring and non-naturally occurring amino acids as well as derivatives thereof. Amino acids also include both D and L forms.

An "isolated" plasmid, nucleic acid, vector, virus, virion, host cell, or other substance refers to a preparation of the substance devoid of at least some of the other components present where the substance or a similar substance naturally occurs or from which it is initially prepared. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

By the term "highly conserved", it is meant at least about 80% identity, preferably at least about 90% identity, and more preferably, over about 97% identity, is conserved. Identity is readily determined by one of skill in the art by resort to algorithms and computer programs known by those of skill in the art.

The term "percent sequence identity" or "identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least one or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to the length of the protein is amino acids.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The terms "pharmaceutically acceptable" and "physiologically acceptable" mean a biologically acceptable formulation, gaseous, liquid or solid, or mixture thereof, suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a variant AAV capsid, an AAV vector, or an AAV virion as disclosed herein, or cell transformed with an AAV, to a subject.

The phrase a "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, produces a desired effect (e.g., prophylactic or therapeutic effect). In some embodiments, unit dosage forms may be within, for example, ampules and vials, including a liquid composition, or a composition in a freeze-dried or lyophilized state; a sterile liquid carrier, for example, can be added prior to administration or delivery in vivo. Individual unit dosage forms can be included in multi-dose kits or containers. Variant AAV capsids, AAV vectors, or AAV virions, and pharmaceutical compositions thereof can be packaged in single or multiple unit dosage form for ease of administration and uniformity of dosage.

A "therapeutically effective amount" will fall in a relatively broad range determinable through experimentation and/or clinical trials. For example, for in vivo injection, e.g., injection directly into the tissue or vaculature of a subject (for example, liver tissue or veins), a therapeutically effective dose will be on the order of from about $10^6$ to about $10^{15}$ AAV virions, e.g., from about $10^8$ to $10^{12}$ AAV virions. Other effective dosages can be readily established by one of ordinary skill in the art through routine trials establishing dose response curves.

An "effective amount" or "sufficient amount" refers to an amount providing, in single or multiple doses, alone or in combination, with one or more other compositions (therapeutic agents such as a drug), treatments, protocols, or therapeutic regimens agents (including, for example, vaccine regimens), a detectable response of any duration of time (long or short term), an expected or desired outcome in or a benefit to a subject of any measurable or detectable degree or for any duration of time (e.g., for minutes, hours, days, months, years, or cured).

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is also a satisfactory outcome.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for the described methods and uses, but the subject may not manifest the disease. Such subjects therefore include those screened positive for an insufficient amount or a deficiency in a functional gene product (protein), or producing an aberrant, partially functional or non-functional gene product (protein), leading to disease; and subjects screening positive for an aberrant, or defective (mutant) gene product (protein) leading to disease, even though such subjects do not manifest symptoms of the disease.

The phrase "enhanced neutralization profile" refers to the ability of an AAV vector or virion to better evade neutralizing antibody binding in the subject. In some instances, fewer neutralization antibodies allow for the AAV infection to allow for higher levels of transduction, making the variant AAV capsid polypeptides, AAV vectors, and AAV virions of the present invention better suited for gene therapy purposes.

The phrases "tropism" and "transduction" are interrelated, but there are differences. The term "tropism" as used herein refers to the ability of an AAV vector or virion to infect one or more specified cell types, but can also encompass how the vector functions to transduce the cell in the one or more specified cell types; i.e., tropism refers to preferential entry of the AAV vector or virion into certain cell or tissue type(s) and/or preferential interaction with the cell surface that facilitates entry into certain cell or tissue types, optionally and preferably followed by expression (e.g., transcription and, optionally, translation) of sequences carried by the AAV vector or virion in the cell, e.g., for a recombinant virus, expression of the heterologous nucleotide sequence(s). As used herein, the term "transduction" refers to the ability of an AAV vector or virion to infect one or more particular cell types; i.e., transduction refers to entry of the AAV vector or virion into the cell and the transfer of genetic material contained within the AAV vector or virion into the cell to obtain expression from the vector genome. In some cases, but not all cases, transduction and tropism may correlate.

The term "tropism profile" refers to the pattern of transduction of one or more target cells, tissues and/or organs. For example, some shuffled AAV capsids (variant AAV capsid polypeptides) provide for efficient transduction of human liver tissue or hepatocyte cells (i.e., human hepatocyte cells). Conversely, some shuffled AAV capsids have only low level transduction of skeletal muscle (e.g., quadriceps muscle), diaphragm muscle and/or cardiac muscle tissue, gonads and/or germ cells. The variant AAV capsid polypeptides disclosed herein provide for efficient and/or enhanced transduction of human liver tissue or hepatocyte cells (i.e., human hepatocyte cells).

Unless indicated otherwise, "efficient transduction" or "efficient tropism," or similar terms, can be determined by reference to a suitable control (e.g., at least about 50%, 60%, 70%, 80%, 85%, 90%, 95%, 100%, 110%, 125%, 150%, 175%, or 200% or more of the transduction or tropism, respectively, of the control). Suitable controls will depend on a variety of factors including the desired tropism profile. Similarly, it can be determined if a capsid and/or virus "does not efficiently transduce" or "does not have efficient tropism" for a target tissue, or similar terms, by reference to a suitable control.

As used herein and in the appended claims, the singular forms "a," "an," and "the" include plural referents unless the context clearly dictates otherwise. Thus, for example, reference to "an AAV virion" includes a plurality of such virions and reference to "a host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

AAV Capsid and Vector Features

AAV vectors of the present invention have numerous features. In some embodiments, the vectors comprise nucleic acid sequences encoding for variant capsid polypeptides. Such AAV vectors and their features are described in detail below.

An exemplary AAV vector of the present invention comprises a nucleic acid encoding for a variant AAV capsid protein differing in amino acid sequence by at least one amino acid from a wild-type or non-variant parent capsid protein. The amino acid difference(s) can be located in a solvent accessible site in the capsid, e.g., a solvent-accessible loop, or in the lumen (i.e., the interior space of the AAV capsid). In some embodiments, the lumen includes the interior space of the AAV capsid. For example, the amino acid substitution(s) can be located in a GH loop in the AAV capsid polypeptide. In some embodiments, the variant capsid polypeptide comprises an amino acid substitution in AAV1, AAV2, AAV3, AAV3b, AAV4, AAV5, AAV6, AAV7, AAV8, or AAV9_hu14 capsid polypeptides.

In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, to non-variant capsid amino acid sequences or to sub-portions of a non-variant parent capsid polypeptide sequence, and exhibits an enhanced neutralization profile as compared to a vector encoding a non-variant parent capsid polypeptide. In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits an enhanced neutralization profile as compared to a vector encoding a non-variant parent capsid polypeptide. In some embodiments, the variant capsid polypeptide comprises one or more regions or sub-portions from non-variant parent capsid polypeptide sequences from AAV serotypes 1, 2, 3b, and 6 (i.e., AAV1, AAV2, AAV3b, and AAV6). In some embodiments, the present invention provides a variant capsid polypeptide according to the above.

In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85%, at least about 90%, at least about 95%, at least about 98%, at least about 99%, or 100%, to non-variant capsid amino acid sequences or to sub-portions of a non-variant parent capsid polypeptide sequence, and exhibits increased transduction or tropism in human liver tissue or hepatocyte cells (i.e., human hepatocyte cells) as compared to a vector encoding a non-variant parent capsid polypeptide. In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85%, at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits increased transduction or tropism in human liver tissue or hepatocyte cells (i.e., human hepatocyte cells) as compared to a vector encoding a non-variant parent capsid polypeptide. In some embodiments, the variant capsid polypeptide comprises one or more regions or sub-portions from non-variant parent capsid polypeptide sequences from AAV serotypes 1, 2, 3b, and 6 (i.e., AAV1, AAV2, AAV3b, and AAV6). In some embodiments, the present invention provides a variant capsid polypeptide according to the above. In some embodiments, the parental serotypes that contributed the most to the variant capsid polypeptides included AAV2, 3b, 1 and 6, in that order. In some embodiments, the variant capsid polypeptide does not comprise one or more regions or sub-portions from AAV4, 5, 8, 9_hu14, bovine or avian. In some embodiments, the variant capsid polypeptide does not comprise one or more regions or sub-portions from AAV8.

In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85%, at least about 90%, at least about 95%, at least about 98%, at least about 99%, or 100%, to non-variant capsid amino acid sequences or to sub-portions of a non-variant parent capsid polypeptide sequence, and exhibits both an enhanced neutralization profile and increased transduction or tropism in human liver tissue or hepatocyte cells (i.e., human hepatocyte cells) as compared to a vector encoding a non-variant parent capsid polypeptide. In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85%, at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits both an enhanced neutralization profile and increased transduction or tropism in human liver tissue or hepatocyte cells (i.e., human hepatocyte cells) as compared to a non-variant parent capsid polypeptide. In some embodiments, the variant capsid polypeptide comprises one or more regions or sub-portions from non-variant parent capsid polypeptide sequences from AAV serotypes 1, 2, 3b, and 6 (i.e., AAV1, AAV2, AAV3b, and AAV6). In some embodiments, the parental serotypes that contributed the most to the variant capsid polypeptides included AAV2, 3b, 1 and 6, in that order. In some embodiments, the variant capsid polypeptide does not comprise one or more regions or sub-portions from AAV4, 5, 8, 9_hu14, bovine or avian. In some embodiments, the variant capsid polypeptide does not comprise one or more regions or sub-portions from AAV8. In some embodiments, the present invention provides a variant capsid polypeptide according to the above.

In some embodiments, a subject AAV vector can encode a variant capsid polypeptide having an amino acid sequence of at least about 85%, at least about 90%, at least about 95%, at least about 98%, or at least about 99%, or 100%, amino acid sequence identity to non-variant parent capsid polypeptide or to sub-portions of a non-variant parent capsid polypeptide. In some embodiments, the variant capsid polypeptide is encoded by other vectors/plasmids known in the art. In some embodiments, the present invention provides a variant capsid polypeptide according to the above.

In some embodiments, the present invention provides a variant adeno-associated virus (AAV) capsid protein, where the variant AAV capsid protein comprises an amino acid sequence having at least about 85%, at least about 90%, at least about 95%, at least about 98%, at least about 99%, or 100%, to non-variant capsid amino acid sequences or to sub-portions of a non-variant parent capsid polypeptide sequence, and exhibits an enhanced neutralization profile as compared a non-variant parent capsid polypeptide. In some embodiments, the present invention provides a variant adeno-associated virus (AAV) capsid protein, where the variant AAV capsid protein comprises an amino acid sequence having at least about 85%, at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits an enhanced neutralization profile as compared to a non-variant parent capsid polypeptide. In some embodiments, the variant capsid polypeptide comprises one or more regions or sub-portions from non-variant parent capsid polypeptide sequences from AAV serotypes 1, 2, 3b, and 6 (i.e., AAV1, AAV2, AAV3b, and AAV6).

In some embodiments, the present invention provides a variant adeno-associated virus (AAV) capsid protein, where the variant AAV capsid protein comprises an amino acid sequence having at least about 85%, at least about 90%, at least about 95%, at least about 98%, at least about 99%, or 100%, to non-variant capsid amino acid sequences or to sub-portions of a non-variant parent capsid polypeptide sequence, and exhibits increased transduction or tropism in human liver tissue or hepatocyte cells (i.e., human hepatocyte cells) as compared to non-variant parent capsid polypeptide. In some embodiments, the present invention provides a variant adeno-associated virus (AAV) capsid protein, where the variant AAV capsid protein comprises an amino acid sequence having at least about 85%, at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits increased transduction or tropism in human liver tissue or hepatocyte cells (i.e., human hepatocyte cells) as compared to a non-variant parent capsid polypeptide. In some embodiments, the variant capsid polypeptide comprises one or more regions or sub-portions from non-variant parent capsid polypeptide sequences from AAV serotypes 1, 2, 3b, and 6 (i.e., AAV1, AAV2, AAV3b, and AAV6). In some embodiments, the parental serotypes that contributed the most to the variant capsid polypeptides included AAV2, 3b, 1 and 6, in that order. In some embodiments, the variant capsid polypeptide does not comprise one or more regions or sub-portions from AAV4, 5, 8, 9_hu14, bovine or avian. In some embodiments, the variant capsid polypeptide does not comprise one or more regions or sub-portions from AAV8.

In some embodiments, the present invention provides a variant adeno-associated virus (AAV) capsid protein, where the variant AAV capsid protein comprises an amino acid sequence having at least about 85%, at least about 90%, at least about 95%, at least about 98%, at least about 99%, or 100%, to non-variant capsid amino acid sequences or to sub-portions of a non-variant parent capsid polypeptide sequence, and exhibits both an enhanced neutralization profile and increased transduction or tropism in human liver tissue or hepatocyte cells (i.e., human hepatocyte cells) as compared to a non-variant parent capsid polypeptide. In some embodiments, the present invention provides a variant adeno-associated virus (AAV) capsid protein, where the variant AAV capsid protein comprises an amino acid sequence having at least about 85%, at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits both an enhanced neutralization profile and increased transduction or tropism in human liver tissue or hepatocyte cells (i.e., human hepatocyte cells) as compared to a non-variant parent capsid polypeptide. In some embodiments, the variant capsid polypeptide comprises one or more regions or sub-portions from non-variant parent capsid polypeptide sequences from AAV serotypes 1, 2, 3b, and 6 (i.e., AAV1, AAV2, AAV3b, and AAV6). In some embodiments, the parental serotypes that contributed the most to the variant capsid polypeptides included AAV2, 3b, 1 and 6, in that order. In some embodiments, the variant capsid polypeptide does not comprise one or more regions or sub-portions from AAV4, 5, 8, 9_hu14, bovine or avian. In some embodiments, the variant capsid polypeptide does not comprise one or more regions or sub-portions from AAV8.

In some embodiments, the variant capsid polypeptides exhibit substantial homology or "substantial similarity," when referring to amino acids or fragments thereof, indicates that, when optimally aligned with appropriate amino acid insertions or deletions with another amino acid (or its complementary strand), there is amino acid sequence identity in at least about 95% to about 99% of the aligned sequences. In some embodiments, the homology is over full-length sequence, or a polypeptide thereof, e.g., a capsid protein, or a fragment thereof of at least 8 amino acids, or more desirably, at least about 15 amino acids in length, including sub-portions of a non-variant parent capsid polypeptide sequence. For example, the variant capsid polypeptide can comprise an amino acid sequence having at least about 85%, at least about 90%, at least about 95%, at least about 98%, at least about 99%, or 100%, amino acid sequence identity to a non-variant parent capsid polypeptide sequence or to sub-portions of a non-variant parent capsid polypeptide. In some embodiments, the variant AAV capsid protein comprises an amino acid sequence having at least about 85%, at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits increased transduction or tropism in human liver tissue or hepatocyte cells (i.e., human hepatocyte cells) as compared to a vector encoding a non-variant parent capsid polypeptide. In some embodiments, the variant AAV capsid protein comprises an amino acid sequence having at least about 85%, at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits an enhanced neutralization profile as compared to a vector encoding a non-variant parent capsid polypeptide. In some embodiments, the variant AAV capsid protein comprises an amino acid sequence having at least about 85% at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV3b, AAV4, AAV5, AAV6, AAV7, AAV8, or AAV9_hu14 capsid polypeptides, and where the variant capsid polypeptide exhibits both an enhanced neutralization profile as compared to a vector encoding a non-variant parent capsid polypeptide and increased transduction or tropism in human liver tissue or hepatocyte cells (i.e., human hepatocyte cells) as compared to a vector encoding a non-variant parent capsid polypeptide. In some embodiments, the variant capsid polypeptide comprises one or more regions or sub-portions from non-variant parent capsid polypeptide sequences from AAV serotypes 1, 2, 3b, and 6 (i.e., AAV1, AAV2, AAV3b, and AAV6). In some embodiments, the parental serotypes that contributed the most to the variant capsid polypeptides included AAV2, 3b, 1 and 6, in that order. In some embodiments, the variant capsid polypeptide does not comprise one or more regions or sub-portions from AAV4, 5, 8, 9_hu14, bovine or avian. In some embodiments, the variant capsid polypeptide does not comprise one or more regions or sub-portions from AAV8. In some embodiments the variant capsid polypeptide sequence comprises SEQ ID NOs:2, 4, 6, or 8, as provided in Table 2 below. In some embodiments, the variant capsid polypeptide sequence is encoded by SEQ ID NOs:1, 3, 5, or 7, as provided in Table 2 below. In some embodiments, the variant AAV capsid polypeptide is selected from the group consisting of AAV-NP84 (SEQ ID NO:2), AAV-NP59 (SEQ ID NO:4), and AAV-NP40 (SEQ ID NO:6). In some embodiments, the variant AAV capsid polypeptide is selected from the group consisting of AAV-NP59 (SEQ ID NO:4), and AAV-NP40 (SEQ ID NO:6). In some embodiments, the variant AAV capsid polypeptide is AAV-NP59 (SEQ ID NO:4). In some embodiments, the variant AAV capsid polypeptide is AAV-NP40 (SEQ ID NO:6).

TABLE 2

Variant Capsid Sequences

| Description SEQ ID NO: | Sequence |
| --- | --- |
| Nucleic acid sequence for AAV-NP84 SEQ ID NO: 1 | >AAV-NP84-nt<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAAGCCTACGACCGGCAGCTCGACAGCGGAGACAACCCGTACCTCAAGTACA<br>ACCACGCCGACGCGGAGTTTCAGGAGCGCCTTAAAGAAGATACGTCTTTTGGGGGCAACCTCGGACGAGC<br>AGTCTTCCAGGCGAAAAAGAGGGTTCTTGAACCTCTGGGCCTGGTTGAGGAACCTGTTAAGACGGCTCCG<br>GGAAAAAAGAGGCCGGTAGAGCACTCTCCTGTGGAGCCAGACTCCTCCTCGGGAACCGGCAAGACAGGCC<br>AGCAGCCCGCTAAAAAGAGACTCAATTTTGGTCAGACTGGCGACTCAGAGTCAGTCCCAGACCCTCAACC<br>TCTCGGAGAACCACCAGCAGCCCCCTCTGGTCTGGGAACTAATACGATGGCTACAGGCAGTGGCGCACCA<br>ATGGCAGACAATAACGAGGGTGCCGATGGAGTGGGTAATTCCTCAGGAAATTGGCATTGCGATTCCCAAT<br>GGCTGGGCGACAGAGTCATCACCACCAGCACCAGAACCTGGGCCCTGCCCACCTACAACAACCATCTCTA<br>CAAGCAAATCTCCAGCCAATCAGGAGCTTCAAACGACAACCACTACTTTGGCTACAGCACCCCTTGGGGG<br>TATTTTGACTTTAACAGATTCCACTGCCACTTCTCACCACGTGACTGGCAGCGACTCATTAACAACAACT<br>GGGGATTCCGGCCCAAGAAACTCAGCTTCAAGCTCTTCAACATCCAAGTTAAAGAGGTCACGCAGAACGA<br>TGGCACGACGACTATTGCCAATAACCTTACCAGCACGGTTCAAGTGTTTACTGACTCGGAGTACCAGCTC<br>CCGTACGTCCTCGGCTCGGCGCATCAAGGATGCCTCCCGCCGTTCCCAGCAGACGTCTTCATGGTGCCAC<br>AGTATGGATACCTCACCCTGAACAACGGGAGTCAGGCAGTAGGACGCTCTTCATTTTACTGCCTGGAGTA<br>CTTTCCTTCTCAGATGCTGCGTACCGGAAACAACTTTACCTTCAGCTACACTTTTGAGGACGTTCCTTTC<br>CACAGCAGCTACGCTCACAGCCAGAGTCTGGACCGTCTCATGAATCCTCTCATCGACCAGTACCTGTATT<br>ACTTGAGCAGAACAAACACTCCAAGTGGAACCACCACGCAGTCAAGGCTTCAGTTTTCTCAGGCCGGAGC<br>GAGTGACATTCGGGACCAGTCTAGGAACTGGCTTCCTGGACCCTGTTACCGCCAGCAGCGAGTATCAAAG<br>ACATCTGCGGATAACAACAACAGTGAATACTCGTGGACTGGAGCTACCAAGTACCACCTCAATGGCAGGA<br>ACTCTCTGGTGAATCCGGGCCCGGCCATGGCAAGCCACAAGGACGATGAAGAAGAGTTTTTTCCTCAGAG<br>CGGGGTTCTCATCTTTGGGAAGCAAGGCTCAGAGAAAACAAATGTGGACATTGAAAAGGTCATGATTACA<br>GACGAAGAGGAAATCAGGACAACCAATCCCGTGGCTACGGAGCAGTATGGTTCTGTATCTACCAACCTCC<br>AGGGAGGCCAACAGACAAGCAGCTACCGCAGATGTCAACACACAAGGCGTTCTTCCAGGCATGGTCTGGCA<br>GGACAGAGATGTGTACCTTCAGGGGCCCATCTGGGCAAAGATTCCACACACGGACGGACATTTTCACCCC<br>TCTCCCCTCATGGGTGGATTCGGACTTAAACACCCTCCTCCACAGATTCTCATCAAGAACACCCCGGTAC<br>CTGCGAATCCTTCGACCACCTTCAGTGCGGCAAAGTTTGCTTCCTTCATCACACAGTACTCCACGGGACA<br>GGTCAGCGTGGAGATCGAGTGGGAGCTGCAGAAGGAAAACAGCAAACGCTGGAATCCCGAAATTCAGTAC<br>ACTTCCAACTACAACAAGTCTGTTAATGTGGACTTTACTGTGGACACTAATGGCGTGTATTCAGAGCCTC<br>GCCCCATTGGCACCAGATACCTGACTCGTAATCTGTAA |
| Amino acid sequence for AAV-NP84 SEQ ID NO: 2 | >AAV-NP84-aa<br>MAADGYLPDWLEDTLSEGIRQWWKLKPGPPPPKPAERHKDDSRGLVLPGYKYLGPFNGLDKGEPVNEADA<br>AALEHDKAYDRQLDSGDNPYLKYNHADAEFQERLKEDTSFGGNLGRAVFQAKKRVLEPLGLVEEPVKTAP<br>GKKRPVEHSPVEPDSSSGTGKTGQQPAKKRLNFGQTGDSESVPDPQPLGEPPAAPSGLGTNTMATGSGAP<br>MADNNEGADGVGNSSGNWHCDSQWLGDRVITTSTRTWALPTYNNHLYKQISSQSGASNDNHYFGYSTPWG<br>YFDFNRFHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFTFSYTFEDVPF<br>HSSYAHSQSLDRLMNPLIDQYLYYLSRTNTPSGTTTQSRLQFSQAGASDIRDQSRNWLPGPCYRQQRVSK |

TABLE 2-continued

Variant Capsid Sequences

| Description SEQ ID NO: | Sequence |
|---|---|
| | TSADNNNSEYSWTGATKYHLNGRDSLVNPGPAMASHKDDEEEFFPQSGVLIFGKQGSEKTNVDIEKVMIT<br>DEEEIRTTNPVATEQYGSVSTNLQGGNRQAATADVNTQGVLPGMVWQDRDVYLQGPIWAKIPHTDGHFHP<br>SPLMGGFGLKHPPPQILIKNTPVPANPSTTFSAAKFASFITQYSTGQVSVEIEWELQKENSKRWNPEIQY<br>TSNYNKSVNVDFTVDTNGVYSEPRPIGTRYLTRNL |
| Nucleic acid sequence for AAV-NP59 SEQ ID NO: 3 | >AAV-NP59-nt<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAAGCCTACGACCGGCAGCTCGACAGCGGAGACAACCCGTACCTCAAGTACA<br>ACCACGCCGACGCGGAGTTTCAGGAGCGCCTTAAAGAAGATACGTCTTTTGGGGGCAACCTCGGACGAGC<br>AGTCTTCCAGGCGAAAAAGAGGGTTCTTGAACCTCTGGGCCTGGTTGAGGAACCTGTTAAGACGGCTCCG<br>GGAAAAAAGAGGCCGGTAGAGCACTCTCCTGTGGAGCCAGACTCCTCCTCGGGAACCGGCAAGACAGGCC<br>AGCAGCCCGCTAAAAAGAGACTCAATTTTGGTCAGACTGGCGACTCAGAGTCAGTCCCAGACCCTCAACC<br>TCTCGGAGAACCACCAGCAGCCCCTCTGGTCTGGGAACTAATACGATGGCTACAGGCAGTGGCGCACCA<br>ATGGCAGACAATAACGAGGGCGCCGACGGAGTGGGTAATTCCTCGGGAAATTGGCATTGCGATTCCACAT<br>GGATGGGCGACAGAGTCATCACCACCAGCACCCGAACCTGGGCCTGCCCACCTACAACAACCATCTCTA<br>CAAGCAAATCTCCAGCCAATCAGGAGCTTCAAACGACAACCACTACTTTGGCTACAGCACCCCTTGGGGG<br>TATTTTGACTTTAACAGATTCCACTGCCACTTCTCACCACGTGACTGGCAGCGACTCATTAACAACAACT<br>GGGGATTCCGGCCCAAGAAACTCAGCTTCAAGCTCTTCAACATCCAAGTTAAAGAGGTCACGCAGAACGA<br>TGGCACGACGACTATTGCCAATAACCTTACCAGCACGGTTCAAGTGTTTACTGACTCGGAGTACCAGCTC<br>CCGTACGTCCTCGGCTCGGCGCATCAAGGATGCCTCCCGCCGTTCCCAGCAGACGTCTTCATGGTGCCAC<br>AGTATGGATACCTCACCCTGAACAACGGGAGTCAGGCAGTAGGACGCTCTTCATTTTACTGCCTGGAGTA<br>CTTTCCTTTCTCAGATGCTGCGTACCGGAAACAACTTTACCTTCAGCTACACTTTTGAGGACGTTCCTTTC<br>CACAGCAGCTACGCTCACAGCCAGAGTCTGGACCGTCTCATGAATCCTCTCATCGACCAGTACCTGTATT<br>ACTTGAGCAGAACAAACACTCCAAGTGGAACCACCACGCAGTCAAGGCTTCAGTTTTCTCAGGCCGGAGC<br>GAGTGACATTCGGGACCAGTCTAGGAACTGGCTTCCTGGACCCTGTTACCGCCAGCAGCGAGTATCAAAG<br>ACATCTGCGGATAACAACAACAGTGAATACTCGTGGACTGGAGCTACCAAGTACCACCTCAATGGCAGAG<br>ACTCTCTGGTGAATCCGGGCCCGGCCATGGCAAGCCACAAGGACGATGAAGAAAAGTTTTTTCCTCAGAG<br>CGGGGTTCTCATCTTTGGGAAGCAAGGCTCAGAGAAAACAAATGTGGACATTGAAAAGGTCATGATTACA<br>GACGAAGAGGAAATCAGGACAACCAATCCCGTGGCTACGGAGCAGTATGGTTCTGTATCTACCAACCTCC<br>AGAGAGGCAACAGACAAGCAGCTACCGCAGATGTCGACACAAGGCGTTCTTCCAGGCATGGTCTGGCA<br>GGACAGAGATGTGTACCTTCAGGGACCCATCTGGGCAAAGATTCCACACACGGACGGACATTTTCACCCC<br>TCTCCCCTCATGGGTGGATTCGGACTTAAACACCCTCCTCCACAGATTCTCATCAAGAACACCCCGGTAC<br>CTGCGAATCCTTCGACCACCTTCAGTGCGGCAAAGTTTGCTTCCTTCATCACACAGTACTCCACGGGACA<br>GGTCAGCGTGGAGATCGAGTGGGAGCTGCAGAAGGAAAACAGCAAACGCTGGAATCCCGAAATTCAGTAC<br>ACTTCCAACTACAACAAGTCTGTTAATGTGGACTTTACTGTGGACACTAATGGCGTGTATTCAGAGCCTC<br>GCCCCATTGGCACCAGATACCTGACTCGTAATCTGTAA |
| Amino acid sequence for AAV-NP59 SEQ ID NO: 4 | >AAV-NP59-aa<br>MAADGYLPDWLEDTLSEGIRQWWKLKPGPPPPKPAERHKDDSRGLVLPGYKYLGPFNGLDKGEPVNEADA<br>AALEHDKAYDRQLDSGDNPYLKYNHADAEFQERLKEDTSFGGNLGRAVFQAKKRVLEPLGLVEEPVKTAP<br>GKKRPVEHSPVEPDSSSGTGKTGQQPAKKRLNFGQTGDSESVPDPQPLGEPPAAPSGLGTNTMATGSGAP<br>MADNNEGADVGNSSGNWHCDSTWMGDRVITTSTRTWALPTYNNHLYKQISSQSGASNDNHYFGYSTPWG<br>YFDFNRFHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFTFSYTFEDVPF<br>HSSYAHSQSLDRLMNPLIDQYLYYLSRTNTPSGTTTQSRLQFSQAGASDIRDQSRNWLPGPCYRQQRVSK<br>TSADNNNSEYSWTGATKYHLNGRDSLVNPGPAMASHKDDEEKFFPQSGVLIFGKQGSEKTNVDIEKVMIT<br>DEEEIRTTNPVATEQYGSVSTNLQRGNRQAATADVDTQGVLPGMVWQDRDVYLQGPIWAKIPHTDGHFHP<br>SPLMGGFGLKHPPPQILIKNTPVPANPSTTFSAAKFASFITQYSTGQVSVEIEWELQKENSKRWNPEIQY<br>TSNYNKSVNVDFTVDTNGVYSEPRPIGTRYLTRNL |
| Nucleic acid sequence for AAV-NP40 SEQ ID NO: 5 | >AAV-NP40-nt<br>ATGGCTGCCGATGGTTATCTTCCAGATTGGCTCGAGGACAACCTTAGTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAAGCCTACGACCGGCAGCTCGACAGCGGAGACAACCCGTACCTCAAGTACA<br>ACCACGCCGACGCGGAGTTTCAGGAGCGCCTTAAAGAAGATACGTCTTTTGGGGGCAACCTCGGACGAGC<br>AGTCTTCCAGGCGAAAAAGAGGGTTCTTGAACCTCTGGGCCTGGTTGAGGAACCTGTTAAGACGGCTCCG<br>GGAAAAAAGAGGCCGGTAGAGCACTCTCCTGTGGAGCCAGACTCCTCCTCGGGAACCGGCAAGACAGGCC<br>AGCAGCCCGCTAAAAAGAGACTCAATTTTGGTCAGACTGGCGACTCAGAGTCAGTCCCAGACCCTCAACC<br>TCTCGGAGAACCACCAGCAGCCCCCTCTGGTCTGGGAACTAATACGATGGCTACAGGCAGTGGCGCACCA<br>ATGGCAGACAATAACGAGGGCGCCGACGGAGTGGGTAATTCCTCGGGAAATTGGCATTGCGATTCCACAT<br>GGATGGGCGACAGAGTCATCACCACCAGCACCAGAACCTGGGCCTGCCCACCTACAACAACCATCTCTA<br>CAAGCAAATCTCCAGCCAATCAGGAGCTTCAAACGACAACCACTACTTTGGCTACAGCACCCCTTGGGGG<br>TATTTTGACTTTAACAGATTCCACTGCCACTTCTCACCACGTGACTGGCAGCGACTCATTAACAACAACT<br>GGGGATTCCGGCCCAAGAAACTCAGCTTCAAGCTCTTCAACATCCAAGTTAAAGAGGTCACGCAGAACGA<br>TGGCACGACGACTATTGCCAATAACCTTACCAGCACGGTTCAAGTGTTTACTGACTCGGAGTACCAGCTC<br>CCGTACGTCCTCGGCTCGGCGCATCAAGGACGCCTCCCGCCGTTCCCAGCAGACGTCTTCATGGTGCCAC<br>AGTATGGATACCTCACCCTGAACAACGGGAGTCAGGCAGTAGGACGCTCTTCATTTTACTGCCTGGAGTA<br>CTTTCCTTTCTCAGATGCTGCGTACCGGAAACAACTTTACCTTCAGCTACACTTTTGAGGACGTTCCTTTC<br>CACAGCAGCTACGCTCACAGCCAGAGTCTGGACCGTCTCATGAATCCTCTCATCGACCAGTACCTGTATT<br>ACTTGAGCAGAACAAACACTCCAAGTGGAACCACCACGCAGTCAAGGCTTCAGTTTTCTCAGGCCGGAGC<br>GAGTGACATTCGGGACCAGTCTAGGAACTGGCTTCCTGGACCCTGTTACCGCCAGCAGCGAGTATCAAAG |

TABLE 2-continued

Variant Capsid Sequences

| Description SEQ ID NO: | Sequence |
|---|---|
| | ACATCTGCGGATAACAACAACAGTGAATACTCGTGGACTGGAGCTACCAAGTACCACCTCAATGGCAGAG<br>ACTCTCTGGTGAATCCGGGCCCGGCCATGGCAAGCCACAAGGACGATGAAGAAGAGTTTTTTCCTCAGAG<br>CGGGGTTCTCATCTTTGGGAAGCAAGGCTCAGAGAAAACAAATGTGGACATTGAAAAGGTCATGATTACA<br>GACGAAGAGGAAATCAGGACAACCAATCCCGTGGCTACGGAGCAGTATGGTTCTGTATCTACCAACCTCC<br>AGAGAGGCAACAGACAAGCAGCTACCGCAGATGTCAACACACAAGGCGTTCTTCCAGGCATGGTCTGGCA<br>GGACAGAGATGTGTACCTTCAGGGGCCCATCTGGGCAAAGATTCCACACACGGACGGACATTTTCACCCC<br>TCTCCCCTCATGGGTGGATTCGGACTTAAACACCCTCCTCCACAGATTCTCATCAAGAACACCCCGGTAC<br>CTGCGAATCCTTCGACCACCTTCAGTGCGGCAAAGTTTGCTTCCTTCATCACACAGTACTCCACGGGACA<br>GGTCAGCGTGGAGATCGAGTGGGAGCTGCAGAAGGAAAACAGCAAACGCTGGAATCCCGAAATTCAGTAC<br>ACTTCCAACTACAACAAGTCTGTTAATGTGGACTTTACTGTGGACACTAATGGCGTGTATTCAGAGCCTC<br>GCCCCATTGGCACCAGATACCTGACTCGTAATCTGTAA |
| Amino acid sequence for AAV-NP40 SEQ ID NO: 6 | >AAV-NP40-aa<br>MAADGYLPDWLEDNLSEGIRQWWKLKPGPPPPKPAERHKDDSRGLVLPGYKYLGPFNGLDKGEPVNEADA<br>AALEHDKAYDRQLDSGDNPYLKYNHADAEFQERLKEDTSGDNLGRAVFQAKKRVLEPLGLVEEPVKTAP<br>GKKRPVEHSPVEPDSSSGTGKTGQQPAKKRLNFGQTGDSESVPDPQPLGEPPAAPSGLGTNTMATGSGAP<br>MADNNEGADGVGNSSGNWHCDSTWMGDRVITTSTRTWALPTYNNHLYKQISSQSGASNDNHYFGYSTPWG<br>YFDFNRFHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFTFSYTFEDVPF<br>HSSYAHSQSLDRLMNPLIDQYLYYLSRTNTPSGTTTQSRLQFSQAGASDIRDQSRNWLPGPCYRQQRVSK<br>TSADNNNSEYSWTGATKYHLNGRDSLVNPGPAMASHKDDEEEFFPQSGVLIFGKQGSEKTNVDIEKVMIT<br>DEEEIRTTNPVATEQYGSVSTNLQRGNRQAATADVNTQGVLPGMVWQDRDVYLQGPIWAKIPHTDGHFHP<br>SPLMGGFGLKHPPPQILIKNTPVPANPSTTFSAAKFASFITQYSTGQVSVEIEWELQKENSKRWNPEIQY<br>TSNYNKSVNVDFTVDTNGVYSEPRPIGTRYLTRNL |
| Nucleic acid sequence for AAV-NP30 SEQ ID NO: 7 | >AAV-NP30-nt<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGCGGTCAACGAGGCAGACGCC<br>GCGGCCCTCGAGCACGACAAAGCCTACGACCGGCAGCTCGACAGCGGAGACAACCCGTACCTCAAGTACA<br>ACCACGCCGACGCGGAGTTTCAGGAGCGCCTTAAAGAAGATACGTCTTTTGGGGGCAACCTCGGACGAGC<br>AGTCTTCCAGGCGAAAAAGAGGGTTCTTGAACCTCTGGGCCTGGTTGAGGAACCTGTTAAGACGGCTCCG<br>GGAAAAAAGAGGCCGGTAGAGCACTCTCCTGTGGAGCCAGACTCCTCCTCGGGAACCGGCAAGACAGGCC<br>AGCAGCCCGCTAAAAAGAGACTCAATTTTGGTCAGACTGGCGACTCAGAGTCAGTCCCAGACCCTCAACC<br>TCTCGGAGAACCACCAGCAGCCCCCTCTGGTCTGGGAACTAATACGATGGCTACAGGCAGTGGCGCACCA<br>ATGGCAGACAATAACGAGGGTGCCGATGGAGTGGGTAATTCCTCAGGAAATTGGCATTGCGATTCCCAAT<br>GGCTGGGCGACAGAGTCATCACCACCAGCACCAGAACCTGGGCCTGCCCACCTACAACAACCATCTCTA<br>CAAGCAAATCTCCAGCCAATCAGGAGCTTCAAACGACAACCACTACTTTGGCTACAGCACCCCTTGGGGG<br>TATTTTGACTTTAACAGATTCCACTGCCACTTCTCACCACGTGACTGGCAGCGACTCATTAACAACAACT<br>GGGGATTCCGGCCCAAGAAACTCAGCTTCAAGCTCTTTAACATCCAAGTTAAAGAGGTCACGCAGAACGA<br>TGGCACGACGACTATTGCCAATAACCTTACCAGCACGGTTCAAGTGTTTACTGACTCGGAGTACCAGCTC<br>CCGTACGTCCTCGGCTCGGCGCATCAAGGATGCCTCCCGCCGTTCCCAGCAGACGTCTTCATGGTGCCAC<br>AGTATGGATACCTCACCCTGAACAACGGGAGTCAGGCAGTAGGACGCTCTTCATTTTACTGCCTGGAGTA<br>CTTTCCTTCTCAGATGCTGCGTACCGGAAACAACTTTACCTTCAGCTACACTTTTGAGGACGTTCCTTTC<br>CACAGCAGCTACGCTCACAGCCAGAGTCTGGACCGTCTCATGAATCCTCTCATCGACCAGTACCTGTATT<br>ACTTGAGCAGAACAAACACTCCAAGTGGAACCACCACGCAGTCAAGGCTTCAGTTTTCTCAGGCCGGAGC<br>GAGTGACATTCGGGACCAGTCTAGGAACTGGCTTCCTGGACCCTGTTACCGCCAGCAGCGAGTATCAAAG<br>ACATCTGCGGATAACAACAACAGTGAATACTCGTGGACTGGAGCTACCAAGTACCACCTCAATGGCAGAG<br>ACTCTCTGGTGAATCCGGGCCCGGCCATGGCAAGCCACAAGGACGATGAAGAAGAGTTTTTTCCTCAGAG<br>CGGGGTTCTCATCTTTGGGAAGCAAGGCTCAGAGAAAACAAATGTGGACATTGAAAAGGTCATGATTACA<br>GACGAAGAGGAAATCAGGACAACCAATCCCGTGGCTACGGAGCAGTATGGTTCTGTATCTACCAACCTCC<br>AGAGAGGCAACAGACAAGCAGCTACCGCAGATGTCAACACACAAGGCGTTCTTCCAGGCATGGTCTGGCA<br>GGACAGAGATGTGTACCTTCAGGGGCCCATCTGGGCAAAGATTCCACACACGGACGGACATTTTCACCCC<br>TCTCCCCTCATGGGTGGATTCGGACTTAAACACCCTCCTCCACAGATTCTCATCAAGAACACCCCGGTAC<br>CTGCGAATCCTTCGACCACCTTCAGTGCGGCAAAGTTTGCTTCCTTCATCACACAGTACTCCACGGGACA<br>GGTCAGCGTGGAGATCGAGTGGGAGCTGCAGAAGGAAAACAGCAAACGCTGGAATCCCGAAATTCAGTAC<br>ACTTCCAACTACAACAAGTCTGTTAATGTGGACTTTACTGTGGACACTAATGGCGTGTATTCAGAGCCTC<br>GCCCCATTGGCACCAGATACCTGACTCGTAATCTGTAA |
| Amino acid sequence for AAV-NP30 SEQ ID NO: 8 | >AAV-NP30-aa<br>MAADGYLPDWLEDTLSEGIRQWWKLKPGPPPPKPAERHKDDSRGLVLPGYKYLGPFNGLDKGEPVNEADA<br>AALEHDKAYDRQLDSGDNPYLKYNHADAEFQERLKEDTSFGGNLGRAVFQAKKRVLEPLGLVEEPVKTAP<br>GKKRPVEHSPVEPDSSSGTGKTGQQPAKKRLNFGQTGDSESVPDPQPLGEPPAAPSGLGTNTMATGSGAP<br>MADNNEGADGVGNSSGNWHCDSQWLGDRVITTSTRTWALPTYNNHLYKQISSQSGASNDNHYFGYSTPWG<br>YFDFNRFHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFTFSYTFEDVPF<br>HSSYAHSQSLDRLMNPLIDQYLYYLSRTNTPSGTTTQSRLQFSQAGASDIRDQSRNWLPGPCYRQQRVSK<br>TSADNNNSEYSWTGATKYHLNGRDSLVNPGPAMASHKDDEEEFFPQSGVLIFGKQGSEKTNVDIEKVMIT<br>DEEEIRTTNPVATEQYGSVSTNLQRGNRQAATADVNTQGVLPGMVWQDRDVYLQGPIWAKIPHTDGHFHP<br>SPLMGGFGLKHPPPQILIKNTPVPANPSTTFSAAKFASFITQYSTGQVSVEIEWELQKENSKRWNPEIQY<br>TSNYNKSVNVDFTVDTNGVYSEPRPIGTRYLTRNL |

TABLE 2-continued

Variant Capsid Sequences

| Description SEQ ID NO: | Sequence |
|---|---|
| Nucleic acid sequence for LK03 SEQ ID NO: 9 | >AAV-LK03-nt<br>ATGGCTGCTGACGGTTATCTTCCAGATTGGCTCGAGGACAACCTTTCTGAAGGCATTCGAGAGTGGTGGG<br>CGCTGCAACCTGGAGCCCCTAAACCCAAGGCAAATCAACAACATCAGGACAACGCTCGGGGTCTTGTGCT<br>TCCGGGTTACAAATACCTCGGACCCGGCAACGGACTCGACAAGGGGGAACCCGTCAACGCAGCGGACGCG<br>GCAGCCCTCGAGCACGACAAGGCCTACGACCAGCAGCTCAAGGCCGGTGACAACCCCTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGATCAGTCTCCTCAGGAACCGGACTCATCATCTGGTGTTGGCAAATCGGGCA<br>AACAGCCTGCCAGAAAAAGACTAAATTTCGGTCAGACTGGCGACTCAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAGGGTGCCGATGGAGTGGGTAATTCCTCAGGAAATTGGCATTGCGATTCCCAAT<br>GGCTGGGCGACAGAGTCATCACCACCAGCACCAGAACCTGGGCCCTGCCCACTTACAACAACCATCTCTA<br>CAAGCAAATCTCCAGCCAATCAGGAGCTTCAAACGACAACCACTACTTTGGCTACAGCACCCCTTGGGGG<br>TATTTTGACTTTAACAGATTCCACTGCCACTTCTCACCACGTGACTGGCAGCGACTCATTAACAACAACT<br>GGGGATTCCGGCCCAAGAAACTCAGCTTCAAGCTCTTCAACATCCAAGTTAAAGAGGTCACGCAGAACGA<br>TGGCACGACGACTATTGCCAATAACCTTACCAGCACGGTTCAAGTGTTTACGGACTCGGAGTATCAGCTC<br>CCGTACGTGCTCGGGTCGGCGCACCAAGGCTGTCTCCCGCCGTTTCCAGCGGACGTCTTCATGGTCCCTC<br>AGTATGGATACCTCACCCTGAACAACGGAAGTCAAGCGGTGGGACGTCTCATCCTTTTACTGCCTGGAGTA<br>CTTCCCTTCGCAGATGCTAAGGACTGGAAATAACTTCCAATTCAGCTATACCTTCGAGGATGTACCTTTT<br>CACAGCAGCTACGCTCACAGCCAGAGTTTGGATCGCTTGATGAATCCTCTTATTGATCAGTATCTGTACT<br>ACCTGAACAGAACGCAAGGAACAACCTCTGGAACAACCAACCAATCACGGCTGCTTTTTAGCCAGGCTGG<br>GCCTCAGTCTATGTCTTTGCAGGCCAGAAATTGGCTACCTGGGCCCTGCTACCGGCAACAGAGACTTTCA<br>AAGACTGCTAACGACAACAACAACAGTAACTTTCCTTGGACAGCGGCCAGCAAATATCATCTCAATGGCC<br>GCGACTCGCTGGTGAATCCAGGACCAGCTATGGCCAGTCACAAGGACGATGAAGAAAAATTTTTCCCTAT<br>GCACGGCAATCTAATATTTGGCAAAGAAGGGACAACGGCAAGTAACGCAGAATTAGATAATGTAATGATT<br>ACGGATGAAGAAGAGATTCGTACCACCAATCCTGTGGCAACAGAGCAGTATGGAACTGTGGCAAATAACT<br>TGCAGAGCTCAAATACAGCTCCCACGACTAGAACTGTCAATGATCAGGGGGCCTTACCTGGCATGGTGTG<br>GCAAGATCGTGACGTGTACCTTCAAGGACCTATCTGGGCAAAGATTCCTCACACGGATGGACACTTTCAT<br>CCTTCTCCTCTGATGGGAGGCTTTGGACTGAAACATCCGCCTCCTCAAATCATGATCAAAAATACTCCGG<br>TACCGGCAAATCCTCCGACGACTTTCAGCCCGGCCAAGTTTGCTTCATTTATCACTCAGTACTCCACTGG<br>ACAGGTCAGCGTGGAAATTGAGTGGGAGCTACAGAAAGAAAACAGCAAACGTTGGAATCCAGAGATTCAG<br>TACACTTCCAACTACAACAAGTCTGTTAATGTGGACTTTACTGTAGACACTAATGGTGTTTATAGTGAAC<br>CTCGCCCCATTGGCACCCGTTACCTTACCCGTCCCCTGTAA |
| Amino acid sequence for LK03 SEQ ID NO: 10 | >AAV-LK03-aa<br>MAADGYLPDWLEDNLSEGIREWWALQPGAPKPKANQQHQDNARGLVLPGYKYLGPGNGLDKGEPVNAADA<br>AALEHDKAYDQQLKAGDNPYLKYNHADAEFQERLKEDTSFGGNLGRAVFQAKKRLLEPLGLVEEAAKTAP<br>GKKRPVDQSPQEPDSSSGVGKSGKQPARKRLNFGQTGDSESVPDPQPLGEPPAAPTSLGSNTMASGGGAP<br>MADNNEGADGVGNSSGNWHCDSQWLGDRVITTSTRTWALPTYNNHLYKQISSQSGASNDNHYFGYSTPWG<br>YFDFNRFHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFQSYTFEDVPF<br>HSSYAHSQSLDRLMNPLIDQYLYYLNRTQGTTSGTTNQSRLLFSQAGPQSMSLQARNWLPGPCYRQQRLS<br>KTANDNNNSNFPWTAASKYHLNGRDSLVNPGPAMASHKDDEEKFFPMHGNLIFGKEGTTASNAELDNVMI<br>TDEEEIRTTNPVATEQYGTVANNLQSSNTAPTTRTVNDQGALPGMVWQDRDVYLQGPIWAKIPHTDGHFH<br>PSPLMGGFGLKHPPPQIMIKNTPVPANPPTTFSPAKFASFITQYSTGQVSVEIEWELQKENSKRWNPEIQ<br>YTSNYNKSVNVDFTVDTNGVYSEPRPIGTRYLTRPL* |
| Nucleic acid sequence for DJ SEQ ID NO: 11 | >AAV-DJ-nt<br>ATGGCTGCCGATGGTTATCTTCCAGATTGGCTCGAGGACACTCTcTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCCTTCAACGGACTCGACAAGGGAGAGCCGTCAACGAGGCAGACGCC<br>GCGGCCCTCGAGCACGACAAAGCCTACGACCGGCAGCTCGACAGCGGAGACAACCCGTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAAAAGAGGCTTCTTGAACCTCTtGGTCTGGTTGAGGAAGCGGCTAAGACGGcTCcT<br>GGAAaGAaGAGgCcTGTAGAGCACTCTCCTGTGGAGCCAGACTCcTCcTCGGgAACCGGAAAgGCGGgCC<br>AGCAGCCTGCAAGAAAAAGATTGAATTTGGTCAGACTGGAGACGCAGACTCAGTCCCAGACCCTCAACC<br>AATCGGAGAACCTCCCGCAGCCCCCTCAGGTGTGGGATCTCTTACAATGGCTGCAGGCGGTGGCGCACCA<br>ATGGCAGACAATAACGAGGGCGCCGACGGAGTGGGTAATTCCTCGGGAAATTGGCATTGCGATTCCACAT<br>GGATGGGCGACAGAGTCATCACCACCAGCACCCGAACCTGGGCCCTGCCCACCTACAACAACCACCTCTA<br>CAAGCAAATCTCCAACAGCACATCTGGAGGATCTTCAAATGACAACCACTACTTCGGCTACAGCACCCCC<br>TGGGGGTATTTTGACTTTAACAGATTCCACTGCCACTTTTCACCACGTGACTGGCAGCGACTCATCAACA<br>ACAACTGGGGATTCCGGCCCAAGAGACTCAGCTTCAAGCTCTTCAACATCCAGGTCAAGGAGGTCACGCA<br>GAATGAAGGCACCAAGACCATCGCCAaTAaCcTCACcAGCACcATCcAGgTGTTtACgGACTCgGAGTAC<br>CAGCTGCCGTACGTcCTCGGCTCTGCcCACCAGGGCTGcCTGCCTCCGTTCCCGGCGGACGTGTTCATGA<br>TTCCCCAGTACGGCTACCTAACACTCAACAACGGTAGTCAGGCCGTGGGACGCTCCTCCTTCTACTGCCT<br>GGAATACTTTCCTTCGCAGATGCTGAGAACCGGCAACAACTTCCAGTTTACTTACACCTTCGAGGACGTG<br>CCTTTCCACAGCAGCTACGCCCACAGCCAGAGCTTGgaCCGGCTGATGAATCCTCTGATTGACCAGTACC<br>TGTACTACTTGTCTCGGACTCAAaCaACAGGAGgCACGAcAaATAcGcAGAATCTGGGCTTCAGCCAaGG<br>TGGGCCTAATACAATGGCCAATCAGGCAaAgAACTGGCTGCCAGGACCCTGTTACCGCCAGCAGCGAGTA<br>TCAAAGACATCTGCGGATAACAACAACAGTGAATACTCGTGGACTGGAGCTACCAAGTACCACCTCAATG<br>GCAGAGACTCTCTGGTGAATCCGGGCCCGGCCATGGCAAGCCACAAGGACGATGAAGAAAAAGTTTTTCC<br>TCAGAGCGGGGTTCTCATCTTTGGGAAGCAAGGCTCAGAGAAAACAAATGTGGACATTGAAAAGGTCATG<br>ATTACAGACGAAGAGGAAATCAGGACAACCAATCCCGTGGCTACGGAGCAGTATGGTTCTGTATCTACCA |

TABLE 2-continued

Variant Capsid Sequences

| Description SEQ ID NO: | Sequence |
|---|---|
| | ACCTCCAGAGAGGCAACAGACAAGCAGCTACCGCAGATGTCAACACACAAGGCGTTCTTCCAGGCATGGT<br>CTGGCAGGACAGAGATGTGTACCTTCAGGGGCCCATCTGGGCAAAGATTCCACACACGGACGGACATTTT<br>CACCCCTCTCCCCTCATGGGTGGATTCGGACTTAAACACCCTCCGCCTCAGATCCTGATCAAGAACACGC<br>CTGTACCTGCGGATCCTCCGACCACCTTCAACCAGTCAAAGCTGAACTCTTTCATCACCCAGTATTCTAC<br>TGGCCAAGTCAGCGTGGAGATCGAGTGGGAGCTGCAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |
| Amino acid sequence for DJ SEQ ID NO: 12 | >AAV-DJ-aa<br>MAADGYLPDWLEDTLSEGIRQWWKLKPGPPPPKPAERHKDDSRGLVLPGYKYLGPFNGLDKGEPVNEADA<br>AALEHDKAYDRQLDSGDNPYLKYNHADAEFQERLKEDTSFGGNLGRAVFQAKKRLLEPLGLVEEAAKTAP<br>GKKRPVEHSPVEPDSSSGTGKAGQQPARKRLNFGQTGDADSVPDPQPIGEPPAAPSGVGSLTMAAGGGAP<br>MADNNEGADGVGNSSGNWHCDSTWMGDRVITTSTRTWALPTYNNHLYKQISNSTSGGSSNDNAYFGYSTP<br>WGYFDFNRFHCHFSPRDWQRLINNNWGFRPKRLSFKLFNIQVKEVTQNEGTKTIANNLTSTIQVFTDSEY<br>QLPYVLGSAHQGCLPPFPADVFMIPQYGYLTLNNGSQAVGRSSFYCLEYFPSQMLRTGNNFQFTYTFEDV<br>PFHSSYAHSQSLDRLMNPLIDQYLYYLSRTQTTGGTTNTQTLGFSQGGPNTMANQAKNWLPGPCYRQQRV<br>SKTSADNNNSEYSWTGATKYHLNGRDSLVNPGPAMASHKDDEEKFFPQSGVLIFGKQGSEKTNVDIEKVM<br>ITDEEEIRTTNPVATEQYGSVSTNLQRGNRQAATADVNTQGVLPGMVWQDRDVYLQGPIWAKIPHTDGHF<br>HPSPLMGGFGLKHPPPQILIKNTPVPADPPTTFNQSKLNSFITQYSTGQVSVEIEWELQKENSKRWNPEI<br>QYTSNYYKSTSVDFAVNTEGVYSEPRPIGTRYLTRNL* |

In some embodiments, the variant AAV capsid polypeptides of the invention exhibit increased transduction in human liver tissue or hepatocyte cells (i.e., human hepatocyte cells) as compared to a non-variant parent capsid polypeptide. In some embodiments, transduction is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction is increased by about 5% to about 80%, about 10% to about 70%, about 20% to about 60%, about 30% to about 60%, or about 40% to about 50%.

In some embodiments, the variant AAV capsid polypeptides of the invention exhibit increased tropism in human liver tissue or hepatocyte cells (i.e., human hepatocyte cells) as compared to a non-variant parent capsid. In some embodiments, tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, tropism is increased by about 5% to about 80%, about 10% to about 70%, about 20% to about 60%, about 30% to about 60%, or about 40% to about 50%.

In some embodiments, the variant AAV capsid polypeptides of the invention exhibit an enhanced neutralization profile as compared to a non-variant parent capsid polypeptide. In some embodiments, the variant capsid polypeptide of the invention further exhibits an enhanced neutralization profile against pooled human immunoglobulins as compared to a non-variant parent capsid polypeptide. In some embodiments, the neutralization profile is enhanced by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the neutralization profile is enhanced by about 5% to about 80%, about 10% to about 70%, about 20% to about 60%, about 30% to about 60%, or about 40% to about 50%. In some embodiments, an enhanced neutralization profile is determined by a reduction in the generation of neutralizing antibodies in a host. In some embodiments, the reduction in generation of neutralizing antibodies is a reduction of about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the reduction in generation of neutralizing antibodies is a reduction of about 5% to about 80%, about 10% to about 70%, about 20% to about 60%, about 30% to about 60%, or about 40% to about 50%.

Figure 6:
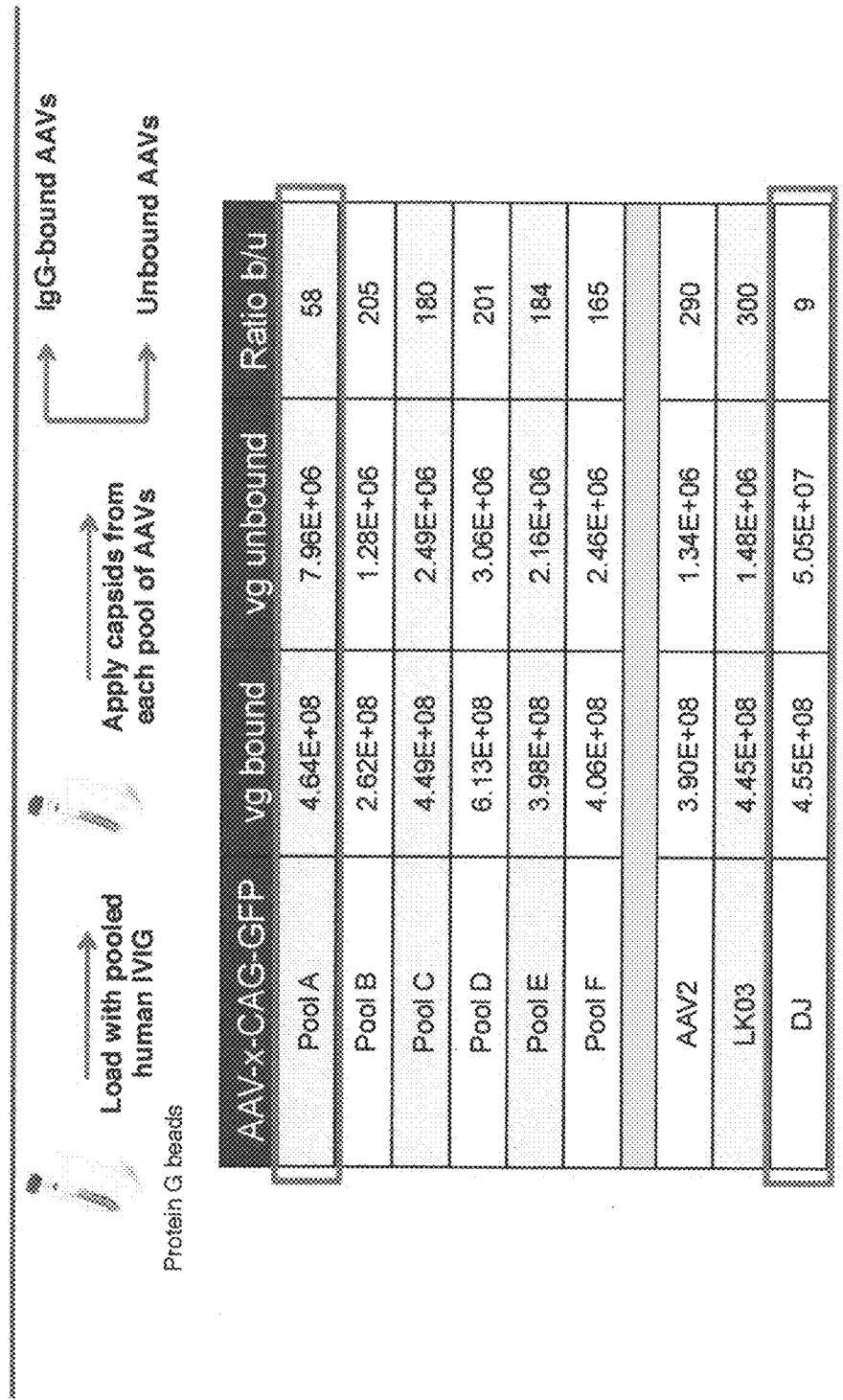
FIG. 6 provides data regarding IVIG binding assays on pools of closely related AAV chimeras.
Figure 7:
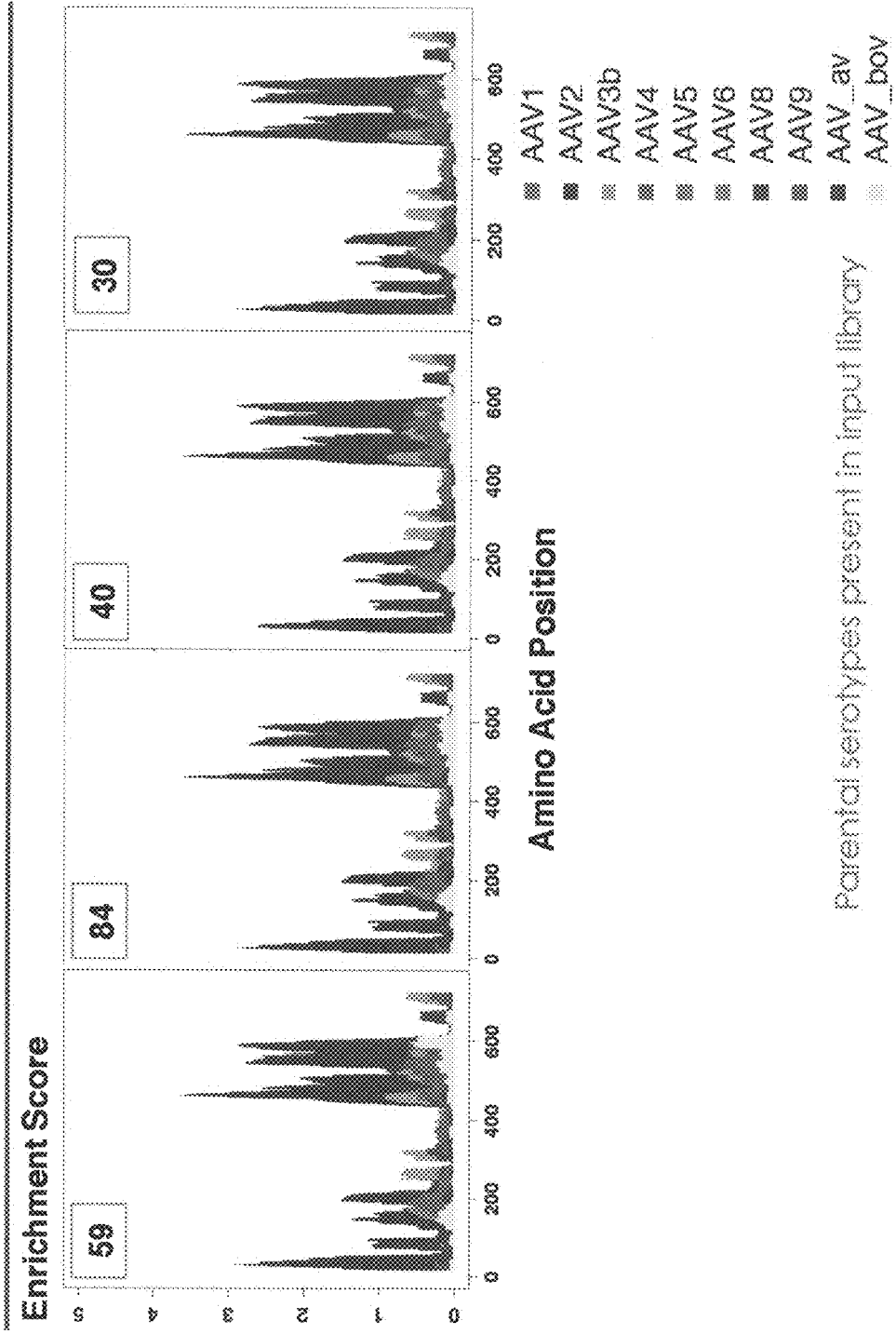
FIG. 7 provides data regarding capsid enrichment scores for 4 variants from Pool A (AAV-NP59 (SEQ ID NO:4), AAV-NP84 (SEQ ID NO:2), AAV-NP40 (SEQ ID NO:6), and AAV-NP30 (SEQ ID NO:8)).
Figure 8:
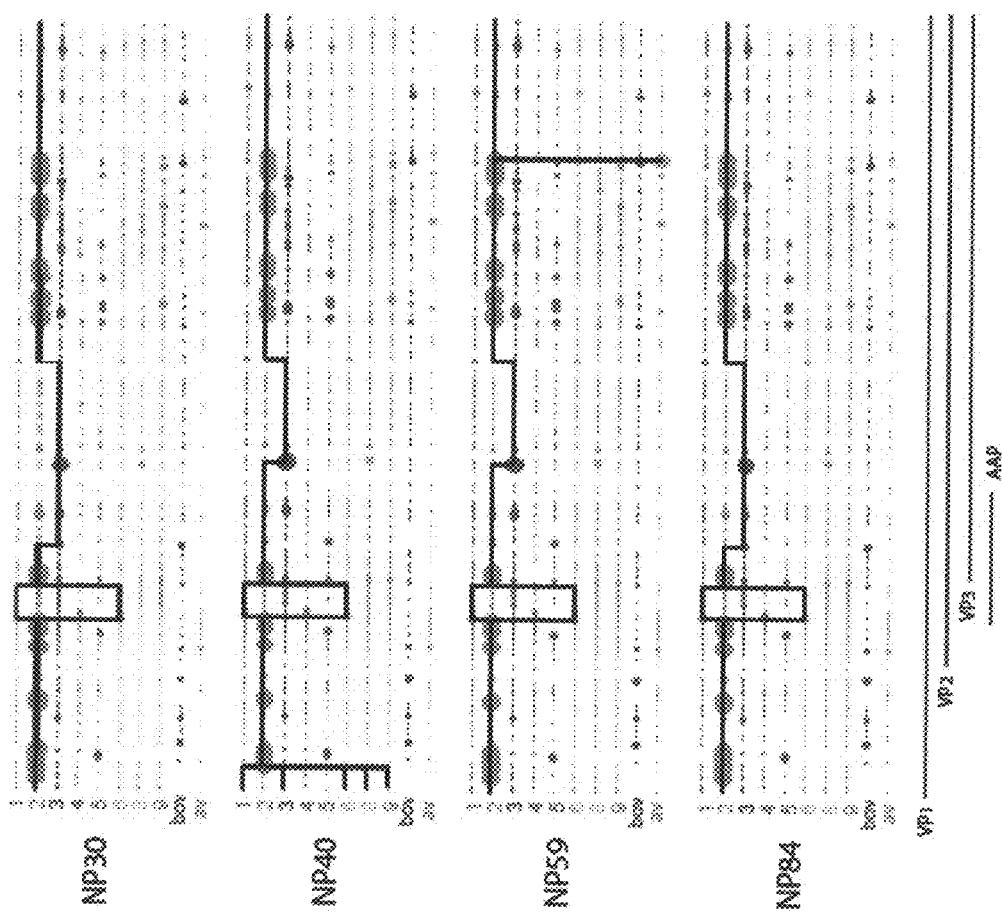
FIG. 8 provides a diagram showing parental contribution to chimeric capsid composition of Pool A variants from the library screens.
Figure 9:
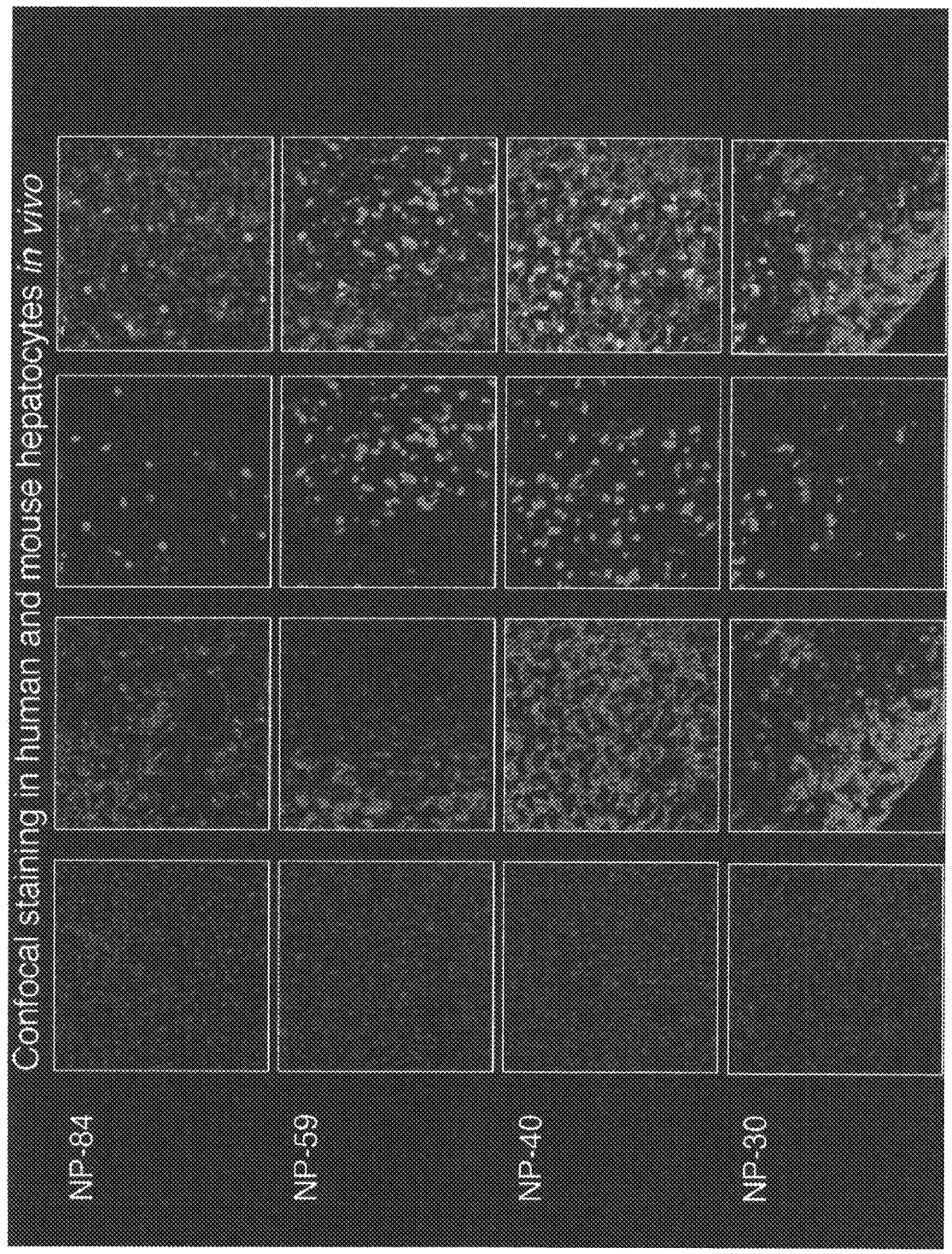
FIG. 9 provides confocal immunofluorescence (IF) staining of human hepatocytes in chimeric mice transplanted with human hepatocytes in vivo. Column 1: Hoechst stained nuclei (blue). Column 2: human hepatocyte staining of human FAH protein (red). Column 3: AAV transduced cells expressing green fluorescent protein (GFP) (green). Column 4: overlay of columns 1, 2, and 3.
Figure 10:
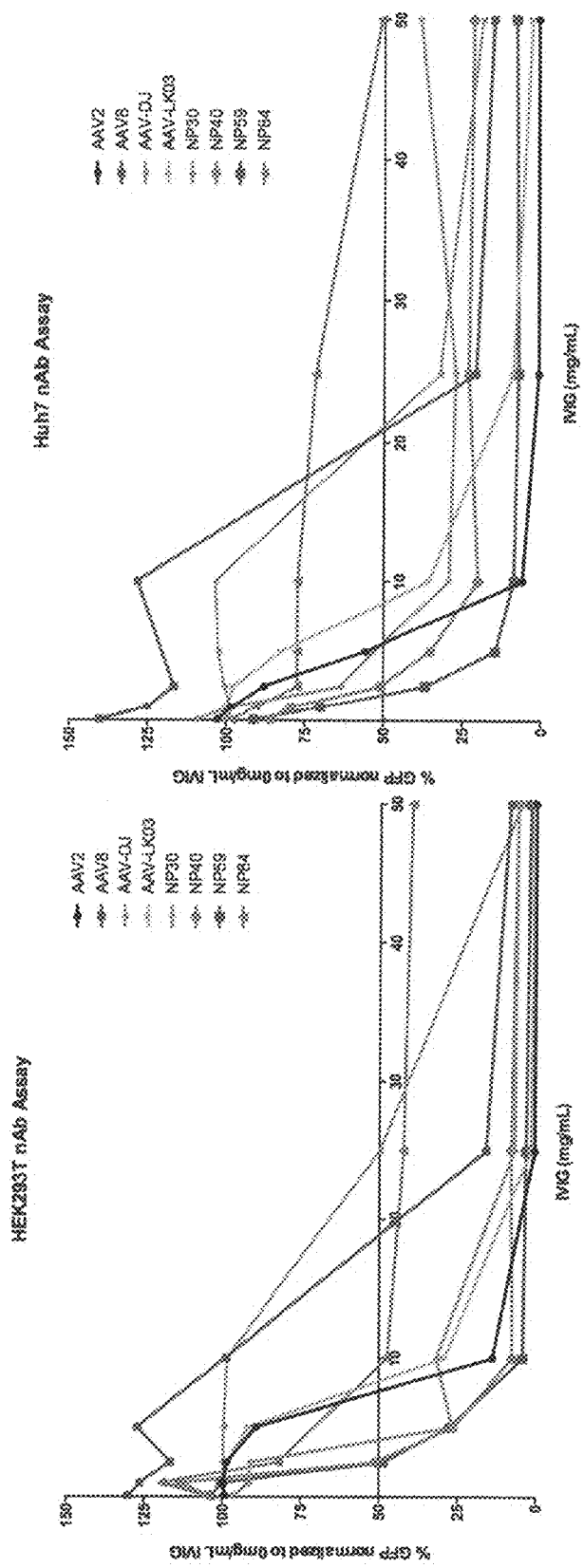
FIG. 10 provides data regarding neutralization assays on human HEK293 and human Huh7 cells with each AAV in the presence of increasing concentrations of pooled human immunoglobulins (IVIG) (AAV-NP59 (SEQ ID NO:4), AAV-NP84 (SEQ ID NO:2), AAV-NP40 (SEQ ID NO:6), and AAV-NP30 (SEQ ID NO:8)). The IVIG neutralization assay was adopted from several previously described methods (Grimm, et al., J. Virol. 82(12): 5887-5911 (2008); Arbetman, et al. J. Virol. 79(24):15238-15245 (2005)), with modifications. Gammagard IVIG Liquid [100 mg/mL] (Baxter, Product Code#LE1500190, Lot#LE12P180AB) was used with a concentration range of 0-50 mg/mL (0, 0.1, 1, 2.5, 5, 10, 25, 50 mg/mL). ssAAV-CAG-GFP was used as the transfer vector. An identical number of genome-containing vector particles (MOI 75,000) of each variant were incubated with increasing concentrations of IVIG at 37° C. for 1-hr. During this hour, the cell culture media on both cell types was changed to that lacking any serum or antibiotics/antimycotics. 80,000 cells (either HEK293 or Huh7) were transduced with the IVIG/AAV mixture and cultures were washed 6-hr later and cultured for 72-hr to allow AAV trafficking, uncoating and GFP expression. Cells were then harvested and analyzed for GFP expression by FACS. Each serotype was normalized to its own "0 mg/mL IVIG" control sample and the concentration of IVIG needed to decrease the signal by 50% (hence why the X and Y axis on the graph cross at 50% instead of 0%) was determined. 10,000 cells were used for each condition to determine the counts/statistics.

In some embodiments, the enhanced neutralization profiles are against pooled human immunoglobulins (i.e., IgG or IVIG, commercially available as Gammagard IVIG). In some embodiments, the ratio of variant AAV capsid polypeptides bound to IVIG is determined as an indicator of an enhanced neutralization profile and methods for determining neutralization profiles are known in the art (see, for example, Grimm, et al., J. Virol. 82(12): 5887-5911 (2008); Arbetman, et al. J. Virol. 79(24):15238-15245 (2005)). In some embodiments, a low ratio of variant AAV capsid polypeptides bound to IVIG as compared to variant AAV capsid polypeptides unbound to IVIG is indicative of an enhanced neutralization profile (see, for example, FIG. 6). In some embodiments, the enhanced neutralization profile is determined by determining the concentration of IVIG needed to decrease the signal generated from a cell transduced by a variant AAV capsid by about 50% as compared to a control sample signal. In some embodiments, the control sample signal is the signal generated from a cell transduced by the variant AAV capsid in the absence of IVIG. In some embodiments, the concentration is a concentration of IVIG sufficient to decrease the signal generated from a cell transduced by a variant AAV capsid by at least about 40%, at least about 45%, at least about 50%, at least about 55%, at least about 60%, at least about 65%, at least about 70%, at least about 75%, at least about 80%, at least about 85%, at least about 90%, or at least about 95% as compared to the control sample signal. In some embodiments, the concentration is a concentration of IVIG sufficient to decrease the signal by at least about 50% as compared to the control sample signal. In some embodiments, the concentration is a concentration of IVIG sufficient to decrease the signal generated from a cell transduced by a variant AAV capsid by at least about 40% to at least about 95% as compared to the control sample signal. In some embodiments, the concentration is a concentration of IVIG sufficient to decrease the signal generated from a cell transduced by a variant AAV capsid by at least about 50% to at least about 90% as compared to the control sample signal. In some embodiments, the concentration is a concentration of IVIG sufficient to decrease the signal generated from a cell transduced by a variant AAV capsid by at least about 50% to at least about 85% as compared to the control sample signal. In some embodiments, the concentration is a concentration of IVIG sufficient to decrease the signal generated from a cell transduced by a variant AAV capsid by at least about 50% to at least about 80% as compared to the control sample signal. In some embodiments, the concentration is a concentration of IVIG sufficient to decrease the signal generated from a cell transduced by a variant AAV capsid by at least about 55% to at least about 75% as compared to the control sample signal. In some embodiments, the concentration is a concentration of IVIG sufficient to decrease the signal generated from a cell transduced by a variant AAV capsid by at least about 50% to at least about 70% as compared to the control sample signal. In some embodiments, the concentration is a concentration of IVIG sufficient to decrease the signal generated from a cell transduced by a variant AAV capsid by at least about 50% to at least about 65% as compared to the control sample signal. In some embodiments, the concentration is a concentration of IVIG sufficient to decrease the signal generated from a cell transduced by a variant AAV capsid by at least about 50% to at least about 60% as compared to the control sample signal. In some embodiments, the concentration is a concentration of IVIG sufficient to decrease the signal generated from a cell transduced by a variant AAV capsid by at least about 50% to at least about 55% as compared to the control sample signal. In some embodiments, the signal generated is any detectable signal. In some embodiments, the signal generated is a fluorescent signal. In some embodiments, the signal generated is from GFP (green fluorescent protein), CFP (cyan fluorescent protein), YFP (yellow fluorescent protein), and RFP (red fluorescent protein). In some embodiments, the signal generated is a bioluminescent signal. In some embodiments, the signal generated is from luciferase (Firefly luciferase or Renilla luciferase).

In some embodiments, the variant AAV capsid polypeptides of the invention further exhibit increased transduction or tropism in one or more human stem cell types as compared to a non-variant parent capsid polypeptide. In some embodiments, the human stem cell types include but are not limited to embryonic stem cells, adult tissue stem cells (i.e., somatic stem cells), bone marrow, progenitor cells, induced pluripotent stem cells, and reprogrammed stem cells. In some embodiments, adult stem cells can include organoid stem cells (i.e., stem cells derived from any organ or organ system of interest within the body). Organs of the body include for example but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

In some embodiments, the variant AAV capsid polypeptides of the invention further exhibit increased transduction or tropism in one or more non-liver human tissues as compared to a non-variant parent capsid polypeptide. In some embodiments, the variant capsid polypeptide further exhibits increased transduction in one or more non-liver human tissues as compared to a vector encoding a non-variant parent capsid polypeptide. In some embodiments, the variant capsid polypeptide further exhibits increased tropism in one or more non-liver human tissues as compared to a vector encoding a non-variant parent capsid polypeptide. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

In some embodiments, the variant AAV capsid polypeptides of the invention further exhibit increased transduction or tropism in one or more non-liver human tissues as compared to a non-variant parent capsid polypeptide. In some embodiments, the variant capsid polypeptide further exhibits increased transduction in one or more non-liver human tissues as compared to a vector encoding a non-variant parent capsid polypeptide. In some embodiments, the variant capsid polypeptide further exhibits increased tropism in one or more non-liver human tissues as compared to a vector encoding a non-variant parent capsid polypeptide. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

In some embodiments, the variant capsid polypeptide contains a VP1 comprising AAV1, AAV3b, AAV6, AAV8 or AAV9_hu14. In some embodiments, the variant capsid polypeptide contains a VP2 comprising AAV2. In some embodiments, the variant capsid polypeptide contains a unique region of VP2 from AAV2. In some embodiments, the variant capsid polypeptide contains a VP3 comprising AAV1, AAV2, AAV3b and AAV6. In some embodiments, the variant capsid polypeptide contains a VP1 comprising AAV2. In some embodiments, the variant capsid polypeptide contains a VP2 comprising AAV2. In some embodiments, the variant capsid polypeptide contains a VP3 comprising AAV1, AAV2, AAV3b and AAV6. In some embodiments, the variant capsid polypeptide is NP-40 (SEQ ID NO:6). In some embodiments, the variant capsid polypeptide is NP-59 (SEQ ID NO:4). In some embodiments, there is a conserved contribution from AAV3b at positions 326-426

(SEQ ID NO: 13)
(NDGTTTIANNLTSTVQVFTDSEYQLPYVLGSAHQGCLPPFPADVFMVPQ

YGYLTLNNGSQAVGRSSFYCLEYFPSQMLRTGNNFQFSYTFEDVPFHSSY

AH).

In some embodiments, the variant capsid polypeptide comprises the amino acid sequence of 326-426 from AAV3b. In some embodiments, the variant capsid polypeptide comprises the amino acid sequence of 326-426 from AAV3b and exhibits enhanced human hepatic transduction. In some embodiments, the variant capsid polypeptide comprises the cylinder (from AAV2). In some embodiments, the variant capsid polypeptide comprises canyon (from AAV3b). In some embodiments, the variant capsid polypeptide comprises one or more substitutions selected from the group consisting of K555E, N622D, and R611G. In some embodiments, the variant capsid polypeptide comprises K555E. In some embodiments, the variant capsid polypeptide comprises N622D. In some embodiments, the variant capsid polypeptide comprises R611G. In some embodiments, the variant capsid polypeptide comprises K555E and R611G. In some embodiments, the variant capsid polypeptide comprises any combination of one or more of the above features.

As an exemplary embodiment of the variant capsid polypeptides of the invention, NP40 is the most shuffled of the three, with the unique region of VP1 from AAV1/3b/6/8/9, the unique region of VP2 derived from AAV2, and finally VP3 with contributions from AAV2 and 3b as well as one de novo mutation (K555E). NP40 exhibits a conserved contribution from AAV3b at positions 326-426. In some embodiments, this is the minimal structural region from AAV3b for enhanced human hepatic transduction. As another exemplary embodiment of the variant capsid polypeptides of the invention, NP59 is similar to NP40 but lacks the diverse VP1 contributions and is instead composed of AAV2 in that sequence stretch. NP59 has the same VP2 and VP3 contributions as NP40 except for one de novo mutation (N622D). As another exemplary embodiment of the variant capsid polypeptides of the invention, NP84 shares the unique regions of VP1 and VP2 with NP59, but has a much larger contribution from AAV3b and less from AAV2 in VP3, as well as two de novo mutations (K555E and R611G).

In some embodiments, the variant capsid polypeptide sequence is selected from the group consisting of AAV-NP84 (SEQ ID NO:2), AAV-NP59 (SEQ ID NO:4), AAV-NP40 (SEQ ID NO:6) and AAV-NP30 (SEQ ID NO:8). For NP84, the unique region of VP1 is composed of AAV2, the unique region of VP2 is composed of AAV2, and VP3 is composed of AAV1, AAV2, AAV3b, AAV6 and several de novo mutations. For NP59, the unique region of VP1 is composed of AAV2, the unique region of VP2 is composed of AAV2, and VP3 is composed of AAV1, AAV2, AAV3b, AAV6 and several de novo mutations. For NP40, the unique region of VP1 is composed of AAV1, AAV3b, AAV6, AAV8 and/or AAV9 at equal probability, the unique region of VP2 is composed of AAV2, and VP3 is composed of AAV1, AAV2, AAV3b, AAV6 and several de novo mutations. For NP30, the unique region of VP1 is composed of AAV2, the unique region of VP2 is composed of AAV2, and VP3 is composed of AAV1, AAV2, AAV3b, AAV6 and several de novo mutations. In some embodiments, the variant capsid polypeptide comprises one or more substitutions (i.e., de novo mutations) selected from the group consisting of K555E, N622D, and R611G. In some embodiments, the variant capsid polypeptide comprises K555E. In some embodiments, the variant capsid polypeptide comprises N622D. In some embodiments, the variant capsid polypeptide comprises R611G. In some embodiments, the variant capsid polypeptide comprises K555E and R611G. In some embodiments, the variant capsid polypeptide comprises any combination of one or more of the above features and/or substitutions (i.e., de novo mutations).

The present invention also provides for generating variant capsid polypeptides, such as AAV-NP84 (SEQ ID NO:2), AAV-NP59 (SEQ ID NO:4), AAV-NP40 (SEQ ID NO:6), and AAV-NP30 (SEQ ID NO:8). These methods employ known techniques of library generation; however, the methods are novel in that they employ replication competent AAV vectors during the variant capsid polypeptide generation (i.e., selection and evolution of the variant capsid polypeptides). The present invention provides methods for generating variant AAV capsid polypeptides, wherein the variant capsid polypeptides exhibits both an enhanced neutralization profile and increased transduction or tropism in human liver tissue or hepatocyte cells (i.e., human hepatocyte cells) as compared to a non-variant parent capsid polypeptide, said method comprising:

a) generating a library of variant AAV capsid polypeptides, wherein said variant AAV capsid polypeptides include a plurality of variant AAV capsid polypeptide sequences from more than one non-variant parent capsid polypeptide;
b) generating an AAV vector library by cloning said variant AAV capsid polypeptide library into AAV vectors, wherein said AAV vectors are replication competent AAV vectors;
c) screening said AAV vector library from b) for variant AAV capsid polypeptides for both an enhanced neutralization profile and increased transduction or tropism in human liver tissue or hepatocyte cells (i.e., human hepatocyte cells) as compared to a non-variant parent capsid polypeptide; and
d) selecting said variant AAV capsid polypeptides from c).

In some embodiments, the method further comprises e) determining the sequence of said variant capsid polypeptides from d).

In some embodiments, the variant AAV capsid polypeptides generated by screening methods of the invention exhibit increased transduction in human liver tissue as compared to a non-variant parent capsid polypeptide. In some embodiments, transduction is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction is increased by about 5% to about 80%, about 10% to about 70%, about 20% to about 60%, about 30% to about 60%, or about 40% to about 50%.

In some embodiments, the variant AAV capsid polypeptide generated by screening methods of the invention exhibits increased tropism in human liver tissue as compared to a non-variant parent capsid. In some embodiments, tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, tropism is increased by about 5% to about 80%, about 10% to about 70%, about 20% to about 60%, about 30% to about 60%, or about 40% to about 50%.

In some embodiments, the variant AAV capsid polypeptides generated by screening methods of the invention exhibit an enhanced neutralization profile as compared to a non-variant parent capsid polypeptide. In some embodiments, the neutralization profile is enhanced by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the neutralization profile is enhanced by about 5% to about 80%, about 10% to about 70%, about 20% to about 60%, about 30% to about 60%, or about 40% to about 50%. In some embodiments, an enhanced neutralization profile is determined by reduced preexisting neutralizing antibodies in a host which cross-react with the new AAV capsid embodiment. In some embodiments, the reduction in preexisting neutralizing antibody cross-reactivity is about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the reduction in generation of neutralizing antibodies is a reduction of about 5% to about 80%, about 10% to about 70%, about 20% to about 60%, about 30% to about 60%, or about 40% to about 50%.

In some embodiments, the variant AAV capsid polypeptide generated by screening methods of the invention further exhibits increased transduction or tropism in one or more non-liver human tissues as compared to a non-variant parent capsid polypeptide. In some embodiments, the variant capsid polypeptide further exhibits increased transduction in one or more non-liver human tissues as compared to a non-variant parent capsid polypeptide. In some embodiments, the variant capsid polypeptide further exhibits increased tropism in one or more non-liver human tissues as compared to a non-variant parent capsid polypeptide. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%.

Transduction can be measured by techniques known in the art, including, for example, immunohistochemical analysis, including those described in Example 1 below, as well as other methods known in the art. In vitro transduction analysis can be performed in human liver tissue cells or hepatocyte cells, including for example by measuring GFP expression (or another marker gene) in order to determine transduction. In vivo or ex vivo transduction analysis can be measured by techniques known in the art, including, for example, Firefly luciferase-based assays, including for example by measuring luciferase expression (or another marker gene) in order to determine transduction. In some embodiments, marker expression from an AAV vector packaged with the variant capsid polypeptides is compared to marker expression from an AAV vector packaged with the non-variant parent capsid polypeptides in order to compare transduction efficiencies. In some embodiments, the transduction is compared for different cell types in order to determine tropism, i.e., compare transduction from an AAV vector packaged with the variant capsid polypeptide to transduction from an AAV packaged with the non-variant capsid polypeptide in at least two different cell types in order to determine tropism for a particular cell type, sometimes referred to as a tropism profile. In some embodiments, at least one cell type is human liver tissue cells or human hepatocyte cells. In some embodiments, at least one cell type is human liver tissue cells. In some embodiments, at least one cell type is human hepatocyte cells.

Figure 3:
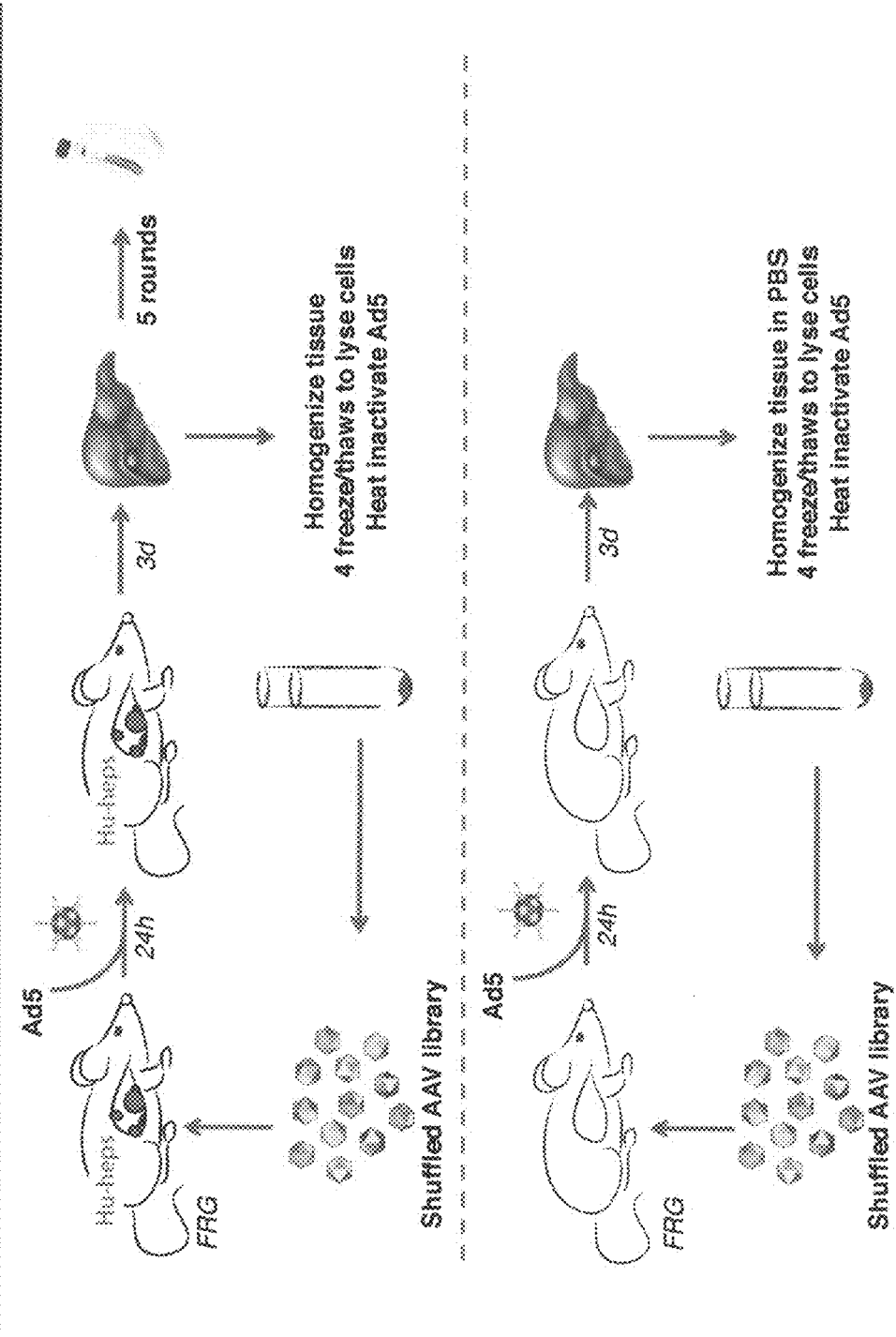
FIG. 3 provides a schematic showing the multiplexed sequential AAV capsid screens for human liver tropism and reduced human immunoglobulin (IgG) binding.
Figure 4:
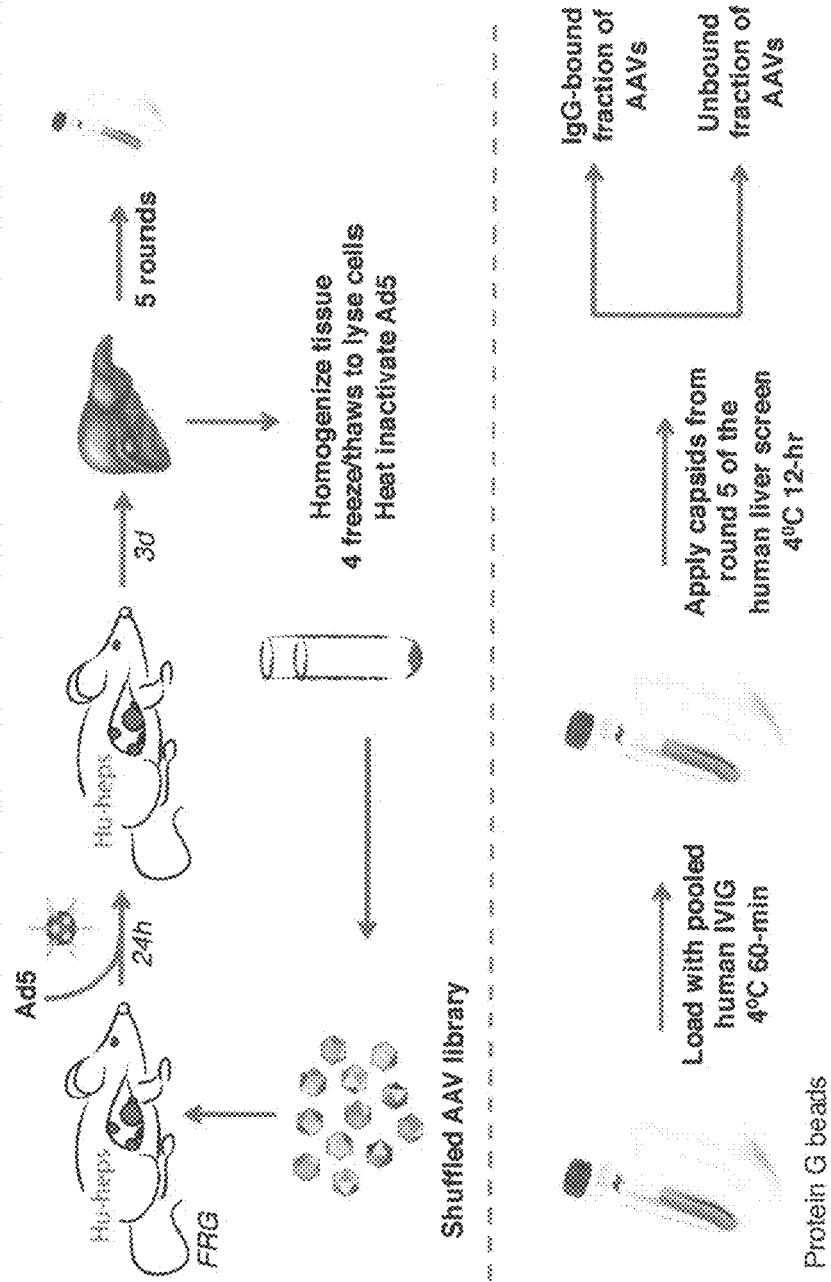
FIG. 4 provides a schematic showing the sequential sub-screen on round 5 selected AAV capsids for reduced humoral neutralization by pooled human IgGs.

Such methods for generating the variant capsid polypeptides include DNA shuffling of capsid proteins, which begins with families of capsid genes from an array or plurality of AAV pseudo-species (for example, AAV1, AAV2, AAV3b, AAV4, AAV5, AAV6, AAV7, AAV8, AAV9, AAV 9_hu14, bovine AAV, avian AAV), that are enzymatically shuffled to create a diverse library of capsid genes that can be cloned back into an AAV shuttle plasmid and utilized to produce live replicating viral libraries (see, for example, FIG. 2). To maximize the likelihood that a shuffled capsid (i.e., variant capsid polypeptides) could functionally transduce human liver tissue or hepatocyte cells (i.e., human hepatocyte cells)—as compared to liver tissue or hepatocyte cells of model organisms typically used for pre-clinical evaluation—the invention contemplates performing a screen in humanized liver mice (see, for example, FIG. 3). To maximize the likelihood that shuffled capsids (i.e., variant capsid polypeptides) exhibit enhanced neutralization profiles, the invention contemplates performing a screen in pooled human immunoglobulins) (see, for example, FIG. 4).

Figure 5:
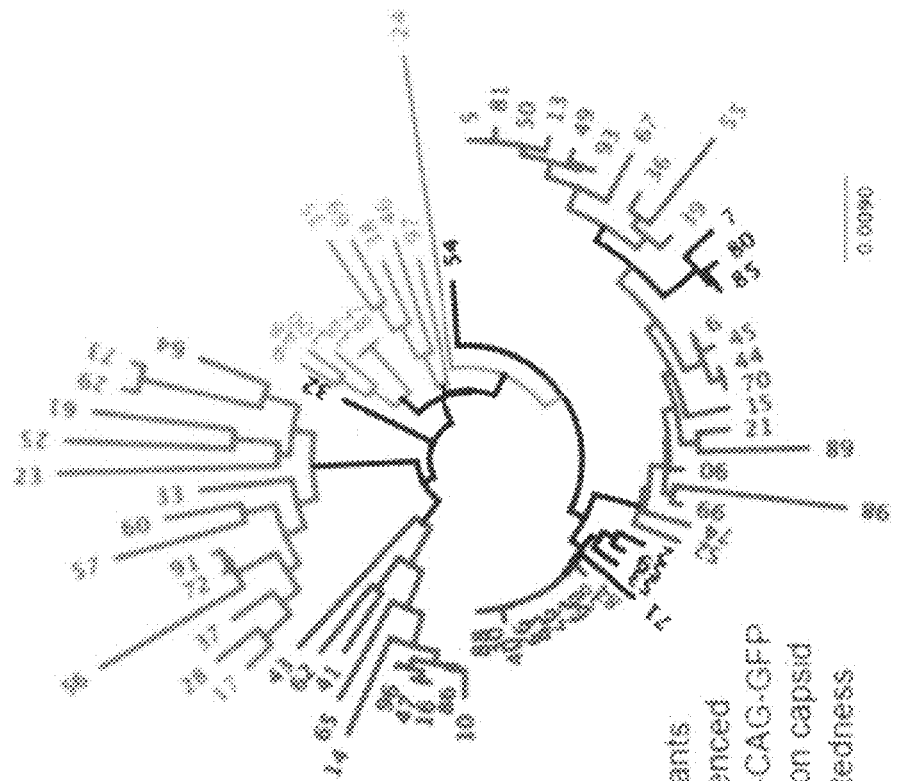
FIG. 5 provides a diagram showing the phylogeny of 100 selected variants and illustrates "families" of related capsids which evolved from the sequential screens.

In some embodiments, at the completion of both screens, variant AAV capsids are chosen from each screen for full Sanger sequencing and phylogenetic comparisons to parental serotypes (i.e., parental non-variant capsid polypeptide sequences). In some embodiments, the parental non-variant capsid polypeptide sequences are those that went into the initial library. The most highly selected variants (for example, those that exhibit the highest increase in transduction and/or tropism in human liver tissue or human hepatocyte cells and an enhanced neutralization profile) from the screens are isolated and vectorized with expression constructs, in some cases for use in subsequent validation experiments. In some embodiments, in order to assess the genetic contribution of each parental AAV serotype (i.e., non-variant parent capsid polypeptide) to the evolved capsids (i.e., variant capsid polypeptides) selected from each screen, crossover mapping can be performed (see, for example, FIG. 5). Both methodologies demonstrate the highly shuffled nature of the evolved capsid variants and highlighted both unique and shared domains present in selected capsids.

In some embodiments, the parental capsids (i.e., non-variant parent capsid polypeptides) that contribute the most to the evolved variants include AAV2, and AAV3b. In some embodiments, the variant capsid polypeptides comprise regions from AAV1, AAV2, AAV3b, AAV6, AAV8, AAV9_hu14 and de novo mutations. In some embodiments, no variants (i.e., variant capsid polypeptide) have capsid fragment regions from AAV4, 5, bovine or avian. In some embodiments, diverse shuffling was achieved and maintained along the length of Cap, including VP1, VP2 and VP3.

In vitro characterizations are used to demonstrate the significant increase in transduction by variant capsid polypeptides over control serotypes (i.e., non-variant parent capsid polypeptides) in various liver-derived cell lines.

For such analyses, large-scale ultrapure productions of AAV vectorized variants (AAV vectors composed of variant capsid polypeptides) can be carried out and those capable of producing high titers sufficient for eventual clinical use (for example, variants AAV-NP84, AAV-NP59, AAV-NP40, and AAV-NP30) can be considered further for validation. In some embodiments, in human liver cells or human hepatocyte cells, shuffled variants (i.e., variant capsid polypeptides) exhibiting significantly increased functional transduction can be selected by the present invention. In some embodiments, the variant AAV capsid polypeptides further exhibit increased transduction or tropism in mouse hepatocytes in vivo.

AAV Vector Elements

The nucleic acid insert (also referred to as a heterologous nucleotide sequence) can be operably linked to control elements directing the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, can also be used. Such promoter sequences are commercially available from, e.g., Stratagene (San Diego, Calif.).

In some embodiments, a cell type-specific or a tissue-specific promoter can be operably linked to nucleic acid insert (also referred to as a heterologous nucleotide sequence) encoding the heterologous gene product, and allowing for selectively or preferentially producing a gene product in a particular cell type(s) or tissue(s). In some embodiments, an inducible promoter can be operably linked to the heterologous nucleic acid.

In some embodiments, the nucleic acid is packaged with the variant capsid polypeptides of the invention. In some embodiments, the nucleic acid insert or packaged nucleic acid is at least 3000 nucleic acids to at least 5000 nucleic acids. In some embodiments, the nucleic acid insert or packaged nucleic acid is at least 3500 nucleic acids to at least 4500 nucleic acids. In some embodiments, the nucleic acid insert or packaged nucleic acid is at least 4000 nucleic acids to at least 5000 nucleic acids. In some embodiments, the nucleic acid insert or packaged nucleic acid is at least 4200 nucleic acids to at least 4900 nucleic acids. In some embodiments, the nucleic acid insert or packaged nucleic acid is at least 4400 nucleic acids to at least 4800 nucleic acids. In some embodiments, the nucleic acid insert or packaged nucleic acid is at least about 4700 nucleic acids.

In some embodiments, the AAV vector packaged by the variant capsid polypeptides is at least about 2000 nucleic acids in total length and up to about 5000 nucleic acids in total length. In some embodiments, the AAV vector packaged by the variant capsid polypeptides is about 2000 nucleic acids, about 2400 nucleic acids, about 2800 nucleic acids, about 3000 nucleic acids, about 3200 nucleic acids, about 3400 nucleic acids, about 3600 nucleic acids, about 3800 nucleic acids, about 4000 nucleic acids, about 4200 nucleic acids, about 4400 nucleic acids, about 4600 nucleic acids, about 4700 nucleic acids, or about 4800 nucleic acids. In some embodiments, the AAV vector packaged by the variant capsid polypeptides is between about 2000 nucleic acids (2 kb) and about 5000 nucleic acids (5 kb). In some embodiments, the AAV vector packaged by the variant capsid polypeptides is between about 2400 nucleic acids (2.4 kb) and about 4800 nucleic acids (4.8 kb). In some embodiments, the AAV vector packaged by the variant capsid polypeptides is between about 3000 nucleic acids (3 kb) and about 5000 nucleic acids (5 kb). In some embodiments, the AAV vector packaged by the variant capsid polypeptides is between about 3000 nucleic acids (3 kb) and about 4000 nucleic acids (4 kb).

The AAV vectors or AAV virions disclosed herein can also include conventional control elements operably linked to the nucleic acid insert (also referred to as a heterologous nucleotide sequence) in a manner permitting transcription, translation and/or expression in a cell transfected with the AAV vector or infected with the AAV virion produced according to the present invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters selected from native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al., Cell, 41:521-530 (1985)), the SV40 promoter, the dihydrofolate reductase promoter, the beta-actin promoter, the phosphoglycerol kinase (PGK) promoter, and the EF1 promoter (Invitrogen). Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clonetech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., (1996) *Proc. Natl. Acad. Sci. USA*, 93:3346-3351), the tetracycline-repressible system (Gossen et al., (1992) *Proc. Natl. Acad. Sci. USA*, 89:5547-5551), the tetracycline-inducible system (Gossen et al., (1995) *Science*, 268:1766-

1769, see also Harvey et al., (1998) *Curr. Opin. Chem. Biol.,* 2:512-518), the RU486-inducible system (Wang et al., (1997) *Nat. Biotech.,* 15:239-243 and Wang et al., (1997) *Gene Ther.,* 4:432-441) and the rapamycin-inducible system (Magari et al., (1997) *J. Clin. Invest.,* 100:2865-2872). Other types of inducible promoters useful in this context are those regulated by a specific physiological state, e.g., temperature, acute phase, a particular differentiation state of the cell, or in replicating cells only.

In another embodiment, the native promoter for the nucleic acid insert (also referred to as a heterologous nucleotide sequence) will be used. The native promoter may be preferred when it is desired that expression of the nucleic acid insert (also referred to as a heterologous nucleotide sequence) should mimic the native expression. The native promoter may be used when expression of the nucleic acid insert (also referred to as a heterologous nucleotide sequence) must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the nucleic acid insert (also referred to as a heterologous nucleotide sequence) includes a gene operably linked to a tissue-specific promoter. For instance, if expression in liver tissue is desired, a promoter active in liver tissue should be used. Examples of promoters that are tissue-specific are known for liver (albumin, Miyatake et al., (1997) *J. Virol.,* 71:5124-32; hepatitis B virus core promoter, Sandig et al., (1996) *Gene Ther.,* 3:1002-9; alpha-fetoprotein (AFP), Arbuthnot et al., (1996) *Hum. Gene Ther.,* 7:1503-14), bone osteocalcin (Stein et al., (1997)*Mol. Biol. Rep.,* 24:185-96); bone sialoprotein (Chen et al., (1996) *J. Bone Miner. Res.,* 11:654-64), lymphocytes (CD2, Hansal et al., (1998) *J. Immunol.,* 161:1063-8; immunoglobulin heavy chain; T cell receptor chain), neuronal such as neuron-specific enolase (NSE) promoter (Andersen et al., (1993) *Cell. Mol. Neurobiol.,* 13:503-15), neurofilament light-chain gene (Piccioli et al., (1991) *Proc. Natl. Acad. Sci. USA,* 88:5611-5), and the neuron-specific vgf gene (Piccioli et al., (1995) *Neuron,* 15:373-84), among others.

In various embodiments, AAV vectors or AAV virions carrying one or more therapeutically useful nucleic acid inserts (also referred to as a heterologous nucleotide sequence) also include selectable markers or reporter genes, e.g., sequences encoding geneticin, hygromycin or puromycin resistance, among others. Selectable reporters or marker genes can be used to signal the presence of the plasmids/vectors in bacterial cells, including, for example, examining ampicillin resistance. Other components of the plasmid may include an origin of replication. Selection of these and other promoters and vector elements are conventional and many such sequences are available (see, e.g., Sambrook et al., and references cited therein).

Host Cells and Packaging

Host cells are necessary for generating infectious AAV vectors as well as for generating AAV virions based on the disclosed AAV vectors. Accordingly, the present invention provides host cells for generation and packaging of AAV virions based on the AAV vectors of the present invention. A variety of host cells are known in the art and find use in the methods of the present invention. Any host cells described herein or known in the art can be employed with the compositions and methods described herein.

The present invention provides host cells, e.g., isolated (genetically modified) host cells, comprising a subject nucleic acid. A subject host cell can be an isolated cell, e.g., a cell in in vitro culture. A subject host cell is useful for producing a subject AAV vector or AAV virion, as described below. Where a subject host cell is used to produce a subject AAV virion, it is referred to as a "packaging cell." In some embodiments, a subject host cell is stably genetically modified with a subject AAV vector. In other embodiments, a subject host cell is transiently genetically modified with a subject AAV vector.

In some embodiments, a subject nucleic acid is introduced stably or transiently into a host cell, using established techniques, including, but not limited to, electroporation, calcium phosphate transfection, liposome-mediated transfection, baculovirus infection, and the like. For stable transformation, a subject nucleic acid will generally further include a selectable marker, e.g., any of several well-known selectable markers such as neomycin resistance, and the like.

Generally, when delivering the AAV vector according to the present invention by transfection, the AAV vector is delivered in an amount from about 5 µg to about 100 µg DNA, about 10 to about 50 µg DNA to about $1 \times 10^4$ cells to about $1 \times 10^{13}$ cells, or about $1 \times 10^5$ cells. However, the relative amounts of vector DNA to host cells may be adjusted, taking into consideration such factors as the selected vector, the delivery method and the host cells selected and such adjustments are within the level of skill of one in the art.

In some embodiments, the host cell for use in generating infectious virions can be selected from any biological organism, including prokaryotic (e.g., bacterial) cells, and eukaryotic cells, including, insect cells, yeast cells and mammalian cells. A subject host cell is generated by introducing a subject nucleic acid (i.e., AAV vector) into any of a variety of cells, e.g., mammalian cells, including, e.g., murine cells, and primate cells (e.g., human cells). Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, CHO, 293, Vero, NIH 3T3, PC12, Huh-7 Saos, C2C12, RAT1, L cells, HT1080, human embryonic kidney (HEK), human embryonic stem cells, human adult tissue stem cells, pluripotent stem cells, induced pluripotent stem cells, reprogrammed stem cells, organoid stem cells, bone marrow stem cells, HLHepG2, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirement for the cell used is it is capable of infection or transfection by an AAV vector. In some embodiments, the host cell is one that has Rep and Cap stably transfected in the cell, including in some embodiments a variant capsid polypeptide as described herein. In some embodiments, the host cell expresses a variant capsid polypeptide of the invention or part of an AAV vector as described herein, such as a heterologous nucleic acid sequence contained within the AAV vector.

In some embodiments, the preparation of a host cell according to the invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods providing the desired nucleotide sequence.

In some embodiments, introduction of the AAV vector into the host cell may also be accomplished using techniques known to the skilled artisan and as discussed throughout the specification. In a preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes providing trans-acting E1 proteins).

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV Rep (replication) proteins. In other embodiments, a subject host cell further comprises an AAV vector. An AAV virion can be generated using a subject host cell. Methods of generating an AAV virion are described in, e.g., U.S. Patent Publication No. 2005/0053922 and U.S. Patent Publication No. 2009/0202490.

In addition to the AAV vector, in exemplary embodiments, the host cell contains the sequences driving expression of the AAV capsid polypeptide (including variant capsid polypeptides and non-variant parent capsid polypeptides) in the host cell and Rep (replication) sequences of the same serotype as the serotype of the AAV Inverted Terminal Repeats (ITRs) found in the nucleic acid insert (also referred to as a heterologous nucleotide sequence), or a cross-complementing serotype. The AAV capsid and Rep (replication) sequences may be independently obtained from an AAV source and may be introduced into the host cell in any manner known to one of skill in the art or as described herein. Additionally, when pseudotyping an AAV vector in an AAV8 capsid for example, the sequences encoding each of the essential Rep (replication) proteins may be supplied by AAV8, or the sequences encoding the Rep (replication) proteins may be supplied by different AAV serotypes (e.g., AAV1, AAV2, AAV3, AAV3b, AAV4, AAV6, AAV7, and/or AAV9).

In some embodiments, the host cell stably contains the capsid protein under the control of a suitable promoter (including, for example, the variant capsid polypeptides of the invention), such as those described above. In some embodiments, the capsid protein is expressed under the control of an inducible promoter. In some embodiments, the capsid protein is supplied to the host cell in trans. When delivered to the host cell in trans, the capsid protein may be delivered via a plasmid containing the sequences necessary to direct expression of the selected capsid protein in the host cell. In some embodiments, when delivered to the host cell in trans, the vector encoding the capsid protein (including, for example, the variant capsid polypeptides of the invention) also carries other sequences required for packaging the AAV, e.g., the Rep (replication) sequences.

In some embodiments, the host cell stably contains the Rep (replication) sequences under the control of a suitable promoter, such as those described above. In some embodiments, the essential Rep proteins are expressed under the control of an inducible promoter. In another embodiment, the Rep proteins are supplied to the host cell in trans. When delivered to the host cell in trans, the Rep proteins may be delivered via a plasmid containing the sequences necessary to direct expression of the selected Rep proteins in the host cell. In some embodiments, when delivered to the host cell in trans, the vector encoding the capsid protein (including, for example, the variant capsid polypeptides of the invention) also carries other sequences required for packaging the AAV vector, e.g., the Rep sequences.

In some embodiments, the Rep and capsid sequences may be transfected into the host cell on a single nucleic acid molecule and exist stably in the cell as an unintegrated episome. In another embodiment, the Rep and capsid sequences are stably integrated into the chromosome of the cell. Another embodiment has the Rep and capsid sequences transiently expressed in the host cell. For example, a useful nucleic acid molecule for such transfection comprises, from 5' to 3', a promoter, an optional spacer interposed between the promoter and the start site of the Rep gene sequence, an AAV Rep gene sequence, and an AAV capsid gene sequence.

Although the molecule(s) providing Rep and capsid can exist in the host cell transiently (i.e., through transfection), in some embodiments, one or both of the Rep and capsid proteins and the promoter(s) controlling their expression be stably expressed in the host cell, e.g., as an episome or by integration into the chromosome of the host cell. The methods employed for constructing embodiments of the invention are conventional genetic engineering or recombinant engineering techniques such as those described in the references above.

In some embodiments, the packaging host cell can require helper functions in order to package the AAV vector of the invention into an AAV virion. In some embodiments, these functions may be supplied by a herpesvirus. In some embodiments, the necessary helper functions are each provided from a human or non-human primate adenovirus source, and are available from a variety of sources, including the American Type Culture Collection (ATCC), Manassas, Va. (US). In some embodiments, the host cell is provided with and/or contains an E1a gene product, an E1b gene product, an E2a gene product, and/or an E4 ORF6 gene product. In some embodiments, the host cell may contain other adenoviral genes such as VAI RNA. In some embodiments, no other adenovirus genes or gene functions are present in the host cell.

Heterologous Nucleic Acid, Nucleic Acid Gene Products, and Polypeptide Gene Products In various embodiments, the invention provides variant capsid polypeptides capable of forming capsids capable of packaging a variety of therapeutic molecules, including nucleic acids and polypeptides. In some embodiments, the therapeutic molecule is a vaccine. In various embodiments, the invention provides for AAV vectors capable of containing nucleic acid inserts, including for example, transgene inserts or other nucleic acid inserts. This allows for vectors capable of expressing polypeptides. Such nucleic acids can comprise heterologous nucleic acid, nucleic acid gene products, and polypeptide gene products. Features of the nucleic acid inserts are described below.

In some embodiments, the AAV vectors described herein contain nucleic acid inserts. In some embodiments, the nucleic acid insert includes but is not limited to nucleic acid sequences selected from the group consisting of a non-coding RNA, a protein coding sequence, an expression cassette, a multi-expression cassette, a sequence for homologous recombination, a genomic gene targeting cassette, and a therapeutic expression cassette.

In some embodiments, the expression cassette is a CRISPR/CAS expression system.

In some embodiments, a nucleic acid insert comprises a heterologous nucleic acid comprising a nucleotide sequence encoding a heterologous gene product, e.g., a nucleic acid gene product or a polypeptide gene product. In some embodiments, the gene product is an interfering RNA (e.g., shRNA, siRNA, miRNA). In some embodiments, the gene product is an aptamer. The gene product can be a self-complementary nucleic acid. In some embodiments, the gene product is a polypeptide.

Suitable heterologous gene product includes interfering RNA, antisense RNA, ribozymes, and aptamers. Where the gene product is an interfering RNA (RNAi), suitable RNAi include RNAi that decrease the level of a target polypeptide in a cell.

In some embodiments, exemplary polypeptides, nucleic acids, or other therapeutic molecules include those useful in the treatment of liver diseases and disorders. Liver disease and disorders include but are not limited to any conditions that stop the liver from functioning properly or prevent it from functioning well (i.e., functioning at normal levels). Symptoms of liver diseases and disorders can include but are not limited to abdominal pain, yellowing of the skin or eyes (jaundice), abnormal results of liver function tests, liver fattening (including, for example, disproportional fattening), and cirrhosis of the liver. Liver diseases and disorders further include but are not limited to amebic liver abscess, autoimmune liver diseases and disorders (including, for example, autoimmune hepatitis, primary biliary cirrhosis (PBC), and primary sclerosing cholangitis (PSC)), biliary atresia, cirrhosis, coccidioidomycosis, delta agent (hepatitis D), drug-induced cholestasis, hemochromatosis, viral hepatitis (including, for example, Hepatitis A, Hepatitis B, and Hepatitis C), neonatal hepatitis, hepatocellular carcinoma (HCC, as well as other liver cancer), fibrolamellar hepatocellular carcinoma, liver disease due to alcohol, pyogenic liver abscess, Reye's syndrome, Sclerosing cholangitis, Wilson's disease, acute liver failure (caused by, for example, drugs, toxins, and various other diseases), alcoholic liver disease, autoimmune-associated diseases, Budd-Chiari syndrome, hypercoagulable disorders, parasitic infection, chronic bile duct obstruction (including, for example, due to tumors, gallstones, inflammation, and trauma), hemochromatosis, alpha-1 antitrypsin (A1A) deficiency, Wilson disease, Alagille Syndrome, cystic disease of the liver, galactosemia, Gilbert's Syndrome, hemochromatosis, liver disease in pregnancy, Lysosomal Acid Lipase Deficiency (LALD), porphyria, sarcoidosis, Type 1 Glycogen Storage Disease, Tyrosinemia, Alveolar hydatid disease, bacillary peliosis, congenital hepatic fibrosis, congestive hepatopathy, gastric antral vascular ectasia, hepatic encephalopathy, hepatolithiasis, hepatopulmonary syndrome, hepatorenal syndrome, hepatosplenomegaly, hepatotoxicity, Indian childhood cirrhosis, Laennec's cirrhosis, Lyngstadaas Syndrome, peliosis hepatis, progressive familial intrahepatic cholestasis, Zahn infarct, Zieve's syndrome, and nonalcoholic fatty liver disease (NAFLD).

In some embodiments, exemplary polypeptides, nucleic acids, or other therapeutic molecules include those useful in the treatment of rare sarcoglycanopathies and dystrophinopathies like Duchenne muscular dystrophy, limb girdle muscle disease, and spinal muscular atrophy, as well as other muscle tissue related diseases. Exemplary muscle tissue related diseases include but are not limited to Acid Maltase Deficiency (AMD), Amyotrophic Lateral Sclerosis (ALS), Andersen-Tawil Syndrome, Becker Muscular Dystrophy (BMD), Becker Myotonia Congenita, Bethlem Myopathy, Bulbospinal Muscular Atrophy (Spinal-Bulbar Muscular Atrophy), Carnitine Deficiency, Carnitine Palmityl Transferase Deficiency (CPT Deficiency), Central Core Disease (CCD), Centronuclear Myopathy, Charcot-Marie-Tooth Disease (CMT), Congenital Muscular Dystrophy (CMD), Congenital Myasthenic Syndromes (CMS), Congenital Myotonic Dystrophy, Cori Disease (Debrancher Enzyme Deficiency), Debrancher Enzyme Deficiency, Dejerine-Sottas Disease (DSD), Dermatomyositis (DM), Distal Muscular Dystrophy (DD), Duchenne Muscular Dystrophy (DMD), Dystrophia Myotonica (Myotonic Muscular Dystrophy), Emery-Dreifuss Muscular Dystrophy (EDMD), Endocrine Myopathies, Eulenberg Disease (Paramyotonia Congenita), Facioscapulohumeral Muscular Dystrophy (FSH or FSHD), Finnish (Tibial) Distal Myopathy, Forbes Disease (Debrancher Enzyme Deficiency), Friedreich's Ataxia (FA), Fukuyama Congenital Muscular Dystrophy, Glycogenosis Type 10, Glycogenosis Type 11, Glycogenosis Type 2, Glycogenosis Type 3, Glycogenosis Type 5, Glycogenosis Type 7, Glycogenosis Type 9, Gowers-Laing Distal Myopathy, Hauptmann-Thanheuser MD (Emery-Dreifuss Muscular Dystrophy), Hereditary Inclusion-Body Myositis, Hereditary Motor and Sensory Neuropathy (Charcot-Marie-Tooth Disease), Hyperthyroid Myopathy, Hypothyroid Myopathy, Inclusion-Body Myositis (IBM), Inherited Myopathies, Integrin-Deficient Congenital Muscular Dystrophy, Kennedy Disease (Spinal-Bulbar Muscular Atrophy), Kugelberg-Welander Disease (Spinal Muscular Atrophy), Lactate Dehydrogenase Deficiency, Lambert-Eaton Myasthenic Syndrome (LEMS), Limb-Girdle Muscular Dystrophy (LGMD), Lou Gehrig's Disease (Amyotrophic Lateral Sclerosis), McArdle Disease (Phosphorylase Deficiency), Merosin-Deficient Congenital Muscular Dystrophy, Metabolic Diseases of Muscle, Mitochondrial Myopathy, Miyoshi Distal Myopathy, Motor Neurone Disease, Muscle-Eye-Brain Disease, Myasthenia Gravis (MG), Myoadenylate Deaminase Deficiency, Myofibrillar Myopathy, Myophosphorylase Deficiency, Myotonia Congenita (MC), Myotonic Muscular Dystrophy (MMD), Myotubular Myopathy (MTM or MM), Nemaline Myopathy, Nonaka Distal Myopathy, Oculopharyngeal Muscular Dystrophy (OPMD), Paramyotonia Congenita, Pearson Syndrome, Periodic Paralysis, Peroneal Muscular Atrophy (Charcot-Marie-Tooth Disease), Phosphofructokinase Deficiency, Phosphoglycerate Kinase Deficiency, Phosphoglycerate Mutase Deficiency, Phosphorylase Deficiency, Phosphorylase Deficiency, Polymyositis (PM), Pompe Disease (Acid Maltase Deficiency), Progressive External Ophthalmoplegia (PEO), Rod Body Disease (Nemaline Myopathy), Spinal Muscular Atrophy (SMA), Spinal-Bulbar Muscular Atrophy (SBMA), Steinert Disease (Myotonic Muscular Dystrophy), Tarui Disease (Phosphofructokinase Deficiency), Thomsen Disease (Myotonia Congenita), Ullrich Congenital Muscular Dystrophy, Walker-Warburg Syndrome (Congenital Muscular Dystrophy), Welander Distal Myopathy, Werdnig-Hoffmann Disease (Spinal Muscular Atrophy), and ZASP-Related Myopathy.

In some embodiments, exemplary polypeptides include neuroprotective polypeptides and anti-angiogenic polypeptides. Suitable polypeptides include, but are not limited to, glial derived neurotrophic factor (GDNF), fibroblast growth factor 2 (FGF-2), nurturin, ciliary neurotrophic factor (CNTF), nerve growth factor (NGF; e.g., nerve growth factor-.beta.), brain derived neurotrophic factor (BDNF), neurotrophin-3 (NT-3), neurotrophin-4 (NT-4), neurotrophin-6 (NT-6), epidermal growth factor (EGF), pigment epithelium derived factor (PEDF), a Wnt polypeptide, soluble Flt-1, angiostatin, endostatin, VEGF, an anti-VEGF antibody, a soluble VEGFR, Factor VIII (FVIII), Factor IX (FIX), and a member of the hedgehog family (sonic hedgehog, Indian hedgehog, and desert hedgehog, etc.).

In some embodiments, useful therapeutic products encoded by the heterologous nucleic acid sequence include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor alpha superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

In some embodiments, useful heterologous nucleic acid sequence products include proteins that regulate the immune system including, without limitation, cytokines and lymphokines such as thrombopoietin (TPO), interleukins (IL) IL-1 through IL-25 (including IL-2, IL-4, IL-12 and IL-18), monocyte chemoattractant protein, leukemia inhibitory factor, granulocyte-macrophage colony stimulating factor, Fas ligand, tumor necrosis factors alpha and .beta., interferons .alpha., .beta., and .gamma., stem cell factor, flk-2/flt3 ligand. Gene products produced by the immune system are also useful in the present invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

In some embodiments, useful heterologous nucleic acid sequence products include any one of the receptors for the hormones, growth factors, cytokines, lymphokines, regulatory proteins and immune system proteins. Useful heterologous nucleic acid sequence s also include receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses the use of gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZFS, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

In some embodiments, useful heterologous nucleic acid sequence products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes useful in enzyme replacement therapy, and which are useful in a variety of conditions resulting from deficient activity of enzyme. For example, enzymes containing mannose-6-phosphate may be utilized in therapies for lysosomal storage diseases (e.g., a suitable gene includes that encoding β-glucuronidase (GUSB)).

In some embodiments, useful heterologous nucleic acid sequence products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 (Wood et al., (1984) Nature, 312:330; Vehar et al., (1984) Nature 312:337; and Toole et al., (1984) Nature, 342:337). Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, releasing the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, used to reduce overexpression of a target.

In some embodiments, the present invention provides methods for treatment of a stem cell disorder, for example a disorder in either bone marrow stem cells or adult tissue stem cells (i.e., somatic stem cells). In some embodiments, adult stem cells can include organoid stem cells (i.e., stem cells derived from any organ or organ system of interest within the body). Organs of the body include for example but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, the disorder for treatment is a disorder in any one or more organoid stem cells (i.e., stem cells derived from any organ or organ system of interest within the body). In some embodiments, the treatment is in vivo (for example, administration of the variant capsid polypeptides is directly to the subject). In some embodiments, the treatment is ex vivo (for example, administration of the variant capsid polypeptides is to stem cells isolated from the subject and the treated stem cells are then returned to the subject).

Reduction and/or modulation of expression of a heterologous nucleic acid sequence is particularly desirable for treatment of hyperproliferative conditions characterized by hyperproliferating cells, such as cancers and psoriasis. Target polypeptides include those polypeptides produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are used as target antigens for autoimmune disease. Other tumor-associated polypeptides can be used as target polypeptides such as polypeptides found at higher levels in tumor cells including the polypeptide recognized by monoclonal antibody 17-1A and folate binding polypeptides.

In some embodiments, suitable therapeutic polypeptides and proteins include those useful for treating individuals suffering from autoimmune diseases and disorders by conferring a broad based protective immune response against targets that are associated with autoimmunity including cell receptors and cells producing "self"-directed antibodies. T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

In some embodiments, heterologous nucleic acid sequences encode for immunogens useful to immunize (i.e., useful as, for example, a vaccine) a human or non-human animal against other pathogens including bacteria, viruses, fungi, parasitic microorganisms or multicellular parasites infecting human and non-human vertebrates, or from a cancer cell or tumor cell. Examples of bacterial pathogens include pathogenic gram-positive cocci include pneumococci; staphylococci (and the toxins produced thereby, e.g., enterotoxin B); and streptococci. Pathogenic gram-negative cocci include meningococcus; gonococcus. Pathogenic enteric gram-negative bacilli include enterobacteriaceae; *pseudomonas*, acinetobacteria and eikenella; melioidosis; *salmonella; shigella; haemophilus; moraxella; H. ducreyi* (causes chancroid); *brucella* species (brucellosis); *Francisella tularensis* (causes tularemia); *Yersinia pestis* (plague) and other *Yersinia* (*pasteurella*); *Streptobacillus moniliformis* and spirillum; Gram-positive bacilli include *Listeria monocytogenes; Erysipelothrix rhusiopathiae; Corynebacterium diphtheria* (causes diphtheria); cholera; *Bacillus. anthracia* (causes anthrax); donovanosis (granuloma inguinale; caused by *Klebsiella granulomatis*); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever; Rocky Mountain spotted fever; Q fever (*Coxiella burnetti*); and Rickettsialpox. Examples of *mycoplasma* and chlamydial infections include: *Mycoplasma pneumoniae*; lymphogranuloma venereum (caused by *Chlamydia trachomatis*); psittacosis; and perinatal chlamydial infections. Pathogenic eukaryotes encompassing pathogenic protozoans and helminths and infections produced thereby include: amebiasis (caused by *Entamoeba histolytica*); malaria (caused by *Plasmodium*); Leishmaniasis (caused by *Leishmania*); trypanosomiasis (caused by *Trypanosoma*); toxoplasmosis (caused by *Toxoplasma gondii*); *Pneumocystis carinii*; babesiosis (caused by *Babesia*); giardiasis (caused by *Giardia lamblia*); trichinosis (caused by roundworms of the genus *Trichinella*); filariasis (caused by roundworms of Filarioidea); schistosomiasis (carried by fresh water snails infected with one of the five varieties of the parasite *Schistosoma*); nematodes (Nematoda); trematodes or flukes (Platyhelminthes); and cestode (Cestoidea; tapeworm) infections. Examples of viruses include but are not limited to human immunodeficiency virus (HIV; e.g., HIV-1 and HIV-2), influenza (e.g., influenza A, influenza B, and influenza C), parainfluenza hepatitis virus (e.g., hepatitis A, hepatitis B, hepatitis C, hepatitis D, and hepatitis E), herpes viruses (HSV; HHV; e.g., herpes virus types 1, 2, 3, 4, 5, 6A, 6B, 7, and 8, including herpes simplex virus types 1 and 2, aka, HSV-1; HSV-2), varicella-zoster virus (HHV-3), Epstein Barr virus (HHV-4), Roseolovirus (HHV-6A and HHV-6B); Rous sarcoma virus, cytomegalovirus (HHV-5), Kaposi's sarcoma-associated herpesvirus; KSHV; HHV-8), papovirus (e.g., human papilloma virus; HPV; HPV-1, HPV-2, HPV-16, and HPV-18), parvovirus (e.g., Parvovirus B19), orthomyxovirus, paramyxovirus (e.g., morbillivirus, respirovirus, rubulavirus, ferlavirus, pneumovirus, and metapneumovirus), picornavirus (e.g., foot-and-mouth disease virus, aquamavirus A, encephalomyocarditis virus, theilovirus, cosavirus A, cadicivirus A, enterovirus A, enterovirus B, enterovirus C, enterovirus D, enterovirus E, enterovirus F, enterovirus G, enterovirus H, enterovirus J, rhinovirus A, rhinovirus B, rhinovirus C, aichivirus A, aichivirus B, aichivirus C, melegrivirus A, human parechovirus, ljungan virus, and salivirus A), togavirus (e.g., flavivirus, alphavirus, and rubivirus), Cowpox virus, Horsepox virus, Crimean-Congo hemorrhagic fever virus, Dengue virus, Eastern equine encephalitis virus, Hantaan virus, Human coronavirus, Human enterovirus 68, Human enterovirus 70, non-HIV retroviruses, rhinovirus, respiratory syncytial virus (RSV), SARS coronavirus, Human spumaretrovirus, Human T-lymphotropic virus, Isfahan virus, Japanese encephalitis virus, Lassa virus, Lymphocytic choriomeningitis virus, MERS coronavirus, measles virus, Mengo encephalomyocarditis virus, Monkeypox virus, mumps virus, Norwalk virus, Pichinde virus, Poliovirus, Rabies virus, rotavirus (e.g., rotavirus A, rotavirus B, and rotavirus C), Rubella virus, St. Louis encephalitis virus, Toscana virus, Uukuniemi virus, Venezuelan equine encephalitis virus, Western equine encephalitis virus, West Nile virus, Yellow fever virus, and Ebola, as well as any other viruses known to those of skill in the art.

Methods for Generating an AAV Virion

In various embodiments, the invention provides a method for generating an AAV virion of the invention. A variety of methods of generating AAV virions are known in the art and can be used to generate AAV virions comprising the AAV vectors described herein. Generally, the methods involved inserting or transducing an AAV vector of the invention into a host cell capable of packaging the AAV vector into and AAV virion. Exemplary methods are described and referenced below; however, any method known to one of skill in the art can be employed to generate the AAV virions of the invention.

An AAV vector comprising a heterologous nucleic acid and used to generate an AAV virion can be constructed using methods that are well known in the art. See, e.g., Koerber et al. (2009) *Mol. Ther.*, 17:2088; Koerber et al. (2008) *Mol. Ther.*, 16: 1703-1709; as well as U.S. Pat. Nos. 7,439,065, 6,951,758, and 6,491,907. For example, the heterologous sequence(s) can be directly inserted into an AAV genome with the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) *Molec. Cell. Biol.* 8:3988-3996; Vincent et al. (1990) Vaccines 90 (Cold Spring Harbor Laboratory Press); Carter, B. J. (1992) *Current Opinion in Biotechnology* 3:533-539; Muzyczka, N. (1992) *Curr. Topics Microbiol. Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

In order to produce AAV virions, an AAV vector is introduced into a suitable host cell using known techniques, such as by transfection. A number of transfection techniques are generally known in the art. See, e.g., Graham et al. (1973) *Virology*, 52:456, Sambrook et al. (1989) *Molecular Cloning, A Laboratory Manual*, Cold Spring Harbor Laboratories, New York, Davis et al. (1986) *Basic Methods in Molecular Biology*, Elsevier, and Chu et al. (1981) *Gene* 13:197. Particularly suitable transfection methods include calcium phosphate co-precipitation (Graham et al. (1973) *Virol.* 52:456-467), direct micro-injection into cultured cells (Capecchi, M. R. (1980) *Cell* 22:479-488), electroporation (Shigekawa et al. (1988) *BioTechniques* 6:742-751), liposome-mediated gene transfer (Mannino et al. (1988) *BioTechniques* 6:682-690), lipid-mediated transduction (Felgner et al. (1987) *Proc. Natl. Acad. Sci. USA* 84:7413-7417), and nucleic acid delivery using high-velocity microprojectiles (Klein et al. (1987) *Nature* 327:70-73).

Suitable host cells for producing AAV virions include microorganisms, yeast cells, insect cells, and mammalian cells, that can be, or have been, used as recipients of a heterologous DNA molecule. The term includes the progeny of the original cell transfected. Thus, a "host cell" as used herein generally refers to a cell transfected with an exogenous DNA sequence. Cells from the stable human cell line, 293 (readily available through, e.g., the American Type Culture Collection under Accession Number ATCC CRL1573) can be used. For example, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a convenient platform in which to produce AAV virions.

Methods of producing an AAV virion in insect cells are known in the art, and can be used to produce a subject AAV virion. See, e.g., U.S. Patent Publication No. 2009/0203071; U.S. Pat. No. 7,271,002; and Chen (2008) *Mol. Ther.* 16:924.

In some embodiments, the AAV virion or AAV vector is packaged into an infectious virion or virus particle, by any of the methods described herein or known in the art.

In some embodiments, the variant capsid polypeptide allows for similar packaging as compared to a non-variant parent capsid polypeptide.

In some embodiments, an AAV vector packaged with the variant capsid polypeptide is transduced into cells in vivo better than a vector packaged with a non-variant parent capsid polypeptide.

In some embodiments, the AAV vector packaged with the variant capsid polypeptide is transduced into cells in vitro better than a vector packaged with a non-variant parent capsid polypeptide.

In some embodiments, the variant capsid polypeptide results in nucleic acid expression higher than a nucleic acid packaged with a non-variant parent capsid polypeptide.

In some embodiments, the AAV vector packaged with said variant capsid polypeptide results in transgene expression better than a transgene packaged with a non-variant parent capsid polypeptide.

Pharmaceutical Compositions & Dosing

The present invention provides pharmaceutical compositions useful in treating subjects according to the methods of the invention as described herein. Further, the present invention provides dosing regimens for administering the described pharmaceutical compositions. The present invention provides pharmaceutical compositions comprising: a) a subject AAV vector or AAV virion, as described herein as well as therapeutic molecules packaged by or within capsids comprising variant polypeptides as described herein; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro, (2000) *Remington: The Science and Practice of Pharmacy,* 20th edition, Lippincott, Williams, & Wilkins; *Pharmaceutical Dosage Forms and Drug Delivery Systems* (1999) H. C. Ansel et al., eds., 7th ed., Lippincott, Williams, & Wilkins; and *Handbook of Pharmaceutical Excipients* (2000) A. H. Kibbe et al., eds., 3rd ed. Amer. Pharmaceutical Assoc.

A subject composition can comprise a liquid comprising a subject variant AAV capsid polypeptide of the invention or AAV virion comprising a variant capsid polypeptide in solution, in suspension, or both. As used herein, liquid compositions include gels. In some cases, the liquid composition is aqueous. In some embodiments, the composition is an in situ gellable aqueous composition, e.g., an in situ gellable aqueous solution. Aqueous compositions have opthalmically compatible pH and osmolality.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound. Preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Useful carriers include Vaseline®, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the AAV vector or AAV virion and methods and uses of are known in the art (see, e.g., *Remington: The Science and Practice of Pharmacy* (2003) 20th ed., Mack Publishing Co., Easton, Pa.; *Remington's Pharmaceutical Sciences* (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., *Drug Delivery Systems* (1980), R. L. Juliano, ed., Oxford, N.Y., pp. 253-315).

Doses can vary and depend upon whether the treatment is prophylactic or therapeutic, the type, onset, progression, severity, frequency, duration, or probability of the disease treatment is directed to, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within about 1 hour to about 2 hours, about 2 hours to about 4 hours, about 4 hours to about 12 hours, about 12 hours to about 24 hours or about 24 hours to about 72 hours after a subject has been identified as having the disease targeted for treatment, has one or more symptoms of the disease, or has been screened and is identified as positive as set forth herein even though the subject does not have one or more symptoms of the disease. In some embodiments, the invention as disclosed herein can be practiced within about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 36 hours, about 48 hours, or about 72 hours or more. Of course, methods and uses of the invention can be practiced about 1 day to about 7 days, about 7 days to about 14 days, about 14 days to about 21 days, about 21 days to about 48 days or more, months or years after a subject has been identified as having the disease targeted for treatment, has one or more symptoms of the disease, or has been screened and is identified as positive as set forth herein. In some embodiments, the invention as disclosed herein can be practiced within about 1 day, about 2 days, about 3 days, about 4 days, about 5 days, about 6 days, about 7 days, about 8 days, about 9 days, about 10 days, about 11 days, about 12 days, about 14 days, about 21 days, about 36 days, or about 48 days or more.

In some embodiments, the present invention provides kits with packaging material and one or more components therein. A kit typically includes a label or packaging insert including a description of the components or instructions for use in vitro, in vivo, or ex vivo, of the components therein. A kit can contain a collection of such components, e.g., a variant AAV capsid polypeptide, an AAV vector, or AAV virion and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying the manufacturer, lot numbers, manufacturer location and date, and expiration dates. Labels or inserts can include information identifying manufacturer information, lot numbers, manufacturer location and date. Labels or inserts can include information on a disease a kit component may be used for. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another incompatible treatment protocol or therapeutic regimen and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Method of Treating a Disease

The present invention also provides methods for treatment of disease in a subject by administering the AAV vectors and/or nucleic acids of the present invention, where AAV vectors and/or nucleic acids described herein packaged within a functional AAV capsid, wherein the functional AAV capsid comprises one or more variant capsid polypeptides of the present invention. In an exemplary embodiment, the invention provides a method of administering a pharmaceutical composition of the invention to a subject in need thereof to treat a disease of a subject. In various embodiments, the subject is not otherwise in need of administration of a composition of the invention. In some embodiments, the invention provides methods for vaccine administration.

In some embodiments, the variant AAV capsid polypeptide packages a therapeutic expression cassette comprised of a heterologous nucleic acid comprising a nucleotide sequence encoding a heterologous gene product, such as for example a therapeutic protein or vaccine. In some embodiments, the AAV virion or AAV vector comprises a therapeutic expression cassette comprised of a heterologous nucleic acid comprising a nucleotide sequence encoding a heterologous gene product, such as for example a therapeutic protein or vaccine.

In some embodiments, the variant capsid polypeptides of the invention are employed as part of vaccine delivery. Vaccine delivery can include delivery of any of the therapeutic proteins as well as nucleic acids described herein. In some embodiments, variant capsid polypeptides of the invention are employed as part of a vaccine regimen and dosed according to the methods described herein.

In some embodiments, the variant AAV capsid polypeptides, the AAV virions, or AAV vectors of the invention are used in a therapeutic treatment regimen.

In some embodiments, the variant AAV capsid polypeptides, the AAV virions, or AAV vectors of the invention are used for therapeutic polypeptide production.

In some cases, a subject variant AAV capsid polypeptide or AAV vector, when introduced into the cells of a subject provides for high-level production of the heterologous gene product packaged by the variant AAV capsid polypeptide or encoded by the AAV. For example, a heterologous polypeptide packaged by the variant AAV capsid polypeptide or encoded by the AAV can be produced at a level of from about 1 µg to about 50 µg or more.

In some cases, a subject variant AAV capsid polypeptide, AAV virion, or AAV vector, when introduced into a subject provides for production of the heterologous gene product packaged by the variant AAV capsid polypeptide or encoded by the AAV vector in at least about 10%, at least about 15%, at least about 20%, at least about 25%, at least about 30%, at least about 35%, at least about 40%, at least about 50% at least about 60%, at least about 70%, at least about 80%, or more than 80%, of the target cells.

In some embodiments, the present invention provides a method of treating a disease, the method comprising administering to an individual in need thereof an effective amount of a therapeutic molecule packaged by the variant AAV capsid polypeptide or subject AAV virion as described above.

A variant AAV capsid polypeptide or subject AAV virion can be administered systemically, regionally or locally, or by any route, for example, by injection, infusion, orally (e.g., ingestion or inhalation), or topically (e.g., transdermally). Such delivery and administration include intravenously, intramuscularly, intraperitoneally, intradermally, subcutaneously, intracavity, intracranially, transdermally (topical), parenterally, e.g. transmucosally or rectally. Exemplary administration and delivery routes include intravenous (i.v.), intraperitoneal (i.p.), intrarterial, intramuscular, parenteral, subcutaneous, intra-pleural, topical, dermal, intradermal, transdermal, parenterally, e.g. transmucosal, intra-cranial, intra-spinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, and intralymphatic.

In some cases, a therapeutically effective amount of a therapeutic molecule packaged by the variant AAV capsid polypeptide or a subject AAV virion is an amount that, when administered to an individual in one or more doses, is effective to slow the progression of the disease or disorder in the individual, or is effective to ameliorate symptoms. For example, a therapeutically effective amount of a therapeutic molecule packaged by the variant AAV capsid polypeptide or a subject AAV virion can be an amount that, when administered to an individual in one or more doses, is effective to slow the progression of the disease by at least about 15%, at least about 20%, at least about 25%, at least about 30%, at least about 40%, at least about 50%, at least about 60%, at least about 70%, at least about 80%, or more than about 80%, compared to the progression of the disease in the absence of treatment with the therapeutic molecule packaged by the variant AAV capsid polypeptide or the AAV virion.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Improvement of clinical symptoms can also be monitored by one or more methods known to the art, and used as an indication of therapeutic effectiveness. Clinical symptoms may also be monitored by any means known by those of skill in the art, including for example measure of liver effectiveness, including for example but not limited to liver enzyme tests, MRI, bile acid profiling, or any other tests known to be useful in examinting and/or determining liver function and/or a defect in liver function. Liver enzyme tests (sometimes refered to as liver function tests, or LFTs) include but are not limited to testing the blood for levels of aspartate aminotransferase (AST or SGOT), alanine aminotransferase (ALT or SGPT), alkaline phosphatase (ALP), 5' nucleotidase, gamma-glutamyl transpeptidase (GGT), bilirubin, albumin, and alpha-1 antitrypsin (A1A). Prothrombin time (PT; clotting time; often expressed as international normalized ratio (INR)) can also be measured, due to the liver's involvement in clotting factor production. Bilirubin levels can also be measured in the urine as a test for liver function.

In some embodiments, a therapeutic molecule (including, for example, a vaccine) packaged by the variant AAV capsid polypeptide, a subject AAV virion, or AAV virus, when introduced into a subject, provides for production of the heterologous gene product for a period of time of from about 2 days to about 6 months, e.g., from about 2 days to about 7 days, from about 1 week to about 4 weeks, from about 1 month to about 2 months, or from about 2 months to about 6 months. In some embodiments, therapeutic molecule (including, for example, a vaccine) packaged by the variant AAV capsid polypeptide, a subject AAV virion or virus, when introduced into a subject provides for production of the heterologous gene product encoded for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years. In some embodiments, the administration regimen is part of a vaccination regimen.

Multiple doses of a subject AAV virion can be administered to an individual in need thereof. Where multiple doses are administered over a period of time, an active agent is administered once a month to about once a year, from about once a year to once every 2 years, from about once every 2 years to once every 5 years, or from about once every 5 years to about once every 10 years, over a period of time. For example, a subject AAV virion is administered over a period of from about 3 months to about 2 years, from about 2 years to about 5 years, from about 5 years to about 10 years, from about 10 years to about 20 years, or more than 20 years. The actual frequency of administration, and the actual duration of treatment, depends on various factors. In some embodiments, the administration regimen is part of a vaccination regimen.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can readily determine a virion dose range to treat a patient having a particular disease or disorder based on the aforementioned factors, as well as other factors. Generally, doses will range from at least about, or more, for example, about $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect. In some embodiments, treatment is administered at a dosage of $5\times10^{10}$ vg/kg. In some embodiments, the variant AAV polypeptides of the present invention can be employed to reduce the amount of total AAV vector or other therapeutic molecule administered to a subject, wherein less total AAV vector or other therapeutic molecule is administered to a subject when said AAV vector or other therapeutic molecule is transduced using a variant capsid polypeptide as compared to the amount of AAV vector or other therapeutic molecule administered to a subject when the AAV vector or other therapeutic molecule is transduced using a non-variant parent capsid polypeptide in order to obtain a similar therapeutic effect (i.e., both dosages induce similar therapeutic effects or indistinguishable therapeutic effects). In some embodiments, the total vector or other therapeutic molecule administered to a subject is reduced by about 5%, about 10%, about 15%, about 20%, about 25%, about 30%, about 35%, about 40%, about 50%, about 55%, about 60%, about 65%, about 70%, about 75%, about 80% or more when an AAV vector or other therapeutic molecule is transduced using a variant capsid polypeptide as compared to when an AAV vector or other therapeutic molecule is transduced using a non-variant parent capsid polypeptide in order to obtain a similar therapeutic effect (i.e., both dosages induce similar therapeutic effects or indistinguishable therapeutic effects). In some embodiments, the total AAV vector or other therapeutic molecule administered to a subject is reduced by about 5% to about 80%, about 10% to about 75%, about 15% to about 65%, about 20% to about 60%, or about 10% to about 50% when the AAV vector or other therapeutic molecule is transduced using a variant capsid polypeptide as compared to when the AAV vector or other therapeutic molecule is transduced using a non-variant parent capsid polypeptide in order to obtain a similar therapeutic effect (i.e., both dosages induce similar therapeutic effects or indistinguishable therapeutic effects).

An effective amount or a sufficient amount can, but need not be, provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein for treatment of a clotting disorder (e.g., hemophilia A or B).

An effective amount or a sufficient amount need not be effective in each and every subject treated, or a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use. Thus, appropriate amounts will depend upon the condition treated, the therapeutic effect desired, as well as the individual subject (e.g., the bioavailability within the subject, gender, age, etc.).

With regard to a disease or symptom thereof, or an underlying cellular response, a detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal, of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods.

Disclosed methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a liver disease disease.

The compound, agent, drug, treatment or other therapeutic regimen or protocol can be administered as a combination composition, or administered separately, such as concurrently or in series or sequentially (prior to or following) delivery or administration of an AAV vector or AAV virion as described herein. The invention therefore provides combinations where a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of an AAV vector or AAV virion as described herein, to a subject. Specific non-limiting examples of combination embodiments therefore include the foregoing or other compound, agent, drug, therapeutic regimen, treatment protocol, process, remedy or composition.

Methods and uses of the invention also include, among other things, methods and uses that result in a reduced need or use of another compound, agent, drug, therapeutic regimen, treatment protocol, process, or remedy. For example, for a blood clotting disease wherein a patient has defective blood clotting secretion from the liver, a method or use of the invention has a therapeutic benefit if, in a given subject, a less frequent or reduced dose or elimination of administration of a recombinant clotting factor protein to supplement for the deficient or defective (abnormal or mutant) endogenous clotting factor secretion from the subject liver. Thus, in accordance with the invention, methods and uses of reducing need or use of another treatment or therapy are provided.

The invention is useful in animals including veterinary medical applications. Suitable subjects therefore include mammals, such as humans, as well as non-human animals. In some embodiments, the human is male. In some embodiments, the human is female. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), experimental animals (mouse, rat, rabbit, guinea pig), as well as other avian species (birds include but are not limited to parrots, parakeets (small and large), penguins, cockatiels, lovebirds, parrotlets, caiques, conures, lories, lorikeets, pionus parrots, Poicephalus, canaries, finches, cockatoos, macaws, crows, doves, pigeons, mynah birds, and toucans). Human subjects include fetal, neonatal, infant, juvenile and adult subjects. Subjects include animal disease models, for example, mouse and other animal models of blood clotting diseases and others known to those of skill in the art.

Non-limiting particular examples of liver diseases and disorders include but are not limited to any conditions that stop the liver from functioning properly or prevent it from functioning well (i.e., functioning at normal levels). Symptoms of liver diseases and disorders can include but are not limited to abdominal pain, yellowing of the skin or eyes (jaundice), abnormal results of liver function tests, liver fattening (including, for example, disproportional fattening), and cirrhosis of the liver. Liver diseases and disorders further include but are not limited to: amebic liver abscess, autoimmune liver diseases and disorders (including, for example, autoimmune hepatitis, primary biliary cirrhosis (PBC), and primary sclerosing cholangitis (PSC)), biliary atresia, cirrhosis, coccidioidomycosis, delta agent (hepatitis D), drug-induced cholestasis, hemochromatosis, viral hepatitis (including, for example, Hepatitis A, Hepatitis B, and Hepatitis C), neonatal hepatitis, hepatocellular carcinoma (HCC, as well as other liver cancer), fibrolamellar hepatocellular carcinoma, liver disease due to alcohol, pyogenic liver abscess, Reye's syndrome, Sclerosing cholangitis, Wilson's disease, acute liver failure (caused by, for example, drugs, toxins, and various other diseases), alcoholic liver disease, autoimmune-associated diseases, Budd-Chiari syndrome, hypercoagulable disorders, parasitic infection, chronic bile duct obstruction (including, for example, due to tumors, gallstones, inflammation, and trauma), hemochromatosis, alpha-1 antitrypsin (A1A) deficiency, Wilson disease, Alagille Syndrome, cystic disease of the liver, galactosemia, Gilbert's Syndrome, hemochromatosis, liver disease in pregnancy, Lysosomal Acid Lipase Deficiency (LALD), porphyria, sarcoidosis, Type 1 Glycogen Storage Disease, Tyrosinemia, Alveolar hydatid disease, bacillary peliosis, congenital hepatic fibrosis, congestive hepatopathy, gastric antral vascular ectasia, hepatic encephalopathy, hepatolithiasis, hepatopulmonary syndrome, hepatorenal syndrome, hepatosplenomegaly, hepatotoxicity, Indian childhood cirrhosis, Laennec's cirrhosis, Lyngstadaas Syndrome, peliosis hepatis, progressive familial intrahepatic cholestasis, Zahn infarct, Zieve's syndrome, and nonalcoholic fatty liver disease (NAFLD).

Non-limiting particular examples of diseases treatable in accordance with the invention include those set forth herein as well as a lung disease (e.g., cystic fibrosis), a blood coagulation or bleeding disorder (e.g., hemophilia A or hemophilia B with or without inhibitors), thalassemia, a blood disorder (e.g., anemia), Alzheimer's disease, Parkinson's disease, Huntington's disease, amyotrophic lateral sclerosis (ALS), epilepsy, lysosomal storage diseases, a copper or iron accumulation disorders (e.g., Wilson's or Menkes disease) lysosomal acid lipase deficiency, a neurological or neurodegenerative disorder, cancer, type 1 or type 2 diabetes, Gaucher's disease, Hurler's disease, adenosine deaminase deficiency, a metabolic defect (e.g., glycogen storage diseases), a retinal degenerative disease (such as RPE65 deficiency or defect, choroideremia, and other diseases of the eye), and a disease of a solid organ (e.g., brain, liver, kidney, heart), as well as muscle diseases including not limited to Acid Maltase Deficiency (AMD), Amyotrophic Lateral Sclerosis (ALS), Andersen-Tawil Syndrome, Becker Muscular Dystrophy (BMD), Becker Myotonia Congenita, Bethlem Myopathy, Bulbospinal Muscular Atrophy (Spinal-Bulbar Muscular Atrophy), Carnitine Deficiency, Carnitine Palmityl Transferase Deficiency (CPT Deficiency), Central Core Disease (CCD), Centronuclear Myopathy, Charcot-Marie-Tooth Disease (CMT), Congenital Muscular Dystrophy (CMD), Congenital Myasthenic Syndromes (CMS), Congenital Myotonic Dystrophy, Cori Disease (Debrancher Enzyme Deficiency), Debrancher Enzyme Deficiency, Dejerine-Sottas Disease (DSD), Dermatomyositis (DM), Distal Muscular Dystrophy (DD), Duchenne Muscular Dystrophy (DMD), Dystrophia Myotonica (Myotonic Muscular Dystrophy), Emery-Dreifuss Muscular Dystrophy (EDMD), Endocrine Myopathies, Eulenberg Disease (Paramyotonia Congenita), Facioscapulohumeral Muscular Dystrophy (FSH or FSHD), Finnish (Tibial) Distal Myopathy, Forbes Disease (Debrancher Enzyme Deficiency), Friedreich's Ataxia (FA), Fukuyama Congenital Muscular Dystrophy, Glycogenosis Type 10, Glycogenosis Type 11, Glycogenosis Type 2, Glycogenosis Type 3, Glycogenosis Type 5, Glycogenosis Type 7, Glycogenosis Type 9, Gowers-Laing Distal Myopathy, Hauptmann-Thanheuser MD (Emery-Dreifuss Muscular Dystrophy), Hereditary Inclusion-Body Myositis, Hereditary Motor and Sensory Neuropathy (Charcot-Marie-Tooth Disease), Hyperthyroid Myopathy, Hypothyroid Myopathy, Inclusion-Body Myositis (IBM), Inherited Myopathies, Integrin-Deficient Congenital Muscular Dystrophy, Kennedy Disease (Spinal-Bulbar Muscular Atrophy), Kugelberg-Welander Disease (Spinal Muscular Atrophy), Lactate Dehydrogenase Deficiency, Lambert-Eaton Myasthenic Syndrome (LEMS), Limb-Girdle Muscular Dystrophy (LGMD), Lou Gehrig's Disease (Amyotrophic Lateral Sclerosis), McArdle Disease (Phosphorylase Deficiency), Merosin-Deficient Congenital Muscular Dystrophy, Metabolic Diseases of Muscle, Mitochondrial Myopathy, Miyoshi Distal Myopathy, Motor Neurone Disease, Muscle-Eye-Brain Disease, Myasthenia Gravis (MG), Myoadenylate Deaminase Deficiency, Myofibrillar Myopathy, Myophosphorylase Deficiency, Myotonia Congenita (MC), Myotonic Muscular Dystrophy (MMD), Myotubular Myopathy (MTM or MM), Nemaline Myopathy, Nonaka Distal Myopathy, Oculopharyngeal Muscular Dystrophy (OPMD), Paramyotonia Congenita, Pearson Syndrome, Periodic Paralysis, Peroneal Muscular Atrophy (Charcot-Marie-Tooth Disease), Phosphofructokinase Deficiency, Phosphoglycerate Kinase Deficiency, Phosphoglycerate Mutase Deficiency, Phosphorylase Deficiency, Phosphorylase Deficiency, Polymyositis (PM), Pompe Disease (Acid Maltase Deficiency), Progressive External Ophthalmoplegia (PEO), Rod Body Disease (Nemaline Myopathy), Spinal Muscular Atrophy (SMA), Spinal-Bulbar Muscular Atrophy (SBMA), Steinert Disease (Myotonic Muscular Dystrophy), Tarui Disease (Phosphofructokinase Deficiency), Thomsen Disease (Myotonia Congenita), Ullrich Congenital Muscular Dystrophy, Walker-Warburg Syndrome (Congenital Muscular Dystrophy), Welander Distal Myopathy, Werdnig-Hoffmann Disease (Spinal Muscular Atrophy), and ZASP-Related Myopathy.

Ocular diseases that can be treated or prevented using a subject method include, but are not limited to, selected from acute macular neuroretinopathy; macular telangiectasia; Behcet's disease; choroidal neovascularization; diabetic uveitis; histoplasmosis; macular degeneration, such as acute macular degeneration, Scorsby's macular dystrophy, early or intermediate (dry) macular degeneration, or a form of advanced macular degeneration, such as exudative macular degeneration or geographic atrophy; edema, such as macular edema, cystoid macular edema and diabetic macular edema; multifocal choroiditis; ocular trauma affecting a posterior ocular site or location; ocular tumors; retinal disorders, such as central retinal vein occlusion, diabetic retinopathy (including proliferative and non-proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy; epiretinal membrane disorders; central or branch retinal vein occlusion; anterior ischemic optic neuropathy, non-retinopathy diabetic retinal dysfunction; retinitis pigmentosa; retinoschisis; and glaucoma.

In one embodiment, a method or use of the invention includes: (a) providing an AAV virion whose capsid comprises the variant AAV capsid polypeptides prepared as described herein, wherein the AAV virion comprises a heterologous nucleic acid sequence, wherein the heterologous nucleic acid sequence is operably linked to an expression control element conferring transcription of said nucleic acid sequence; and (b) administering an amount of the AAV virion to the subject such that said heterologous nucleic acid is expressed in the subject.

In one embodiment, a method or use of the invention includes: (a) providing a therapeutic molecule (including, for example, a vaccine) packaged by variant AAV capsid polypeptides prepared as described herein, wherein the therapeutic molecule comprises a heterologous nucleic acid sequence, wherein the heterologous nucleic acid sequence is operably linked to an expression control element conferring transcription of said nucleic acid sequence; and (b) administering an amount of the therapeutic molecule (including, for example, a vaccine) packaged by variant AAV capsid polypeptides to the mammal such that said heterologous nucleic acid is expressed in the mammal.

In another embodiment, a method or use of the invention includes delivering or transferring a heterologous polynucleotide sequence into a mammal or a cell of a mammal, by administering a heterologous polynucleotide packaged by a variant AAV capsid polypeptide, a plurality of heterologous polynucleotides packaged by variant AAV capsid polypeptides, an AAV virion prepared as described herein, or a plurality of AAV virions comprising the heterologous nucleic acid sequence to a mammal or a cell of a mammal, thereby delivering or transferring the heterologous polynucleotide sequence into the mammal or cell of the mammal. In some embodiments, the heterologous nucleic acid sequence encodes a protein expressed in the mammal, or where the heterologous nucleic acid sequence encodes an inhibitory sequence or protein that reduces expression of an endogenous protein in the mammal.

By way of example, respecting hemophilia, it is believed that, in order to achieve a therapeutic effect, the liver must secrete a level of circulating blood coagulation factor to a concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a circulating blood coagulation factor concentration greater than about 5% of normal is needed. With respect to treating such a hemophilic subject, a typical dose is at least $1\times10^{10}$ AAV vector genomes (vg) per kilogram (vg/kg) of the weight of the subject, or between about $1\times10^{10}$ to about $1\times10^{11}$ vg/kg of the weight of the subject, or between about $1\times10^{11}$ to about $1\times10^{12}$ vg/kg of the weight of the subject, or between about $1\times10^{12}$ to about $1\times10^{13}$ vg/kg of the weight of the subject, to achieve a desired therapeutic effect. In some embodiments, treatment is administered at a dosage of $5\times10^{10}$ vg/kg.

EXAMPLES

Example 1: Novel Recombinant Adeno-Associated Virus Capsids Resistant to Pre-Existing Human Neutralizing Antibodies Purpose:

To evolve new recombinant AAV (rAAV) capsids which have the combined ability to both transduce human cells, but also the ability to evade neutralization by pre-existing anti-capsid antibodies in patients. Creation and identification of rAAV vectors that are resilient to neutralization by pre-existing antibody titers would have great utility in human gene therapy as these vectors are used in clinical trials for nucleic acid delivery. There is a high percentage of the human population (varies between 25 to 75%) who have pre-existing anti-AAV antibodies that would preclude successful gene transfer for the treatment of the intended disease. As such, pre-screened patients often have to be excluded from clinical trials and not receive the therapeutic treatment.

Technical Description (Abstract):

Wild-type replicating AAV libraries of 10e5 (aka, 105) variants via DNA shuffling of ten different parental AAV capsids (AAVs 1, 2, 3b, 4, 5, 6, 8, 9_hu14, avian, bovine) were utilized. The AAV capsid libraries selectively replicate in human cells when co-administered with wild-type adenovirus type 5, making chimeric humanized liver mice an excellent tool to allow for selection of capsids with tropism for human liver. Screens were carried out for five rounds of selection in xenotransplanted humanized liver mice and rather than waiting for the screen to go to completion, the screen ended with some library diversity remaining for use in a subsequent screen for neutralizing antibody evasion. All variants from round five of the human liver screen were carried forward and screened for two additional rounds for their ability to resist binding to pooled human immunoglobulins in IgG immunocapture assays. The top 100 highly selected variants were sequenced and vectorized into CAG promoter-driven GFP preparations in seven pools based on capsid relatedness at the amino acid level. Each pool was then resubjected to additional pooled human immunoglobulin screening and the best pool was chosen. The top seven candidates from this pool were tested alongside control serotypes that represent the extremes for humoral neutralization: highest neutralization (AAV-2), lowest neutralization (AAV-DJ), as well as LK03 that falls in between. The most relevant variants from these pools for clinical use were identified to be AAV-NP84 (SEQ ID NO:2), AAV-NP40 (SEQ ID NO:6) and AAV-NP59 (SEQ ID NO:4). AAV-NP84 (SEQ ID NO:2) has neutralization profiles on par with AAV-DJ and subsequent transduction tests in humanized liver mice in vivo demonstrated a high tropism and specificity for human hepatocytes with AAV-NP84 (SEQ ID NO:2). In comparison, AAV-NP40 (SEQ ID NO:6) has modest neutralization profiles but also shows high human hepatocyte tropism and specificity in vivo. Finally, AAV-NP59 (SEQ ID NO:4) also displays a modest neutralization profile but is capable of transducing both human and mouse hepatocytes. This could be very useful as AAV-NP59 (SEQ ID NO:4) could be used to model both pre-clinical studies in mouse as well as used clinically in humans due to its combined transduction capabilities.

Such Variant AAV Capsid Polypeptides Find Use in Human Gene Therapy.

AAV Vectors:

Current AAV capsids with excellent tropism to liver hepatocytes include: AAV-8, AAV-DJ, and AAV-LK03. However, both AAV-8 and AAV-DJ largely only transduce mouse heptocytes, not human hepatocytes. Although AAV-LK03 transduces human hepatocytes well in humanized mice in vivo, about ⅓ of potential patients have pre-existing antibodies against it, limiting its ability to be useful in these patients. The new AAV capsids AAV-NP84 (SEQ ID NO:2), AAV-NP40 (SEQ ID NO:6) and AAV-NP59 (SEQ ID NO:4) show robust human hepatocyte transduction in humanized mice in vivo. AAV-NP84 (SEQ ID NO:2) also shows what appears to be a favorable antibody neutralization profile.

Variations in capsid sequence might enhance the neutralization profile even further, enhance transduction of human tissues and/or expand transduction of various human cell types that are good targets for therapeutic interventions.

Capsid sequences AAV-NP84 (SEQ ID NO:2), AAV-NP40 (SEQ ID NO:6) and AAV-NP59 (SEQ ID NO; 4), as well as AAV-NP30 (SEQ ID NO:8) have been identified in the present invention.

Novel variant AAV capsids that exhibit both human hepatocyte tropism and human immune evasion abilities are provided in the present invention.

Example 2: Bioengineered AAV Capsids with Combined High Human Liver Transduction In Vivo and Unique Humoral Seroreactivity Abstract:

Existing recombinant adeno-associated virus (rAAV) serotypes for delivering in vivo gene therapy treatments for human liver diseases have not yielded combined high-level human hepatocyte transduction and favorable humoral neutralization properties. Yet, these combined properties are important for therapeutic efficacy. To bioengineer capsids that exhibit both unique seroreactivity profiles and functionally transduce human hepatocytes at therapeutically relevant levels, multiplexed sequential directed evolution screens were performed using diverse capsid libraries in both primary human hepatocytes in vivo and with pooled human sera from thousands of patients. AAV libraries were subjected to five rounds of in vivo selection in mice with humanized livers to isolate an enriched human-hepatotropic library that was then used as input for a sequential on-bead screen against pooled human immunoglobulins. Evolved variants were vectorized and validated against existing hepatotropic serotypes. Two of the evolved AAV serotypes—NP40 and NP59—exhibited both improved functional human hepatocyte transduction in vivo in chimeric humanized liver mice, along with favorable human seroreactivity profiles. These novel capsids represent enhanced vector delivery systems for future human liver gene therapy applications.

Introduction:

Despite decades of liver gene therapy research, no liver disorder treated with rAAV gene transfer to date has reached curative, rather than therapeutic, levels. Although there has been substantial progress in treating patients with rAAV vectors expressing human Factor IX in hemophilia B[1,2], transduction was low but compensated for with supraphysiologic levels of expression from the few transduced hepatocytes[3,4]. For non-cell autonomous diseases like hemophilia B that have the benefit of secreted elements, these low transduction levels may be sufficient when paired with transfer vectors optimized for high expression. However, such transduction levels will be suboptimal for liver diseases with more demanding cell autonomous phenotypes. Numerous hurdles remain for improving long-term functional human liver transduction including increasing total functional hepatocyte transduction levels, pre-existing neutralizing antibodies (nAbs) against rAAV capsids, and cellular immune responses to capsid peptides presented on transduced hepatocytes. Suboptimal transduction to date likely stems from the fact that preclinical rAAV selection and validation has historically been performed in animal models that neither recapitulate the hepatocellular tropism in humans, nor the kinetics and strength of expression which can be reached[1,5]. Humoral neutralization of rAAV in the bloodstream arises from patient exposure to parental serotypes in nature[6-11]. Immune-mediated destruction of transduced hepatocytes is due to CD8+ T-cell responses to rAAV capsid components[12], but this can largely be managed via corticosteroid administration[1] and reduced dosing. Thus, high-level, functional human hepatocyte transduction and evading humoral neutralization remain the leading barriers to truly efficacious clinical liver gene therapy today.

Importantly, rAAV vectors can be bioengineered to achieve transduction and neutralization potentials not possible with parental serotypes through directed evolution of diverse capsid libraries[13-15]. This technique utilizes replicating AAV throughout the entire selection and evolution process. In contrast to non-replicating screens which only select for receptor binding and uptake[16,17], approaches that use replicating AAV select for every step in the intrahepatocellular trafficking and expression cascade, all of which can heavily influence the efficiency of transduction post-entry[5,18-20]. Even single amino acid capsid mutations have been shown to affect functional transduction post-entry and post-uncoating[21]. Taken together, these data support the use of replicating AAV screens whenever possible.

Here each of these important parameters were combined: utilizing replicating AAV libraries that allow for selection beyond just hepatocyte receptor binding and entry, evolving human hepatocyte tropism in human rather than mouse hepatocytes in vivo, screening for humoral evasion against pools of human immunoglobulins from thousands of patients, and assessing transduction using clinically meaningful methodologies. The result is a panel of novel rAAV variants with superior human hepatic transduction and unique humoral neutralization compared to previously characterized serotypes.

Results:

No Existing rAAV Serotype Fulfills all the Necessary Criteria for Ideal Liver Delivery in Human There exists in the gene therapy field no ideal rAAV vector candidate that satisfies the combinatorial needs of high functional human hepatocyte transduction and low neutralization potential. While several candidates have demonstrated detectable human hepatocyte transduction in either clinical trials or in xenograft models, none exhibit favorable neutralization profiles and vice versa (see Table 3, below). Any rAAV that has not been tested in either a human liver trial or in humanized liver mice was excluded from this list, as assessing human hepatocyte transduction solely in cell lines (rAAV-F series[22]) or non-humanized mice (rAAV1[23,24]) has been shown to have poor correlation with human liver transduction[1,5]. The two candidates with the most favorable extremes are rAAV-LK03 which has high human hepatocyte transduction[4] but also elicits substantial nAb levels[9], and rAAV-DJ which elicits low nAb levels[13] but has yet to be assessed for human hepatocyte transduction. To address this, six humanized FRG[25] mice were treated with ssAAV-DJ-CAG-GFP and measured transduction in mouse and human hepatocytes. Liver immunohistochemistry for human FAH and viral GFP demonstrated low levels of functional human hepatocyte transduction (<5%) in all treated mice (see FIG. 17a, b). The results from GFP RNA FISH followed by sequential GFP DNA FISH on treated liver sections demonstrated that the block to functional human transduction occurred post-uncoating (see FIG. 17c-e). Although both strong nuclear GFP DNA as well as nuclear and cytoplasmic GFP RNA were detected, there was no GFP protein, indicating a translational block to functional expression.

TABLE 3

Literature Comparison

| AAV Serotype | Estimated human hepatocyte transduction in clinical trials | Human hepatocyte transduction in humanized mice | Mouse hepatocyte transduction | Levels of pre-existing nAb in humans |
|---|---|---|---|---|
| AAV2 | Low[2] | Low[4] | Low[4,18,52] | Medium[27,35]-high[9,10,27,28,34] |
| AAV3b | ND | Medium[3] | Low[3,24,53] | High[9,28] |
| AAV5 | Low[54,55]* | Low[3] | Low[3,18,24,56] | Low[35,55]*-medium[10,28,34,35]-high[28] |
| AAV8 | Low[1,5] | Low[3,4] | Medium[3]-high[4,57] | Medium[27,34]-high[9,10,28] |
| AAV9 | ND | Low[3] | Medium[3] | Medium[34] |
| AAV-LK03 | ND | High[4] | Low[4] | High[9] |
| AAV-DJ | ND | Low (see FIG. S1) | High[13,58] | Low[13] (and see FIG. 5) |

Table 3 provides a literature comparison of functional hepatocyte transduction and pre-existing neutralizing antibody levels in humans with existing hepatotropic AAV serotypes. The ability to functionally transduce hepatocytes in vivo in different settings was compared. Column 1 shows estimated functional percent human hepatocyte transduction from clinical trials. All values are estimates since no biopsies assessing functional transduction (protein expression rather than vector copy number) post-treatment have been performed. Of note, while expression levels from AAV8 were therapeutic in some patients (sustained 5-7% of normal human FIX levels), previous data showing supraphysiologic expression per transduced hepatocyte suggests <10% of patient hepatocytes were transduced. Column 2 shows actual percent human hepatocyte functional transduction in vivo measured from treated xenografted liver mice. Column 3 shows actual percent mouse hepatocyte functional transduction in vivo from non-xenografted mice of varying genotypes and strain backgrounds. Column 4 shows levels of pre-existing neutralizing antibodies (nAb) measured from human sera in neutralization assays. ND=not determined. *=predicted (data acquired from a non-peer-reviewed press release prior to the end of the study). For the three transduction columns, low=0-10%, medium=10-50%, high=50-100% of liver hepatocytes. For the neutralization column, low=0-10%, medium=10-50%, high=50-100% of patients whose sera showed neutralization for that AAV capsid.

Diverse AAV Capsid Library Screening in Primary Human Hepatic Xenografts In Vivo The ideal rAAV capsid for liver-directed gene therapy in humans would combine high functional hepatic transduction with immune evasion. To evolve such a variant, a directed evolution approach that bioengineered diverse capsids through DNA shuffling of capsid genes from numerous genetically and functionally diverse parental AAV serotypes was employed. Enzymatic fragmentation followed by assembly of shuffled full-length capsid genes was used to generate a diverse capsid library. Those were then cloned into an AAV shuttle vector and utilized to produce live replicating AAV libraries (see FIG. 2a, 18). The library was produced from 10 different parental capsid serotypes: 1, 2, 3b, 4, 5, 6, 8, 9_hu14, avian and bovine. To maximize the likelihood that the shuffled capsids could both evade humoral neutralization and functionally transduce human hepatocytes, multiplexed sequential screens using primary human tissues were performed. First, primary human surgical liver specimens were digested and purified to isolate populations of human hepatocytes for transplantation into FRG mice (see FIG. 2b). 5E10 vector genomes (vg) of AAV library was administered intravenously into xenografted mice (see FIG. 2c) followed by live Adenovirus-5 (Ad-5) 24-hrs later. Replicated AAV variants that trafficked successfully to the liver were isolated after 2 days post-Ad5 administration, minimally purified and re-titered, and again injected at 5E10 vg/mouse into new xenotransplanted mice. This in vivo screening cycle was carried out for five rounds of selection. Diversity monitoring via Sanger sequencing began at round 3, and each round thereafter, until round 5 when sufficient pressure for human hepatic transduction had been selected but some library diversity remained. This enriched human-hepatotropic AAV library was then used as input for a series of sequential on-bead screens against pooled human immunoglobulins from thousands of patients to select variants with reduced humoral neutralization potential across the general population (see FIG. 2d). After two rounds of binding selection, those variants that remained unbound were subjected to stringent characterization for potential clinical utility.

Figure 12:
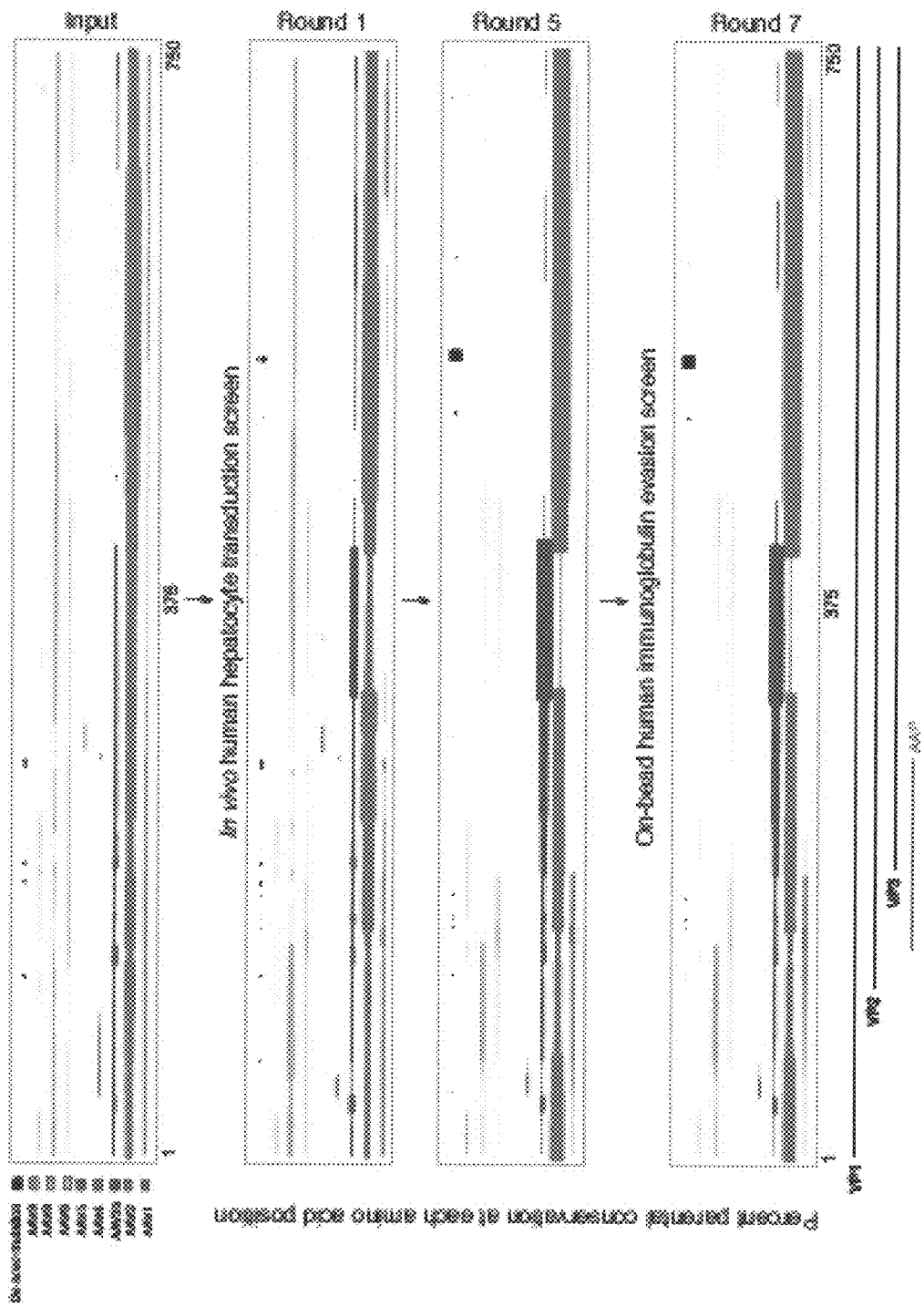
FIG. 12 provides percent parental conservation at each amino acid position during the progression of each screen. Using PacBio single-molecule sequencing and bioinformatic analyses, positional enrichment assessments were performed to calculate percent conservation among amino acids from parental serotypes (AAVs 1, 2, 3b, 4, 5, 6, 8, 9_hu14) or de novo mutations for each amino acid position among all capsids at key rounds during the screen (input, rounds 1 and 5 in vivo and round 7 unbound). Bovine and avian were removed from the plot since few variants showed any appreciable contribution from those two serotypes. The maximum square size indicates that 100% of variants share that amino acid from that parent at that position. All other square sizes are proportional to the percent of variants from 0-100% that have that amino acid at that position from that parent. Each parent is colored as is shown in the legend (same color scheme is used in FIG. 3A, B) and de novo mutations that evolved during the screen are shown in black. VP1, VP2, VP3 and AAP ORFs are diagrammed below for reference.

Identifying Functionally Important Residues Via Structural and Comparative Computational Modeling At the completion of the second sequential screen, capsid sequences amplified from the input library and several selection rounds were deep sequenced using PacBio single-molecule sequencing. Round-to-round positional analyses from thousands of capsids identified the selection for key residues (see FIG. 12). This approach was more revealing than classic phylogenetic trees that root on the nearest full-length parental sequence, effectively masking functionally important residues within full-length capsid relatedness (see FIG. 19). Interestingly, although rAAV2 is known to be a poor functional transducer of human hepatocytes, several structural fragments from AAV2 were highly selected in the initial screen during the early rounds of screening, most notably residues in the C-terminal end of VP3. However, many stretches of AAV2 sequence were strongly selected against including: a portion of the unique region of VP1 and the unique region of VP2 (aligned residues 67-to-146), which instead selected for AAV8 residues; a large stretch of VP3 (aligned residues 321-to-423) which selected for AAV3b residues; and several high frequency de novo mutation hot spots (aligned residues 42, 158, 165, 181, 290, 515 and 555) which contained various amino acids not present in any of the parental serotypes used for library generation. As the experiments transitioned into the second screen to select capsid variants capable of humoral evasion, the IgG-bound and unbound AAV variants exhibited a high degree of structural mean similarity. Only a few key regions were different between them that are likely necessary in combination to achieve the improved IgG evasion. Here, the global differences were more easily seen with the individual, rather than aggregate, full-length capsid sequences from PacBio single-molecule sequencing (see FIG. 19a).

Figure 13B:
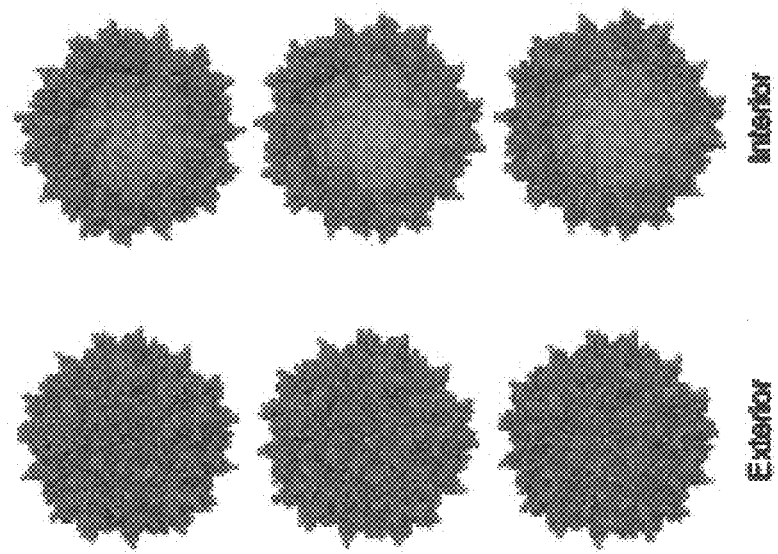
FIG. 13A-FIG. 13B provides sequence and structural composition of new human hepatotropic shuffled AAV capsid variants. (A) Crossover mapping analysis of capsid fragment crossovers in vectorized variants from the parental AAV serotypes (AAVs 1, 2, 3b, 4, 5, 6, 8, 9_hu14) used in the library. The maximum circle size indicates a 100% match for that amino acid from that parent at that position. All other circle sizes are proportional to the percent likelihood that that amino acid at that position matches that parent. The solid black line for each chimera represents the most likely parental serotype match identified across each crossover. Thin parallel lines between crossovers indicate multiple parental matches at an equal probability. Vertical spikes indicate a mutation from within the parental sequence space, while an overhead asterisk indicates an evolved de novo mutation for which no parent has that amino acid at that position. VP1, VP2, VP3 and AAP ORFs are diagrammed below for reference. (B) Shuffled variants were 3D false-color mapped onto the crystal structure of AAV2. Color-coding indicates parental contribution using the same colors as in (A).
Figure 13A:
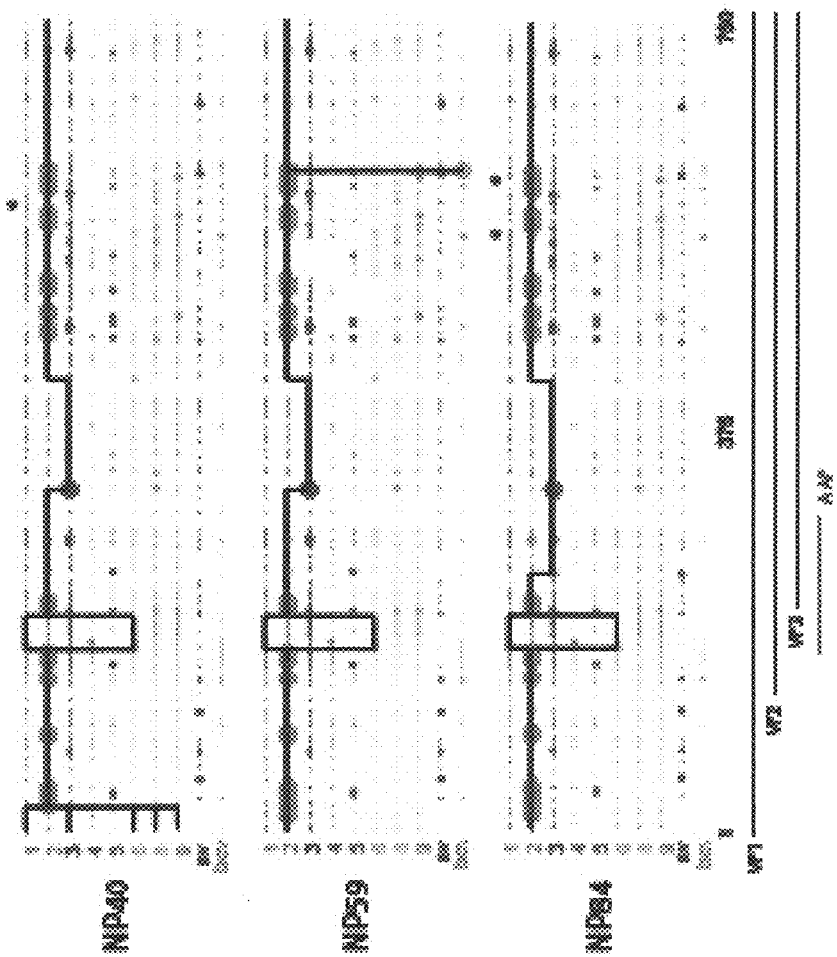
Figures 20A, 20B:
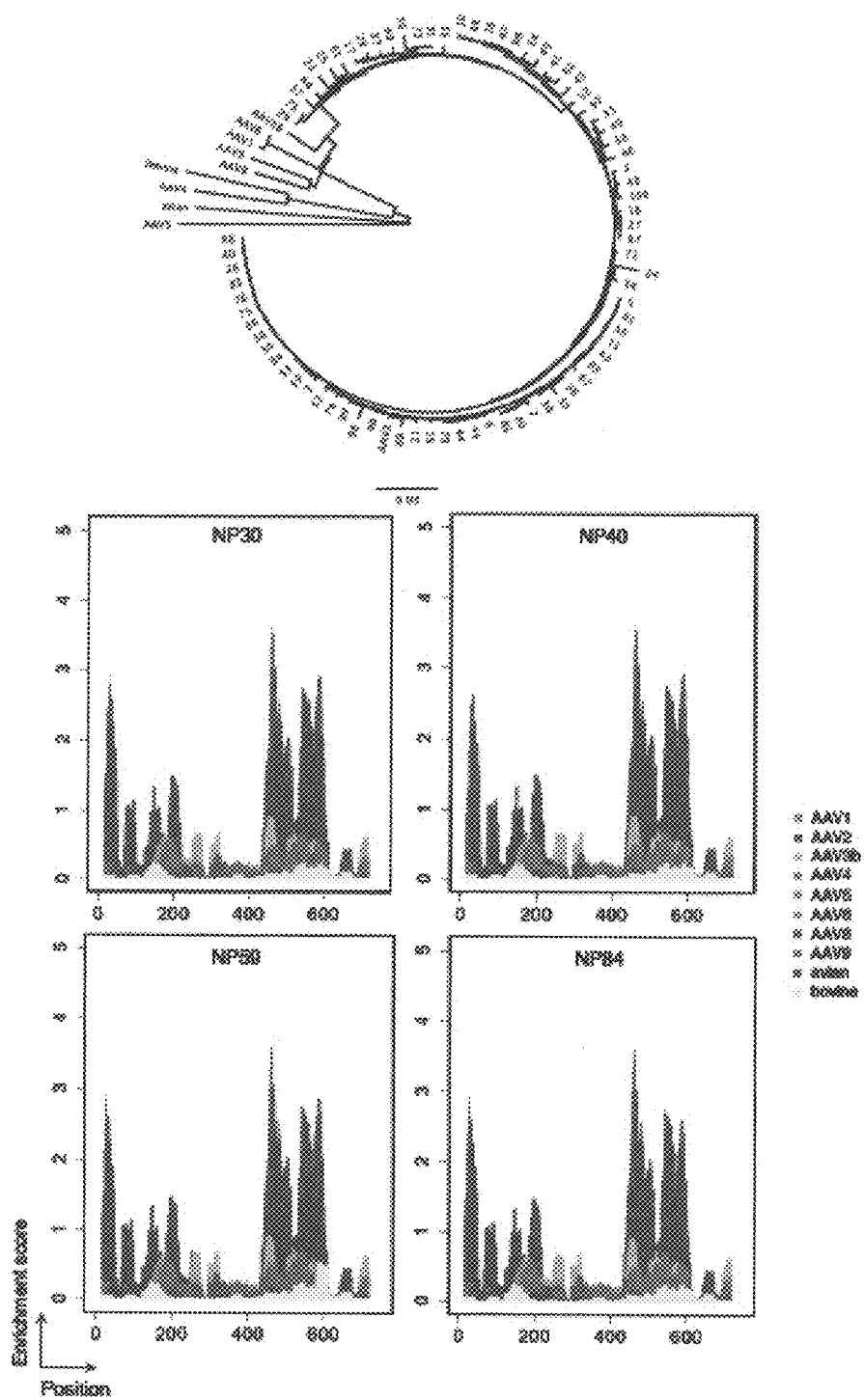
FIG. 20A-FIG. 20B provides phylogeny and enrichment scores of top variants from screen completion. (A) Phylogenetic tree showing genetic relatedness at the amino acid level among the parental serotypes in the library (AAVs 1, 2, 3b, 4, 5, 6, 8, 9_hu14) and the top 100 selected variants from the final round of the second screen for immune evasion from the unbound AAV fraction. (B) Enrichment scores were calculated for each amino acid position in the sequence of each chimera by comparison of sequences from parental serotypes based on maximum likelihood. Library parents are depicted in different colors as shown.

To further probe the evolved variants, several of the most highly selected capsid variants obtained after the final screen were chosen (see FIG. 20a) and vectorized with GFP or Firefly Luciferase (FLuc) expression constructs for subsequent validation experiments. To determine the genetic contribution of each parental AAV serotype to the evolved capsids fragment crossover mapping (see FIG. 13a), structural capsid mapping (see FIG. 13b) and predictive fragment conservation analyses (see FIG. 20b) were performed. These complementary methodologies demonstrated selection for certain residues and highlighted both unique and shared domains. Shuffling was achieved along the length of Cap, including VP1, VP2, VP3 and AAP. The parental serotypes that contributed the most to the evolved variants included AAV2, 3b, 1 and 6 in that order. None of the selected variants had appreciable contributions from AAV4, 5, 8, 9_hu14, bovine or avian. It is interesting to note the lack of selection for almost any unique AAV8 sequence in variants selected for their ability to transduce human as opposed to mouse hepatocytes. This supports previous findings of some of the inventors[4] and that of others in the field[3] that rAAV8 is a poor functional transducer of human hepatocytes in vivo, and is much better suited for mouse transduction studies.

Shuffled NP40, NP59 and NP84 capsid sequences (see FIG. 13a, 23) contained many fragments from parental serotypes with known liver tropism, and these variants were selected for in the initial in vivo screen in humanized liver xenografts. Each of these 3 shuffled capsids would be predicted to have similar comparative structures to one another given their highly similar capsid sequences (see FIG. 13a, b). NP40 is the most shuffled of the three, with the unique region of VP1 from AAV1/3b/6/8/9, the unique region of VP2 derived from AAV2, and finally VP3 with contributions from AAV2 and 3b as well as one de novo mutation (K555E). As with the other variant capsids, a conserved contribution from AAV3b at positions 326-426 suggesting that this is the minimal structural region from AAV3b required for enhanced human hepatic transduction was observed. NP59 is similar to NP40 but lacks the diverse VP1 contributions and is instead composed of AAV2 in that sequence stretch. NP59 has the same VP2 and VP3 contributions as NP40 except for one de novo mutation (N622D). NP84 shares the unique regions of VP1 and VP2 with NP59, but has a much larger contribution from AAV3b and less from AAV2 in VP3, as well as two de novo mutations (K555E and R611G). Looking globally at all three variant capsids, structural mapping highlighted the subtle structural heterogeneity in hypervariable regions but also macro-conservation within key structural domains such as the cylinder (from AAV2), canyon (from AAV3b) and various symmetry axes.

Figures 14A, 14B, 14C:
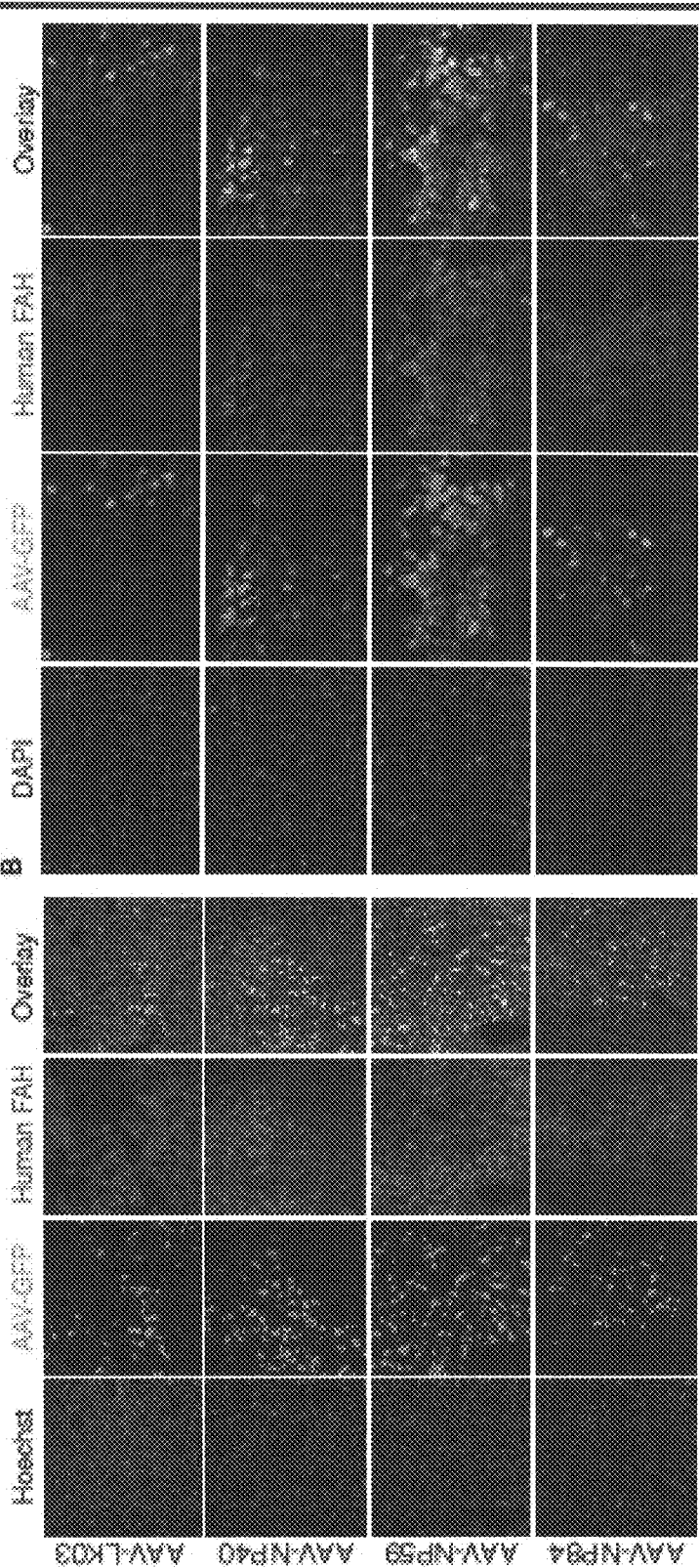
FIG. 14A-FIG. 14C provides validation and comparative quantitation of human hepatocyte transduction in humanized liver mice in vivo. (A) Representative immunohistochemical images from treated humanized liver mice from OHSU transduced with ssAAV-CAG-GFP at 2E11 vg IV with varying capsid serotypes. Human-specific FAH (violet), viral-GFP (green), Hoechst (blue) on liver cross-sections. Scale=100-µM. (B) Representative immunohistochemical images from treated humanized liver mice from CMRI transduced with ssAAV-LSP1-GFP at 2E11 vg IV with varying capsid serotypes. Human-specific albumin (red), viral-GFP (green), DAPI (blue) on liver cross-sections. Scale=100 µM. (C) Summary of analysis from transduced xenografted mice. The percentage of transduced human hepatocytes was determined by individually analyzing and comparing cell counts from images of GFP fluorescence and human FAH immunostaining as described previously[4].
Figure 21A:
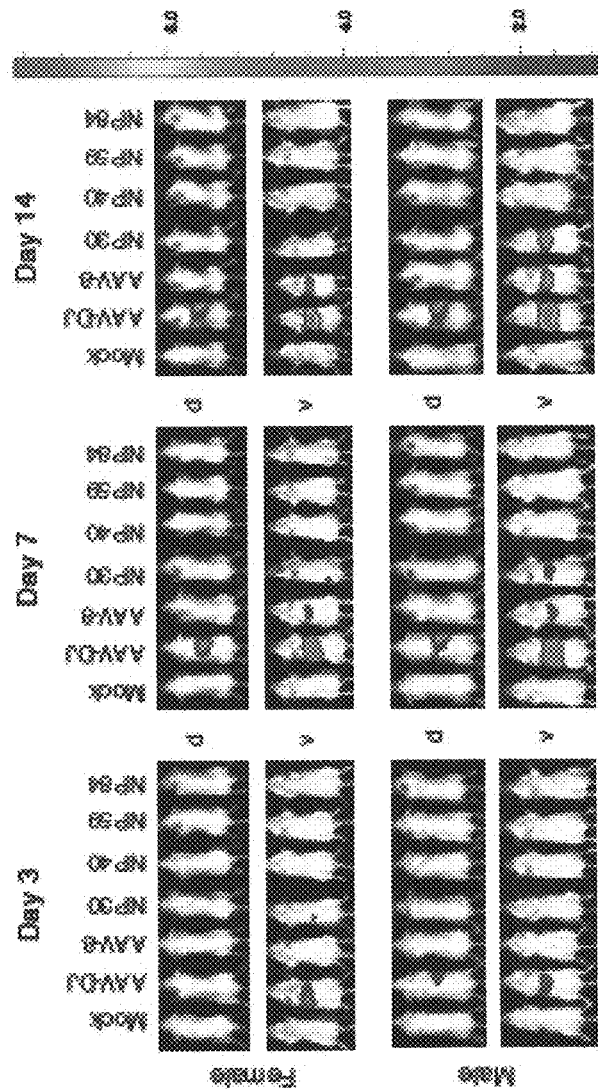
FIG. 21A-FIG. 21B provides short in vivo transduction time-course in non-humanized mice. (A) Live imaging FLuc transduction time course in non-transplanted wildtype Balb/cJ mice treated with PBS, AAV-DJ, AAV8, AAV-NP30 (SEQ ID NO:8), AAV-NP40 (SEQ ID NO;6), AAV-NP59 (SEQ ID NO:4) or AAV-NP84 (SEQ ID NO:2) expressing ssAAV-EF1α-FLuc after IV tail vein administration (2E11 vg/mouse). Mean radiance (p/s/cm2/sr) is displayed with all mice imaged on the same, shared scale. All mice were imaged on both the dorsal (d) and ventral (v) sides. (B) Quantified dorsal and ventral radiance at day 14 from mice from (A).
Figure 21B:
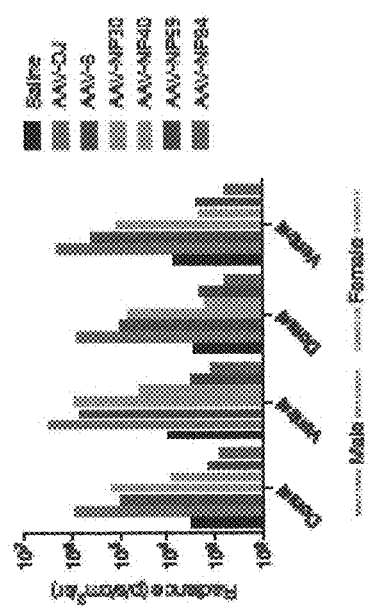

Liver Xenografts are an Accurate Surrogate for Assessing Human Hepatic Transduction To rigorously assess the functional human hepatic transduction capabilities of the shuffled capsids in an appropriate in vivo setting, humanized FRG xenograft mice were transduced. To reduce bias and maximize stringency, cohorts of xenografted liver mice were produced in two different labs and administered variant (NP40, NP59 and NP84) or control (LK03 and DJ) rAAV capsids expressing GFP. Humanized mice at each of the two locations were administered rAAV at the same dose (2E11/mouse), via the same delivery method (intravenous lateral tail vein injection), and assessed for transduction via GFP immunohistochemistry 14-days post-AAV administration (see FIG. 14a, b). Although different promoters were used, both CAG and LSP1 have been shown to express at equivalent levels in hepatocytes[26]. To assess the potential impact of repopulation percentage on transduction, one cohort was transduced at high repopulation levels and the other with low repopulation levels. The independent results from two blinded labs demonstrated that shuffled variants NP40 and NP59 (and in the high repopulation cohort, also NP84) had significantly increased functional human hepatocyte transduction over control serotypes LK03 and DJ (see FIG. 14c, 17a, b). Although the trend for increased transduction by variants over controls held regardless of the degree of repopulation, the average transduction level varied depending on the availability of human hepatocytes and limiting rAAV virions. Transduction was seen across the hepatic lobule where gradients in metabolic activity, and possibly expression and secretion of transgene products exist. The new shuffled variants are highly specific for transduction of human hepatocytes. When injected IV into non-humanized Balb-CJ mice, the shuffled variants either functionally transduced the liver very poorly or not at all (see FIG. 21a, b). This is in sharp contrast to rAAV-DJ which outperformed even rAAV8 at functional mouse liver transduction.

Immunologic Properties of Evolved Hepatotropic AAV Variant

To predict the likelihood of rAAV neutralization in patients with pre-existing and potentially cross-reacting anti-AAV capsid antibodies, both seroreactivity assays and transduction neutralization assays using serum from a variety of patient groups and nonhuman primates was performed. First, individual human serum samples from 50 healthy U.S. adults of each gender (see Table 4, below) were assessed for their seroreactivity to the shuffled capsid variants and control serotypes (see FIG. 15a, 22a, b, Table 5, below). Shuffled variants NP40, NP59, NP84 and DJ all had significantly reduced seroreactivity profiles compared to rAAV8 and LK03 (P<0.001-0.0001), known to have high human neutralization frequencies[9,10,27,28]. Separately assessing seroreactivity by gender demonstrated a statistically significant difference in seroreactivity against the different capsids in men and women, however sample numbers were low and must be interpreted with caution (see Table 5). While both men and women showed significantly improved seroreactivity to all shuffled variants over rAAV8, only males had significant improvements compared to LK03 (n=33). Female patients did not demonstrate significant seroreactivity differences between LK03 and each of the three new variant capsids (NP40, NP59 and NP84), albeit from low patient numbers (n=17).

TABLE 4

Details for normal off-clot human serum samples

| DOS | Age | Gender | Ethnicity | Smoke | ABO | DOS | Age | Gender | Ethnicity | Smoke | ABO |
|---|---|---|---|---|---|---|---|---|---|---|---|
| Jan. 29, 2016 | 34 | Male | Black | Yes | B+ | Jan. 29, 2016 | 55 | Male | Black | Yes | A+ |
| Feb. 8, 2016 | 23 | Female | Caucasian | Yes | O+ | Jan. 29, 2016 | 22 | Male | Black | Yes | O+ |
| Feb. 8, 2016 | 37 | Female | Black | No | A+ | Jan. 29, 2016 | 52 | Male | Black | Yes | B+ |

TABLE 4-continued

Details for normal off-clot human serum samples

| DOS | Age | Gender | Ethnicity | Smoke | ABO | DOS | Age | Gender | Ethnicity | Smoke | ABO |
|---|---|---|---|---|---|---|---|---|---|---|---|
| Feb. 8, 2016 | 21 | Female | Black | No | O+ | Jan. 29, 2016 | 22 | Male | Black | No | A+ |
| Feb. 8, 2016 | 37 | Female | Caucasian | Yes | A− | Jan. 29, 2016 | 24 | Male | Black | Yes | A+ |
| Feb. 8, 2016 | 24 | Female | Caucasian | No | A− | Feb. 5, 2016 | 18 | Female | Black | Yes | A+ |
| Jan. 29, 2016 | 21 | Male | Black | No | O+ | Jan. 29, 2016 | 40 | Male | Black | No | B+ |
| Jan. 29, 2016 | 23 | Male | Black | Yes | O+ | Jan. 29, 2016 | 33 | Male | Black | Yes | A+ |
| Jan. 29, 2016 | 25 | Female | Black | Yes | O+ | Jan. 12, 2016 | 42 | Male | Black | No | B+ |
| Jan. 29, 2016 | 25 | Male | Black | Yes | O+ | Jan. 29, 2016 | 22 | Male | Black | No | O+ |
| Feb. 5, 2016 | 27 | Female | Black | No | A+ | Jan. 29, 2016 | 22 | Female | Black | No | A+ |
| Jan. 29, 2016 | 21 | Male | Black | Yes | B+ | Jan. 29, 2016 | 41 | Male | Caucasian | Yes | A− |
| Feb. 8, 2016 | 21 | Female | Black | Yes | O+ | Jan. 29, 2016 | 23 | Male | Black | Yes | O+ |
| Jan. 29, 2016 | 20 | Male | Black | Yes | O+ | Jan. 12, 2016 | 39 | Male | Caucasian | Yes | A− |
| Jan. 12, 2016 | 31 | Male | Black | Yes | A+ | Jan. 29, 2016 | 18 | Male | Black | No | O+ |
| Jan. 29, 2016 | 29 | Male | Black | No | B+ | Jan. 29, 2016 | 19 | Male | Black | Yes | O+ |
| Jan. 29, 2016 | 42 | Male | Black | Yes | A+ | Jan. 29, 2016 | 23 | Female | Black | No | O+ |
| Jan. 29, 2016 | 20 | Male | Black | Yes | O+ | Jan. 29, 2016 | 18 | Female | Black | No | A+ |
| Jan. 29, 2016 | 39 | Female | Black | Yes | B+ | Jan. 29, 2016 | 42 | Male | Black | Yes | A+ |
| Jan. 29, 2016 | 30 | Male | Black | Yes | B+ | Jan. 29, 2016 | 24 | Male | Black | Yes | O+ |
| Jan. 29, 2016 | 22 | Male | Black | Yes | A+ | Jan. 29, 2016 | 53 | Male | Black | Yes | A+ |
| Jan. 29, 2016 | 35 | Male | Black | Yes | A+ | Jan. 12, 2016 | 24 | Male | Black | No | B+ |
| Jan. 29, 2016 | 24 | Male | Black | No | A+ | Jan. 29, 2016 | 59 | Female | Black | Yes | B+ |
| Feb. 5, 2016 | 18 | Female | Caucasian | No | O+ | Jan. 29, 2016 | 22 | Female | Black | Yes | O+ |
| Feb. 5, 2016 | 36 | Female | Black | No | B+ | Jan. 29, 2016 | 43 | Male | Black | No | A+ |

Table 4 provides details for normal off-clot human serum samples. Details on 50 US serum donors from FIG. 15A including date of sample blood draw (DOS), age at time of donation, gender, ethnicity, smoker status and ABO blood type. All donors were negative for HBV, HCV and HIV (data not shown).

TABLE 5

Human seroreactivity statistics

| Comparisons | Mean Diff. | 95.00% CI of diff. | Significant | Summary | P Value |
|---|---|---|---|---|---|
| STATISTICS FOR FIG. 15A | | | | | |
| AAV8 vs. LK03 | 0.508 | −0.017 to 1.033 | No | ns | 0.0644 |
| AAV8 vs. DJ | 2.085 | 1.56 to 2.61 | Yes | **** | <0.0001 |
| AAV8 vs. NP40 | 1.702 | 1.177 to 2.227 | Yes | **** | <0.0001 |
| AAV8 vs. NP59 | 1.56 | 1.035 to 2.085 | Yes | **** | <0.0001 |
| AAV8 vs. NP84 | 1.232 | 0.707 to 1.757 | Yes | **** | <0.0001 |
| LK03 vs. DJ | 1.577 | 1.052 to 2.102 | Yes | **** | <0.0001 |
| LK03 vs. NP40 | 1.194 | 0.669 to 1.719 | Yes | **** | <0.0001 |
| LK03 vs. NP59 | 1.052 | 0.5275 to 1.577 | Yes | **** | <0.0001 |
| LK03 vs. NP84 | 0.724 | 0.199 to 1.249 | Yes | ** | 0.0013 |
| DJ vs. NP40 | −0.382 | −0.908 to 0.143 | No | ns | 0.2947 |
| DJ vs. NP59 | −0.524 | −1.049 to 0.001 | No | ns | 0.0504 |
| DJ vs. NP84 | −0.853 | −1.378 to −0.328 | Yes | **** | <0.0001 |
| NP40 vs. NP59 | −0.142 | −0.667 to 0.383 | No | ns | 0.9712 |
| NP40 vs. NP84 | −0.47 | −0.995 to 0.055 | No | ns | 0.1083 |
| NP59 vs. NP84 | −0.328 | −0.853 to 0.197 | No | ns | 0.4709 |
| STATISTICS FOR FIG. 22A | | | | | |
| AAV8 vs. LK03 | 0.129 | −0.528 to 0.787 | No | ns | 0.9930 |
| AAV8 vs. DJ | 2.043 | 1.386 to 2.701 | Yes | **** | <0.0001 |
| AAV8 vs. NP40 | 1.536 | 0.879 to 2.193 | Yes | **** | <0.0001 |
| AAV8 vs. NP59 | 1.461 | 0.804 to 2.119 | Yes | **** | <0.0001 |
| AAV8 vs. NP84 | 0.915 | 0.257 to 1.572 | Yes | ** | 0.0013 |
| LK03 vs. DJ | 1.914 | 1.257 to 2.572 | Yes | **** | <0.0001 |
| LK03 vs. NP40 | 1.407 | 0.749 to 2.064 | Yes | **** | <0.0001 |
| LK03 vs. NP59 | 1.332 | 0.675 to 1.99 | Yes | **** | <0.0001 |
| LK03 vs. NP84 | 0.786 | 0.128 to 1.443 | Yes | ** | 0.0092 |
| DJ vs. NP40 | −0.508 | −1.165 to 0.150 | No | ns | 0.2316 |
| DJ vs. NP59 | −0.582 | −1.239 to 0.075 | No | ns | 0.1151 |
| DJ vs. NP84 | −1.129 | −1.786 to −0.471 | Yes | **** | <0.0001 |
| NP40 vs. NP59 | −0.074 | −0.732 to 0.583 | No | ns | 0.9995 |
| NP40 vs. NP84 | −0.621 | −1.278 to 0.036 | No | ns | 0.0759 |
| NP59 vs. NP84 | −0.547 | −1.204 to 0.111 | No | ns | 0.1633 |
| STATISTICS FOR FIG. 22B | | | | | |
| AAV8 vs. LK03 | 1.321 | 0.606 to 2.037 | Yes | **** | <0.0001 |
| AAV8 vs. DJ | 2.166 | 1.45 to 2.881 | Yes | **** | <0.0001 |
| AAV8 vs. NP40 | 1.967 | 1.251 to 2.682 | Yes | **** | <0.0001 |
| AAV8 vs. NP59 | 1.638 | 0.922 to 2.353 | Yes | **** | <0.0001 |

TABLE 5-continued

Human seroreactivity statistics

| Comparisons | Mean Diff. | 95.00% CI of diff. | Significant | Summary | P Value |
|---|---|---|---|---|---|
| AAV8 vs. NP84 | 1.888 | 1.172 to 2.603 | Yes | **** | <0.0001 |
| LK03 vs. DJ | 0.845 | 0.1291 to 1.56 | Yes | * | 0.0113 |
| LK03 vs. NP40 | 0.646 | −0.070 to 1.361 | No | ns | 0.1008 |
| LK03 vs. NP59 | 0.317 | −0.399 to 1.032 | No | ns | 0.7885 |
| LK03 vs. NP84 | 0.567 | −0.149 to 1.282 | No | ns | 0.2011 |
| DJ vs. NP40 | −0.199 | −0.915 to 0.5165 | No | ns | 0.9645 |
| DJ vs. NP59 | −0.528 | −1.244 to 0.188 | No | ns | 0.2706 |
| DJ vs. NP84 | −0.278 | −0.993 to 0.438 | No | ns | 0.8657 |
| NP40 vs. NP59 | −0.329 | −1.045 to 0.387 | No | ns | 0.7605 |
| NP40 vs. NP84 | −0.079 | −0.794 to 0.637 | No | ns | 0.9995 |
| NP59 vs. NP84 | 0.250 | −0.465 to 0.966 | No | ns | 0.9097 |

Table 5 provides human seroreactivity statistics. Comparative statistical data for all patients (FIG. 15A); separated male patients (FIG. 22A); and separated female patients (FIG. 22B).

To support future pre-clinical testing in nonhuman primates, seroreactivity with serum from a small cohort of 6 rhesus macaques (see Table 6, below) against the same panel of AAVs (see FIG. 15b) was assessed. Given the small cohort size, no statistically significant difference was seen for mean seroreactivity between the tested capsids (see Table 7, below) with the exception that seroreactivity against DJ was significantly lower than AAV8 ($P<0.01$). In vitro neutralization assays in human 2V6.11 permissive cells using serum from a limited cohort of 21 healthy human donors from the E.U. found mean similarity across all serotypes (see FIG. 15c, Table 8, below). Although all shuffled variants had lower mean levels of neutralization than LK03, only rAAV8 reached statistical significance ($P<0.001$) in this small cohort (n=21). One important potential application of these capsids relates to hemophilia B trials. Thus, seroreactivity assays with serum from 21 adult males with hemophilia B (see Table 9, below) was performed. Due to sample limitations, the variants to only the leading candidate, LK03, was compared. Results showed that compared to LK03, NP59 had more favorable mean seroreactivity in 66% of patients, while both NP84 and NP40 were more favorable in 53% of patients, although did not reach statistical significance in this small cohort (see FIG. 15d, Table 9). Cumulatively, these findings highlight the unique immunological features of variant capsids NP40, NP59, NP84 and DJ, particularly when it comes to seroprevalence and antibody-mediated neutralization.

TABLE 6

Nonhuman primate samples

| ID | Age at collection | Date of birth | Gender | Country of origin | Supplier |
|---|---|---|---|---|---|
| 2 | 24 months | Oct. 23, 2013 | Male | Maurice | BIOPRIM (France) |
| 3 | 24 months | Oct. 26, 2013 | Male | Maurice | BIOPRIM (France) |
| 7 | 24 months | Nov. 8, 2013 | Male | Maurice | BIOPRIM (France) |
| 9 | 23 months | Nov. 14, 2013 | Male | Maurice | BIOPRIM (France) |
| 11 | 23 months | Nov. 17, 2013 | Male | Maurice | BIOPRIM (France) |
| 19 | 23 months | Nov. 13, 2013 | Male | Maurice | BIOPRIM (France) |

Table 6 provides details for nonhuman primate serum samples from healthy adult rhesus *Macaca fascicularis* monkeys. Monkey ID, age at time of blood draw, date on birth (month/day/year), gender, country of origin and supplier are shown.

TABLE 7

Additional statistics from FIG. 15

| Comparisons | Mean Diff. | 95.00% CI of diff. | Significant | Summary | P Value |
|---|---|---|---|---|---|
| STATISTICS FOR FIG. 15B | | | | | |
| AAV8 vs. LK03 | 0.117 | −0.141 to 0.375 | No | ns | 0.7285 |
| AAV8 vs. DJ | 0.293 | 0.035 to 0.551 | Yes | * | 0.0196 |
| AAV8 vs. NP40 | 0.228 | −0.030 to 0.486 | No | ns | 0.1065 |
| AAV8 vs. NP59 | 0.163 | −0.095 to 0.421 | No | ns | 0.4014 |
| AAV8 vs. NP84 | 0.197 | −0.062 to 0.455 | No | ns | 0.2132 |
| LK03 vs. DJ | 0.176 | −0.082 to 0.434 | No | ns | 0.3192 |
| LK03 vs. NP40 | 0.111 | −0.1474 to 0.369 | No | ns | 0.7701 |
| LK03 vs. NP59 | 0.046 | −0.2125 to 0.304 | No | ns | 0.9936 |
| LK03 vs. NP84 | 0.080 | −0.179 to 0.338 | No | ns | 0.9290 |
| DJ vs. NP40 | −0.065 | −0.323 to 0.193 | No | ns | 0.9688 |
| DJ vs. NP59 | −0.130 | −0.389 to 0.128 | No | ns | 0.6343 |
| DJ vs. NP84 | −0.096 | −0.355 to 0.162 | No | ns | 0.8558 |
| NP40 vs. NP59 | −0.065 | −0.323 to 0.193 | No | ns | 0.9690 |
| NP40 vs. NP84 | −0.031 | −0.289 to 0.227 | No | ns | 0.9990 |
| NP59 vs. NP84 | 0.034 | −0.224 to 0.292 | No | ns | 0.9984 |
| STATISTICS FOR FIG. 15C | | | | | |
| AAV8 vs. LK03 | −0.725 | −1.032 to −0.418 | Yes | **** | <0.0001 |
| AAV8 vs. DJ | −0.466 | −0.773 to −0.159 | Yes | *** | 0.0004 |
| AAV8 vs. NP40 | −0.422 | −0.729 to −0.115 | Yes | ** | 0.0018 |
| AAV8 vs. NP59 | −0.567 | −0.874 to −0.260 | Yes | **** | <0.0001 |

TABLE 7-continued

Additional statistics from FIG. 15

| Comparisons | Mean Diff. | 95.00% CI of diff. | Significant | Summary | P Value |
|---|---|---|---|---|---|
| AAV8 vs. NP84 | −0.433 | −0.740 to −0.126 | Yes | ** | 0.0012 |
| LK03 vs. DJ | 0.258 | −0.049 to 0.565 | No | ns | 0.1506 |
| LK03 vs. NP40 | 0.303 | −0.004 to 0.610 | No | ns | 0.0550 |
| LK03 vs. NP59 | 0.158 | −0.149 to 0.465 | No | ns | 0.6682 |
| LK03 vs. NP84 | 0.292 | −0.015 to 0.599 | No | ns | 0.0720 |
| DJ vs. NP40 | 0.045 | −0.262 to 0.352 | No | ns | 0.9982 |
| DJ vs. NP59 | −0.10 | −0.408 to 0.206 | No | ns | 0.9308 |
| DJ vs. NP84 | 0.034 | −0.273 to 0.341 | No | ns | 0.9995 |
| NP40 vs. NP59 | −0.146 | −0.453 to 0.162 | No | ns | 0.7389 |
| NP40 vs. NP84 | −0.011 | −0.318 to 0.296 | No | ns | >0.9999 |
| NP59 vs. NP84 | 0.134 | −0.173 to 0.441 | No | ns | 0.7983 |
| STATISTICS FOR FIG. 15D | | | | | |
| NP40 vs. NP59 | 0.179 | −0.093 to 0.451 | No | ns | 0.3108 |
| NP40 vs. NP84 | 0.051 | −0.221 to 0.323 | No | ns | 0.9606 |
| NP40 vs. LK03 | 0.041 | −0.231 to 0.313 | No | ns | 0.9782 |
| NP59 vs. NP84 | −0.129 | −0.401 to 0.143 | No | ns | 0.5970 |
| NP59 vs. LK03 | −0.138 | −0.410 to 0.134 | No | ns | 0.5390 |
| NP84 vs. LK03 | −0.010 | −0.282 to 0.262 | No | ns | 0.9997 |

Table 7 provides additional statistics from FIG. 16. Comparative statistical data for seroreactivity from 6 adult rhesus macaques (FIG. 15B); neutralization from 21 healthy adults from the E.U. (FIG. 15C); and seroreactivity from 21 adult hemophilia B patients (FIG. 15D).

TABLE 8

Human serum samples - healthy donors

| | Country of origin | Gender | Age |
|---|---|---|---|
| 1 | France | Male | 10 |
| 2 | France | Male | 3 |
| 3 | France | Male | 7 |
| 4 | France | Female | 46 |
| 5 | France | Female | 7 |
| 6 | France | Female | 22 |
| 7 | France | Female | 39 |
| 8 | France | Female | 30 |
| 9 | Netherlands | Female | 28 |
| 30 | France | Male | 38 |
| 31 | France | Male | 39 |
| 32 | France | Male | 31 |
| 33 | France | Male | 39 |
| 34 | France | Male | 63 |
| 35 | France | Female | 50 |
| 36 | France | Female | 39 |
| 37 | France | Female | 47 |
| 38 | France | Male | 37 |
| 39 | France | Male | 62 |
| 40 | France | Female | 46 |
| 41 | France | Male | 53 |

Table 8 provides details for human serum samples from 21 healthy donors from the E.U. used for the neutralization studies. Subject ID, country of origin, gender and age (in years) at time of donation are shown.

TABLE 9

Human serum samples - hemophilia B

| ID | Age | Gender |
|---|---|---|
| 1 | 19 | Male |
| 3 | 45 | Male |
| 5 | 19 | Male |
| 6 | 24 | Male |
| 7 | 27 | Male |

TABLE 9-continued

Human serum samples - hemophilia B

| ID | Age | Gender |
|---|---|---|
| 9 | 37 | Male |
| rf206 | 51 | Male |
| rf209 | 20 | Male |
| rf211 | 30 | Male |
| rf212 | 28 | Male |
| rf210 | 27 | Male |
| rf012 | 25 | Male |
| rf016 | 31 | Male |
| rf013 | 32 | Male |
| rf010 | 22 | Male |
| rf011 | 30 | Male |
| rf208 | 41 | Male |
| rf205 | 53 | Male |
| sj008 | 22 | Male |
| rf009 | 28 | Male |
| rf014 | 66 | Male |

Table 9 provides details for human serum samples from 21 donors with confirmed hemophilia B. Patient ID, age at time of donation and gender are shown.

Comparative Human Hepatic Organoid Transduction Assays Support Differential Transduction In addition to treating liver diseases in vivo with intravenous delivery of rAAV, ex vivo gene delivery or gene correction studies in transplantable human hepatic organoids represents a potential future therapy for some liver diseases. To establish whether the evolved liver variants could also be used ex vivo, GFP transduction assessments in primary human liver organoids were performed. In duplicate organoid transduction time course assessments spanning 14 days (see FIG. 16a, b), shuffled variant NP40 showed significantly greater functional human liver organoid transduction over rAAV2 and rAAV8 by mean fluorescent intensity (MFI) imaging of GFP, and had equivalent MFI to that seen from the high-level transduction achieved with LK03 and DJ—known strong in vitro transducers. NP59 had similar transduction levels as rAAV2 and had much greater MFI than rAAV8. NP84 was not a strong transducer of human hepatic organoids ex vivo.

Discussion

Choosing the best rAAV serotype for optimum human hepatic delivery has grown increasingly complex and controversial in recent years stemming from differences in experimental setup, data interpretation and reproducibility[3,4,29,30]. Given the number of altered variables in experimental design by different groups, this is perhaps not surprising. No two studies have been performed identically, thus comparisons have and will continue to be confounded. At its simplest, use of different model systems for assessment has created difficulties. It is well known that rAAV transduction in in vitro culture systems does not correlate with in vivo transduction levels, thus testing in these lines for the purposes of establishing functional in vivo transduction without other supportive data should be abandoned. Even with in vivo transduction measurements, use of different species with no human xenograft (mice), has been shown to not recapitulate transduction outcomes in humans[1,5] and such results should be interpreted with caution. While no model organism perfectly recapitulates a human liver, current evidence demonstrates that assessing functional transduction in xenograft liver models engrafted with primary human hepatocytes has best recapitulated existing patient data[3,4] and should be the collective model moving forward. Similarly, quantifying functional transduction by vector copy number is grossly inaccurate as it measures all genomes post-entry irrespective of functionality. This is critically important quantitatively as most AAV genomes do not complete the intracellular trafficking and expression cascade[31,32] required for therapeutic relevance, thus leading to large over-estimations of transduction.

In this study, the potential importance of controlling for and reporting the repopulation levels in humanized mice since the relative ratio of mouse to human hepatocytes was likely critical to overall transduction efficiency levels when rAAV virions were limiting was demonstrated. To date, it has been challenging to even attempt to reproduce studies published in the field due to poor methods reporting and low numbers of treated subjects. To facilitate comparisons between future studies, additional variables should also be stringently controlled and reported including: detailed mouse maintenance conditions, strain backgrounds of mice or other animal models, human hepatocyte donor characteristics (age, gender, disease state, location), method of injection, AAV production and purification methods employed, detailed transfer vector descriptions (including promoter, transgene, enhancer, polyA, genome type, etc.), method of titration, final resuspension solution, method of quantifying vector transduction and any normalizations performed.

High levels of preexisting nAbs against parental serotypes in patients treated to date have made pre-screening a requirement for all future trials. Prevalence of nAbs varies with patient geography, health status, gender, age and likely many other variables[33]. Among known hepatotropic serotypes, the limited human studies to date have shown highest nAb levels against rAAV2[9,10,27,28,34], rAAV5[10,28,34,35], rAAV8[10,28,27] and rAAV3b[9,28] along with the highly related rAAV-LK03 capsid[9]. New capsids with different parentage and reduced susceptibility to neutralization are needed to enable future liver gene therapy trials with maximum patient enrollment. Few antigenic epitopes have been characterized for parental serotypes or shuffled variants, thus precluding rational design attempts that still maximize capsid library diversity. Screening future capsid variants in preclinical validations against pools of patient antibodies represents an unbiased approach to improve the ultimate utility of variants moving into the clinic.

An exciting possibility with the new capsid variants that transduce human liver at such high levels would be to decrease patient doses while still enabling desired expression levels. This could bypass several hurdles to rAAV being an effective vector for future liver gene therapy trials: a) reduced probability for neutralization as fewer circulating capsids would be present; b) reduced production costs to offset the staggering treatment costs that can reach $1 million dollars per patient[36,37]; and c) reduced probability for capsid-specific T-cell responses against transduced hepatocytes[38]. Similarly, high-level functional transduction will be key for the field as those in the field collectively transition from treating simple non-cell autonomous liver diseases like Crigler-Najjar and the hemophilias, to cell-autonomous diseases like ornithine transcarbamylase deficiency and other urea cycle disorders which will require at least 20-50% of human hepatocytes to be functionally transduced for clinical efficacy.

Methods

Shuffled AAV Capsid Plasmid Library Generation.

The shuffled AAV capsid library was generated as described previously[4] with modifications described below. The AAV capsid genes from serotypes 1, 2, 3b, 4, 5, 6, 8, 9_hu14, avian and bovine were PCR-amplified with high-fidelity polymerase and cloned using a Zero Blunt TOPO PCR Cloning Kit (Invitrogen Cat#K2800) followed by Sanger sequencing of individual clones. Capsid genes were excised, mixed at 1:1 ratios and digested using DNaseI at various intervals from 1-30 min. These pooled reactions were separated on a 1% (w/v) agarose gel, and fragments <1,000-bp were excised and used in a primer-less PCR reassembly step, followed by a second round of PCR using primers binding outside the capsid gene:

```
                                          (SEQ ID NO: 14)
           Fwd: 5'-GTCTGAGTGACTAGCATTCG-3'

(SEQ ID NO: 15)
           Rev: 5'-GCTTACTGAAGCTCACTGAG-3'
```

Figure 18:
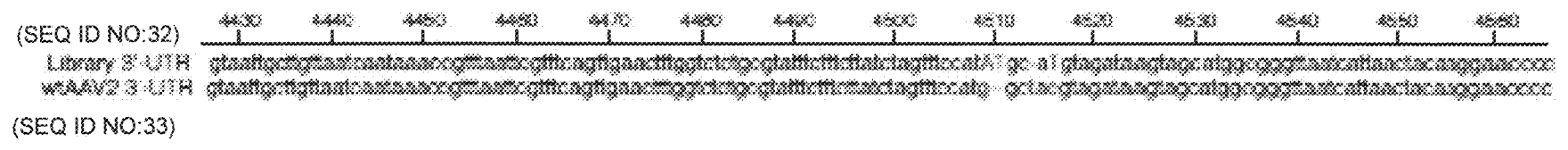

Full-length shuffled capsid genes were cloned into a modified pAAV2 host plasmid (ITR-Rep2-Cap cloning site-AAV2 3'UTR sequence-ITR) with SwaI/NsiI restriction sites flanking the CAP insertion site and a modified portion of the AAV2 VP1 3' UTR (see FIG. 18). Ligations were transformed into numerous independent electro-competent cell aliquots and diluted 1:40 in LB culture with low ampicillin (50-g/mL) for minimal expansion. An aliquot was plated, and 100 clones were picked and Sanger sequenced to validate library diversity. The pool of library plasmids was purified using an EndoFree Plasmid Mega Kit (Qiagen Cat#123811) and used to produce libraries of replication-competent AAV virions.

AAV Library Production, Vector Production and Titration.

AAV library productions were produced using a $Ca_3(PO_4)_2$ transfection protocol (wtAAV library plasmid pool and pAdS helper) in HEK293T cells (ATCC Cat#CRL-3216) followed by double cesium chloride density gradient purification, dialysis as previously described[39], and resuspended in dPBS with 5% sorbitol (w/v) and 0.001% Pluronic F-68 (v/v). AAV libraries were titered for Rep by TaqMan qPCR with the following primer/probe set:

```
                                          (SEQ ID NO: 16)
     Fwd:     5'-TTCGATCAACTACGCAGACAG-3'

(SEQ ID NO: 17)
     Rev:     5'-GTCCGTGAGTGAAGCAGATATT-3'
```

```
                                              (SEQ ID NO: 18)
Probe:    5'/FAM/TCTGATGCTGTTTCCCTGCAGACA/BHQ-1/-3'
```

Recombinant AAV vector productions were similarly produced as above but as triple transfections (PEI or Ca$_3$(PO$_4$)$_2$) with pAdS helper, AAV transfer vector (ssAAV-CAG-GFP-WPRE-SV40 pA from Addgene #37825; ssAAV-EF1α-FLuc-WPRE-HgHpA cloned in-house; ssAAV-LSP1-GFP-WPRE-BgHpA from Ian Alexander[40]), and pseudotyping plasmids for each capsid of interest. AAV-GFP vectors were titered on GFP by TaqMan qPCR with the following primer/probe set:

```
                                              (SEQ ID NO: 19)
Fwd:      5'-GACGTAAACGGCCACAAGTT-3'

(SEQ ID NO: 20)
Rev:      5'-GAACTTCAGGGTCAGCTTGC-3'

(SEQ ID NO: 21)
Probe:    5'/FAM/CGAGGGCGATGCCACCTACG/BHQ-1/-3'
```

AAV-FLuc vectors were titered by TaqMan qPCR with the following primer/probe set:

```
                                              (SEQ ID NO: 22)
Fwd:      5'-CACATATCGAGGTGGACATTAC-3'

(SEQ ID NO: 23)
Rev:      5'-TGGTTTGTATTCAGCCCATAG-3'

(SEQ ID NO: 24)
Probe:    5'/FAM/ACTTCGAGATGAGCGTTCGGCTG/BHQ-1/-3'
```

Mice.

Fah/Rag2/Il2rgc (FRG) deficient mice[25] on a C57BL/6J background and FRG mice on a NOD-strain background (FRGN) were housed and maintained in specific-pathogen-free barrier facilities at either Oregon Health & Science University (U.S.), Stanford University (U.S.), or the Children's Medical Research Institute (Australia). FRG/N mice were maintained on irradiated high-fat low-protein mouse chow (U.S.: Lab Diet Cat#Picolab-5LJ5; Australia: Specialty Feeds Cat#5415-024) ad libitum to decrease flux through the tyrosine pathway. Beginning on the day of transplantation, FRG/N mice in the U.S. were maintained on 1-week of acidified water to prevent bacterial growth, while mice in Australia received acidified water supplemented with 25-mg/mL Baytril antibiotic. The following week, mice in the U.S. were switched to 1-week of 8-mg/L SMX-TMP antibiotic water (supplemented with 0.7-mol/L dextrose for palatability), while mice in Australia were switched to 1-mg/L NTBC water. Thereafter, at each location, FRG/N mice were cycled on and off 1-mg/L NTBC water as described[25,41]. Adult Balb/cJ mice were purchased from The Jackson Laboratories (Cat#00651) for imaging studies. The Institutional Animal Care & Use Committees of Stanford University, Oregon Health & Science University and the Children's Medical Research Institute approved all mouse procedures.

Hepatocyte Transplantation.

Donor human hepatocytes for transduction studies were acquired from either Celsis (Cat#F00995, Lot#LTS) from a 17-year-old Caucasian female for U.S. studies, or from Lonza (Cat#CC-25915, Lot#9F3097) from a Caucasian male for Australian studies. Weanling FRG/N mice were pre-conditioned with administration of recombinant human adenovirus expressing urokinase (1.25E9 PFU by tail vein in Australia and 5E10 PFU retroorbitally in U.S.) 24-hr prior to transplant to promote human cell engraftment. 5E5-1E6 human hepatocytes were injected intrasplenically into anesthetized recipient FRG/N mice and cycled on/off NTBC to promote human hepatocyte engraftment and expansion[25]. Broad-spectrum antibiotic (Ceftiofur 4-mg/kg in U.S.; Baytril 5.6-mg/kg in Australia) was given by intraperitoneal injection immediately prior to surgery and for two days following surgery. Several weeks post-transplant, circulating human albumin levels were used to assess percent human engraftment from several microliters of peripheral mouse blood.

Human Albumin ELISA.

To assess percent human engraftment in chimeric mice, several microliters of peripheral blood were used to measure human albumin using the Bethyl Quantitative Human Albumin ELISA kit (Cat#E88-129) per manufacturer's protocol. This same kit was used to detect secreted human albumin levels in the media supernatant during human hepatic organoid differentiation as a marker of successful differentiation.

Replication-Competent AAV Library Selection in Humanized FRG Mice.

Female FRG mice with confirmed humanization were transduced with 5E10 vg/mouse of AAV library by intravenous tail vein administration. 5E9 PFU of wild-type replication competent human Adenovirus-5 (hAd5) (ATCC Cat#VR-5) in 20-μl volume was administered by intravenous retroorbital injection 24-hr later. Transduced humanized livers were harvested 48-hr after hAd5 administration. Livers were minced, subjected to three freeze-thaw cycles and further homogenization to ensure complete lysis of remaining hepatocytes. Liver lysates were then subjected to 65° C. for 30-min to heat inactivate the hAd5, and spun at 14,000 RPM at 4° C. to separate viral-containing supernatants from cellular debris. Viral supernatants were dot-blot titered after each round to ensure continual administration of 5E10 vg/mouse at each subsequent round of in vivo selection for a total of 5 rounds.

Sequential Sub-Screen on Evolved Human-Liver Library Against Pooled Human Immunoglobulins.

PureProteome protein-G magnetic beads (Millipore Cat#LSKMAGG02) were pre-loaded with pooled human immunoglobulins (Baxter Gammagard IVIG Liquid™, Cat #LE1500190, Lot #LE12J338AB) for 60-min at 4° C. per bead manufacturer instructions for direct immunoprecipitation protocols. The AAV library from round 5 of the in vivo screen was applied to the IgG-loaded beads for 12-hr rotating at 4° C. Bound and unbound fractions were natively eluted per manufacturer instructions and run over a new set of IgG-loaded beads to enrich for true IgG-bound and unbound AAV populations. Viral gDNA was extracted from each fraction using the MinElute Virus Spin Kit (Qiagen Cat#57704), followed by PCR amplification using:

```
                                              (SEQ ID NO: 25)
     Fwd: 5'-TGGATGACTGCATCTTTGAA-3'

(SEQ ID NO: 26)
     Rev: 5'-TGCTTACCCGGGTTACGAGTCAGGTATCTG-3'
```

AAV capsid ORFs from round 2 of the subscreen for IgG evasion were cloned using a Zero Blunt TOPO Kit and 100 clones were sent for full Sanger sequencing to assess diversity with primers:

Fwd-1: 5'-TGGATGACTGCATCTTTGAA-3' (SEQ ID NO: 27)

Fwd-2: 5'-ATTGGCATTGCGATTCC-3' (SEQ ID NO: 28)

Vectorization and Sequence Contribution Analysis of Evolved AAV Capsids.

Contigs were assembled using Geneious R7 v7.1.9 software and clones selected for vectorization were amplified using:

Fwd: 5'-AAATCAGGTATGGCTGCCGATG-3' (SEQ ID NO: 30)

Rev: 5'-GCTTCCCGGGATGGAAACTAGATAAGAAAG-3' (SEQ ID NO: 31)

PCR amplicons were cloned in-frame, downstream of Rep, into predigested recipient pCap packaging plasmid containing AAV2 Rep without ITRs using SwaI and XmaI restriction sites. AAV capsid genes were sequence verified and resultant contigs were analyzed using a custom Perl pipeline that assesses multiple sequence alignments using Clustal Omega (EMBL-EBI) to generate the overall serotype composition of the shuffled AAVs by comparison of DNA and amino acid sequences with the parental AAV serotypes based on maximum likelihood. Xover 3.0 DNA/protein shuffling pattern analysis software was used to generate parental fragment crossover maps of shuffled variants[42]. Each parental serotype was color coded as follows: AAV1: red; AAV2: forest green; AAV3b: marine blue; AAV4: magenta; AAV5: tv blue; AAV6: green cyan; AAV8: orange; AAV9: pale green; avian: purple; bovine: deep salmon).

PacBio Library Preparation and Full-Length Single-Molecule Capsid Sequencing.

Pacific Biosciences (PacBio) SMRT bell libraries were prepared following the "Procedure and Checklist-2 kb Template Preparation and Sequencing" protocol from PacBio using the SMRTbell Template Prep Kit v1.0 (PacBio Cat#100-259-100). PacBio 'Binding and Annealing' calculator was used to determine appropriate concentrations for annealing and binding of SMRTbell libraries. SMRTbell libraries were annealed and bound to P6 DNA polymerase for sequencing using the DNA/Polymerase Binding Kit P6 v2.0 (PacBio Cat#100-372-700). Bound SMRTbell libraries were loaded onto SMRT cells using standard MagBead protocols and the MagBead Buffer Kit v2.0 (PacBio Cat#100-642-800). The standard MagBead sequencing protocol was followed with the DNA Sequencing Kit 4.0 v2 (PacBio Cat#100-612-400, also known as P6/C4 chemistry). Sequencing data was collected for 6-hour movie times with 'Stage Start' not enabled. Circular consensus sequence (CCS) reads were generated using the PacBio SMRT portal and the RS_ReadsOfinsert.1 protocol, with filtering set at Minimum Full Pass=3 and Minimum Predicted Accuracy=95%.

Bioinformatic Assessment of PacBio Sequence Reads.

CCS reads with sequence lengths from 2,300-2,350 nucleotides were included in downstream bioinformatics analyses. Indels in CCS reads were corrected using an in-house algorithm that first assesses parental fragment identity to determine correct parental nucleotide sequences to compare for determining indels for correction. Single nucleotide polymorphisms that did not result in indels, were maintained. Corrected sequences in FASTA format were then aligned with MUSCLE[43]. Phylogenetic analyses were conducted using the maximum-likelihood method in RAxML[44]. Percent parental conservation was determined using an in-house algorithm that identifies the percentage of each parent on each aligned position in the shuffled library. The maximum square size indicates that 100% of variants share that amino acid from that parent at that position. All other square sizes are proportional to the percent of variants from 0-100% that have that amino acid at that position from that parent.

Transduction Mouse Experiments.

All mice received normodynamic intravenous lateral tail vein injections of 2E11 vg/mouse of ssAAV-CAG-GFP or ssAAV-LSP1-GFP pseudotyped with various capsid serotypes. Treated mice were monitored for 14-days and livers were harvested under inhalation isoflurane anesthesia. Liver tissue was cut into several 2×5-mm pieces from several lobes and fixed in 10× volume of 4% PFA for 5-hr at 25° C. protected from light. Fixed tissue was washed 1× in PBS and put through a sucrose cryoprotection and rehydration series (10% w/v sucrose for 2-hr at 25° C., 20% w/v sucrose overnight at 4° C., 30% w/v sucrose for 4-hr at 25° C.). Liver pieces were rinsed in PBS, blotted dry and mounted in cryomolds (Tissue-Tek Cat#4557) with OCT (Tissue-Tek Cat#4583) and frozen in a liquid nitrogen-cooled isopentane bath. Cryomolds were placed at −80° C. until sectioning.

Liver Immunohistochemistry.

Fluorescent staining of liver sections for human FAH was performed per established protocols[45] with minor modifications. Modifications included: fixing slides in ice-cold methanol for 10 minutes rather than acetone at room temperature; blocking with 10% rather than 5% donkey serum (Santa Cruz, Cat#sc-2044) in dPBS for 30-min at RT in a humidified chamber; primary antibody solution was 100-μl of monoclonal rabbit anti-human FAH IgG antibody (Sigma, Cat#HPA-04137) at 1:100 (Australia) or 1:500 (U.S.) in 10% donkey serum incubated overnight at 4° C. (U.S.) or for 2-hrs at RT (Australia); secondary antibody solution was 100-μl of donkey anti-rabbit AlexaFluor 647 IgG antibody (Invitrogen, Cat#A31573) at 1:500 along with Hoechst 33342 (Molecular Probes, Cat#H-3570) at 1:1,000 in PBST for 1-hr at RT in dark conditions (U.S.), or 100-μl of donkey anti-rabbit AlexaFluor 594 IgG antibody (Invitrogen, Cat#A21207) at 1:500 in PBS for 1-hr at RT in dark conditions followed by DAPI at 80-ng/mL in PBS; slides were mounted with 3 drops of ProLong Gold Antifade (Invitrogen, Cat#P36934) (U.S.) or ProLong Diamond Antifade (Invitrogen, Cat#P36961) (Australia). Antibody validity controls included secondary-only staining, and demonstration on positive control frozen human liver tissue sections (Zyagen, Cat#HF-314) and negative control frozen untreated mouse liver sections. Confocal imaging in the U.S. was performed on a Leica TCS SP8-X WLL inverted confocal microscope with a 20× oil immersion objective and imaged with Leica AF software v3.3.0.10134, while confocal imaging in Australia was performed on an inverted Zeiss Axio with 20× objective and imaged with Zen Pro software. Z-stacks were compressed using ImageJ v2.0.0 and overlaid in Adobe Photoshop CS6 v13.0. Signal co-localization of AAV-GFP signal with mouse or human hepatocytes was done using Volocity v6.3 software and re-validated with counts by eye on a subset of sections.

Hepatic Fluorescent In Situ Hybridization (FISH).

Sequential RNA and DNA FISH on OCT-embedded frozen liver sections from treated humanized mice was performed as described[46]. To localize RNA FISH signals, slides were analyzed by acquiring multiple 3D images, recording coordinates of all imaged fields, and combining planes from each field using an EDF (extended depth of focus) function into a series of single-focused images for each imaged field. Subsequent DNA FISH was completed as described[46] and the previously imaged fields were imaged again, in the same manner. Comparing the image sets allows one to determine the relative position of RNA and DNA signals. The addition of GFP immunostaining showed the relationship between transcription and translation of AAV transfer vector DNA. Images were taken on a Nikon Eclipse E800 wide-field microscope (60× Plan Apochromat objective with 1.4-NA) with a Photometrics Coolsnap ES camera and Nikon NIS Elements software v4.2.

Functional Validation of Human Hepatic Organoid Cultures.

Human liver non-parenchymal cells from a 23-year-old male were cultured as described[47,48] with minor modifications (gastrin was omitted and ALKS inhibitor SB431542 was added). To functionally demonstrate hepatic origin of organoids, media from organoid cultures was tested for the presence of human albumin by ELISA (human albumin=58.3-ng/mL).

Human Hepatic Organoid Transduction with AAV.

Initiated hepatic organoid cultures were passaged at a ratio of 1:4 into standard organoid conditions (embedding in >95% Matrigel followed by addition of liquid media) in 24-well suspension plates after two weeks of growth. After the fifth organoid passage, ssAAV-CAG-GFP preparations of each serotype were added at MOI 500K to each well. Media was changed after a 3-day incubation and daily thereafter, and the emergence of GFP expression was monitored daily by fluorescence microscopy and brightfield imaging. After 14 days of imaging on an EVOS F1 Imaging System (ThermoFisher Cat#AMF4300), single hepatic cells were dissociated from the organoid with TrypLE Express (ThermoFisher, Cat#1797945) and 100K dissociated cells were analyzed for GFP positivity by flow cytometry (BD Canto II).

Indirect Seroreactivity ELISA Assay for Anti-AAV Antibodies in Human Serum.

Off-clot serum collected from peripheral blood of 50 healthy U.S. adults (see Table 4) was used as the primary antibody in an indirect ELISA. Pooled human IgG (Baxter, Cat#LE1500190, Lot#LE12P180AB) from thousands of donors was used to prepare a standard curve (sixteen 2-fold dilutions of 100-mg/ml stock IVIG in blocking buffer). Shuffled and parental AAV capsids served as antigens (5E8 vector genomes/well). Human IgG standards were assessed in replicates of six and all AAV samples were assessed in triplicate. IgG standards and AAV samples were fixed to wells of a 96-well immunoplate with 50-µl coating solution (13 mM $Na_2CO_3$, 35 mM $NaHCO_3$ in water, pH 9.6), plates were sealed and incubated overnight at 4° C. Plates were washed 2× with PBST containing 0.05% Tween-20 and blocked with blocking buffer (PBS, 6% BSA, 0.05% Tween-20) for 1-hr at 25° C. Plates were washed 2× with PBST. Each of the 50 human sera samples was diluted in blocking buffer (1:100-1:2,000), and 50-µl was added to experimental wells. Plates were incubated for 2-hr at 37° C. and then washed 2× in PBST. Polyclonal sheep anti-human IgG-HRP secondary antibody (GE Bioscience Cat#NA933V) was diluted 1:500 in wash buffer and 100-µl added to each well to detect bound antibodies in the human sera. Plates were incubated for 2-hr at 37° C. and washed 2× in PBST. OPD substrate (o-phenylenediaminedihydrochloride, Sigma Cat#P4664) was added at 100-µl/well in a 0.1M sodium citrate buffer and plates were incubated at 25° C. for exactly 10-min. The reaction was stopped with 50-4/well of 3M $H_2SO_4$ and the absorbance determined at 490-nm on a microplate reader (Bio-Rad). A set of blank wells was used to subtract background for non-specific binding of antibodies to the immunoplate. Standards were plotted using Four Parameter Logistic curve fitting to determine sample concentrations that fall within the linear range of the dilution series and detection limits using Prism v6.0 software. The same assay was performed on a cohort of 21 adult males with hemophilia B (see Table 9).

Indirect Seroreactivity ELISA Assay for Anti-AAV Antibodies in Normal Rhesus Macaque Serum.

The seroreactivity ELISA was performed as previously described[49] with plates coated at 1E9 vp/well. Off-clot serum was collected from peripheral blood from 6 rhesus macaques (see Table 6).

Luminescence-Based AAV Neutralization Assay with Individual Human Serum Samples.

The neutralization assay was performed as previous described[50]. Off-clot serum was collected from peripheral blood of 21 healthy E.U. individuals (see Table 8). ssAAV-CMV-FLuc vector was used as the transfer vector at an MOI of 200.

False-Colored Structural Capsid Mapping.

Chimeric capsids were false-color mapped onto the AAV2 capsid structure 1LP3[51] using Pymol v1.7.6.0. Mapped colors correspond to parental serotype colors used in the parental fragment crossover maps. Exterior capsid views have all chains represented, while cross-section views have chains surrounding a cylinder at the 5-fold symmetry axis removed exposing the capsid interior lumen.

Statistics.

Statistical analyses were conducted with Prism v6 and Excel v14.5.8 software. Experimental values for each panel in FIG. 15 were log+1 transformed before being assessed via two-way ANOVA using Tukey's multiple comparisons test. P values <0.05 were considered statistically significant. Additional experimental differences were evaluated using a Student's unpaired two-tailed t-test assuming equal variance.

REFERENCES

1 Nathwani, A. C. et al. Long-term safety and efficacy of factor IX gene therapy in hemophilia B. *The New England journal of medicine* 371, 1994-2004, doi:10.1056/NEJMoa1407309 (2014).

2 Manno, C. S. et al. Successful transduction of liver in hemophilia by AAV-Factor IX and limitations imposed by the host immune response. *Nature medicine* 12, 342-347, doi:10.1038/nm1358 (2006).

3 Vercauteren, K. et al. Superior In vivo Transduction of Human Hepatocytes Using Engineered AAV3 Capsid. *Molecular therapy: the journal of the American Society of Gene Therapy* 24, 1042-1049, doi:10.1038/mt.2016.61 (2016).

4 Lisowski, L. et al. Selection and evaluation of clinically relevant AAV variants in a xenograft liver model. *Nature* 506, 382-386, doi:10.1038/nature12875 (2014).

5 Nathwani, A. C. et al. Adenovirus-associated virus vector-mediated gene transfer in hemophilia B. *The New England journal of medicine* 365, 2357-2365, doi:10.1056/NEJMoa1108046 (2011).

6 Li, C. et al. Neutralizing antibodies against adeno-associated virus examined prospectively in pediatric patients with hemophilia. *Gene therapy* 19, 288-294, doi:10.1038/gt.2011.90 (2012).

7 Erles, K., Sebokova, P. & Schlehofer, J. R. Update on the prevalence of serum antibodies (IgG and IgM) to adeno-associated virus (AAV). *Journal of medical virology* 59, 406-411 (1999).

8 Calcedo, R. et al. Adeno-associated virus antibody profiles in newborns, children, and adolescents. *Clinical and vaccine immunology: CVI* 18, 1586-1588, doi:10.1128/CVI.05107-11 (2011).

9 Ling, C. et al. Prevalence of neutralizing antibodies against liver-tropic adeno-associated virus serotype vectors in 100 healthy Chinese and its potential relation to body constitutions. *Journal of integrative medicine* 13, 341-346, doi:10.1016/S2095-4964(15)60200-X (2015).

10 Liu, Q. et al. Neutralizing antibodies against AAV2, AAV5 and AAV8 in healthy and HIV-1-infected subjects in China: implications for gene therapy using AAV vectors. *Gene therapy* 21, 732-738, doi:10.1038/gt.2014.47 (2014).

11 Liu, Q. et al. The prevalence of neutralizing antibodies against AAV serotype 1 in healthy subjects in China: implications for gene therapy and vaccines using AAV1 vector. *Journal of medical virology* 85, 1550-1556, doi:10.1002/jmv.23647 (2013).

12 Mingozzi, F. et al. CD8(+) T-cell responses to adeno-associated virus capsid in humans. *Nature medicine* 13, 419-422, doi:10.1038/nm1549 (2007).

13 Grimm, D. et al. In vitro and in vivo gene therapy vector evolution via multispecies interbreeding and retargeting of adeno-associated viruses. *Journal of virology* 82, 5887-5911, doi:10.1128/JVI.00254-08 (2008).

14 Li, W. et al. Engineering and selection of shuffled AAV genomes: a new strategy for producing targeted biological nanoparticles. *Molecular therapy: the journal of the American Society of Gene Therapy* 16, 1252-1260, doi:10.1038/mt.2008.100 (2008).

15 Kotterman, M. A. & Schaffer, D. V. Engineering adeno-associated viruses for clinical gene therapy. *Nature reviews. Genetics* 15, 445-451, doi:10.1038/nrg3742 (2014).

16 Gray, S. J. et al. Directed evolution of a novel adeno-associated virus (AAV) vector that crosses the seizure-compromised blood-brain barrier (BBB). *Molecular therapy: the journal of the American Society of Gene Therapy* 18, 570-578, doi:10.1038/mt.2009.292 (2010).

17 Jang, J. H. et al. An evolved adeno-*associated viral variant enhances gene delivery and gene targeting in neural stem cells. Molecular therapy: the journal of the American Society of Gene Therapy* 19, 667-675, doi:10.1038/mt.2010.287 (2011).

18 Davidoff, A. M. et al. Comparison of the ability of adeno-associated viral vectors pseudotyped with serotype 2, 5, and 8 capsid proteins to mediate efficient transduction of the liver in murine and nonhuman primate models. *Molecular therapy: the journal of the American Society of Gene Therapy* 11, 875-888, doi:10.1016/j.ymthe.2004.12.022 (2005).

19 Nathwani, A. C. et al. Safe and efficient transduction of the liver after peripheral vein infusion of self-complementary AAV vector results in stable therapeutic expression of human FIX in nonhuman primates. *Blood* 109, 1414-1421, doi:10.1182/blood-2006-03-010181 (2007).

20 Nathwani, A. C. et al. Self-complementary adeno-associated virus vectors containing a novel liver-specific human factor IX expression cassette enable highly efficient transduction of murine and nonhuman primate liver. *Blood* 107, 2653-2661, doi:10.1182/blood-2005-10-4035 (2006).

21 Salganik, M. et al. Adeno-associated virus capsid proteins may play a role in transcription and second-strand synthesis of recombinant genomes. *Journal of virology* 88, 1071-1079, doi:10.1128/JVI.02093-13 (2014).

22 Chatterjee, S., Smith, L. & Wong, K. Adeno-associated virus vector variants for high efficiency genome editing and methods thereof. United States patent (2015).

23 Xiao, W. D. et al. Gene therapy vectors based on adeno-associated virus type 1. *Journal of virology* 73, 3994-4003 (1999).

24 Zincarelli, C., Soltys, S., Rengo, G. & Rabinowitz, J. E. Analysis of AAV serotypes 1-9 mediated gene expression and tropism in mice after systemic injection. *Molecular Therapy* 16, 1073-1080, doi:10.1038/mt.2008.76 (2008).

25 Azuma, H. et al. Robust expansion of human hepatocytes in Fah-/-/Rag2-/-/Il2rg-/- mice. *Nature biotechnology* 25, 903-910, doi:10.1038/nbt1326 (2007).

26 Turunen, T. A. et al. Sleeping Beauty Transposon Vectors in Liver-directed Gene Delivery of LDLR and VLDLR for Gene Therapy of Familial Hypercholesterolemia. *Molecular therapy: the journal of the American Society of Gene Therapy* 24, 620-635, doi:10.1038/mt.2015.221 (2016).

27 Calcedo, R., Vandenberghe, L. H., Gao, G., Lin, J. & Wilson, J. M. Worldwide epidemiology of neutralizing antibodies to adeno-associated viruses. *The Journal of infectious diseases* 199, 381-390, doi:10.1086/595830 (2009).

28 van der Marel, S. et al. Neutralizing antibodies against adeno-associated viruses in inflammatory bowel disease patients: implications for gene therapy. *Inflammatory bowel diseases* 17, 2436-2442, doi:10.1002/ibd.21673 (2011).

29 Wang, L. et al. Comparative Study of Liver Gene Transfer With AAV Vectors Based on Natural and Engineered AAV Capsids. *Molecular therapy: the journal of the American Society of Gene Therapy* 23, 1877-1887, doi:10.1038/mt.2015.179 (2015).

30 Kay, M. A. Selecting the Best AAV Capsid for Human Studies. *Molecular therapy: the journal of the American Society of Gene Therapy* 23, 1800-1801, doi:10.1038/mt.2015.206 (2015).

31 Zen, Z., Espinoza, Y., Bleu, T., Sommer, J. M. & Wright, J. F. Infectious titer assay for adeno-associated virus vectors with sensitivity sufficient to detect single infectious events. *Human gene therapy* 15, 709-715, doi:10.1089/1043034041361262 (2004).

32 Grimm, D. et al. Titration of AAV-2 particles via a novel capsid ELISA: packaging of genomes can limit production of recombinant AAV-2. *Gene therapy* 6, 1322-1330, doi:10.1038/sj.gt.3300946 (1999).

33 Calcedo, R. & Wilson, J. M. Humoral Immune Response to AAV. *Frontiers in immunology* 4, 341, doi:10.3389/fimmu.2013.00341 (2013).

34 Boutin, S. et al. Prevalence of serum IgG and neutralizing factors against adeno-associated virus (AAV) types 1, 2, 5, 6, 8, and 9 in the healthy population: implications for gene therapy using AAV vectors. *Human gene therapy* 21, 704-712, doi:10.1089/hum.2009.182 (2010).

35 Halbert, C. L. et al. Prevalence of neutralizing antibodies against adeno-associated virus (AAV) types 2, 5, and 6 in cystic fibrosis and normal populations: Implications for gene therapy using AAV vectors. *Human gene therapy* 17, 440-447, doi:10.1089/hum.2006.17.440 (2006).

36 Han, X. & Ni, W. Cost-Effectiveness Analysis of Glybera for The Treatment of Lipoprotein Lipase Deficiency. *Value in health: the journal of the International Society* for Pharmacoeconomics and Outcomes Research 18, A756, doi:10.1016/j.jval.2015.09.2461 (2015).
37 Morrison, C. $1-million price tag set for Glybera gene therapy. *Nature biotechnology* 33, 217-218, doi:10.1038/nbt0315-217 (2015).
38 Mingozzi, F. & High, K. A. Immune responses to AAV vectors: overcoming barriers to successful gene therapy. *Blood* 122, 23-36, doi:10.1182/blood-2013-01-306647 (2013).
39 Grimm, D. Production methods for gene transfer vectors based on adeno-associated virus serotypes. *Methods* 28, 146-157 (2002).
40 Cunningham, S. C., Dane, A. P., Spinoulas, A., Logan, G. J. & Alexander, I. E. Gene delivery to the juvenile mouse liver using AAV2/8 vectors. *Molecular therapy: the journal of the American Society of Gene Therapy* 16, 1081-1088, doi:10.1038/mt.2008.72 (2008).
41 Wilson, E. M. et al. Extensive double humanization of both liver and hematopoiesis in FRGN mice. *Stem cell research* 13, 404-412, doi:10.1016/j.scr.2014.08.006 (2014).
42 Huang, W., Johnston, W. A., Boden, M. & Gillam, E. M. ReX: A suite of computational tools for the design, visualization, and analysis of chimeric protein libraries. *BioTechniques* 60, 91-94, doi:10.2144/000114381 (2016).
43 Edgar, R. C. MUSCLE: multiple sequence alignment with high accuracy and high throughput. *Nucleic Acids Res* 32, 1792-1797, doi:10.1093/nar/gkh340 (2004).
44 Stamatakis, A., Ludwig, T. & Meier, H. RAxML-III: a fast program for maximum likelihood-based inference of large phylogenetic trees. *Bioinformatics* 21, 456-463, doi:10.1093/bioinformatics/bti191 (2005).
45 Barzel, A. et al. Promoterless gene targeting without nucleases ameliorates haemophilia B in mice. *Nature* 517, 360-364, doi:10.1038/nature13864 (2015).
46 Namekawa, S. H., Payer, B., Huynh, K. D., Jaenisch, R. & Lee, J. T. Two-step imprinted X inactivation: repeat versus genic silencing in the mouse. *Molecular and cellular biology* 30, 3187-3205, doi:10.1128/MCB.00227-10 (2010).
47 Huch, M. et al. In vitro expansion of single Lgr5+ liver stem cells induced by Wnt-driven regeneration. *Nature* 494, 247-250, doi:10.1038/nature11826 (2013).
48 Dorrell, C. et al. The organoid-initiating cells in mouse pancreas and liver are phenotypically and functionally similar. *Stem cell research* 13, 275-283, doi:10.1016/j.scr.2014.07.006 (2014).
49 Mingozzi, F. et al. Prevalence and pharmacological modulation of humoral immunity to AAV vectors in gene transfer to synovial tissue. *Gene therapy* 20, 417-424, doi:10.1038/gt.2012.55 (2013).
50 Meliani, A. et al. Determination of anti-adeno-associated virus vector neutralizing antibody titer with an in vitro reporter system. *Human gene therapy methods* 26, 45-53, doi:10.1089/hgtb.2015.037 (2015).
51 Xie, Q. et al. The atomic structure of adeno-associated virus (AAV-2), a vector for human gene therapy. *Proceedings of the National Academy of Sciences of the United States of America* 99, 10405-10410, doi:10.1073/pnas.162250899 (2002).
52 Dane, A. P., Wowro, S. J., Cunningham, S. C. & Alexander, I. E. Comparison of gene transfer to the murine liver following intraperitoneal and intraportal delivery of hepatotropic AAV pseudo-serotypes. *Gene therapy* 20, 460-464, doi:10.1038/gt.2012.67 (2013).
53 Li, S. Y. et al. Efficient and Targeted Transduction of Nonhuman Primate Liver With Systemically Delivered Optimized AAV3B Vectors. *Molecular Therapy* 23, 1867-1876, doi:10.1038/mt.2015.174 (2015).
54 D'Avola, D. et al. Phase I open label liver-directed gene therapy clinical trial for acute intermittent porphyria. *Journal of hepatology* 65, 776-783, doi:10.1016/j.jhep.2016.05.012 (2016).
55 uniQure. Press release: uniQure announces first clinical data from second dose cohort of AMT-060 in ongoing phase I/II trial in patients with severe hemophilia B. (2016).
56 Paneda, A. et al. Effect of Adeno-Associated Virus Serotype and Genomic Structure on Liver Transduction and Biodistribution in Mice of Both Genders. *Human gene therapy* 20, 908-917, doi:10.1089/hum.2009.031 (2009).
57 Nakai, H. et al. Unrestricted hepatocyte transduction with adeno-associated virus serotype 8 vectors in mice. *Journal of virology* 79, 214-224, doi:10.1128/1V1.79.1.214-224.2005 (2005).
58 Mao, Y. et al. Single point mutation in adeno-associated viral vectors—DJ capsid leads to improvement for gene delivery in vivo. *BMC biotechnology* 16, 1, doi:10.1186/s12896-015-0230-0 (2016).

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. An adeno-associated virus (AAV) vector comprising a nucleic acid sequence encoding a variant AAV capsid polypeptide, wherein said variant AAV capsid polypeptide exhibits increased transduction or tropism in human liver tissue or hepatocyte cells as compared to a non-variant parent capsid polypeptide, wherein said variant AAV capsid polypeptide sequence comprises a sequence selected from the group consisting of AAV-NP84 (SEQ ID NO:2), AAV-NP59 (SEQ ID NO:4), AAV-NP40 (SEQ ID NO:6), and AAV-NP30 (SEQ ID NO:8).

2. The AAV vector of claim 1, wherein said variant AAV capsid polypeptide sequence is AAV-NP84 (SEQ ID NO:2).

3. The AAV vector of claim 1, wherein said variant AAV capsid polypeptide sequence is AAV-NP59 (SEQ ID NO:4).

4. The AAV vector of claim 1, wherein said variant AAV capsid polypeptide sequence is AAV-NP40 (SEQ ID NO:6).

5. The AAV vector of claim 1, wherein said variant AAV capsid polypeptide sequence is AAV-NP30 (SEQ ID NO:8).

6. The AAV vector of claim 1, wherein said nucleic acid sequence encoding said variant AAV capsid polypeptide comprises a sequence selected from the group consisting of AAV-NP84 (SEQ ID NO:1), AAV-NP59 (SEQ ID NO:3), AAV-NP40 (SEQ ID NO:5), and AAV-NP30 (SEQ ID NO:7).

7. A method of using the AAV vector of claim 1, in a therapeutic treatment regimen or vaccine.

8. A method of using the AAV vector of claim 1 to reduce the amount of total AAV vector administered to a subject, said method comprising administering less total AAV vector amount to said subject when said AAV vector is transduced by a variant AAV capsid polypeptide as compared to the amount of AAV vector administered to said subject when said AAV vector is transduced by a non-variant parent capsid polypeptide in order to obtain a similar therapeutic effect.

9. An adeno-associated virus (AAV) vector comprising a nucleic acid sequence encoding a variant AAV capsid polypeptide, wherein said variant AAV capsid polypeptide exhibits an enhanced neutralization profile as compared to a non-variant parent capsid polypeptide, wherein said variant AAV capsid polypeptide exhibits increased transduction of human liver organoids in 3-dimensional cultures in vitro as compared to a non-variant parent capsid polypeptide, wherein said variant AAV capsid polypeptide sequence comprises a sequence selected from the group consisting of AAV-NP84 (SEQ ID NO:2), AAV-NP59 (SEQ ID NO:4), AAV-NP40 (SEQ ID NO:6), and AAV-NP30 (SEQ ID NO:8).

10. The AAV vector of claim 1, wherein said variant AAV capsid polypeptide exhibits an enhanced neutralization profile against pooled human immunoglobulins as compared to a non-variant parent capsid polypeptide.

11. The AAV vector of claim 1, wherein said variant AAV capsid polypeptide exhibits increased transduction or tropism in human liver tissue or hepatocyte cells.

12. The AAV vector of claim 1, wherein said variant AAV capsid polypeptide exhibits increased transduction as compared to a non-variant parent capsid polypeptide.

13. The AAV vector of claim 1, wherein said variant AAV capsid polypeptide exhibits increased tropism as compared to a non-variant parent capsid polypeptide.

14. The AAV vector of claim 1, wherein said variant AAV capsid polypeptide further exhibits increased transduction or tropism in one or more non-liver human tissues or non-hepatocyte human cells as compared to a non-variant parent capsid polypeptide.

15. The AAV vector of claim 1, wherein said variant AAV capsid polypeptide exhibits increased transduction of human liver tissue or hepatocyte cells in vivo as compared to a non-variant parent capsid polypeptide.

16. The AAV vector of claim 1, wherein said variant AAV capsid polypeptide exhibits increased transduction of human liver tissue or hepatocyte cells in vitro as compared to a non-variant parent capsid polypeptide.

17. An adeno-associated virus (AAV) vector comprising a nucleic acid sequence encoding a variant AAV capsid polypeptide, wherein said variant AAV capsid polypeptide exhibits an enhanced neutralization profile as compared to a non-variant parent capsid polypeptide, wherein said vector further comprises a nucleic acid sequence comprising a therapeutic expression cassette, wherein said expression cassette is a CRISPR/CAS expression system, wherein said variant AAV capsid polypeptide sequence comprises a sequence selected from the group consisting of AAV-NP84 (SEQ ID NO:2), AAV-NP59 (SEQ ID NO:4), AAV-NP40 (SEQ ID NO:6), and AAV-NP30 (SEQ ID NO:8).

18. The AAV vector of claim 17, wherein said therapeutic expression cassette encodes a therapeutic protein or antibody.

19. An adeno-associated virus (AAV) vector comprising a nucleic acid sequence encoding a variant AAV capsid polypeptide, wherein said variant AAV capsid polypeptide exhibits an enhanced neutralization profile as compared to a non-variant parent capsid polypeptide, wherein said variant AAV capsid polypeptide sequence comprises a sequence selected from the group consisting of AAV-NP84 (SEQ ID NO:2), AAV-NP59 (SEQ ID NO:4), AAV-NP40 (SEQ ID NO:6), and AAV-NP30 (SEQ ID NO:8).

20. The AAV vector of claim 19, wherein said variant AAV capsid polypeptide sequence is AAV-NP84 (SEQ ID NO:2).

21. The AAV vector of claim 19, wherein said variant AAV capsid polypeptide sequence is AAV-NP59 (SEQ ID NO:4).

22. The AAV vector of claim 19, wherein said variant AAV capsid polypeptide sequence is AAV-NP40 (SEQ ID NO:6).

23. The AAV vector of claim 19, wherein said variant AAV capsid polypeptide sequence is AAV-NP30 (SEQ ID NO:8).

24. An adeno-associated virus (AAV) vector comprising a nucleic acid sequence encoding a variant AAV capsid polypeptide, wherein said nucleic acid sequence encoding said variant AAV capsid polypeptide comprises a sequence selected from the group consisting of AAV-NP84 (SEQ ID NO:1), AAV-NP59 (SEQ ID NO:3), AAV-NP40 (SEQ ID NO:5), and AAV-NP30 (SEQ ID NO:7).

25. A method of using the AAV vector of claim 24 in a therapeutic treatment regimen or vaccine.

26. A method of using the AAV vector of claim 24 to reduce the amount of total AAV vector administered to a subject, said method comprising administering less total AAV vector amount to said subject when said AAV vector is transduced by a variant AAV capsid polypeptide as compared to the amount of AAV vector administered to said subject when said AAV vector is transduced by a non-variant parent capsid polypeptide in order to obtain a similar therapeutic effect.

27. The AAV vector of claim 24, wherein said nucleic acid sequence encoding said variant AAV capsid polypeptide is AAV-NP84 (SEQ ID NO:1).

28. The AAV vector of claim 24, wherein said nucleic acid sequence encoding said variant AAV capsid polypeptide is AAV-NP59 (SEQ ID NO:3).

29. The AAV vector of claim 24, wherein said nucleic acid sequence encoding said variant AAV capsid polypeptide is AAV-NP40 (SEQ ID NO:5).

30. The AAV vector of claim 24, wherein said nucleic acid sequence encoding said variant AAV capsid polypeptide is AAV-NP30 (SEQ ID NO:7).

31. The AAV vector of claim 6, wherein said nucleic acid sequence encoding said variant AAV capsid polypeptide is AAV-NP84 (SEQ ID NO:1).

32. The AAV vector of claim 6, wherein said nucleic acid sequence encoding said variant AAV capsid polypeptide is AAV-NP59 (SEQ ID NO:3).

33. The AAV vector of claim 6, wherein said nucleic acid sequence encoding said variant AAV capsid polypeptide is AAV-NP40 (SEQ ID NO:5).

34. The AAV vector of claim 6, wherein said nucleic acid sequence encoding said variant AAV capsid polypeptide is AAV-NP30 (SEQ ID NO:7).

35. The AAV vector of claim 24, wherein said variant AAV capsid polypeptide exhibits an enhanced neutralization profile against pooled human immunoglobulins as compared to a non-variant parent capsid polypeptide.

36. The AAV vector of claim 24, wherein said variant AAV capsid polypeptide exhibits increased transduction or tropism in human liver tissue or hepatocyte cells.

37. The AAV vector of claim 24, wherein said variant AAV capsid polypeptide exhibits increased transduction as compared to a non-variant parent capsid polypeptide.

38. The AAV vector of claim 24, wherein said variant AAV capsid polypeptide exhibits increased tropism as compared to a non-variant parent capsid polypeptide.

39. The AAV vector of claim 24, wherein said variant AAV capsid polypeptide further exhibits increased transduction or tropism in one or more non-liver human tissues or non-hepatocyte human cells as compared to a non-variant parent capsid polypeptide.

40. The AAV vector of claim 24, wherein said variant AAV capsid polypeptide exhibits increased transduction of human liver tissue or hepatocyte cells in vivo as compared to a non-variant parent capsid polypeptide.

41. The AAV vector of claim 24, wherein said variant AAV capsid polypeptide exhibits increased transduction of human liver tissue or hepatocyte cells in vitro as compared to a non-variant parent capsid polypeptide.

42. An adeno-associated virus (AAV) vector comprising a nucleic acid sequence encoding a variant AAV capsid polypeptide, wherein said variant AAV capsid polypeptide exhibits increased transduction or tropism in human liver tissue or hepatocyte cells as compared to a non-variant parent capsid polypeptide, wherein said variant AAV capsid polypeptide exhibits increased transduction of human liver organoids in 3-dimensional cultures in vitro as compared to a non-variant parent capsid polypeptide, wherein said variant AAV capsid polypeptide sequence comprises a sequence selected from the group consisting of AAV-NP84 (SEQ ID NO:2), AAV-NP59 (SEQ ID NO:4), AAV-NP40 (SEQ ID NO:6), and AAV-NP30 (SEQ ID NO:8).

43. The AAV vector of claim 42, wherein said variant AAV capsid polypeptide exhibits an enhanced neutralization profile.

44. The AAV vector of claim 42, wherein said variant AAV capsid polypeptide exhibits an enhanced neutralization profile against pooled human immunoglobulins as compared to a non-variant parent capsid polypeptide.

45. The AAV vector of claim 42, wherein said variant AAV capsid polypeptide exhibits increased transduction or tropism in human liver tissue or hepatocyte cells.

46. The AAV vector of claim 42, wherein said variant AAV capsid polypeptide exhibits increased transduction as compared to a non-variant parent capsid polypeptide.

47. The AAV vector of claim 42, wherein said variant AAV capsid polypeptide exhibits increased tropism as compared to a non-variant parent capsid polypeptide.

48. The AAV vector of claim 42, wherein said variant AAV capsid polypeptide further exhibits increased transduction or tropism in one or more non-liver human tissues or non-hepatocyte human cells as compared to a non-variant parent capsid polypeptide.

49. The AAV vector of claim 42, wherein said variant AAV capsid polypeptide exhibits increased transduction of human liver tissue or hepatocyte cells in vivo as compared to a non-variant parent capsid polypeptide.

50. The AAV vector of claim 42, wherein said variant AAV capsid polypeptide exhibits increased transduction of human liver tissue or hepatocyte cells in vitro as compared to a non-variant parent capsid polypeptide.

* * * * *

SEQUENCE LISTING

<160> NUMBER OF SEQ ID NOS: 33

<210> SEQ ID NO 1
<211> LENGTH: 2208
<212> TYPE: DNA
<213> ORGANISM: Artificial Sequence
<220> FEATURE:
<223> OTHER INFORMATION: capsid polypeptide

<400> SEQUENCE: 1

| | | | | | |
|---|---|---|---|---|---|
| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | gcataaggac | 120 |
| gacagcaggg | gtcttgtgct | tcctgggtac | aagtacctcg | acccttcaa | cggactcgac | 180 |
| aagggagagc | cggtcaacga | ggcagacgcc | gcggccctcg | agcacgacaa | agcctacgac | 240 |
| cggcagctcg | acagcggaga | caacccgtac | ctcaagtaca | accacgccga | cgcggagttt | 300 |
| caggagcgcc | ttaaagaaga | tacgtctttt | gggggcaacc | tcggacgagc | agtcttccag | 360 |
| gcgaaaaaga | gggttcttga | acctctgggc | ctggttgagg | aacctgttaa | gacggctccg | 420 |
| ggaaaaaaga | ggccggtaga | gcactctcct | gtggagccag | actcctcctc | gggaaccggc | 480 |
| aagacaggcc | agcagcccgc | taaaaagaga | ctcaattttg | gtcagactgg | cgactcagag | 540 |
| tcagtcccag | accctcaacc | tctcggagaa | ccaccagcag | cccctctgg | tctgggaact | 600 |
| aatacgatgg | ctacaggcag | tggcgcacca | atggcagaca | ataacgaggg | tgccgatgga | 660 |
| gtgggtaatt | cctcaggaaa | ttggcattgc | gattcccaat | ggctgggcga | cagagtcatc | 720 |
| accaccagca | ccagaacctg | ggccctgccc | acctacaaca | accatctcta | caagcaaatc | 780 |
| tccagccaat | caggagcttc | aaacgacaac | cactactttg | gctacagcac | ccttggggg | 840 |
| tattttgact | taacagatt | ccactgccac | ttctcaccac | gtgactggca | gcgactcatt | 900 |
| aacaacaact | ggggattccg | gcccaagaaa | ctcagcttca | agctcttcaa | catccaagtt | 960 |
| aaagaggtca | cgcagaacga | tggcacgacg | actattgcca | ataaccttac | cagcacggtt | 1020 |
| caagtgttta | ctgactcgga | gtaccagctc | ccgtacgtcc | tcggctcggc | gcatcaagga | 1080 |
| tgcctcccgc | cgttcccagc | agacgtcttc | atggtgccac | agtatggata | cctcaccctg | 1140 |
| aacaacggga | gtcaggcagt | aggacgctct | tcattttact | gcctggagta | cttccttct | 1200 |
| cagatgctgc | gtaccggaaa | caactttacc | ttcagctaca | cttttgagga | cgttcctttc | 1260 |
| cacagcagct | acgctcacag | ccagagtctg | gaccgtctca | tgaatcctct | catcgaccag | 1320 |
| tacctgtatt | acttgagcag | aacaaacact | ccaagtggaa | ccaccacgca | gtcaaggctt | 1380 |
| cagtttctc | aggccggagc | gagtgacatt | cgggaccagt | ctaggaactg | gcttcctgga | 1440 |
| ccctgttacc | gccagcagcg | agtatcaaag | acatctgcgg | ataacaacaa | cagtgaatac | 1500 |
| tcgtggactg | gagctaccaa | gtaccacctc | aatggcagag | actctctggt | gaatccgggc | 1560 |
| ccggccatgg | caagccacaa | ggacgatgaa | gaaagttttt | tccctcagag | cggggttctc | 1620 |
| atctttggga | agcaaggctc | agagaaaaca | aatgtggaca | ttgaaaaggt | catgattaca | 1680 |
| gacgaagagg | aaatcaggac | aaccaatccc | gtggctacgg | agcagtatgg | ttctgtatct | 1740 |
| accaacctcc | aggaggcaa | cagacaagca | gctaccgcag | atgtcaacac | acaaggcgtt | 1800 |
| cttccaggca | tggtctggca | ggacagagat | gtgtaccttc | aggggcccat | ctgggcaaag | 1860 |
| attccacaca | cggacggaca | ttttcacccc | tctcccctca | tgggtggatt | cggacttaaa | 1920 |
| cacccctcctc | cacagattct | catcaagaac | accccggtac | ctgcgaatcc | ttcgaccacc | 1980 |
| ttcagtgcgg | caaagtttgc | ttccttcatc | acacagtact | ccacgggaca | ggtcagcgtg | 2040 |

```
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa                2208

<210> SEQ ID NO 2
<211> LENGTH: 735
<212> TYPE: PRT
<213> ORGANISM: Artificial Sequence
<220> FEATURE:
<223> OTHER INFORMATION: capsid polypeptide

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Phe Pro Ala Asp
            355                 360             365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Gly Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 3
<211> LENGTH: 2208
```

<212> TYPE: DNA
<213> ORGANISM: Artificial Sequence
<220> FEATURE:
<223> OTHER INFORMATION: capsid polypeptide

<400> SEQUENCE: 3

| | | | | | |
|---|---|---|---|---|---|
| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | gcataaggac | 120 |
| gacagcaggg | gtcttgtgct | tcctgggtac | aagtacctcg | gacccttcaa | cggactcgac | 180 |
| aagggagagc | cggtcaacga | ggcagacgcc | gcggccctcg | agcacgacaa | agcctacgac | 240 |
| cggcagctcg | acagcggaga | caacccgtac | ctcaagtaca | accacgccga | cgcggagttt | 300 |
| caggagcgcc | ttaaagaaga | tacgtctttt | gggggcaacc | tcggacgagc | agtcttccag | 360 |
| gcgaaaaaga | gggttcttga | acctctgggc | ctggttgagg | aacctgttaa | gacggctccg | 420 |
| ggaaaaaaga | ggccggtaga | gcactctcct | gtggagccag | actcctcctc | gggaaccggc | 480 |
| aagacaggcc | agcagcccgc | taaaaagaga | ctcaattttg | gtcagactgg | cgactcagag | 540 |
| tcagtcccag | accctcaacc | tctcggagaa | ccaccagcag | cccctctgg | tctgggaact | 600 |
| aatacgatgg | ctacaggcag | tggcgcacca | atggcagaca | taacgagggg | cgccgacgga | 660 |
| gtgggtaatt | cctcgggaaa | ttggcattgc | gattccacat | ggatgggcga | cagagtcatc | 720 |
| accaccagca | cccgaacctg | gcccctgccc | acctacaaca | accatctcta | caagcaaatc | 780 |
| tccagccaat | caggagcttc | aaacgacaac | cactactttg | gctacagcac | cccttggggg | 840 |
| tattttgact | ttaacagatt | ccactgccac | ttctcaccac | gtgactggca | gcgactcatt | 900 |
| aacaacaact | ggggattccg | gcccaagaaa | ctcagcttca | agctcttcaa | catccaagtt | 960 |
| aaagaggtca | cgcagaacga | tggcacgacg | actattgcca | ataacttac | cagcacggtt | 1020 |
| caagtgttta | ctgactcgga | gtaccagctc | ccgtacgtcc | tcggctcggc | gcatcaagga | 1080 |
| tgcctcccgc | cgttcccagc | agacgtcttc | atggtgccac | agtatggata | cctcaccctg | 1140 |
| aacaacggga | gtcaggcagt | aggacgctct | tcattttact | gcctggagta | ctttccttct | 1200 |
| cagatgctgc | gtaccggaaa | caactttacc | ttcagctaca | cttttgagga | cgttcctttc | 1260 |
| cacagcagct | acgctcacag | ccagagtctg | gaccgtctca | tgaatcctct | catcgaccag | 1320 |
| tacctgtatt | acttgagcag | aacaaacact | ccaagtggaa | ccaccacgca | gtcaaggctt | 1380 |
| cagtttttctc | aggccggagc | gagtgacatt | cgggaccagt | ctaggaactg | gcttcctgga | 1440 |
| ccctgttacc | gccagcagcg | agtatcaaag | acatctgcgg | ataacaacaa | cagtgaatac | 1500 |
| tcgtggactg | gagctaccaa | gtaccacctc | aatggcagag | actctctggt | gaatccgggc | 1560 |
| ccggccatgg | caagccacaa | ggacgatgaa | gaaaagtttt | tccctcagag | cggggttctc | 1620 |
| atctttggga | agcaaggctc | agagaaaaca | aatgtggaca | ttgaaaaggt | catgattaca | 1680 |
| gacgaagagg | aaatcaggac | aaccaatccc | gtggctacgg | agcagtatgg | ttctgtatct | 1740 |
| accaacctcc | agagaggcaa | cagacaagca | gctaccgcag | atgtcgacac | acaaggcgtt | 1800 |
| cttccaggca | tggtctggca | ggacagagat | gtgtaccttc | agggacccat | ctgggcaaag | 1860 |
| attccacaca | cggacggaca | ttttcacccc | tctcccctca | tgggtggatt | cggacttaaa | 1920 |
| caccctcctc | cacagattct | catcaagaac | accccggtac | ctgcgaatcc | ttcgaccacc | 1980 |
| ttcagtgcgg | caaagtttgc | ttccttcatc | acacagtact | ccacgggaca | ggtcagcgtg | 2040 |
| gagatcgagt | gggagctgca | gaaggaaaac | agcaaacgct | ggaatcccga | aattcagtac | 2100 |
| acttccaact | acaacaagtc | tgttaatgtg | gactttactg | tggacactaa | tggcgtgtat | 2160 |

-continued tcagagcctc gccccattgg caccagatac ctgactcgta atctgtaa         2208

<210> SEQ ID NO 4
<211> LENGTH: 735
<212> TYPE: PRT
<213> ORGANISM: Artificial Sequence
<220> FEATURE:
<223> OTHER INFORMATION: capsid polypeptide

<400> SEQUENCE: 4

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
```

```
                355                 360                 365
Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asp Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 5
<211> LENGTH: 2208
<212> TYPE: DNA
<213> ORGANISM: Artificial Sequence
<220> FEATURE:
<223> OTHER INFORMATION: capsid polypeptide
```

<400> SEQUENCE: 5

```
atggctgccg atggttatct tccagattgg ctcgaggaca accttagtga aggaataaga      60
cagtggtgga agctcaaacc tggcccacca ccaccaaagc ccgcagagcg gcataaggac     120
gacagcaggg gtcttgtgct tcctgggtac aagtacctcg gacccttcaa cggactcgac     180
aagggagagc cggtcaacga ggcagacgcc gcggccctcg agcacgacaa agcctacgac     240
cggcagctcg acagcggaga caacccgtac ctcaagtaca accacgccga cgcggagttt     300
caggagcgcc ttaaagaaga tacgtctttt gggggcaacc tcggacgagc agtcttccag     360
gcgaaaaaga gggttcttga acctctgggc ctggttgagg aacctgttaa gacggctccg     420
ggaaaaaaga ggccggtaga gcactctcct gtggagccag actcctcctc gggaaccggc     480
aagacaggcc agcagcccgc taaaaagaga ctcaattttg gtcagactgg cgactcagag     540
tcagtcccag accctcaacc tctcggagaa ccaccagcag cccctctgg tctgggaact     600
aatacgatgg ctacaggcag tggcgcacca atgcgagaca ataacgaggg cgccgacgga     660
gtgggtaatt cctcgggaaa ttggcattgc gattccacat ggatgggcga cagagtcatc     720
accaccagca ccagaacctg ggccctgccc acctacaaca accatctcta caagcaaatc     780
tccagccaat caggagcttc aaacgacaac cactactttg ctacagcac ccttgggg     840
tattttgact ttaacagatt ccactgccac ttctcaccac gtgactggca gcgactcatt     900
aacaacaact ggggattccg gcccaagaaa ctcagcttca agctcttcaa catccaagtt     960
aaagaggtca cgcagaacga tggcacgacg actattgcca ataaccttac cagcacggtt    1020
caagtgttta ctgactcgga gtaccagctc ccgtacgtcc tcggctcggc gcatcaagga    1080
tgcctcccgc cgttcccagc agacgtcttc atggtgccac agtatggata cctcacccctg    1140
aacaacggga gtcaggcagt aggacgctct tcatttttact gcctggagta ctttccttct    1200
cagatgctgc gtaccggaaa caactttacc ttcagctaca cttttgagga cgttcctttc    1260
cacagcagct acgctcacag ccagagtctg gaccgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaagagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attcacacac cggacggaca tttttcacccc tctccctca tggtggattt cggacttaaa    1920
caccctcctc acagatcttc catcaagaac acccgtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatcccga aattcagtac    2100
acttccaact acaacaagtc tgttaatgtg gactttactg tggacactaa tggcgtgtat    2160
tcagagcctc gcccccattgg caccagatac ctgactcgta atctgtaa                 2208
```

<210> SEQ ID NO 6
<211> LENGTH: 735

-continued

```
<212> TYPE: PRT
<213> ORGANISM: Artificial Sequence
<220> FEATURE:
<223> OTHER INFORMATION: capsid polypeptide

<400> SEQUENCE: 6

Met Ala Ala Asp Gly Tyr Leu Pro Asp Trp Leu Glu Asp Asn Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380
```

```
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
        420                 425                 430

Leu Met Asn Pro Leu Ile Asp Gln Tyr Leu Tyr Tyr Leu Ser Arg Thr
    435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 7
<211> LENGTH: 2208
<212> TYPE: DNA
<213> ORGANISM: Artificial Sequence
<220> FEATURE:
<223> OTHER INFORMATION: capsid polypeptide

<400> SEQUENCE: 7
atggctgccg atggttatct tccagattgg ctcgaggaca ctctctctga aggaataaga      60
cagtggtgga agctcaaacc tggcccacca ccaccaaagc ccgcagagcg gcataaggac     120
```

```
gacagcaggg gtcttgtgct tcctgggtac aagtacctcg acccttcaa cggactcgac    180 aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa dacggctccg    420
ggaaaaaaga ggccggtaga gcactctcct gtggagccag actcctcctc gggaaccggc    480
aagacaggcc agcagcccgc taaaaagaga ctcaattttg gtcagactgg cgactcagag    540
tcagtcccag accctcaacc tctcggagaa ccaccagcag cccctctgg tctgggaact    600 aatacgatgg ctacaggcag tggcgcacca atggcagaca ataacgaggg tgccgatgga    660
gtgggtaatt cctcaggaaa ttggcattgc gattcccaat ggctgggcga cagagtcatc    720
accaccagca ccagaacctg ggccctgccc acctacaaca accatctcta caagcaaatc    780
tccagccaat caggagcttc aaacgacaac cactactttg gctacagcac cccttggggg    840
tattttgact ttaacagatt ccactgccac ttctcaccac gtgactggca gcgactcatt    900
aacaacaact ggggattccg gcccaagaaa ctcagcttca agctctttaa catccaagtt    960
aaagaggtca cgcagaacga tggcacgacg actattgcca ataaccttac cagcacggtt   1020
caagtgttta ctgactcgga gtaccagctc ccgtacgtcc tcggctcggc gcatcaagga   1080
tgcctcccgc cgttcccagc agacgtcttc atggtgccac agtatggata cctcaccctg   1140
aacaacggga gtcaggcagt aggacgctct tcattttact gcctggagta ctttccttct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccactc aatggcagag actctctggt gaatccgggc   1560
ccggccatgg caagccacaa ggacgatgaa gaagagttt tccctcagag cgggggttctc   1620 atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac acccccgtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa             2208
```

<210> SEQ ID NO 8
<211> LENGTH: 735
<212> TYPE: PRT
<213> ORGANISM: Artificial Sequence
<220> FEATURE:
<223> OTHER INFORMATION: capsid polypeptide

```
<400> SEQUENCE: 8

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415
```

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Glu Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 9
<211> LENGTH: 2211
<212> TYPE: DNA
<213> ORGANISM: Artificial Sequence
<220> FEATURE:
<223> OTHER INFORMATION: capsid polypeptide

<400> SEQUENCE: 9
atggctgctg acggttatct tccagattgg ctcgaggaca acctttctga aggcattcga     60
gagtggtggg cgctgcaacc tggagcccct aaacccaagg caaatcaaca acatcaggac    120
aacgctcggg gtcttgtgct tccgggttac aaatacctcg acccggcaa cggactcgac    180 aaggggaac ccgtcaacgc agcggacgcg gcagccctcg agcacgacaa ggcctacgac    240

```
cagcagctca aggccggtga caaccoctac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga tcagtctcct caggaaccgg actcatcatc tggtgttggc    480
aaatcgggca acagcctgc agaaaaaga ctaaatttcg gtcagactgg cgactcagag    540
tcagtcccag accctcaacc tctcggagaa ccaccagcag cccccacaag tttgggatct    600
aatacaatgg cttcaggcgg tggcgcacca atggcagaca ataacgaggg tgccgatgga    660
gtgggtaatt cctcaggaaa ttggcattgc gattcccaat ggctgggcga cagagtcatc    720
accaccagca ccagaacctg ggccctgccc acttacaaca accatctcta caagcaaatc    780
tccagccaat caggagcttc aaacgacaac cactactttg ctacagcac cccttggggg    840
tattttgact ttaacagatt ccactgccac ttctcaccac gtgactggca gcgactcatt    900
aacaacaact ggggattccg gcccaagaaa ctcagcttca agctcttcaa catccaagtt    960
aaagaggtca cgcagaacga tggcacgacg actattgcca ataaccttac cagcacggtt    1020
caagtgttta cggactcgga gtatcagctc ccgtacgtgc tcgggtcggc gcaccaaggc    1080
tgtctcccgc cgtttccagc ggacgtcttc atggtccctc agtatggata cctcaccctg    1140
aacaacggaa gtcaagcggt gggacgctca tccttttact gcctggagta cttcccttcg    1200
cagatgctaa ggactggaaa taacttccaa ttcagctata ccttcgagga tgtacctttt    1260
cacagcagct acgctcacag ccagagtttg gatcgcttga tgaatcctct tattgatcag    1320
tatctgtact acctgaacag aacgcaagga acaacctctg aacaaccaa ccaatcacgg    1380
ctgcttttta gccaggctgg gcctcagtct atgtctttgc aggccagaaa ttggctacct    1440
gggccctgct accggcaaca gagactttca aagactgcta cgacaacaa caacagtaac    1500
tttccttgga cagcggccag caaatatcat ctcaatggcc gcgactcgct ggtgaatcca    1560
ggaccagcta tggccagtca caggacgat gaagaaaaat ttttccctat gcacggcaat    1620
ctaatatttg gcaaagaagg gacaacggca agtaacgcag aattagataa tgtaatgatt    1680
acggatgaag aagagattcg taccaccaat cctgtggcaa cagagcagta tggaactgtg    1740
gcaaataact tgcagagctc aaatacagct cccacgacta gaactgtcaa tgatcagggg    1800
gccttacctg catggtgtg gcaagatcgt gacgtgtacc ttcaaggacc tatctgggca    1860
aagattcctc acacggatgg acactttcat ccttctcctc tgatgggagg ctttggactg    1920
aaacatccgc ctcctcaaat catgatcaaa aatactccgg taccgcaaa tcctccgacg    1980
actttcagcc cggccaagtt tgcttcattt atcactcagt actccactgg acaggtcagc    2040
gtggaaattg agtgggagct acagaaagaa aacagcaaac gttggaatcc agagattcag    2100
tacacttcca actacaacaa gtctgttaat gtggacttta ctgtagacac taatggtgtt    2160
tatagtgaac ctcgccccat tggcacccgt taccttaccc gtcccctgta a    2211
```

<210> SEQ ID NO 10
<211> LENGTH: 736
<212> TYPE: PRT
<213> ORGANISM: Artificial Sequence
<220> FEATURE:
<223> OTHER INFORMATION: capsid polypeptide

<400> SEQUENCE: 10

Met Ala Ala Asp Gly Tyr Leu Pro Asp Trp Leu Glu Asp Asn Leu Ser
1               5                   10                  15

-continued

```
Glu Gly Ile Arg Glu Trp Trp Ala Leu Gln Pro Gly Ala Pro Lys Pro
             20                  25                  30

Lys Ala Asn Gln Gln His Gln Asp Asn Ala Arg Gly Leu Val Leu Pro
         35                  40                  45

Gly Tyr Lys Tyr Leu Gly Pro Gly Asn Gly Leu Asp Lys Gly Glu Pro
     50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
             100                 105                 110

Asn Leu Gly Arg Ala Val Phe Gln Ala Lys Lys Arg Leu Leu Glu Pro
         115                 120                 125

Leu Gly Leu Val Glu Glu Ala Ala Lys Thr Ala Pro Gly Lys Lys Arg
     130                 135                 140

Pro Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                 165                 170                 175

Gly Asp Ser Glu Ser Val Pro Asp Pro Gln Pro Leu Gly Glu Pro Pro
             180                 185                 190

Ala Ala Pro Thr Ser Leu Gly Ser Asn Thr Met Ala Ser Gly Gly Gly
         195                 200                 205

Ala Pro Met Ala Asp Asn Asn Glu Gly Ala Asp Gly Val Gly Asn Ser
     210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                 245                 250                 255

Tyr Lys Gln Ile Ser Ser Gln Ser Gly Ala Ser Asn Asp Asn His Tyr
             260                 265                 270

Phe Gly Tyr Ser Thr Pro Trp Gly Tyr Phe Asp Phe Asn Arg Phe His
         275                 280                 285

Cys His Phe Ser Pro Arg Asp Trp Gln Arg Leu Ile Asn Asn Asn Trp
     290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                 325                 330                 335

Thr Ser Thr Val Gln Val Phe Thr Asp Ser Glu Tyr Gln Leu Pro Tyr
             340                 345                 350

Val Leu Gly Ser Ala His Gln Gly Cys Leu Pro Pro Phe Pro Ala Asp
         355                 360                 365

Val Phe Met Val Pro Gln Tyr Gly Tyr Leu Thr Leu Asn Asn Gly Ser
     370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                 405                 410                 415

Asp Val Pro Phe His Ser Ser Tyr Ala His Ser Gln Ser Leu Asp Arg
             420                 425                 430

Leu Met Asn Pro Leu Ile Asp Gln Tyr Leu Tyr Tyr Leu Asn Arg Thr
```

```
             435                 440                 445
Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
                515                 520                 525

Asp Asp Glu Glu Lys Phe Phe Pro Met His Gly Asn Leu Ile Phe Gly
530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735

<210> SEQ ID NO 11
<211> LENGTH: 2214
<212> TYPE: DNA
<213> ORGANISM: Artificial Sequence
<220> FEATURE:
<223> OTHER INFORMATION: capsid polypeptide

<400> SEQUENCE: 11
atggctgccg atggttatct tccagattgg ctcgaggaca ctctctctga aggaataaga      60
cagtggtgga agctcaaacc tggcccacca ccaccaaagc ccgcagagcg cataaggac     120 gacagcaggg gtcttgtgct tcctgggtac aagtacctcg acccttcaa cggactcgac     180 aagggagagc cggtcaacga ggcagacgcc gcggccctcg agcacgacaa agcctacgac    240
cggcagctcg acagcggaga caaccccgtac ctcaagtaca accacgccga cgccgagttc    300
caggagcggc tcaaagaaga tacgtctttt ggggggcaacc tcgggcgagc agtcttccag    360
gccaaaaaga ggcttcttga acctcttggt ctggttgagg aagcggctaa gacggctcct    420
```

```
ggaaagaaga ggcctgtaga gcactctcct gtggagccag actcctcctc gggaaccgga    480
aaggcgggcc agcagcctgc aagaaaaaga ttgaattttg gtcagactgg agacgcagac    540
tcagtcccag accctcaacc aatcggagaa cctcccgcag cccctcagg tgtgggatct     600 cttacaatgg ctgcaggcgg tggcgcacca atggcagaca taacgagggg cgccgacgga    660
gtgggtaatt cctcgggaaa ttggcattgc gattccacat ggatgggcga cagagtcatc    720
accaccagca cccgaacctg ggccctgccc acctacaaca accacctcta caagcaaatc    780
tccaacagca catctggagg atcttcaaat gacaacgcct acttcggcta cagcaccccc    840 tggggggtatt ttgactttaa cagattccac tgccactttt caccacgtga ctggcagcga    900
ctcatcaaca caactgggg attccggccc aagagactca gcttcaagct cttcaacatc    960
caggtcaagg aggtcacgca gaatgaaggc accaagacca tcgccaataa cctcaccagc   1020
accatccagg tgtttacgga ctcggagtac cagctgccgt acgttctcgg ctctgcccac   1080
cagggctgcc tgcctccgtt cccggcggac gtgttcatga ttccccagta cggctaccta   1140
acactcaaca acggtagtca ggccgtggga cgctcctcct tctactgcct ggaatacttt   1200
ccttcgcaga tgctgagaac cggcaacaac ttccagttta cttacacctt cgaggacgtg   1260
cctttccaca gcagctacgc ccacagccag agcttggacc ggctgatgaa tcctctgatt   1320
gaccagtacc tgtactactt gtctcggact caaacaacag gaggcacgac aaatacgcag   1380
actctgggct tcagccaagg tgggcctaat acaatggcca atcaggcaaa gaactggctg   1440
ccaggaccct gttaccgcca gcagcgagta tcaaagacat ctgcggataa caacaacagt   1500
gaatactcgt ggactggagc taccaagtac cacctcaatg gcagagactc tctggtgaat   1560 ccgggccccgg ccatggcaag ccacaaggac gatgaagaaa agttttttcc tcagagcggg   1620
gttctcatct ttgggaagca aggctcagag aaaacaaatg tggacattga aaaggtcatg   1680
attacagacg aagaggaaat caggacaacc aatcccgtgg ctacggagca gtatggttct   1740
gtatctacca acctccagag aggcaacaga caagcagcta ccgcagatgt caacacacaa   1800
ggcgttcttc caggcatggt ctggcaggac agagatgtgt accttcaggg gcccatctgg   1860
gcaaagattc acacacggga cggacatttt caccctctc ccctcatggg tggattcgga   1920
cttaaacacc ctcgcctca gatcctgatc aagaacacgc ctgtacctgc ggatcctccg   1980
accaccttca accagtcaaa gctgaactct ttcatcaccc agtattctac tggccaagtc   2040
agcgtggaga tcgagtggga gctgcagaag gaaaacagca gcgctggaa ccccgagatc    2100 cagtacacct ccaactacta caaatctaca agtgtggact tgctgttaa tacagaaggc    2160 gtgtactctg aaccccgccc cattggcacc cgttacctca cccgtaatct gtaa          2214
```

<210> SEQ ID NO 12
<211> LENGTH: 737
<212> TYPE: PRT
<213> ORGANISM: Artificial Sequence
<220> FEATURE:
<223> OTHER INFORMATION: capsid polypeptide

<400> SEQUENCE: 12

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45
```

```
Gly Tyr Lys Tyr Leu Gly Pro Phe Asn Gly Leu Asp Lys Gly Glu Pro
     50                  55                  60

Val Asn Glu Ala Asp Ala Ala Leu Glu His Asp Lys Ala Tyr Asp
 65              70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Ile Gly Glu Pro Pro
            180                 185                 190

Ala Ala Pro Ser Gly Val Gly Ser Leu Thr Met Ala Ala Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Thr Asn Thr Gln Thr Leu Gly Phe
450                 455                 460
```

```
Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Lys Thr Ser Ala Asp
            485                 490                 495

Asn Asn Asn Ser Glu Tyr Ser Trp Thr Gly Ala Thr Lys Tyr His Leu
                500                 505                 510

Asn Gly Arg Asp Ser Leu Val Asn Pro Gly Pro Ala Met Ala Ser His
            515                 520                 525

Lys Asp Asp Glu Glu Lys Phe Phe Pro Gln Ser Gly Val Leu Ile Phe
530                 535                 540

Gly Lys Gln Gly Ser Glu Lys Thr Asn Val Asp Ile Glu Lys Val Met
545                 550                 555                 560

Ile Thr Asp Glu Glu Glu Ile Arg Thr Thr Asn Pro Val Ala Thr Glu
                565                 570                 575

Gln Tyr Gly Ser Val Ser Thr Asn Leu Gln Arg Gly Asn Arg Gln Ala
                580                 585                 590

Ala Thr Ala Asp Val Asn Thr Gln Gly Val Leu Pro Gly Met Val Trp
            595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 13
<211> LENGTH: 101
<212> TYPE: PRT
<213> ORGANISM: Artificial Sequence
<220> FEATURE:
<223> OTHER INFORMATION: capsid polypeptide

<400> SEQUENCE: 13

Asn Asp Gly Thr Thr Thr Ile Ala Asn Asn Leu Thr Ser Thr Val Gln
1               5                   10                  15

Val Phe Thr Asp Ser Glu Tyr Gln Leu Pro Tyr Val Leu Gly Ser Ala
                20                  25                  30

His Gln Gly Cys Leu Pro Pro Phe Pro Ala Asp Val Phe Met Val Pro
            35                  40                  45

Gln Tyr Gly Tyr Leu Thr Leu Asn Asn Gly Ser Gln Ala Val Gly Arg
        50                  55                  60

Ser Ser Phe Tyr Cys Leu Glu Tyr Phe Pro Ser Gln Met Leu Arg Thr
65                  70                  75                  80

Gly Asn Asn Phe Gln Phe Ser Tyr Thr Phe Glu Asp Val Pro Phe His
```

Ser Ser Tyr Ala His
        100

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gtctgagtga ctagcattcg                                        20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gcttactgaa gctcactgag                                        20

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
ttcgatcaac tacgcagaca g                                      21

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
gtccgtgagt gaagcagata tt                                     22

<210> SEQ ID NO 18
<211> LENGTH: 24
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: modified by FAM
<220> FEATURE:
<221> NAME/KEY: misc_feature
<222> LOCATION: (24)..(24)
<223> OTHER INFORMATION: modified by BHQ-1/-3'

<400> SEQUENCE: 18
tctgatgctg tttccctgca gaca                                   24

<210> SEQ ID NO 19
<211> LENGTH: 20
<212> TYPE: DNA
<213> ORGANISM: Artificial Sequence
<220> FEATURE:

<223> OTHER INFORMATION: primer

<400> SEQUENCE: 19
gacgtaaacg gccacaagtt                                               20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
gaacttcagg gtcagcttgc                                               20

<210> SEQ ID NO 21
<211> LENGTH: 20
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: modified by FAM
<220> FEATURE:
<221> NAME/KEY: misc_feature
<222> LOCATION: (20)..(20)
<223> OTHER INFORMATION: modified by BHQ-1/-3'

<400> SEQUENCE: 21
cgagggcgat gccacctacg                                               20

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
cacatatcga ggtggacatt ac                                            22

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
tggtttgtat tcagcccata g                                             21

<210> SEQ ID NO 24
<211> LENGTH: 23
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: modified by FAM
<220> FEATURE:
<221> NAME/KEY: misc_feature
<222> LOCATION: (1)..(1)
<223> OTHER INFORMATION: modified by BHQ-1/-3'

<400> SEQUENCE: 24

```
acttcgagat gagcgttcgg ctg                                          23

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
tggatgactg catctttgaa                                              20

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
tgcttacccg ggttacgagt caggtatctg                                   30

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
tggatgactg catctttgaa                                              20

<210> SEQ ID NO 28
<211> LENGTH: 17
<212> TYPE: DNA
<213> ORGANISM: Artificial Sequence
<220> FEATURE:
<223> OTHER INFORMATION: primer

<400> SEQUENCE: 28
attggcattg cgattcc                                                 17

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
atggaaacta gataagaaag aa                                           22

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
aaatcaggta tggctgccga tg                                           22

<210> SEQ ID NO 31
<211> LENGTH: 30
<212> TYPE: DNA
```

```
<213> ORGANISM: Artificial Sequence
<220> FEATURE:
<223> OTHER INFORMATION: primer

<400> SEQUENCE: 31
gcttcccggg atggaaacta gataagaaag                              30

<210> SEQ ID NO 32
<211> LENGTH: 137
<212> TYPE: DNA
<213> ORGANISM: Artificial Sequence
<220> FEATURE:
<223> OTHER INFORMATION: modified AAV2 VP1 3'UTR sequence

<400> SEQUENCE: 32
gtaattgctt gttaatcaat aaaccgttta attcgtttca gttgaacttt ggtctctgcg    60
tatttctttc ttatctagtt tccatatgca tgtagataag tagcatggcg ggttaatcat   120
taactacaag gaacccc                                                  137

<210> SEQ ID NO 33
<211> LENGTH: 137
<212> TYPE: DNA
<213> ORGANISM: Artificial Sequence
<220> FEATURE:
<223> OTHER INFORMATION: modified AAV2 VP1 3'UTR sequence

<400> SEQUENCE: 33
gtaattgctt gttaatcaat aaaccgttta attcgtttca gttgaacttt ggtctctgcg    60
tatttctttc ttatctagtt tccatggcta cgtagataag tagcatggcg ggttaatcat   120
taactacaag gaacccc                                                  137
```